US006214355B1

(12) United States Patent
Guo et al.

(10) Patent No.: US 6,214,355 B1
(45) Date of Patent: Apr. 10, 2001

(54) DBPA COMPOSITIONS

(75) Inventors: Betty P. Guo, Boston, MA (US); Magnus Höök, Houston, TX (US)

(73) Assignee: Texas A & M University System, College Station, TX (US)

( * ) Notice: Subject to any disclaimer, the term of this patent is extended or adjusted under 35 U.S.C. 154(b) by 0 days.

(21) Appl. No.: 09/117,257

(22) PCT Filed: Oct. 22, 1996

(86) PCT No.: PCT/US96/17081

§ 371 Date: Oct. 29, 1998

§ 102(e) Date: Oct. 29, 1998

(87) PCT Pub. No.: WO97/27301

PCT Pub. Date: Jul. 31, 1997

Related U.S. Application Data

(63) Continuation-in-part of application No. 08/945,476, filed as application No. PCT/US96/05886 on Apr. 24, 1996, which is a continuation-in-part of application No. 08/589,711, filed on Jan. 22, 1996, now Pat. No. 5,853,987, which is a continuation-in-part of application No. 08/427,023, filed on Apr. 24, 1995, now abandoned.

(51) Int. Cl.[7] .......................... A16K 39/02; A16K 38/16; C07K 14/20; C07K 16/12
(52) U.S. Cl. .................... 424/234.1; 530/388.4; 530/350; 514/2
(58) Field of Search ................ 530/350, 388.4; 504/2; 424/234.1

(56) References Cited

U.S. PATENT DOCUMENTS

| 5,460,955 | 10/1995 | Mosher et al. | 435/69.7 |
|---|---|---|---|
| 5,853,987 | 12/1998 | Gou et al. | 435/6 |

FOREIGN PATENT DOCUMENTS

| WO 90/04411 | 5/1990 | (WO) | C12Q/1/68 |
|---|---|---|---|
| WO 92/00055 | 1/1992 | (WO) | C12N/15/31 |
| WO 95/04145 | 2/1995 | (WO) | C12N/15/31 |
| WO 96/34106 | 10/1996 | (WO) | C12N/15/30 |
| WO 97/27301 | 7/1997 | (WO) | C12N/15/30 |
| 98/06850 | * 2/1998 | (WO) . | |

OTHER PUBLICATIONS de Silva, et al., "*Borrelia Burgdorferi* OspA is an Arthopod–Specific Transmission–Blocking Lyme Disease Vaccine," *J. Exp. Med.*, 183:271–275, 1996.

Jauris–Heipke, et al., "Genetic Heterogeneity of the Genes Coding for the Outer Surface Protein C(OspC) and the Flagellin of Borrelia Burgdorferi," *Med. Microbial. Immunol. (Berl)*, 182(1):37–50, 1993.

Mayer, et al., "Block Oligopeptides (L–Lysyl)$_m$–(L–Alanyl)$_n$–L–Tyrosyl–(L–Alanyl)$_n$–(L–Lysyl)$_m$–II. Circular Dichroism and Pulsefluorimetry Conformational Studies," *Biopolymers*, 17:337–360, 1978.

O'Brian, et al., HIV–1 Tropism for Mononuclear Phagocytes can be Determined by Regions of gp120 Outside the CD4–Binding Domain, *Nature*, 1990.

Schönherr, et al., "Interaction of Biglycan with Type I Collagen," *J. Biol. Chem.*, 270(6):2776–2783, 1995.

Schönherr, et al., "Decorin–Type I Collagen Interaction," *J. Biol. Chem.*, 270(15):8877–8883, 1995.

Stuber, et al., "Assessment of Major Histocompatibility Complex Class I Interaction with Epstein–Barr Virus and Human Immunodeficiency Virus Peptides by Elevation of Membrane H–2 and HLA in Peptide Loading–Deficient Cell," *Eur. J. Immunol.*, 22:2697–2703, 1992.

Takeuchi, et al., "Bone Matrix Decorin Binds Transforming Growth Factor–β and Enhances its Bioactivity," *J. Biol. Chem.*, 269:32634–32638, 1994.

Yaron, et al., "Synthesis and Immunological Properties of the Oligolysyl–N–Dinitrophenyllysine and Oligolysylalanylalany–N–Dinitrophenyllysine Peptides Series," *Biochemistry*, 13(2):347–354, 1974.

Alon, R., Bayer, E.A. and Wilchek, M., "Biotin–Containing Protein as a Cause of False Positive Clones in Gene Probing with Streptavidin/Biotin," *BioTechniques*, 14(2):209–210, 1993.

Isberg, R. R., "Discrimination Between Intracellular Uptake and Surface Adhesion of Bacterial Pathogens," *Science*, 252:934–938, May 17, 1991.

Sambrook, J., Fritsch, E. F. and Maniatis, T., In: *Molecular Cloning, A Laboratory Manual*, 2d Ed., Cold Spring Harbor Laboratory Press, New York, pp. 12.16–12.24, 1989.

Kantor, F. S., "Disarming Lyme Disease," *Scientific American*, pp. 34–39, Sep., 1994.

Langermann, S., Palaszynski, S., Sadziene, A., Stover, C. K. and Keonig, S., "Systemic and Mucosal Immunity Induced by BCG Vector Expressing Outer–Surface Protein A of *Borrielia burgdorferi*," *Nature*, 372:552–555, Dec. 8, 1994.

(List continued on next page.)

Primary Examiner—Stephanie W. Zitomer
(74) Attorney, Agent, or Firm—Williams, Morgan and Amerson

(57) ABSTRACT

Disclosed are the dbp gene and dbp-derived nucleic acid segments from *Borrelia burgdorferi*, the etiological agent of Lyme disease, and DNA segments encoding dbp from related borrelias. Also disclosed are decorin binding protein compositions and methods of use. The DBP protein and antigenic epitopes derived therefrom are contemplated for use in the treatment of pathological Borrelia infections, and in particular, for use in the prevention of bacterial adhesion to decorin. DNA segments encoding these proteins and anti-(decorin binding protein) antibodies will also be of use in various screening, diagnostic and therapeutic applications including active and passive immunization and methods for the prevention of Borrelia colonization in an animal. These DNA segments and the peptides derived therefrom are contemplated for use in the preparation of vaccines and, also, for use as carrier proteins in vaccine formulations, and in the formulation of compositions for use in the prevention of Lyme disease.

39 Claims, 31 Drawing Sheets

OTHER PUBLICATIONS

Figure 1A:
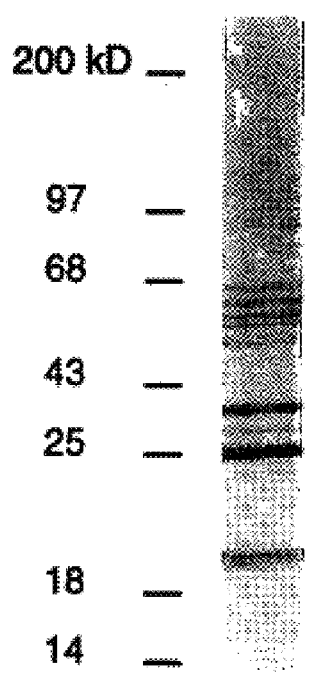

Philipp, M. T. and Johnson B. J. B., "Animal Models of Lyme Diseases: Pathogensis and Immunoprophylaxis," *Trends in Microbiology*, 2(11):431–437, Nov., 1994.

Sharon, N. and Lis, H., "Carbohydrates in Cell Recognition," *Scientific American*, pp. 82–89, Jan., 1993.

Steere, A. C., "Lyme Disease: A Growing Threat to Urban Populations," *Proc. Natl. Acad. Sci. USA*, 91:2378–2382, Mar., 1994.

Guo, B., Norris, S.J., Howell, J. and Höök, M., "Identification of Decorin Binding Proteins on the Outer Membrane Surface of *Borrelia burgdorferi*," Abstr. Annu. Meet. Am. Soc. Microbiol., D–161, p. 124, May, 1994 (listed in C10).

Guo. B., Norris, S.J., Rosenberg, L. C. and Hook, M., "Adherence of *Borrelia burdorferi* to the Proteoglycan Decorin," *Infect. Immun.*, 63(9):3467–3472, 1995 (listed in C10).

Bidanset et al., "Binding of the Proteoglycan Decorin to Collagen Type VI," *J. Biol. Chem.* 267(8):5250–5256, Mar. 15,1992.

Guo et al., "Evidence that the decorin binding protein of *Borrelia burgdorferi* is an adhesin," 96th General Meeting of the American Society for Microbiology, New Orleans, Louisiana, ISSN: 1060–2011, XP 000618881, Abstract No. D–38, p. 248, May 19–23, 1996 (listed in C13).

Probert et al., "Immunization with the outer surface proteins of *Borrelia burgdorferi* provides limited cross–protection," 95th General Meeting of the American Society for Microbiology, Washington, D.C., 144 ISSN 0067–2777, Abstract No. E–56, p. 290, May 21–25, 1995.

Yamaguchi et al., "Negative regulation of tranforming growth factor–$\beta$ by the proteoglycan decorin," *Nature*, 346:281–284, Jul. 19, 1990.

Barbour, A. G., "Isolation and cultivation of lyme disease spirochetes," *Yale J. Biol. Med.* 57:521–525, 1984.

Genovese, C., Rowe, D. and Kream, B., "Construction of DNA sequences complementary to rat $\alpha_1$ and $\alpha_2$ collagen mRNA and their use in studying the regulation of type I collagen synthesis by 1,25–dihydroxyvitaminD," *Biochemistry* 23:6210–6216, 1984.

Guo, B., Höök, M., Norris, S. J. and Howell, J. "*Borrelia burgdorferi*: Adherence of Two Outer Surface Proteins to the Proteoglycan, Decorin," Meeting of the Texas Branch of The American Society for Microbiology, Austin, Texas, Abstract No. 15, Nov. 11–13, 1993.

Oldberg,A., Antonsson,P., Lindblom,K. and Heinegard,D., "A collagen–binding59–kd protein (fibromodulin)is structurally related to the small interstitial proteoglycansPG–S1 and PG–S2 (decorin)," *EMBO J.* 8:2601–2604,1989.

* cited by examiner

```
CTCGATCTATTTTTAAATATATAATAAATTAATAAAATAAGTGGTAAAAGGAGAAAGAATATTAAAACAAAATATAT
TCTGTTGCCAGTAATAACATTATTGTGTAATATGTATAGTGAGGTATTACTCAAAGAGCAAGAAACAAAAATCAAAAA
ATCGTTGTTAACGAACAAAATGAAAGATTAAAACGCTTAATAAAGCTTATGGAAAAATACATCTAGTAAAAGTTAAAA
GACATGACAATTAAAGTAAAAAACAAAATAGCCTCAGGAGCAAGCAAAAAAGGATACTTCTTTAAAGGCCTAAAGGGTAT
TTTTATGCCTTTAAGCCTGCCAATCCTTATACTCCTAATTAAAAAATAAAGCAATATCAAAATAGTCAAAATACTCA
AAAGAGAAGCCAATAAATTGCGGGAGATGGCTTCTCTTTTATTTTTAAGACCTAATTATTTTAGACTTTGATTCAATTG
CAAAATAACCAATTTGAAATATTTGGCAAACTGGAAACAAGTCTTAAATTACAAGCCAGATGATAGAAACTTGTAATT
CCAAACAATGTTACTGCTATATATTTGCATATAAAACAAATTCACACTAACAATAAAATATAAAACTTAAACTGATA
CGCTTTTAAAATAAAAGTTTTAAACTTTAGTACAAATCTAGACATTATATATTAACTTTTTACATCAACATACTAACTAATT
TATTTTATTTATTTTCATAAGTGGGCTAAAATTTAAATTTAACTAAATTTAATAGAAGGAGAAAAATGAAAATTG
GAAAGCTAAATTCAATAGTTATAGCCTTGTTGTTTTTTAAACTATTGGTCGCATGTAGTATTGGATTAGTAGAAGAACAAAT
GCAGCTCTTGAATCGTCCTCTAAGGATTTAAAAAAACAAATTTAAAATAAAACAAGTGGTGACTAGCCTTAAGAAGCAAAGTACAAG
TTTTGAAGCTTTTACAGGTCTTAAAACCGGTTCCAAGTAACAAGTGGTGACTAGCCTTAAGAAGCAAAGTACAAG
CCATTGTTGAAACAGGAAAGTTCCTTAAGATAATAGAAGAAGAAGCTTAAAGCTTAAAGAACAACAGTGGTCAA
TTCTTGGCTATGTTTGACTTAATGCTTGAGGTTGTAGAATCGCTAGAAGACGTTGAATAATAGGCTTAAAAGCCCGTGT
TTTAGAGGAATCTAAAAATAATCCTATAAACACAGCTGAAAGATTGCTTGCGGCTAAAGCTCAAATAGAAAATCAACTTA
AAGTGGTTAAGGAAAACAAAATATTGGAGAGAAAAATGGTGGAGAAAAATAACAAAGCAAAAAATAAGAAATAAATATTA
AAAATATTGTCATTAGAATGGACTAAAAGTAAAATTTTTA
```

FIG. 2A

GCTCGTCCTAATATTTACAATTTAATAATAATATTGGTTTATTGCTTTTACTAAAATACAAAAAAAGGATAATGTTATGATTA
AATGTAATAATAAACTTTTAACAATTACTTAAACTATACTTGTTAACCTACTACTTATATCATGTGGACTAACAGGA
GCAACAAAAATCAAATTAGAATCATCAGCTAAAGCCATTGTAGATGAAATAGATGCAATTAAAAAAAAGGCTGCTTCTAT
GGGTGTAAATTTGATGCCTTTAAAGATAAAAAAACGGGTAGTGGGGTATCAGAAAATCCATTCATACTTGAAGCAAAAG
TGCGAGCTACTACAGTAGCGGAAAATTCGTAATAGCAATAGAAGAGGAAGCTACTAAACTTAAAGAAACTGGAAGTAGT
GGTGAATTCTCAGCAATGTATGATTTAATGTTTGAAGTCTCAAAACCATTACAAGAATTGGGAATACAAGAGATGACAAA
AACAGTCTCAATGCAGCTGAAGAGAATCCTCCAACTACAGCTCAAGGAGTGCTTGAAATTGCAAAAAAAATGAGAGAAA
AATTACAAAGGGTTCACAAGAAAAACCAAGACACACTTAAAGAAAAAAATACCGAAGACAGCACTGCTAAATCGTAATAA
ACACCATTTTATATGCAACTCAAAATAACAAATATTAAGCTCTTCAACCAGCATTCAAAAGCTAAATTAAGGTTAAAGCAATTAACC
TAATTCTGCAATGCAAAAAACAAAAAACAAATATTAAGCTCTTCAACCAGCATTCAAAAGCTAAATTAAGGTTAAAGCAATTAACC
CAAAGGATTAAAATTTAAAAAAATACTGTAATAAATTAAAAATGTAATTATTATTTCAAACAAAATAAT
TAAATATCCTTTTTGATGTTATTGGAATTTCTTTCCTTTAGACTTTAAATCAAGACTGTCGTAAAGCACCTTATTATTA
TCCATTACAAGAAAATGCACAAAAACCCTTGGAAAAATATTTTATAACTAAGAATTTTACATGGATTAAAATATAACAATCCT
AAGTGGACTCTCTGATCTAACCTTGGAAAAATATTTTATAACTAAGAATTTTACATGGATTAAAATATAACAATCCT
TTCTAATGTAGCCTAATTCCAAAACCGCTGATAATTTAAATTAACGTCTTTTTGCTGTAAATCAAACCCCTTTAAAACA
AATATCAATAGTGCAAAGACAAAAAATAACATCGGACTTTTGAATGTCTTTAAACA

FIG. 2B

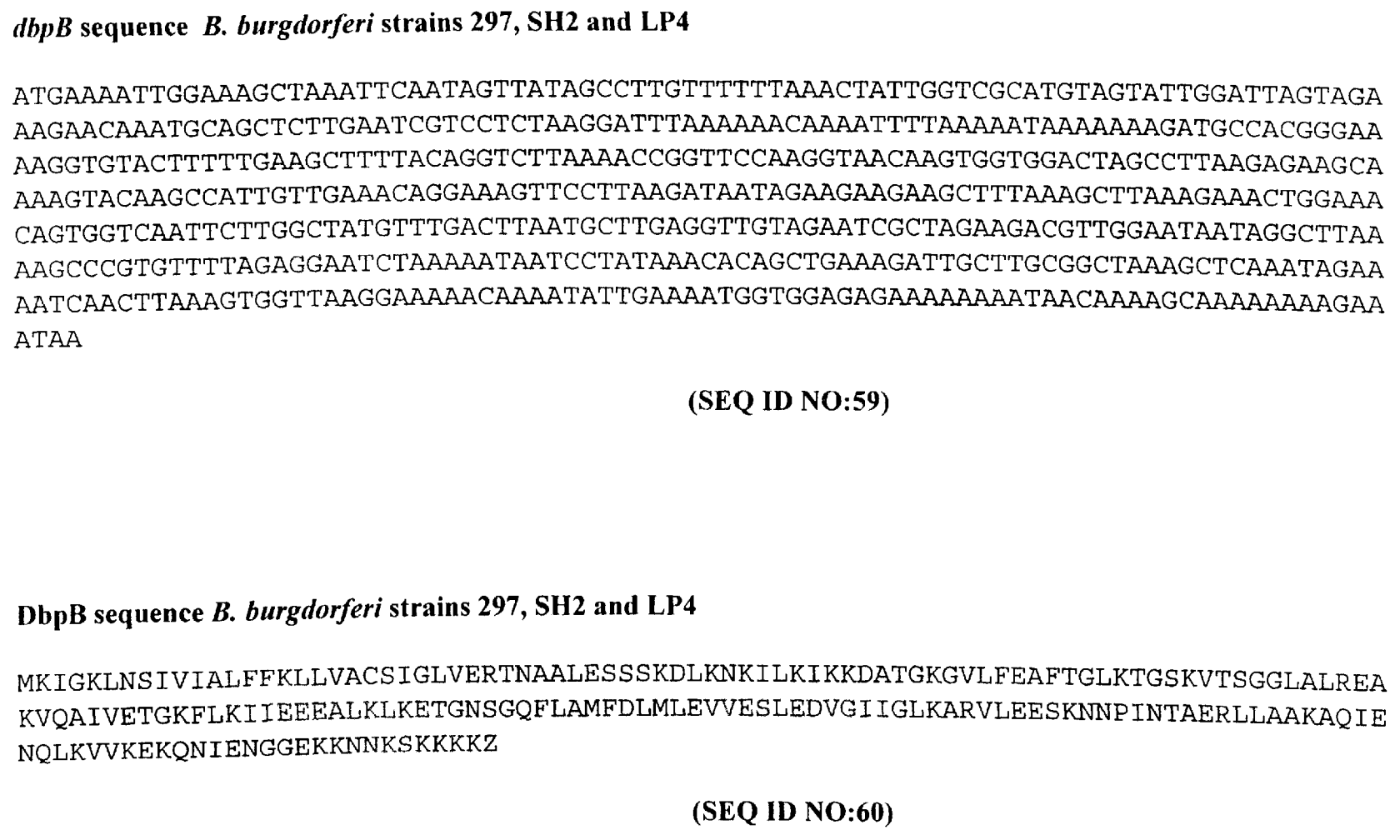

*dbpB* **sequence *B. burgdorferi* strains 297, SH2 and LP4**

ATGAAAATTGGAAAGCTAAATTCAATAGTTATAGCCTTGTTTTTTAAACTATTGGTCGCATGTAGTATTGGATTAGTAGA
AAGAACAAATGCAGCTCTTGAATCGTCCTCTAAGGATTTAAAAAACAAAATTTTAAAAATAAAAAAAGATGCCACGGGAA
AAGGTGTACTTTTTGAAGCTTTTACAGGTCTTAAAACCGGTTCCAAGGTAACAAGTGGTGGACTAGCCTTAAGAGAAGCA
AAAGTACAAGCCATTGTTGAAACAGGAAAGTTCCTTAAGATAATAGAAGAAGAAGCTTTAAAGCTTAAAGAAACTGGAAA
CAGTGGTCAATTCTTGGCTATGTTTGACTTAATGCTTGAGGTTGTAGAATCGCTAGAAGACGTTGGAATAATAGGCTTAA
AAGCCCGTGTTTTAGAGGAATCTAAAAATAATCCTATAAACACAGCTGAAAGATTGCTTGCGGCTAAAGCTCAAATAGAA
AATCAACTTAAAGTGGTTAAGGAAAAACAAAATATTGAAAATGGTGGAGAGAAAAAAAATAACAAAAGCAAAAAAAAGAA
ATAA

(SEQ ID NO:59)

**DbpB sequence *B. burgdorferi* strains 297, SH2 and LP4**

MKIGKLNSIVIALFFKLLVACSIGLVERTNAALESSSKDLKNKILKIKKDATGKGVLFEAFTGLKTGSKVTSGGLALREA
KVQAIVETGKFLKIIEEEALKLKETGNSGQFLAMFDLMLEVVESLEDVGIIGLKARVLEESKNNPINTAERLLAAKAQIE
NQLKVVKEKQNIENGGEKKNNKSKKKKZ

(SEQ ID NO:60)

FIG. 3

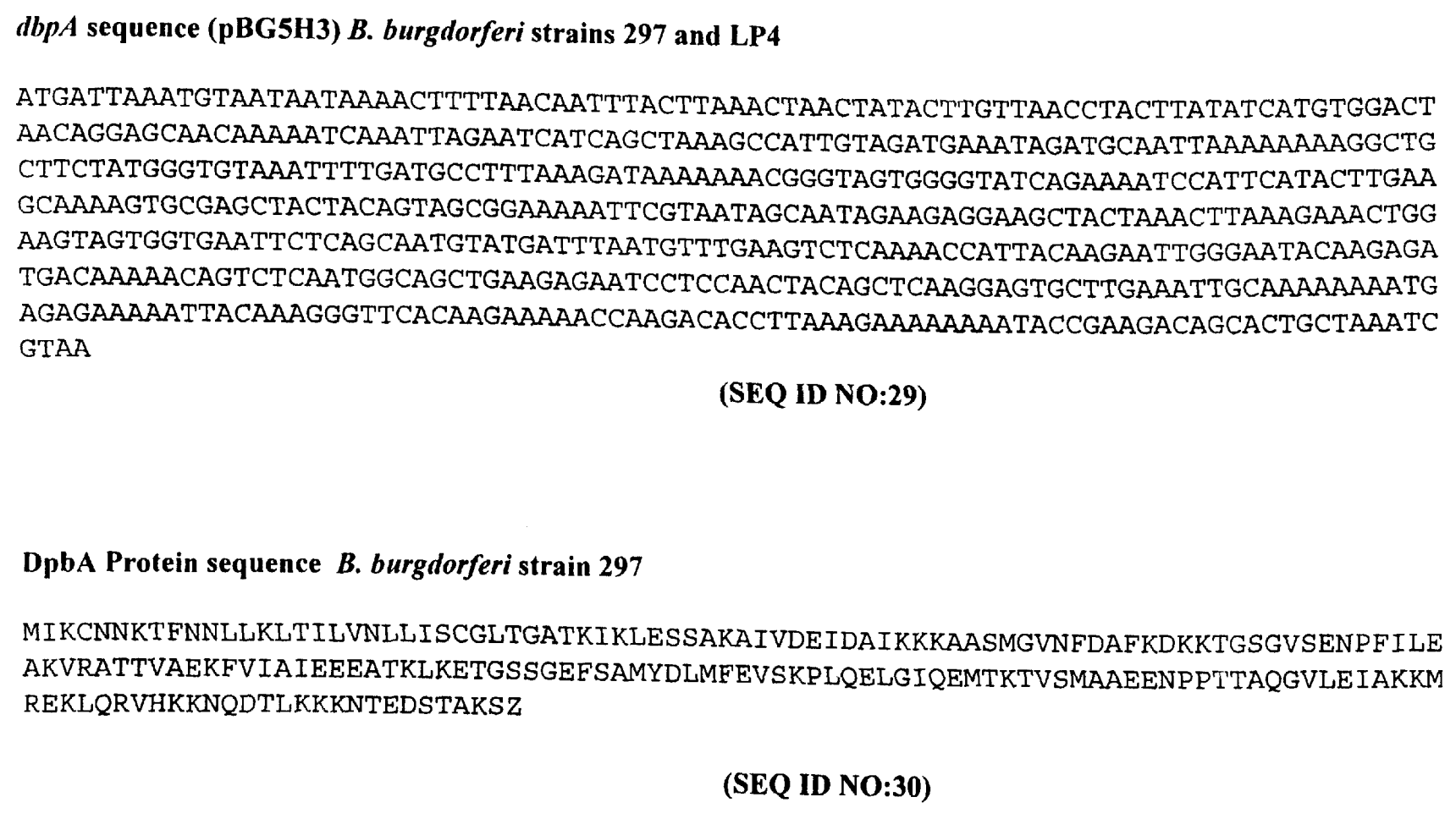

*dbpA* sequence (pBG5H3) *B. burgdorferi* strains 297 and LP4

ATGATTAAATGTAATAATAAAACTTTTAACAATTTACTTAAACTAACTATACTTGTTAACCTACTTATATCATGTGGACT
AACAGGAGCAACAAAAATCAAATTAGAATCATCAGCTAAAGCCATTGTAGATGAAATAGATGCAATTAAAAAAAAGGCTG
CTTCTATGGGTGTAAATTTTGATGCCTTTAAAGATAAAAAAACGGGTAGTGGGGTATCAGAAAATCCATTCATACTTGAA
GCAAAAGTGCGAGCTACTACAGTAGCGGAAAAATTCGTAATAGCAATAGAAGAGGAAGCTACTAAACTTAAAGAAACTGG
AAGTAGTGGTGAATTCTCAGCAATGTATGATTTAATGTTTGAAGTCTCAAAACCATTACAAGAATTGGGAATACAAGAGA
TGACAAAAACAGTCTCAATGGCAGCTGAAGAGAATCCTCCAACTACAGCTCAAGGAGTGCTTGAAATTGCAAAAAAAATG
AGAGAAAAATTACAAAGGGTTCACAAGAAAAACCAAGACACCTTAAAGAAAAAAAATACCGAAGACAGCACTGCTAAATC
GTAA

(SEQ ID NO:29)

DpbA Protein sequence *B. burgdorferi* strain 297

MIKCNNKTFNNLLKLTILVNLLISCGLTGATKIKLESSAKAIVDEIDAIKKKAASMGVNFDAFKDKKTGSGVSENPFILE
AKVRATTVAEKFVIAIEEEATKLKETGSSGEFSAMYDLMFEVSKPLQELGIQEMTKTVSMAAEENPPTTAQGVLEIAKKM
REKLQRVHKKNQDTLKKKNTEDSTAKSZ

(SEQ ID NO:30)

FIG. 4

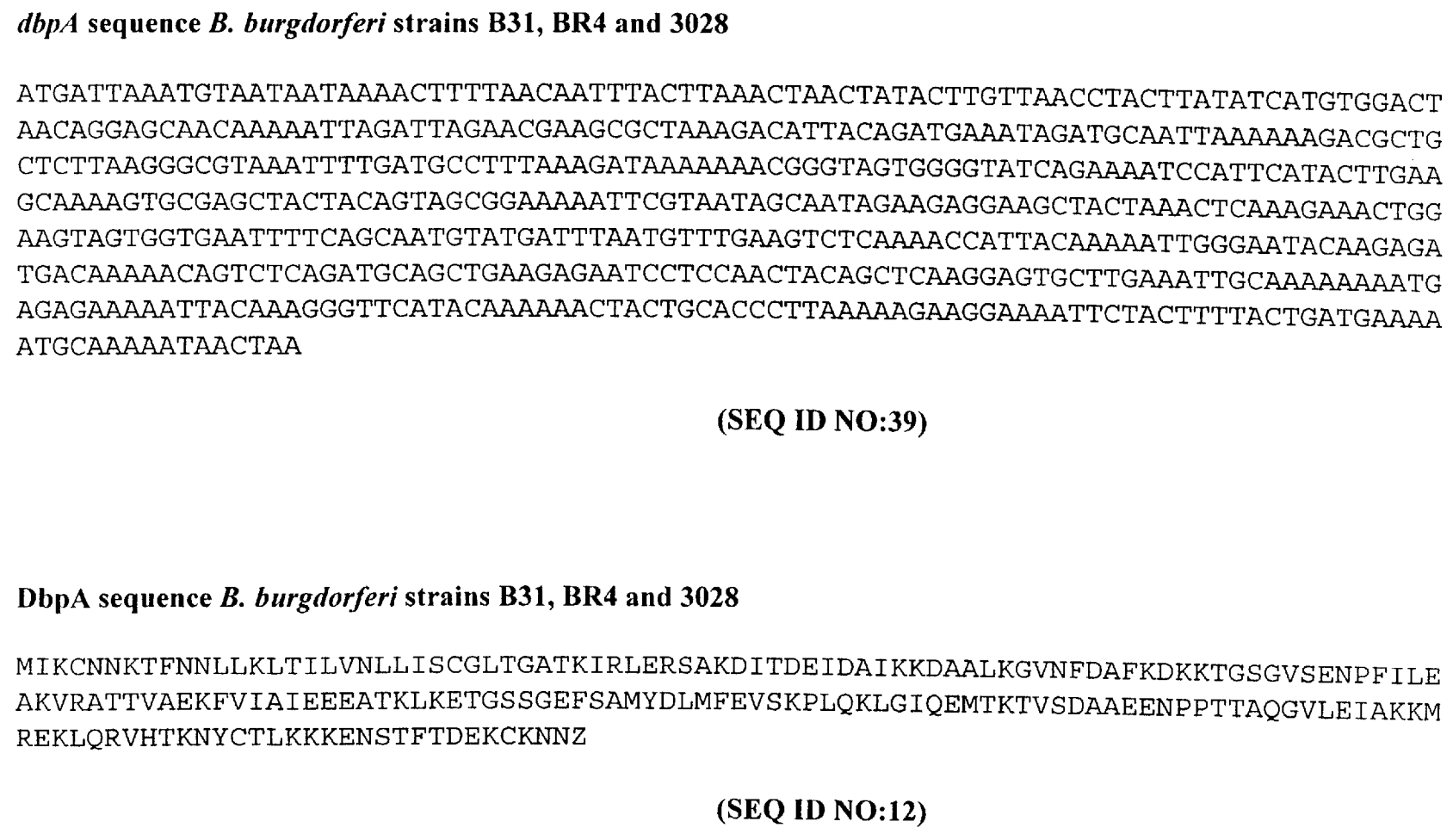

***dbpA* sequence *B. burgdorferi* strains B31, BR4 and 3028**

ATGATTAAATGTAATAATAAAACTTTTAACAATTTACTTAAACTAACTATACTTGTTAACCTACTTATATCATGTGGACT
AACAGGAGCAACAAAAATTAGATTAGAACGAAGCGCTAAAGACATTACAGATGAAATAGATGCAATTAAAAAGACGCTG
CTCTTAAGGGCGTAAATTTTGATGCCTTTAAAGATAAAAAAACGGGTAGTGGGGTATCAGAAAATCCATTCATACTTGAA
GCAAAAGTGCGAGCTACTACAGTAGCGGAAAAATTCGTAATAGCAATAGAAGAGGAAGCTACTAAACTCAAAGAAACTGG
AAGTAGTGGTGAATTTTCAGCAATGTATGATTTAATGTTTGAAGTCTCAAAACCATTACAAAAATTGGGAATACAAGAGA
TGACAAAAACAGTCTCAGATGCAGCTGAAGAGAATCCTCCAACTACAGCTCAAGGAGTGCTTGAAATTGCAAAAAAAATG
AGAGAAAAATTACAAAGGGTTCATACAAAAAACTACTGCACCCTTAAAAAGAAGGAAAATTCTACTTTTACTGATGAAAA
ATGCAAAAATAACTAA

(SEQ ID NO:39)

**DbpA sequence *B. burgdorferi* strains B31, BR4 and 3028**

MIKCNNKTFNNLLKLTILVNLLISCGLTGATKIRLERSAKDITDEIDAIKKDAALKGVNFDAFKDKKTGSGVSENPFILE
AKVRATTVAEKFVIAIEEEATKLKETGSSGEFSAMYDLMFEVSKPLQKLGIQEMTKTVSDAAEENPPTTAQGVLEIAKKM
REKLQRVHTKNYCTLKKKENSTFTDEKCKNNZ

(SEQ ID NO:12)

FIG. 5

*dbpB* sequence *B. burgdorferi* strains HB19, G3940, LP5, ZS7, NCH-1 and FRED; *B. garinii* strain 20047

ATGAAAATTGGAAAGCTAAATTCAATAGTTATAGCCCTTGTTTTTAAACTATTGGTCGCATGTAGTATTGGATTAGTAGA
AGAACAAAATGCAGCTCTTGAATCGTCTCCTCTAAGGATTTAAAACAAATTTAAAAATAAAAGAAGCCACGGGAA
AAGGTGTACTTTTTGAAGCTTTTACAGTCTTAAAACCGGTTCCAAGTAACAAGTGGTGGACTAGCCTTAAGAGAAGCA
AAAGTACAAGCCATTGTTGAAACAGGAAAGTTCCTTAAGATAATAGAAGAAGCTTAAAGATGAAAACTGGAAA
CAGTGGTCAATTCTTGGCTATGTTTGACTTAATGCTTGAGGTTGTAGAATCGCTAGAGACGTTGGAATAATAGGCTTAA
AAGCCCGTGTTTTAGAGGAATCTAAAAATAATCCTATAAACACAGCTGAAAGATTGCTTGCGGCTAAAGCTCAAATAGAA
AATCAACTTAAAGTGGTTAAGGAAAAACAAAATATTGAAAATGTGGAGAGAAAAAAATAACAAAAGCAAAAAAAGAA
ATAA (SEQ ID NO:63)

DbpB sequence *B. burgdorferi* strains HB19, G3940, LP5, ZS7, NCH-1 and FRED; *B. garinii* strain 20047

MKIGKLNSIVIALFFKLLVACSIGLVERTNAALESSSKDLKNKILKIKKEATGKGVLFEAFTGLKTGSKVTSGGLALREA
KVQAIVETGKFLKIIEEEALKLKETGNSGQFLAMFDLMLEVVESLEDVGIIGLKARVLEESKNNPINTAERLLAAKAQIE
NQLKVVKEKQNIENGGEKKNNKSKKKK (SEQ ID NO:64)

FIG. 6

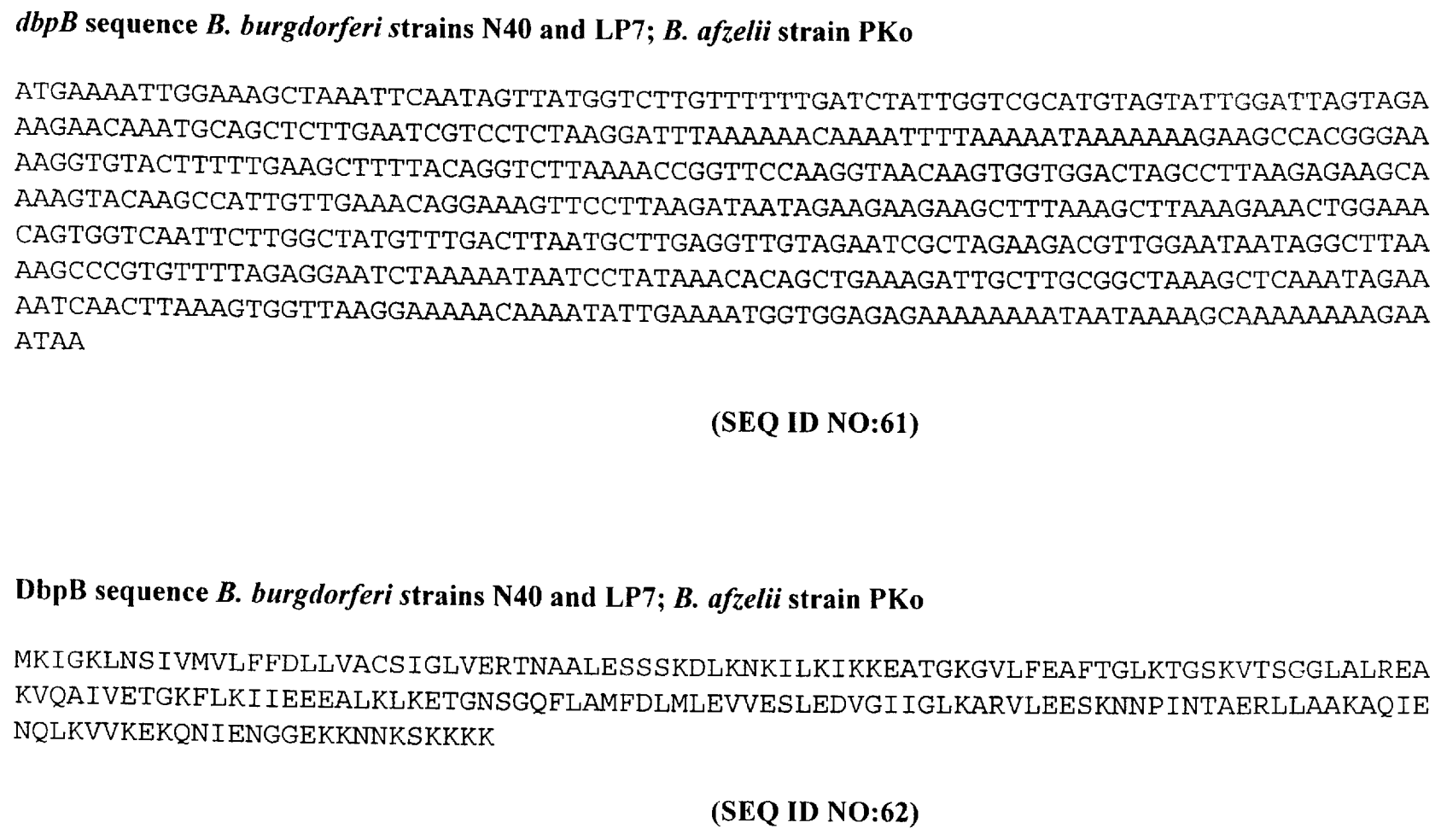

*dbpB* sequence *B. burgdorferi* strains N40 and LP7; *B. afzelii* strain PKo

ATGAAAATTGGAAAGCTAAATTCAATAGTT

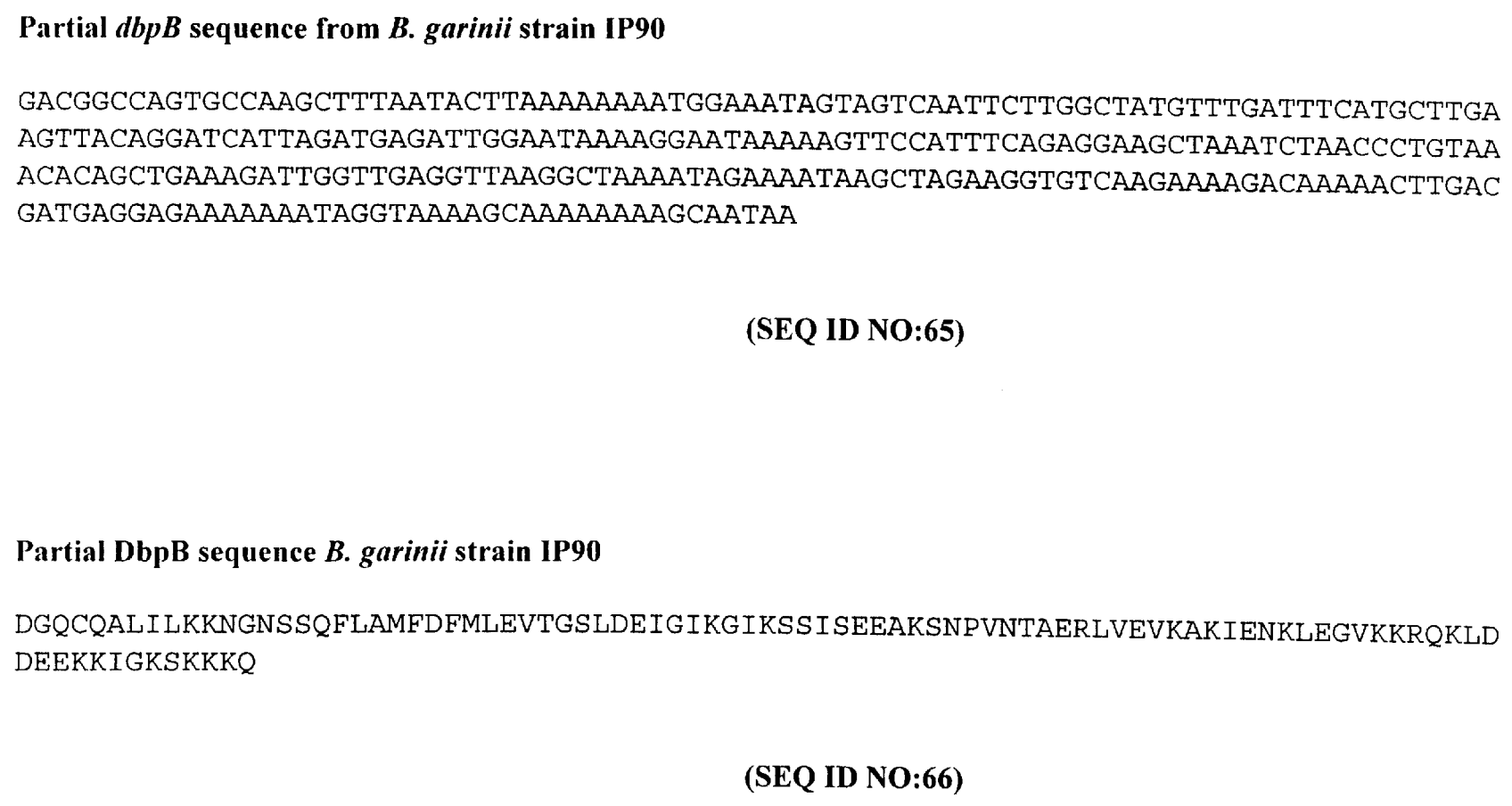

**Partial *dbpB* sequence from *B. garinii* strain IP90**

GACGGCCAGTGCCAAGCTTTAATAC

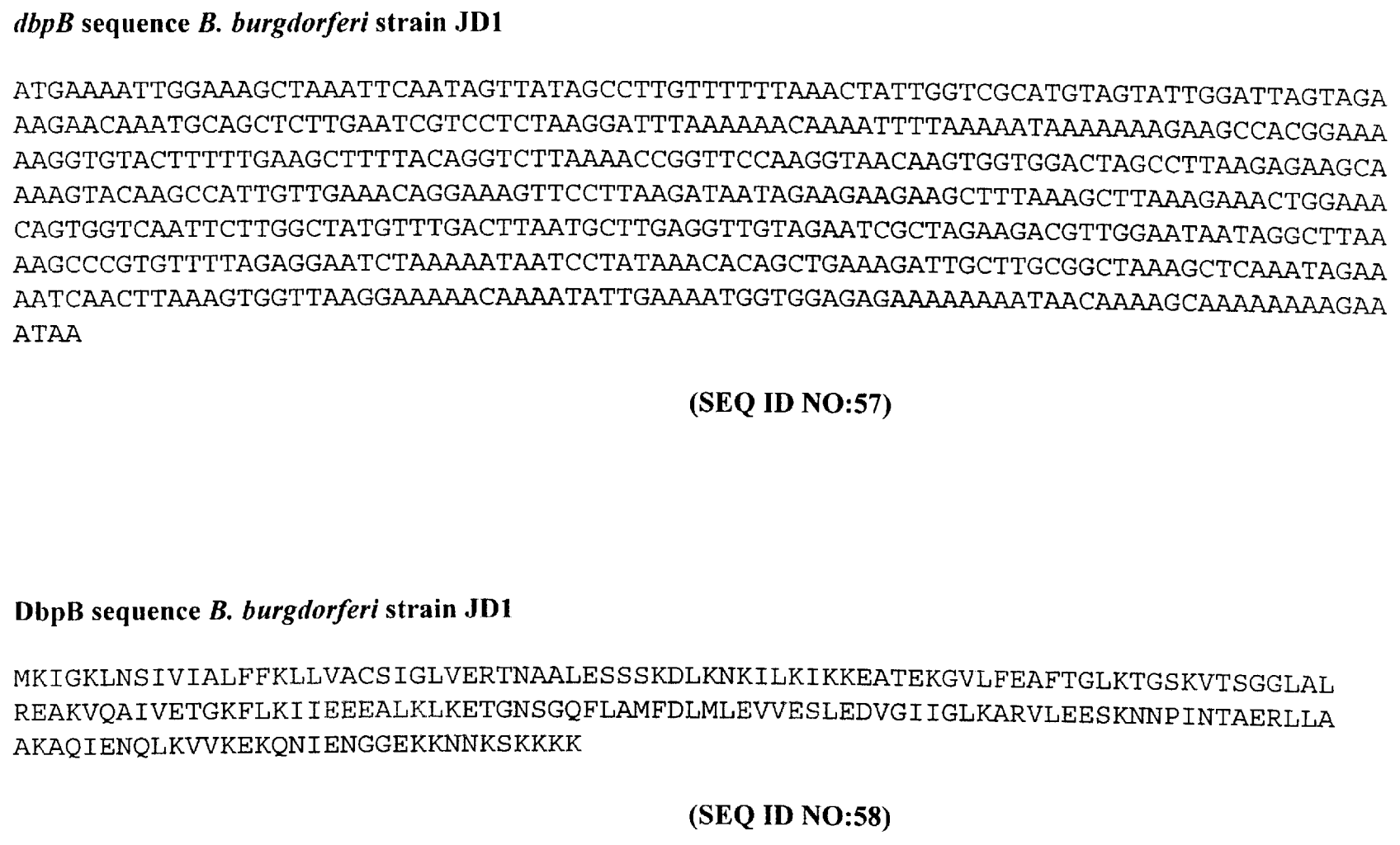

*dbpB* sequence *B. burgdorferi* strain JD1

ATGAAAATT

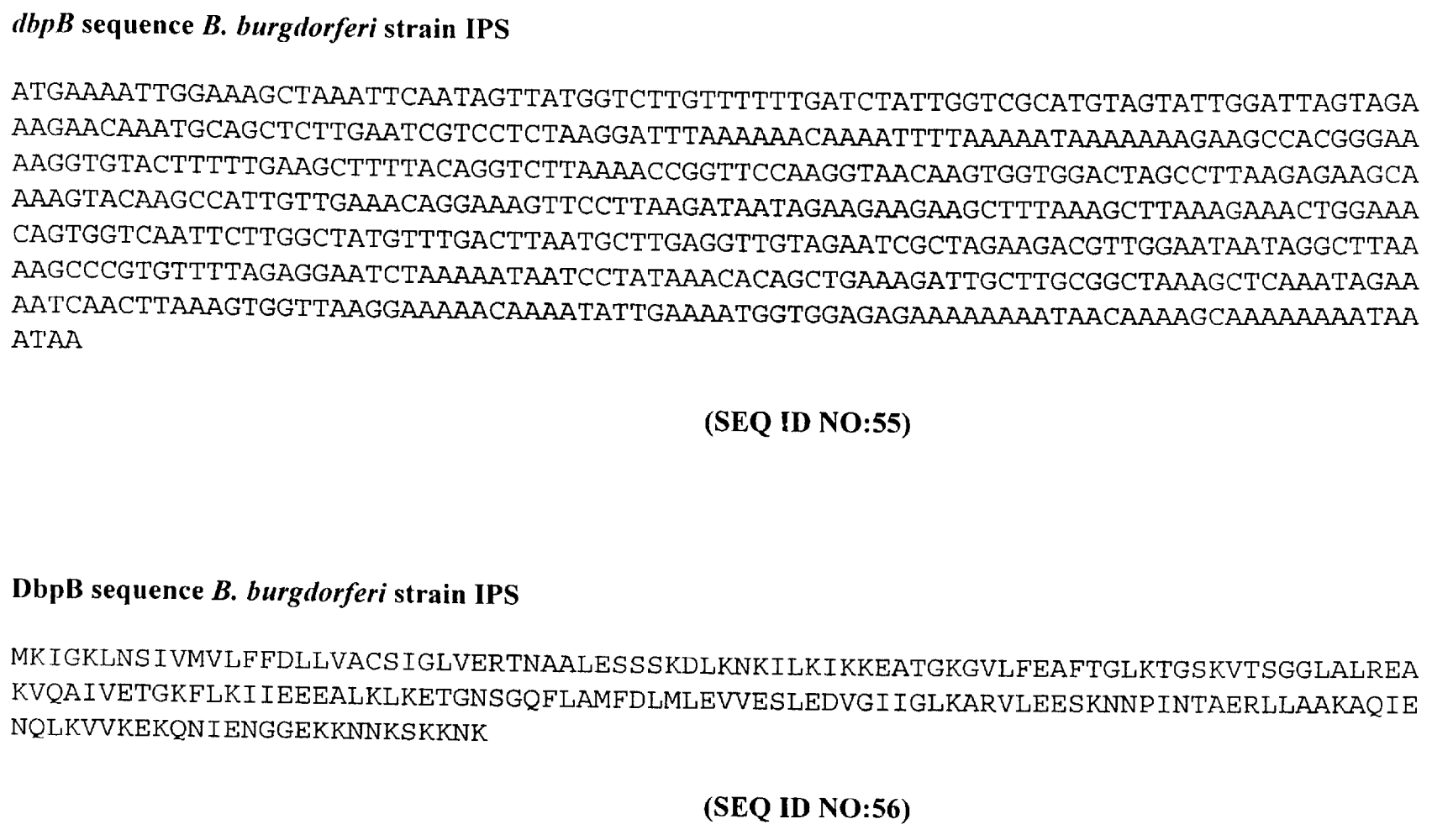

*dbpB* sequence *B. burgdorferi* strain IPS

ATGAAAATTGGAAAGCTAAAATTCAATAGTTATGGT

*dbpB* sequence *B. burgdorferi* strain CA287

ATGAAAATTGGAAAGCTAAATTCAATAGTTATGTCTCTTGTTTTTGATCTATTGGTCGCATGTAGTATTGGATTAGTAGA
AGAACAAATACAGCTCTTGAATCGTCCTCTCTAAGGATTTAAAAACAAAATTTAAAATAAAAAAGAAGCCACGGGAA
AAGGTGTACTTTTTGAAGCTTTTACAGTCTTAAAACCGGTTCCAAGTAACAAGTGGTGGACTAGCCTTAAGAGAAGCA
AAAGTACAAGCCATTGTTGAAACAGGAAAGTTCCTTAAGATAATAGAAGAAGCTTTAAAGCTTAAAGAAACTGGAAA
CAGTGGTCAATTCTTGGCTATGTTTGACTTAATGCTTGAGGTTGTAGAATCGTGAGGTTGTAGAGACGTTGGAATAATAGGCTTAA
AAGCCCGTGTTTTAGAGGAATCTAAAAATAATCCTATAAACACAGCTGAAAGATTGCTTGCGGCTAAAGCTCAAATAGAA
AATCAACTTAAAGTGGTTAAGGAAAAACAAATATTGAAAATGTGGAGAGAAAAAAATAACAAAAGCAAAAAAAATAA
ATAA (SEQ ID NO:53)

DbpB sequence *B. burgdorferi* strain CA287

MKIGKLNSIVMVLFFDLLVACSIGLVERTNTALESSSKDLKNKILKIKKEATGKGVLFEAFTGLKTGSKVTSGGLALREA
KVQAIVETGKFLKIIEEEALKLKETGNSGQFLAMFDLMLEVVESLEDVGIIGLKARVLEESKNNPINTAERLLAAKAQIE
NQLKVVKEKQNIENGGEKKNNKSKKNK (SEQ ID NO:54)

FIG. 11

*dbpA* sequence *B. garinii* strain IP90

ATGACTAAACACCACCAAAAATTTACTTAAACTAAGTTTAATTGTTAGCCTGTTAGTAGCATGTGGCTTAACAGGAGAAAC
TAAAATCAAATTAGAATCATCAGCTCAAGAAATTAAAGATGAAATAAATTAAAGCTAATGCTAAAAAGAAGGCG
TAAATTCGAGGCTTTCACAGATAAACAAGGCAGTAAGGTATCAAAAAAGCCTGAATTCATACTTAAAGCAAAATA
CAAGCTATTCAAGTGGCAGGAAAATTTGTAAAGCAATAAAAGAGGAAGCAGAAAACTTAAAAGAGTGGAAGTAGCGG
TGCATTCTCGGCAATGTATGATTTAATGCTTGATGTATCAAACCACTAGAGAGATTGGAATACAAAAATGACAGGAA
CAGTTACACAGGCAGCTGAAAAAACCCCTCCAACTACAGCTGAGGGGATACTTGCTATTGCAAAAGCAATGGAAGATAAA
TTAAACAATGTTAATACAAAACAACACGAGGCTCTCAAAAACCTCGAGGGAAAAGAAGCCAAAACTCCTAAATAA (SEQ ID NO:51)

DbpA sequence *B. garinii* strain IP90

MTKHTKNLLKLSLIVSLLVACGLTGETKIKLESSAQEIKDEINKIKANAKKEGVNFEAFTDKQTGSKVSKKPEFILKAKI
QAIQVAGKFVKAIKEEAEKLKKSGSSGAFSAMYDLMLDVSKPLEEIGIQKMTGTVTQAAEKTPPTTAEGILAIAKAMEDK
LNNVNTKQHEALKNLEGKEAKTPKZ (SEQ ID NO:52)

FIG. 12

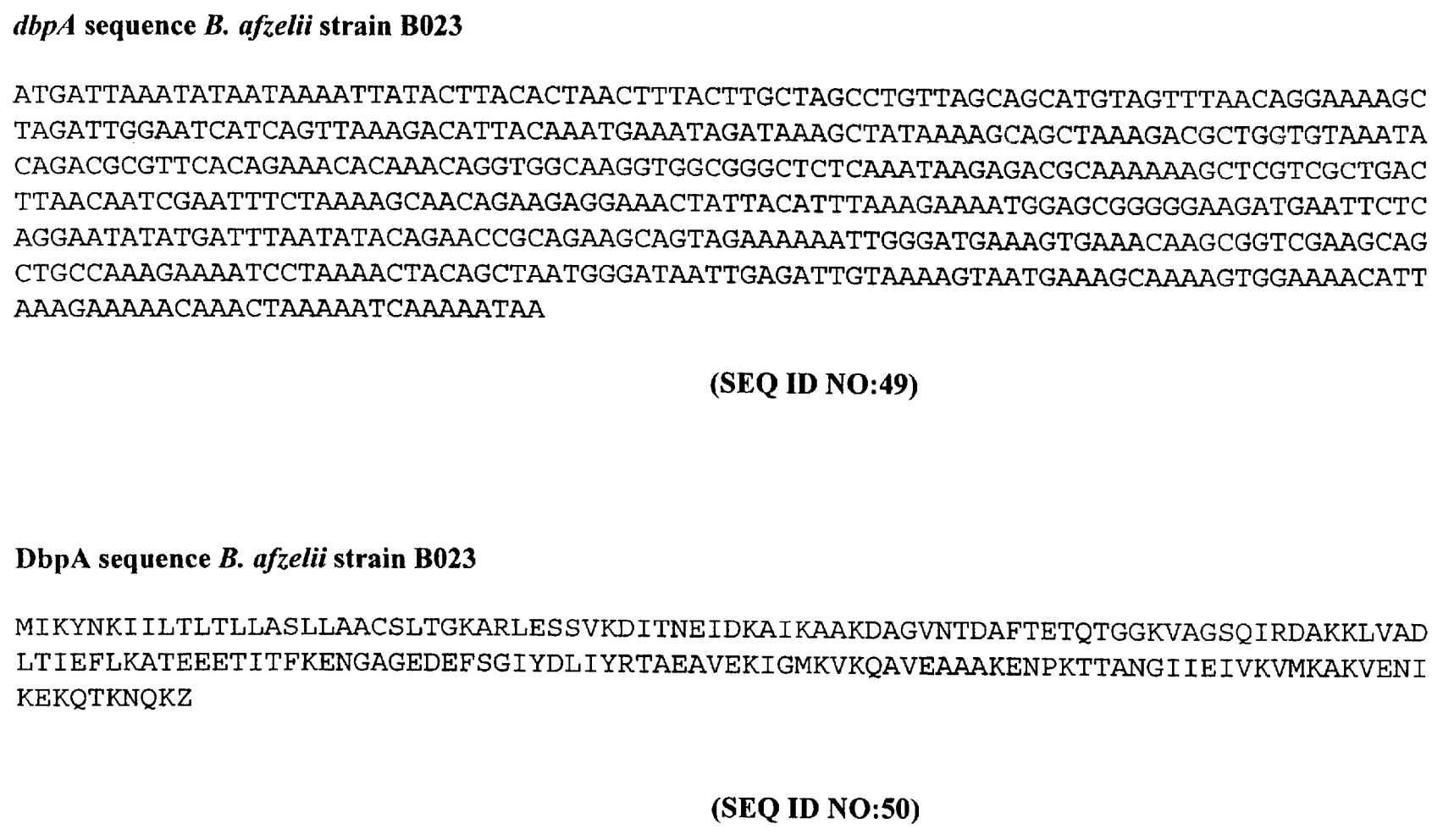

*dbpA* sequence *B. afzelii* strain B023

ATGATTAAATATAATAAAATTATACTTACACTA

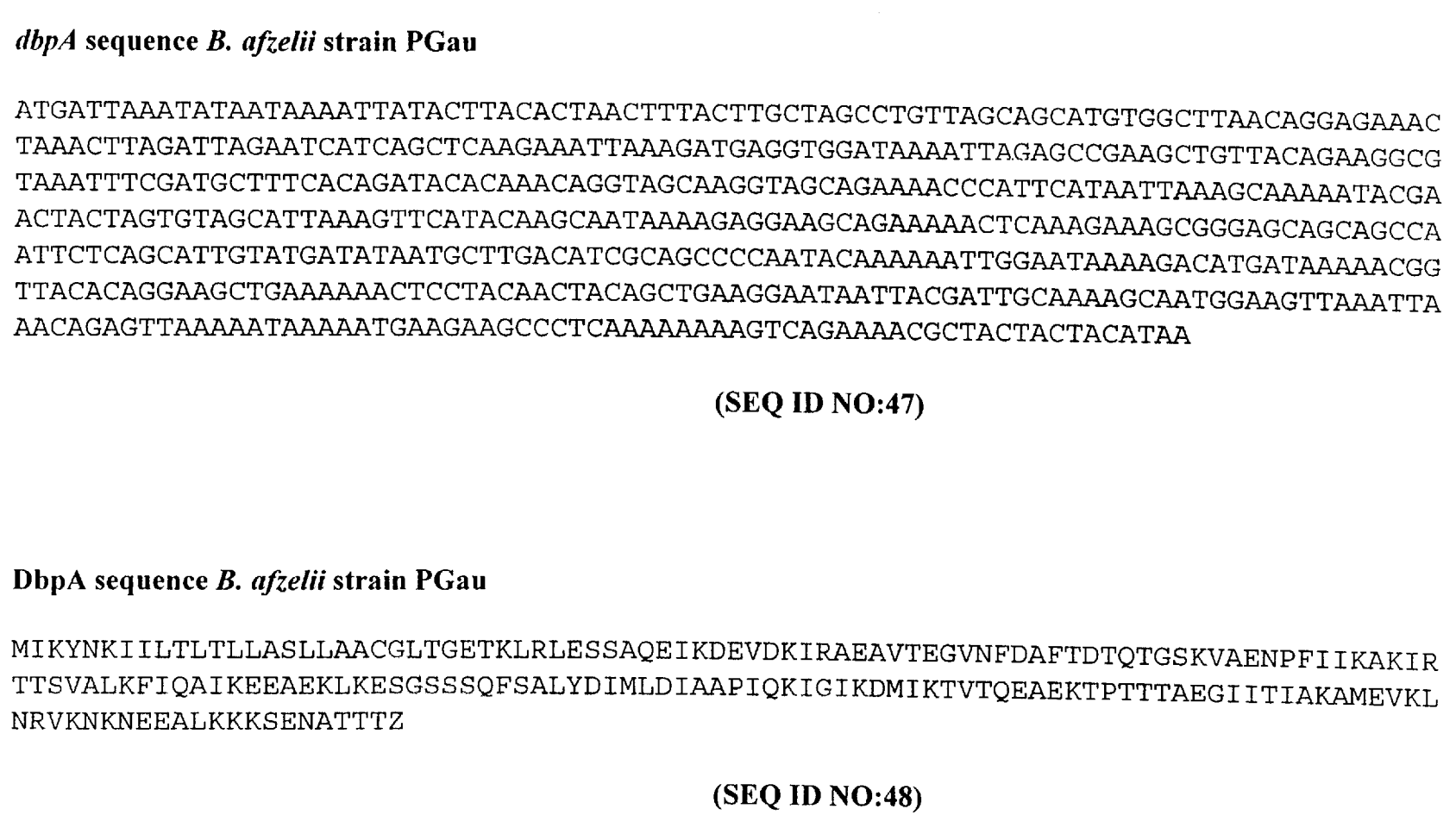

*dbpA* sequence *B. afzelii* strain PGau

ATGATTAAATATAAATAAATTATAC

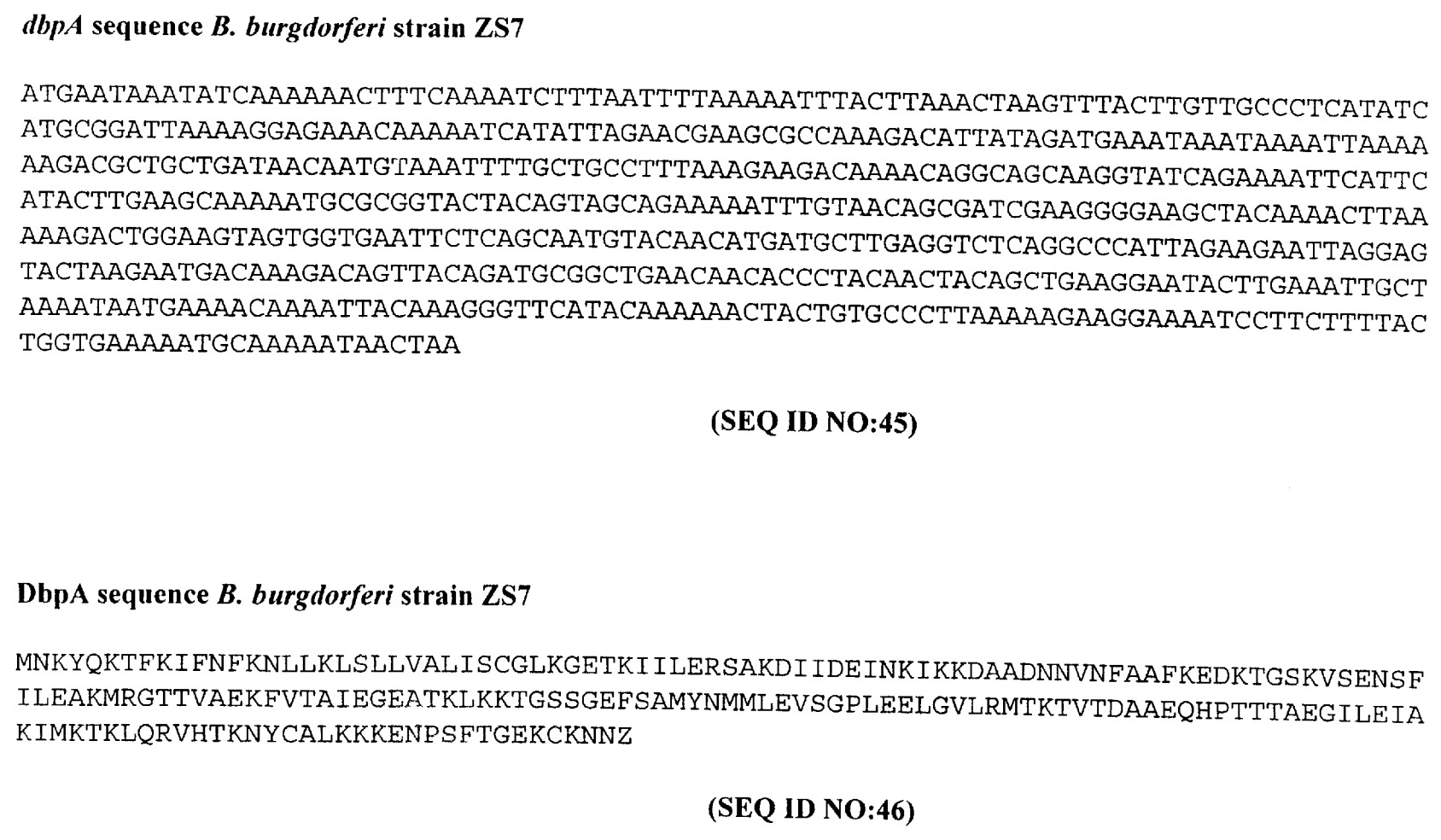

*dbpA* sequence *B. burgdorferi* strain ZS7

ATGAATAAATATCAAAAAACTTTCAAAATCTT

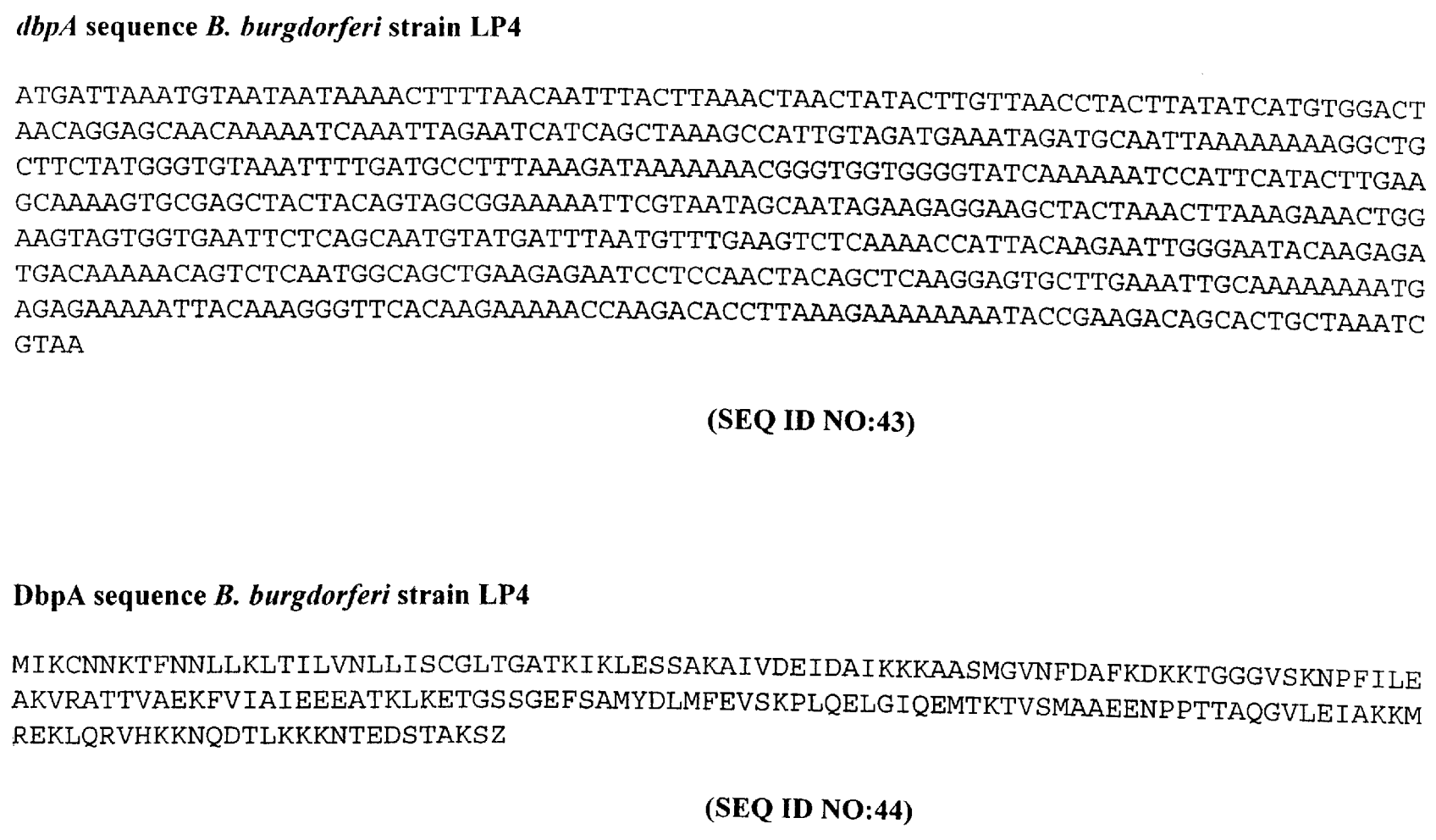

*dbpA* sequence *B. burgdorferi* strain LP4

ATGATTAAATGTAATAATAAAACTTTAAC

*dbpA* sequence *B. burgdorferi* strain G3940

ATGATTAAATGTAATAATAAAACTTTTAACAATTTACTTAAACTATACTTGTTAACCTACTTATATCATGTGGACT
AACAGGAGCAACAAAAATCAAATTAGAATCATCAGCTAAAGCCATTGTGAGATGAAATAGATGCAATTAAAAAGAGGCTG
CTTCTATGGGTGTAAATTTTGAAGCCTTTACAGATAGTGAAACAGGTAGAAAGGCAGCAGGATCAGGAGGGGATTTCATA
AAACAAGCAAAAGTACGAGCTATTAAAGTAGCAGAAAACTTCTTAACAGCAATAGAGAGGAGGCTACTAAACTTAAAGA
AACTGGAAGTAGTGGTGAATTTTCAGCAATGTATGATTTAATGTTTGAAGTCTCAGAACCATTAGAAAGAATTGGGGTAC
AAAAATGAAAAAACAGTCTCAATGGCAGCTGAAGAGAATCCTCCAACTACAGCTCAAGGAGTGCTTGAAATTGCAAAA
AAAATGAGAGAAAAATTAATACAAGTTAAAGGAAAACAAAAATTAAATCCAGAAACTACTACGGAATAA (SEQ ID NO:41)

DbpA sequence *B. burgdorferi* strain G3940

MIKCNNKTFNNLLKLTILVNLLISCGLTGATKIKLESSAKAIVDEIDAIKKEAASMGVNFEAFTDSETGRKAAGSGGDFI
KQAKVRAIKVAENFLTAIEEEATKLKETGSSGEFSAMYDLMFEVSEPLERIGVQKMKKTVSMAAEENPPTTAQGVLEIAK
KMREKLIQVKGKQKLNPETTTEZ (SEQ ID NO:42)

FIG. 17

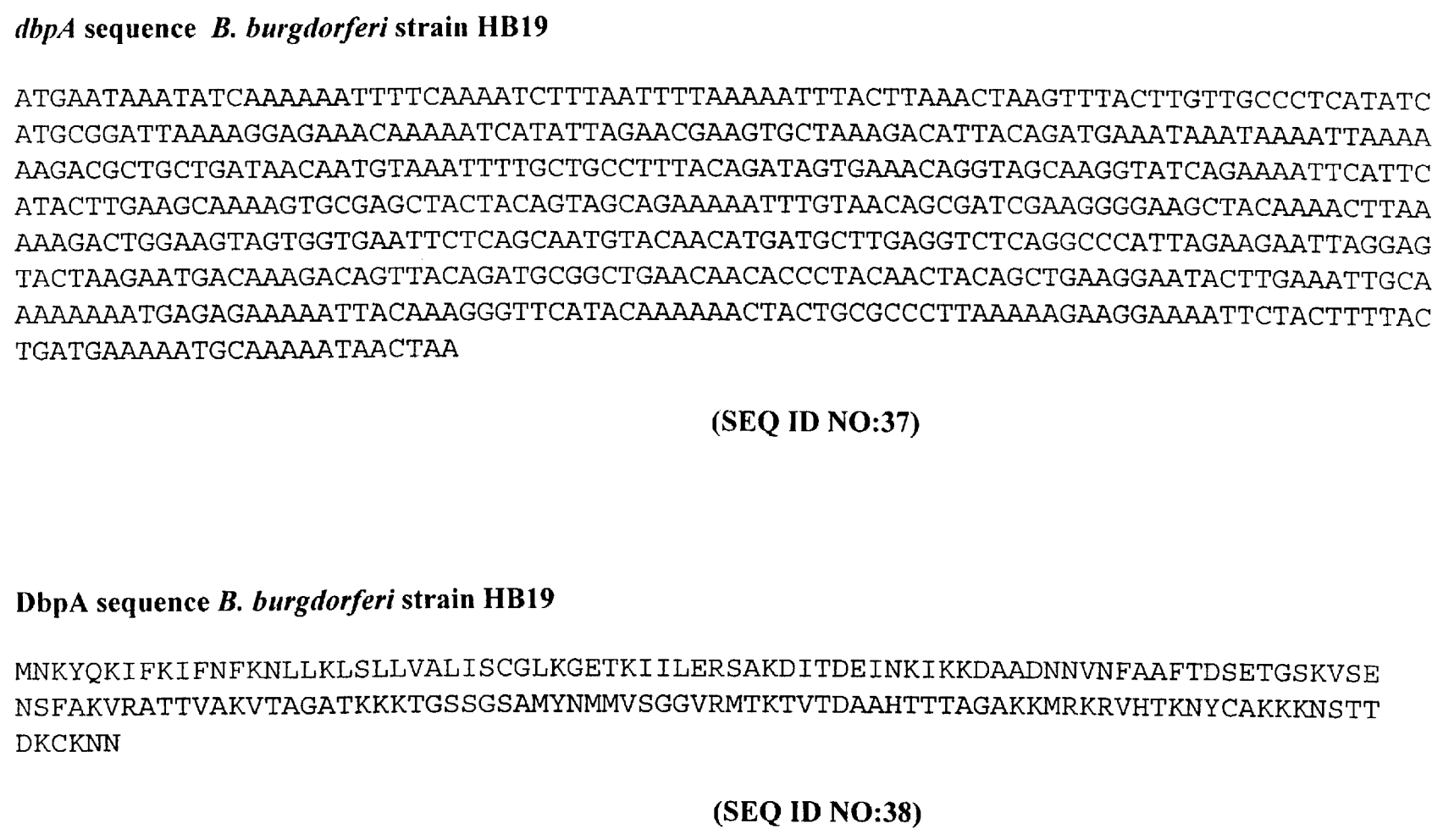

*dbpA* sequence *B. burgdorferi* strain HB19

ATGAAT

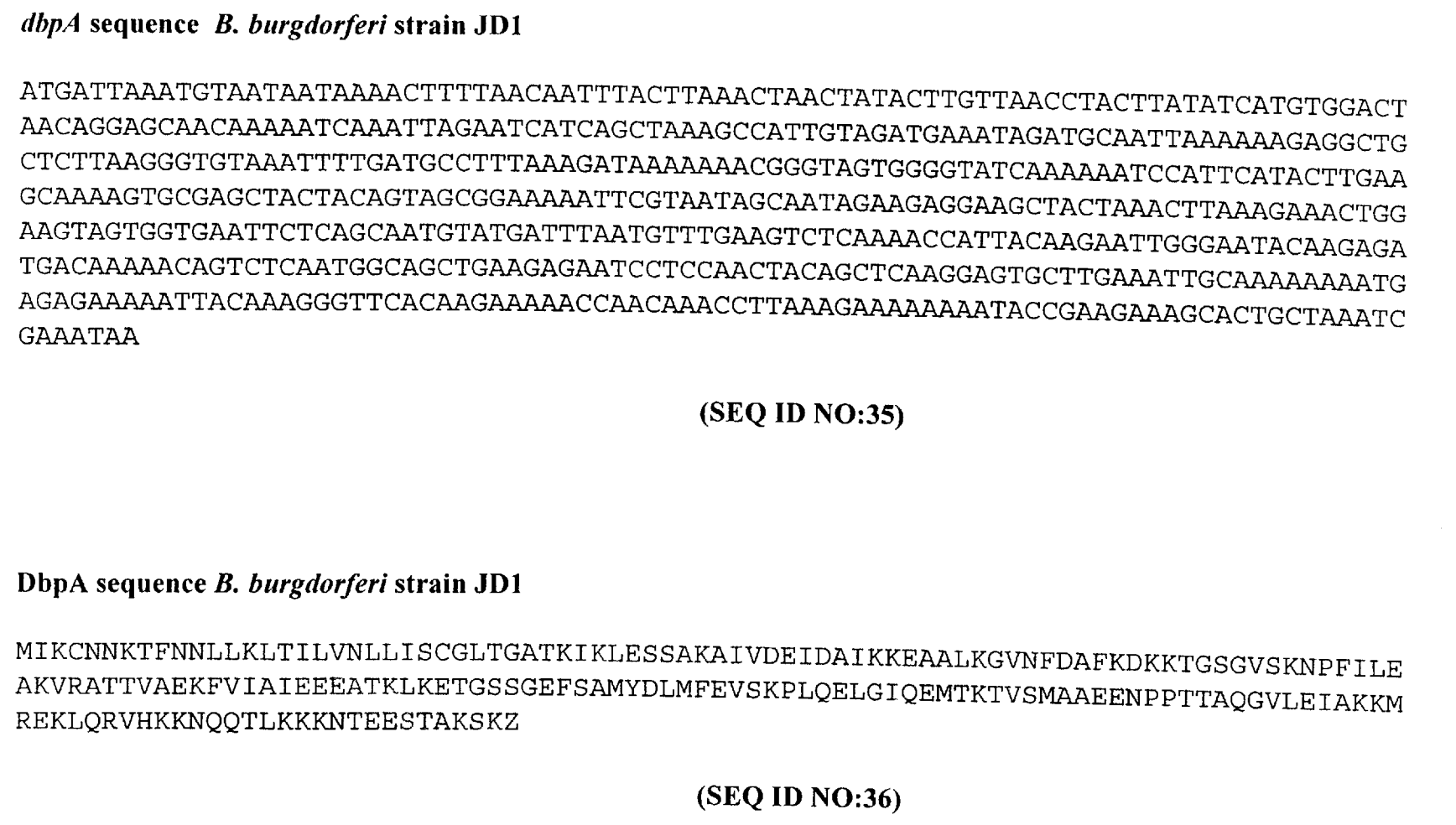

*dbpA* sequence *B. burgdorferi* strain JD1

ATGATTAAATGTAATAATAAACTTTTAACAATTACTT

*dbpA* sequence *B. burgdorferi* strain N40

ATGAATAAATATCAAAAAATCTTTAATTTTAAAAATTTACTTAAACTAAGTTTACTTGTTGCCCTCATATC
ATGCGGATTAAAAGGAGAAACAAAAATCATATTAGAACGAAGCGCTAAAGACATTACAGATGAAATAAATAAAA
AAGACGCTGCTGATAACAATGTAAATTTTGCTGCCTTTACAGATAGTGAAACAGGTAGCAAGGTATCAGAAAATTCATTC
ATACTTGAAGCAAAAGTGCGAGCTACTACAGTAGCAGAGAAAAATTTGTAACACGGATCGAAGGGGAAGCTACAAAACTTAA
AAAGACTGGAAGTAGTGCTGTGAATTCTCAGCAATGTACAACATGATGCTTGAGGTCTCAGGCCCATTAGAAGAATTAGGAG
TACTAAGAATGACAAAGACAGTTACAGATGCGGCTGAACAACACCCTACAACACTCTGAAGGAATACTTGAAATTGCT
AAATAATGAAAACAAAATTACAAGGGTTCATACAAAAAACTACTGCGCCCTTGAAAAGAAGAAAAATCCTAATTTTAC
TGATGAAAAATGCAAAAATAACTAA (SEQ ID NO:33)

DbpA sequence *B. burgdorferi* strain N40

MNKYQKTFKIFNFKNLLKLSLLVALISCGLKGETKIILERSAKDITDEINKIKKDAADNNVNFAAFTDSETGSKVSENSF
ILEAKVRATTVAEKFVTAIEGEATKLKKTGSSGEFSAMYNMMLEVSGPLEELGVLRMTKTVTDAAEQHPTTTAEGILEIA
KIMKTKLQRVHTKNYCALEKKKNPNFTDEKCKNNZ (SEQ ID NO:34)

FIG. 20

***dbpA* sequence *B. burgdorferi* strain SH2**

ATGATTAAATGTAATAATAAAACTTTTAACAATTTACTTAAACTAACTATACTTGTTAACCTACTTATATCATGTGGACT
AACAGGAGCAACAAAAATCAAATTAGAATCATCAGCTAAAGCCATTGTAGATGAAATAGATGCAATTAAAAAAAAGGCTG
CTTCTATGGGTGTAAATTTTGATGCCTCTAAAGATAAAAAAACGGGTAGTGGGGTATCAGAAAATCCATTCATACTTGAA
GCAAAAGTGCGAGCTACTACAGTAGCGGAAAAATTCGTAATAGCAATAGAAGAGGAAGCTACTAAACTTAAAGAAACTGG
AAGTAGTGGTGAATTCTCAGCAATGTATGATTTAATGTTTGAAGTCTCAAAACCATTACAAGAATTGGGAATACAAGAGA
TGACAAAAACAGTCTCAATGGCAGCTGAAGAGAATCCTCCAACTACAGCTCAAGGAGTGCTTGAAATTGCAAAAAAAATG
AGAGAAAAATTACAAAGGGTTCACAAGAAAAACCAAGACACCTTAAAGAAAAAAAATACCGAAGACAGCACTGCTAAATC
GTAA

(SEQ ID NO:31)

**DbpA sequence *B. burgdorferi* strain SH2**

MIKCNNKTFNNLLKLTILVNLLISCGLTGATKIKLESSAKAIVDEIDAIKKKAASMGVNFDASKDKKTGSGVSENPFILE
AKVRATTVAEKFVIAIEEEATKLKETGSSGEFSAMYDLMFEVSKPLQELGIQEMTKTVSMAAEENPPTTAQGVLEIAKKM
REKLQRVHKKNQDTLKKKNTEDSTAKS

(SEQ ID NO:32)

FIG. 21

DbpA amino acid sequence identities (in %)

B. burgdorferi / B. afzellii / B. garinii

| | 297 | LP7 | SH2 | LP4 | JD1 | B31 | BR4 | G3940 | ZS7 | HB19 | N40 | PGAU | B023 | IP90 |
|---|---|---|---|---|---|---|---|---|---|---|---|---|---|---|
| 297 | - | | | | | | | | | | | | | |
| LP7 | 100 | - | | | | | | | | | | | | |
| SH2 | 99.5 | 99.46 | - | | | | | | | | | | | |
| LP4 | 99.46 | 99.47 | 98.93 | - | | | | | | | | | | |
| JD1 | 97.34 | 97.30 | 96.81 | 97.87 | - | | | | | | | | | |
| B31 | 90.37 | 90.37 | 89.84 | 89.84 | 92.06 | - | | | | | | | | |
| BR4 | 90.37 | 90.37 | 89.84 | 89.84 | 92.06 | 100 | - | | | | | | | |
| G3940 | 84.53 | 84.53 | 83.98 | 84.53 | 84.44 | 83.43 | 83.43 | - | | | | | | |
| ZS7 | 77.42 | 77.42 | 76.88 | 76.88 | 78.19 | 82.72 | 82.72 | 73.33 | - | | | | | |
| HB19 | 76.34 | 76.34 | 75.80 | 75.80 | 77.13 | 84.29 | 84.29 | 77.13 | 95.38 | - | | | | |
| N40 | 74.73 | 74.73 | 74.19 | 74.19 | 70.06 | 81.15 | 81.15 | 75.00 | 96.41 | 96.41 | - | | | |
| PGAU | 69.78 | 69.78 | 69.23 | 69.23 | 69.78 | 72.37 | 72.37 | 69.32 | 70.17 | 73.33 | 70.71 | - | | |
| B023 | 59.76 | 59.76 | 59.17 | 59.27 | 59.17 | 62.13 | 62.13 | 66.27 | 60.12 | 76.41 | 62.87 | 65.68 | - | |
| IP90 | 69.94 | 69.94 | 69.39 | 70.49 | 70.49 | 69.78 | 69.78 | 67.79 | 70.95 | 72.63 | 72.62 | 74.72 | 59.17 | - |

FIG. 22

DBPA COMPOSITIONS

The present application is a nationalization of PCT application No. PCT/US96/17081, filed Oct. 22, 1996; which is a continuation-in-part of co-pending U.S. application Ser. No. 08/945,476, filed Dec. 24, 1997; which is a nationalization of PCT application No. PCT/US96/05886, filed Apr. 24, 1996; which is a continuation-in-part of U.S. application Ser. No. 08/589,711, filed Jan. 22, 1996, which issued as U.S. Pat. No. 5,853,987 on Dec. 29, 1998; which is a continuation-in-part of U.S. Ser. No. 08/427,023, filed Apr. 24, 1995, now abandoned. The entire texts and figures of each of which disclosures are specifically incorporated herein by reference without disclaimer.

1. BACKGROUND OF THE INVENTION

1.1 Field of the Invention

The present invention relates generally to the field of molecular biology. More particularly, certain embodiments concern methods and compositions comprising DNA segments, and proteins derived from bacterial species. More particularly, the invention provides gene compositions encoding the decorin (Dcn) binding proteins (DBPs) from *Borrelia burgdorferi* and the corresponding peptide epitopes and protein sequences comprising native and synthetically-modified Dcn binding site domains. Various methods for making and using these DNA segments, DNA segments encoding synthetically-modified ligand binding site domains, and native and synthetic DbpA and DbpB proteins are disclosed, such as, for example, the use of dbpA and dbpB DNA segments as diagnostic probes and templates for protein production, and the use of proteins, fusion protein carriers and peptides in various pharmacological and immunological applications.

1.2 Description of the Related Art

1.2.1 Lyme Disease

Lyme disease (Steere, 1989), or Lyme borreliosis, is transmitted by ticks, particularly of the genus Ixodes, and caused by spirochetes of the genus Borrelia. Lyme disease agents, that is borrelias isolated from humans or animals with clinical Lyme disease, are currently classified into at least four phylogenetic groups: *B. burgdorferi* sensu stricto, *B. garinii*, *B. andersonii*, and *B. afzelii*. Strains potentially representing other phylogenetic groups of Lyme disease agents as well, such as group 25015, have been also isolated from ixodid ticks. Collectively these spirochetes are referred to as *B. burgdorferi* sensu lato, or simply *B. burgdorferi*. The genotypic and phenotypic variation among Lyme disease agents supporting the designation of these phylogenetic subgroupings is a major complicating factor for the design of effective vaccines or immunotherapeutic strategies for Lyme disease.

Lyme disease is transmitted through the bite of a tick which attaches itself to the host and, upon feeding, deposits the spirochetes into the dermis of the skin. In the skin, *B. burgdorferi* replicates before endovascular dissemination to organs. Typically, an annular spreading skin lesion, erythema migrans, forms from the site of the tick bite. Early symptoms of Lyme disease are flu-like and may include fatigue and lethargy. Left untreated, Lyme disease can develop into a chronic, multisystemic disorder involving the skin, joints, heart, and central nervous system.

Once deposited in the dermis, the spirochetes become associated with and appear to colonize the collagen fibers. Skin is the most consistent site of spirochete-positive culture. In persistent infection, the skin may provide a protective niche for replication, thereby acting as a reservoir of spirochetes for subsequent distribution to other tissues.

As *B. burgdorferi* disseminates to other organs, the organisms appear to localize to the extracellular spaces of these tissues as well. In several organs, including tendon (Barthold et al., 1993; 1991), ligament (Häupl et al., 1993), heart (Zimmer et al., 1990), and muscle (Barthold et al., 1992; Duray, 1992), *B. burgdorferi* spirochetes are found primarily in close association with collagen fibers, suggesting that this association is an important mechanism of tissue adherence in different stages of infection. Although the association of *B. burgdorferi* with collagen fibers has been reported previously by several investigators, the molecular mechanism responsible is not known. Lyme disease is typically treated with antibiotics, which are generally effective in the early stages of the disease. Later stages involving cardiac, arthritic, and nervous system disorders are often non-responsive.

1.2.2 Existing Vaccines for Prevention of Lyme Disease

Several proteins present on the outer surface of *B. burgdorferi* have been identified, including OspA (31 kDa), OspB (34 kDa), OspC (22 kDa), OspD, OspE, and OspF. Laboratory studies have shown that passively-administered antibodies (Schaible et al., 1990) reactive with the *B. burgdorferi* outer surface protein A (OspA), or immunization with recombinant OspA (Fikrig et al., 1990), protect mice from challenge with in vitro-grown or tick-borne *B. burgdorferi*. Based largely on the protective efficacy of experimental OspA vaccines in rodent models of Lyme borreliosis, three monovalent OspA-based vaccines are currently in clinical trials. However, recent findings suggest that broad, sustained protection of humans may be difficult to achieve with vaccines based solely on OspA.

Three observations, however, suggest that OspA-based vaccines may prove to have limited efficacy in treating Lyme disease in humans:

a) Modulation of OspA expression by *B. burgdorferi* may limit the site of action of OspA-specific antibodies to spirochetes residing in the tick midgut as these antibodies are ineffective shortly after infection;

b) Human immune responses to OspA subunit vaccines have not matched those of rodents in level or duration; and c) OspA is serologically diverse, particularly among European and Asian *B. garinii* and *B. afzelii* isolates. Reactivity with panels of OspA monoclonal antibodies (mAbs), and DNA sequence analysis has shown that as many as seven different OspA subgroups can be distinguished (Wilske et al., 1991; 1993).

Moreover, these variations will no doubt affect the cross-protection to be anticipated with OspA vaccines. Cross-protection was seen by one group using an immunocompetent mouse model (Fikrig et al., 1995), but cross-protection was weak or absent in SCID mouse or hamster models used by other (Schaible et al., 1993; Lovrich et al., 1995). An additional concern is that as many as 10% of *B. burgdorferi* isolates fail to express OspA in culture (Wilske et al., 1991; 1993).

Another problem with the use of OspA as antigens for stimulation of an immune response in an affected patient is the fact that OspA protein is either poorly immunogenic in humans, or not expressed by *B. burgdorferi* in vivo until late in infection. Lyme disease patients, mice, hamsters, and dogs infected by tick bite or low-doses of cultured *B. burgdorferi* fail to mount substantial anti-OspA immune responses for many months following infection although they do mount early responses to other *B. burgdorferi* antigens (flagellin, OspC, etc.) (Steere, 1989; Barthold and Bockenstedt, 1993). OspA is expressed by *B. burgdorferi* within ticks (Barbour et al., 1983), but detection of OspA on borrelias in tissue early after infection is difficult. Passive immunization of mice with OspA antibody (Schaible et al., 1990), or immunization with recombinant OspA, after challenge does not eliminate infection and only partially alters disease.

Unfortunately, OspA-immunized mice are not protected from a challenge with host-adapted spirochetes delivered in the form of skin biopsy transplants from infected mice (Barthold et al., 1995). The bacteria appear to express OspA in vivo only at later stages when the infection becomes disseminated. This would be explained by down-regulation of OspA expression by borrelia shortly after initiation of feeding by the tick.

de Silva et al. (1996) demonstrated that when OspA-specific antibodies were administered to mice before or at the time of attachment of borrelia-infected ticks these mice were protected from spirochetal infection. However, when OspA-specific antibody was administered 48-hr after tick attachment no protection was observed.

Modulation of borrelia antigen expression within feeding ticks has recently been reported for OspC; initially low in resting ticks, OspC levels increase on *B. burgdorferi* after initiation of tick feeding (Schwan et al., 1995). OspC might appear to be a promising in vivo target, but its high level of antigenic variation complicates its development as a vaccine (Probert and LeFebvre, 1995).

In vitro cultivation of *B. burgdorferi* suggests that the genes for OspA and OspC are inversely regulated. Preliminary findings of some researchers do suggest that OspA levels similarly decrease after initiation of tick feeding. If these findings are confirmed, OspA antibodies will need to pre-exist at high levels in human or animal hosts prior to the tick bite to be effective against OspA-expressing borrelias in the tick, and may receive little or no boosting upon delivery of the spirochetes into the skin within the milieu of immunosuppressive components of the tick saliva (Urioste et al., 1994).

Telford et al. (1995) describes the efficacy of human Lyme disease vaccine formulations in a mouse model. The authors speculate that "(i)t is likely that titer of circulating antibody to OspA critically determines protection because of the unique mode of action of antispirochetal immunity, wherein antibody or other effectors interfere with the process of transmission within the gut of the infecting tick, before inoculation of the pathogen." Consistent with this hypothesis it has been shown that anti-borrelia serum can protect mice from infection by tick bite if administered within two days after initiation of feeding by borrelia-infected ticks, but not when passively administered at later times (Shih et al., 1995). The antibody levels in response to recombinant OspA subunit vaccinations seen to date in Phase II trials have been moderate, with serum ELISA titers <3,000, and drop off to near baseline levels within five months (Keller et al., 1994). The results in these studies indicate that it will be necessary to include additional antigens to achieve a protective vaccine for Lyme disease.

1.3 Deficiencies in the Prior Art

It is clear that while several approaches to the treatment of bacterial diseases have experienced some success, many problems remain, including antibiotic resistance, variability of antigens between species and species variation through mutation of antigens, as well as the need to protect susceptible groups such as young children, the elderly and other immunocompromised patients. Thus, there exists an immediate need for an effective treatment for *B. burgdorferi*, and vaccines against the causative agent of Lyme disease.

Although attempts have been made to utilize the Osps as vaccines to confer protection against *B. burgdorferi*, the results have been disappointing. Because these proteins have demonstrated strain specificity, e.g., variance among isolates and among different passages, and some lack of cross protection between strains, their potential use as vaccines remains very limited.

Because currently known antigens are not sufficient to elicit a protective immune response over a broad spectrum of *B. burgdorferi* strains, there continues to be an urgent need to develop novel prevention and treatment methods as well as novel antigens able to elicit a broad-spectrum immune response and useful diagnostic methods for the prevention, treatment, and diagnosis of Lyme disease.

2. SUMMARY OF THE INVENTION

The present invention overcomes one or more of these and other drawbacks inherent in the prior art by providing novel compositions and methods for their use in the treatment of Lyme disease using non-antibiotic strategies. Disclosed are methods for the use of novel peptides and antibody compositions in the treatment of Lyme disease mediated by the inhibition of *B. burgdorferi* binding to the host cell ECM component, Dcn. Also disclosed are methods for active and passive immunization against *B. burgdorferi* and related borrelias including *B. afzelii, B. andersonii, B. japonica*, and *B. garinii* using novel native and site-specifically-altered DBP compositions and DBP-derived epitopic peptides from *B. burgdorferi, B. andersonii, B. afzelii, B. japonica*, and *B. garinii*. Particular aspects of the invention relate to novel nucleic acid segments encoding these peptides and epitopes, and methods for the use of such nucleic acid segments in a variety of diagnostic and therapeutic regimens.

Biochemical and immunological characterization of the *B. burgdorferi* DBPs show that Lyme disease vaccines comprising DbpA and/or DbpB compositions overcome the limitations of the prior art involving OspA and, are, indeed, superior to those formulations based on OspA regimens.

2.1 dbp Nucleic Acid Compositions

The invention provides nucleic acid sequences encoding DbpA and DbpB proteins. As used herein, a "dbp gene" means a nucleic acid sequence encoding a DBP. Preferred dbp genes include the dbpA and dbpB genes, in particular those from *B. burgdorferi, B. japonica, B. andersonii, B. afzelii*, and *B. garinii*.

A preferred nucleic acid sequence encoding a dbpA gene is the nucleotide sequence of SEQ ID NO:7, SEQ ID NO:10, SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:29, SEQ ID NO:31, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:50, or SEQ ID NO:52, and more preferably, the nucleotide sequence of the approximately 0.6-kb open reading frame (ORF) of the *B. burgdorferi* dbpA gene (from position 1471 to 2031 of SEQ ID NO:7), or strain variants or active fragments thereof.

A preferred nucleic acid sequence encoding a dbpB gene is the nucleotide sequence of SEQ ID NO:53, SEQ ID NO:55, SEQ ID NO:57, SEQ ID NO:59, SEQ ID NO:61, SEQ ID NO:63, and SEQ ID NO:65, and more preferably, the nucleotide sequence of the approximately 0.6-kb open reading frame (ORF) of the *B. burgdorferi* dbpB gene (from position 791 to 1351 of SEQ ID NO:7) or strain variants or active fragments thereof.

It is expected that the genes encoding DBPs will vary in nucleic acid sequence from strain to strain, but that the variation in nucleic acid sequence will not preclude hybridization between sequences encoding the DBPs of each strain under moderate to strict hybridization conditions. It is also contemplated that the genes encoding DbpAs from various strains may vary in nucleic acid sequences, but that the variation will not preclude hybridization between sequences encoding a DbpA from each strain under moderate to strict hybridization conditions. Likewise, it is contemplated that the genes encoding DbpBs from various strains may vary in nucleic acid sequences, but that the variation will not preclude hybridization between sequences encoding a DbpB from each strain under moderate to strict hybridization conditions.

As used herein, a strain variant of a DBP means any polypeptide encoded, in whole or in part, by a nucleic acid sequence which hybridizes under moderate to strict hybridization conditions to the nucleic acid sequence of SEQ ID NO:7, SEQ ID NO:10, SEQ ID NO:11, SEQ ID NO:12, SEQ ID NO:14, SEQ ID NO:16, SEQ ID NO:18, SEQ ID NO:20, SEQ ID NO:22, SEQ ID NO:24, or SEQ ID NO:26 encoding the DbpA protein of strains 297, B31, Sh.2.82, HB-19, PGau, IP90, LP4, LP7, and JD1, respectively, or to the nucleic acid sequence of SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, or SEQ ID NO:51, encoding the DbpA protein of strains 297/LP4, SH2, N40, JD1, HB19, B31/BR4/3028, G3940, LP4, ZS7, PGau, B023, and IP90, respectively.

Likewise, as also used herein, a strain variant of a DBP means any polypeptide encoded, in whole or in part, by a nucleic acid sequence which hybridizes under moderate to strict hybridization conditions to the nucleic acid sequence of SEQ ID NO:7, SEQ ID NO:10, SEQ ID NO:11, or to the nucleic acid sequence of SEQ ID NO:53, SEQ ID NO:55, SEQ ID NO:57, SEQ ID NO:59, SEQ ID NO:61, SEQ ID NO:63, or SEQ ID NO:65, encoding the DbpB protein of strains CA287 (DbpB protein: SEQ ID NO:54), IPS (DbpB protein: SEQ ID NO:56), JD1 (DbpB protein: SEQ ID NO:58), 297, SH2, and LP4 (DbpB protein: SEQ ID NO:60), N40, LP7, and PKo (DbpB protein: SEQ ID NO:62), HB19, G3940, LP5, ZS7, NCH-1, FRED, and 20047 (DbpB protein: SEQ ID NO:64) and IP90 (DbpB protein: SEQ ID NO:66), respectively.

One of skill in the art will understand that strain variants of DBPs include those proteins encoded by nucleic acid sequences which may be amplified using one or more of the dbpA-encoding nucleic acid sequences of SEQ ID NO:7, SEQ ID NO:8, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, or SEQ ID NO:51, and more preferably from the nucleic acid sequence of SEQ ID NO:7, and most preferably, the nucleic acid sequence of the 0.6-kb ORF (from position 1471 to 2031 of SEQ ID NO:7) encoding the *B. burgdorferi* 297 DbpA protein.

One of skill in the art will also understand that strain variants of DBPs include those proteins encoded by nucleic acid sequences which may be amplified using one or more of the dbpB-encoding nucleic acid sequences of SEQ ID NO:53, SEQ ID NO:55, SEQ ID NO:57, SEQ ID NO:59, SEQ ID NO:61, SEQ ID NO:63, or SEQ ID NO:65, and more preferably from the nucleic acid sequence of SEQ ID NO:7, and most preferably, the nucleic acid sequence of the 0.6-kb ORF (from position 791 to 1351 of SEQ ID NO:7) encoding the *B. burgdorferi* 297 DbpB protein.

SEQ ID NO:7 lists the nucleotide sequence of a 2.5-kb insert of borrelia genomic DNA cloned in pBlueScript™ which comprises the dbpA and dbpB genes of *B. burgdorferi* 297. This recombinant clone, designated BG26:pB/2.5(5), has been deposited with the American Type Culture collection in *E. coli* strain JM101, and has been given the ATCC accession number ATCC69791. Contained within the 2.5-kb DNA insert from position 1471 to 2031 is the approximately 0.6-kb ORF encoding the *B. burgdorferi* DbpA protein (SEQ ID NO:8) and from position 791 to position 1351, the approximately 0.6-kb ORF encoding the *B. burgdorferi* DbpB protein (SEQ ID NO:28).

In related embodiments, the invention also comprises strain variants of DBPs and nucleic acid segments encoding DBPs, in particular, the dbpA and dbpB genes which encode the DbpA and DbpB proteins, respectively. Strain variants are those nucleic acid compositions and polypeptide compositions expressed by various strains of *B. burgdorferi* and related borrelias including *B. afzelii, B. andersonii, B. japonica*, and *B. garinii* which specifically encode DBPs.

These DBPs also bind Dcn and related proteoglycans and share similarity of structure and function with the DbpA and DbpB proteins of *B. burgdorferi* strain 297. Such DbpA amino acid sequences include those DbpA sequences of related borrelia strains B31, Sh.2.82, HB-19, LP4, LP7, and JD1 of *B. burgdorferi* (SEQ ID NO:12, SEQ ID NO:14, SEQ ID NO:16, SEQ ID NO:22, SEQ ID NO:24, and SEQ ID NO:26, respectively); strain pGau (SEQ ID NO:18) of *B. afzelii*; or strain IP90 (SEQ ID NO:20) of *B. garinii*. DbpA amino acid sequences are also disclosed in SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, and SEQ ID NO:52.

DbpB amino acid sequences are disclosed in SEQ ID NO:54, SEQ ID NO:56, SEQ ID NO:58, SEQ ID NO:60, SEQ ID NO:62, SEQ ID NO:64, and SEQ ID NO:56.

Aspects of the invention concern the identification of such strain variants using diagnostic methods and kits described herein. In particular, methods utilizing dbpA and dbpB gene sequences as nucleic acid hybridization probes and/or anti-DbpA and anti-DbpB antibodies in western blots or related analyses are useful for the identification of such strain variants. The identity of potential strain variants of DBPs may be confirmed by Dcn binding assays, e.g., by blot analysis with labeled Dcn, or alternatively by the demonstrating the ability of the strain-variant DBPs to lessen or prevent adherence of *B. burgdorferi* and related borrelias including *B. afzelii, B. andersonii, B. japonica*, and *B. garinii* to Dcn.

As used herein, a DBP means a purified and isolated protein including a strain variant or an active fragment thereof, derived from *B. burgdorferi* or a similar species which induces Lyme disease in a similar way, and having the ability to bind Dcn. Preferably, a DBP is a DbpA or DbpB protein encoded by a nucleic acid sequence contained within the *B. burgdorferi* DNA insert shown in SEQ ID NO:7, and more preferably a DbpA or DbpB protein which comprises the amino acid sequence of SEQ ID NO:8 or SEQ ID NO:28, which encode DbpA and DbpB from 297, respectively.

Preferred DbpA-encoding DNA sequences are those shown in SEQ ID NO:12, SEQ ID NO:14, SEQ ID NO:16, SEQ ID NO:18, SEQ ID NO:20, SEQ ID NO:22, SEQ ID NO:24, and SEQ ID NO:26, as well as those DbpA-encoding DNA sequences disclosed in SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, and SEQ ID NO:51, and all strain variants or active fragments thereof encoding all or portions of a borrelial DbpA protein.

Preferred DbpB-encoding DNA sequences are those shown in FIG. 3 (SEQ ID NO:60), FIG. 6 (SEQ ID NO:64), FIG. 7 (SEQ ID NO:62), FIG. 8 (SEQ ID NO:66), FIG. 9 (SEQ ID NO:58), FIG. 10 (SEQ ID NO:56), and FIG. 11 (SEQ ID NO:54) or strain variants or active fragments thereof encoding all or portions of a borrelial DbpB protein.

In the present invention, a DBP composition is also understood to comprise one or more polypeptides that are immunologically reactive with antibodies generated against *B. burgdorferi, B. garinii, B. afzelii, B. andersonii, B. japonica*, or related Borrelia spp. and in particular antibodies generated against a DbpA or DbpB protein, particularly those encoded by the dbpA nucleic acid sequences of any of SEQ ID NO:7, SEQ ID NO:10, SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, and SEQ ID NO:51; or the dbpB nucleic acid sequences disclosed in any of SEQ ID NO:53, SEQ ID NO:55, SEQ ID NO:57, SEQ ID NO:59, SEQ ID NO:61, SEQ ID NO:63, or SEQ ID NO:65, or to active fragments, or to strain variants thereof.

Likewise, a DBP composition of the present invention is understood to comprise one or more polypeptides that are capable of eliciting antibodies that are immunologically reactive with one or more DbpA or DbpB proteins encoded by one or more dbpA nucleic acid sequences contained in SEQ ID NO:7, SEQ ID NO:10, SEQ ID NO :11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, or SEQ ID NO:51, or by one or more dbpB nucleic acid sequences contained in SEQ ID NO:53, SEQ ID NO:55, SEQ ID NO:57, SEQ ID NO:59, SEQ ID NO:61, SEQ ID NO:63, or SEQ ID NO:65, or to active fragments, or to strain variants thereof, or to one or more nucleic acid sequences which hybridize to one or more of these sequences under conditions of moderate to high stringency. Particularly preferred DbpA proteins include one or more of the DbpA amino acid sequences disclosed in any of SEQ ID NO:8, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, and SEQ ID NO:52. Particularly preferred DbpB proteins include one or more of the DbpB amino acid sequences disclosed in any of SEQ ID NO:54, SEQ ID NO:56, SEQ ID NO:58, SEQ ID NO:60, SEQ ID NO:62, SEQ ID NO:64, and SEQ ID NO:66.

A DBP composition of the present invention is also understood to comprise one or more polypeptides that elicit an immune response in a treated animal, this immune response being effective to lessen or prevent symptomatic disorders associated with Lyme disease or related borrelioses, or which polypeptides are capable of eliciting antibodies that are immunologically reactive with a DbpA encoded by a nucleic acid sequence of any of SEQ ID NO:7, SEQ ID NO:10, SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, or SEQ ID NO:51, or with an active fragment, or with one or more strain variants thereof, or which polypeptides are capable of eliciting antibodies that are immunologically reactive with a DbpB encoded by a nucleic acid sequence of any of SEQ ID NO:7, SEQ ID NO:53, SEQ ID NO:55, SEQ ID NO:57, SEQ ID NO:59, SEQ ID NO:61, SEQ ID NO:63, or SEQ ID NO:65, or with an active fragment, or with one or more strain variants thereof.

As used herein, an active fragment of a DBP includes a whole or a portion of a DBP which is modified by conventional techniques, e.g., mutagenesis, or by addition, deletion, or substitution, but which active fragment exhibits substantially the same structure and function as a native DBP as described herein. For example, portions of the protein not required to block adherence of *B. burgdorferi* to Dcn may be deleted or altered; additions to the protein may be made to enhance the protein's antigenicity according to conventional methods.

As used herein, a DBP composition which confers protection against Lyme disease means a DBP composition which prevents or lessens adhesion of *B. burgdorferi* to Dcn, or prevents or lessens adhesion the severity of any of the disorders associated with *B. burgdorferi* infection, including erythema migrans, arthritis, carditis, neurological disorders, or any other Lyme disease-related disorder.

Other aspects of the present invention concern isolated DNA segments and recombinant vectors encoding one or more DBPs, in particular, the DbpA and DbpB proteins from Borrelia such as *B. burgdorferi, B. afzelii, B. andersonii, B. garinii*, and *B. japonica*, and the creation and use of recombinant host cells through the application of DNA technology, that express one or more dbp gene products, and in particular, the dbpA and dbpB genes from Borrelia such as *B. burgdorferi, B. afzelii, B. andersonii, B. garinii*, and *B. japonica*. As such, the invention concerns DNA segments comprising an isolated gene that encodes a DbpA protein or peptide that includes an amino acid sequence essentially as set forth by a contiguous sequence from SEQ ID NO:9, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, or SEQ ID NO:52. These DNA segments are represented by those that include a dbpA nucleic acid sequence essentially as set forth by a contiguous sequence from SEQ ID NO:7, SEQ ID NO:10, SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, or SEQ ID NO:53.

Compositions that include a purified DbpA protein that has an amino acid sequence essentially as set forth by the amino acid sequence of SEQ ID NO:9, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, or SEQ ID NO:52 are also encompassed by the invention.

Likewise, the invention also concerns DNA segments comprising an isolated gene that encodes a DbpB protein or peptide that includes an amino acid sequence essentially as set forth by a contiguous sequence from SEQ ID NO:54, SEQ ID NO:56, SEQ ID NO:58, SEQ ID NO:60, SEQ ID NO:62, SEQ ID NO:64, or SEQ ID NO:66. These DNA segments are represented by those that include a dbpB nucleic acid sequence essentially as set forth by a contiguous sequence from SEQ ID NO:7, SEQ ID NO:10, SEQ ID NO:11, SEQ ID NO:53, SEQ ID NO:55, SEQ ID NO:57, SEQ ID NO:59, SEQ ID NO:61, SEQ ID NO:63, or SEQ ID NO:65.

Compositions that include a purified DbpB protein that has an amino acid sequence essentially as set forth by the amino acid sequence of SEQ ID NO:28, SEQ ID NO:54, SEQ ID NO:56, SEQ ID NO:58, SEQ ID NO:60, SEQ ID NO:62, SEQ ID NO:64, or SEQ ID NO:66 are also encompassed by the invention. Regarding the novel DBPs, the present invention concerns DNA segments, that can be isolated from virtually any bacterial source, that are free from total genomic DNA and that encode proteins having DBP-like activity. DNA segments encoding one or more DBP-like species may prove to encode proteins, polypeptides, subunits, functional domains, and the like.

As used herein, the term "DNA segment" refers to a DNA molecule that has been isolated free of total genomic DNA of a particular species. Therefore, a DNA segment encoding a DBP refers to a DNA segment that contains one or more DBP coding sequences yet is isolated away from, or purified free from, total genomic DNA of the species from which the DNA segment is obtained. Included within the term "DNA segment", are DNA segments and smaller fragments of such segments, and also recombinant vectors, including, for example, plasmids, cosmids, phagemids, phage, viruses, and the like.

Similarly, a DNA segment comprising an isolated or purified dbp gene refers to a DNA segment including DBP coding sequences and, in certain aspects, regulatory sequences, isolated substantially away from other naturally occurring genes or protein encoding sequences. Preferably the sequence encodes a DbpA or DbpB protein, and more preferably, comprises a dbpA or dbpB gene, in particular, a dbpA or dbpB gene from Borrelia such as *B. burgdorferi, B. afzelii, B. andersonii, B. garinii,* or *B. japonica.* In this respect, the term "gene" is used for simplicity to refer to a functional protein, polypeptide or peptide encoding unit. As will be understood by those in the art, this functional term includes both genomic sequences, extra-genomic and plasmid-encoded sequences and smaller engineered gene segments that express, or may be adapted to express, proteins, polypeptides or peptides. Such segments may be naturally isolated, or modified synthetically by the hand of man. "Isolated substantially away from other coding sequences" means that the gene of interest, in this case, a gene encoding a DBP, forms the significant part of the coding region of the DNA segment, and that the DNA segment does not contain large portions of naturally-occurring coding DNA, such as large chromosomal fragments or other functional genes or polypeptide coding regions. Of course, this refers to the DNA segment as originally isolated, and does not exclude genes or coding regions later added to the segment by the hand of man.

In particular embodiments, the invention concerns isolated DNA segments and recombinant vectors incorporating DNA sequences that encode a DBP species that comprises an amino acid sequence essentially as set forth in any of SEQ ID NO:8, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, or SEQ ID NO:66, or biologically-functional equivalents thereof. In other particular embodiments, the invention concerns isolated DNA segments and recombinant vectors incorporating DNA sequences that comprises a sequence essentially as set forth in SEQ ID NO:7, SEQ ID NO:7, SEQ ID NO:10, SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, or SEQ ID NO:65, or biologically-functional equivalents or strains variants thereof.

The term "a sequence essentially as set forth in SEQ ID NO:7, SEQ ID NO:7, SEQ ID NO:10, SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, or SEQ ID NO:65," means that the sequence substantially corresponds to a portion of the DNA sequence listed in any of SEQ ID NO:7, SEQ ID NO:7, SEQ ID NO:10, SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, or SEQ ID NO:65, and has relatively few nucleotides that are not identical to, or a biologically functional equivalent of, the nucleic acid sequences of SEQ ID NO:7, SEQ ID NO:7, SEQ ID NO: 10, SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, or SEQ ID NO:65. Such nucleotide sequences are also considered to be essentially as those disclosed herein when they encode essentially the same amino acid sequences as disclosed, or that they encode biologically functional equivalent amino acids tot hose as disclosed herein. In particular, preferred nucleotide sequences are those which encode the amino acid sequences of any of SEQ ID NO:8, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, or SEQ ID NO:66, or biologically functional equivalents thereof.

The term "biologically functional equivalent" is well understood in the art and is further defined in detail herein (e.g., see Illustrative Embodiments). Accordingly, sequences that have between about 70% and about 80%; or more preferably, between about 81% and about 90%; or even more preferably, between about 91% and about 99%; of amino acids that are identical or functionally equivalent to the amino acids disclosed herein, will be sequences that are "essentially as set forth in SEQ ID NO:8, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64 or SEQ ID NO:66".

In certain other embodiments, the invention concerns isolated DNA segments and recombinant vectors that include within their sequence a nucleic acid sequence essentially as set forth in SEQ ID NO:7, SEQ ID NO:10, SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63 or SEQ ID NO:65. The term "essentially as set forth in SEQ ID NO:7, SEQ ID NO:10, SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63 or SEQ ID NO:65" is used in the same sense as described above and means that the nucleic acid sequence substantially corresponds to a portion of SEQ ID NO:7, SEQ ID NO:10, SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63 or SEQ ID NO:65 and has relatively few nucleotides residues that are not identical, or functionally equivalent, to the nucleotide residues of SEQ ID NO:7, SEQ ID NO:10, SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63 or SEQ ID NO:65. Again, DNA segments that encode proteins exhibiting a DBP-like activity will be most preferred.

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various upstream or downstream regulatory or structural genes.

Naturally, the present invention also encompasses DNA segments that are complementary, or essentially complementary, to one or more of the sequences set forth in SEQ ID NO:7, SEQ ID NO:10, SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63 or SEQ ID NO:65. Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to one or more of the nucleic acid segments of SEQ ID NO:7, SEQ ID NO:10, SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63 or SEQ ID NO:65, under relatively stringent conditions such as those described herein.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared that include a short contiguous stretch identical to or complementary to one or more of SEQ ID NO:7, SEQ ID NO:10, SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63 or SEQ ID NO:65, such as about 14 nucleotides, and that are up to about 10,000 or about 5,000 base pairs in length, with segments of about 3,000 being preferred in certain cases. DNA segments with total lengths of about 2,000, about 1,000, about 500, about 200, about 100 and about 50 base pairs in length (including all intermediate lengths) are also contemplated to be useful.

It will be readily understood that "intermediate lengths", in these contexts, means any length between the quoted ranges, such as 14, 15, 16, 17, 18, 19, 20, etc.; 21, 22, 23, etc.; 30, 31, 32, etc.; 50, 51, 52, 53, etc.; 100, 101, 102, 103, etc.; 150, 151, 152, 153, etc.; including all integers through the 200–500; 500–1,000; 1,000–2,000; 2,000–3,000; 3,000–5,000; 5,000–10,000 ranges, up to and including sequences of about 12,001, 12,002, 13,001, 13,002 and the like.

It will also be understood that this invention is not limited to the particular nucleic acid sequences as disclosed in SEQ ID NO:7, SEQ ID NO:10, SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63 or SEQ ID NO:65 or to the amino acid sequences as disclosed in SEQ ID NO:8, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, and SEQ ID NO:66. Recombinant vectors and isolated DNA segments may therefore variously include the DbpA and/or DbpB coding regions themselves, coding regions bearing selected alterations or modifications in the basic coding region, or they may encode larger polypeptides that nevertheless include a DBP coding region or may encode biologically functional equivalent proteins or peptides that have variant amino acids sequences.

The DNA segments of the present invention encompass biologically functional equivalent DBPs and DBP peptides, in particular those DBPs isolated from prokaryotic sources such as bacteria. DNA segments isolated from species of Borrelia and related bacteria which are shown to bind Dcn are particularly preferred for use in the methods disclosed herein. Such sequences may arise as a consequence of codon redundancy and functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test mutants in order to examine activity at the molecular level.

If desired, one may also prepare fusion proteins and peptides, e.g., where the DBP coding regions are aligned within the same expression unit with other proteins or peptides having desired functions, such as for purification or immunodetection purposes (e.g., proteins that may be purified by affinity chromatography and enzyme label coding regions, respectively).

Recombinant vectors form further aspects of the present invention. Particularly useful vectors are contemplated to be those vectors in which the coding portion of the DNA segment, whether encoding a full length protein or smaller peptide, is positioned under the control of a promoter. The promoter may be in the form of the promoter that is naturally associated with a DBP gene, as may be obtained by isolating the 5' non-coding sequences located upstream of the coding segment, for example, using recombinant cloning and/or PCR™ technology, in connection with the compositions disclosed herein.

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a DBP gene in its natural environment. Such promoters may include dbpA or dbpB promoters normally associated with other genes, and/or promoters isolated from any bacterial, viral, eukaryotic, or mammalian cell. Naturally, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al. (1989). The promoters employed may be constitutive, or inducible, and can be used under the appropriate conditions to direct high level expression of the introduced DNA segment, such as is advantageous in the large-scale production of recombinant proteins or peptides.

Prokaryotic expression of nucleic acid segments of the present invention may be performed using methods known to those of skill in the art, and will likely comprise expression vectors and promotor sequences such as those provided by tac, trp, lac, lacUV5 or T7. When expression of the recombinant DBP proteins is desired in eukaryotic cells, a number of expression systems are available and known to those of skill in the art. An exemplary eukaryotic promoter system contemplated for use in high-level expression is the Pichia expression vector system (Pharmacia LKB Biotechnology).

In connection with expression embodiments to prepare one or more recombinant DBPs or DbpA- or DbpB-derived peptides, it is contemplated that longer DNA segments will most often be used, with DNA segments encoding an entire DBP or one or more functional domains, epitopes, ligand binding domains, subunits, etc. therefore being most preferred. However, it will be appreciated that the use of shorter DNA segments to direct the expression of a DBP or a DBP-derived peptide or epitopic core region, such as may be used to generate anti-DbpA or anti-DbpB antibodies, also falls within the scope of the invention. DNA segments that encode peptide antigens from about 15 to about 100 amino acids in length, or more preferably, from about 15 to about 50 amino acids in length are contemplated to be particularly useful.

The dbpA and dbpB genes and DNA segments derifed therefrom may also be used in connection with somatic expression in an animal or in the creation of a transgenic animal. Again, in such embodiments, the use of a recombinant vector that directs the expression of the full length or active DBP is particularly contemplated. Expression of dbpA and or dbpB transgene in animals is particularly contemplated to be useful in the production of anti-DbpA or anti-DbpB antibodies for use in passive immunization methods for prevention of borrelial adhesion to Dcn, and treatment of infections due to Borrelia invasion, and particularly invasion by *B. burgdorferi, B. afzelii, B. andersonii, B. garinii*, or *B. japonica*. Such anti-DbpA or anti-DbpB antibodies are also contemplated for use in passive immunization methods for prevention of bacterial adhesion to Dcn, and treatment of infections caused by any bacterial species which binds to Dcn upon invasion.

An important aspect of the invention is the identification of nucleic acid sequences encoding DbpA proteins which do not share significant sequence homology with nucleic acid sequences encoding DbpB proteins, and vice versa. Methods are provided for determining such sequences based on nucleic acid hybridization. In a preferred embodiment, the invention discloses and claims a nucleic acid segment which comprises the nucleic acid sequence from between position 791 and position 1351 of SEQ ID NO:7, or the complement thereof, or a sequence that hybridizes to the sequence from between position 791 and position 1351 of SEQ ID NO:7, but not to the sequence from between position 1471 and position 2031 of SEQ ID NO:7 under the same hybridization conditions. Such methods permit the identification of dbpB genes which do not cross-hybridize with dbpA gene sequences and vice versa.

2.2 Recombinant Expression of DbpA and DbpB

The present invention also concerns recombinant host cells for expression of one or more isolated dbpA or dbpB genes. It is contemplated that virtually any host cell may be employed for this purpose, but certain advantages may be found in using a bacterial host cell such as *E. Coli, S. typhimurium, B. subtilis*, or others. Expression in eukaryotic cells is also contemplated such as those derived from yeast, insect, or mammalian cell lines. These recombinant host cells may be employed in connection with "overexpressing" DBPs, that is, increasing the level of expression over that found naturally in Borrelia, in particular, *B. burgdorferi, B. afzelii, B. andersonii, B. garinii, B. japonica*, or related spirochete.

Proteins having amino acid sequences derived from, or similar to the DbpA or DbpB proteins of the present invention are contemplated to have affinity for Dcn and may be purified from other constituents of Borrelia, in particular, *B. burgdorferi, B. afzelii, B. andersonii, B. garinii*, or *B. japonica*, or recombinant host cells by chromatography on matrices containing Dcn, so-called "affinity chromatography." DBPs may also be purified by methodologies not relying on affinity for Dcn such as ion exchange chromatography, size exclusion chromatography, metal chelation chromatography, or the like. Buffer, detergent, and other conditions may be dissimilar from those optimal for "affinity chromatography." In a preferred embodiment, an affinity matrix comprising Dcn or a related proteoglycan may be used for the isolation of DBPs from solution, or alternatively, isolation of intact bacteria expressing DBPs, or even membrane fragments of bacteria expressing DBPs.

A particular aspect of this invention provides novel ways in which to utilize recombinant DBPs or DBP-derived peptides, nucleic acid segments encoding these peptides, recombinant vectors and transformed host cells comprising one or more dbp genes or dbp-derived nucleic acid segments, recombinant vectors and transformed host cells comprising one or more dbp genes or dbp-derived DNA segments, and recombinant vectors and transformed host cells comprising one or more Borrelia dbp-derived nucleic acid segments, in particular one or more dbpA or dbpB nucleic acid segments from *B. burgdorferi, B. afzelii, B. andersonii, B. garinii*, or *B. japonica*. As is well known to those of skill in the art, many such vectors and host cells are readily available, one particular detailed example of a suitable vector for expression in mammalian cells is that described in U.S. Pat. No. 5,168,050, incorporated herein by reference. However, there is no requirement that a highly purified vector be used, so long as the coding segment employed encodes a protein or peptide of interest (e.g., a DbpA or DbpB protein from Borrelia, and particularly a DbpA or DbpB protein from *B. burgdorferi, B. afzelii, B. andersonii, B. japonica*, or *B. garinii*, and does not include any coding or regulatory sequences that would have an adverse effect on cells. Therefore, it will also be understood that useful nucleic acid sequences may include additional residues, such as additional non-coding sequences flanking either of the 5' or 3' portions of the coding region or may include various regulatory sequences.

After identifying an appropriate epitope-encoding nucleic acid molecule, it may be inserted into any one of the many vectors currently known in the art, so that it will direct the expression and production of the protein or peptide epitope of interest (e.g., a DbpA or DbpB protein from Borrelia and in particular, from *B. burgdorferi, B. afzelii, B. andersonii, B. garinii*, or *B. japonica*) when incorporated into a host cell. In a recombinant expression vector, the coding portion of the DNA segment is positioned under the control of a promoter. The promoter may be in the form of the promoter which is naturally associated with a DBP-encoding nucleic acid segment, as may be obtained by isolating the 5' non-coding sequences located upstream of the coding segment, for example, using recombinant cloning and/or PCR™ technology, in connection with the compositions disclosed herein. Direct amplification of nucleic acids using the PCR™ technology of U.S. Pat. Nos. 4,683,195 and 4,683,202 (herein incorporated by reference) are particularly contemplated to be useful in such methodologies.

In certain embodiments, it is contemplated that particular advantages will be gained by positioning one or more DBP-encoding DNA segments under the control of one or more recombinant, or heterologous, promoters. As used herein, a recombinant or heterologous promoter is intended to refer to a promoter that is not normally associated with a dbpA, dbpB, or dbp-like gene segment in its natural environment. A "dbp-like gene segment" is intended to mean any nucleic acid segment which hybridizes to a dbpA and/or dbpB gene under conditions of moderate to high stringency. Such promoters may include those normally associated with other MSCRAMM-encoding genes, and/or promoters isolated from any other bacterial, viral, eukaryotic, or mammalian cell. Naturally, it will be important to employ a promoter that effectively directs the expression of the DNA segment in the particular cell containing the vector comprising one or more DBP-encoding nucleic acid segments.

The use of recombinant promoters to achieve protein expression is generally known to those of skill in the art of molecular biology, (see e.g., Sambrook et al., 1989). The promoters employed may be constitutive, or inducible, and can be used under the appropriate conditions to direct high level or regulated expression of the introduced DNA segment. For eukaryotic expression, the currently preferred promoters are those such as CMV, RSV LTR, the SV40 promoter alone, and the SV40 promoter in combination with the SV40 enhancer. In preferred embodiments, the expression of recombinant DBPs may be carried out using prokaryotic expression systems, and in particular bacterial systems such as *E. coli, B. burgdorferi*. Such prokaryotic expression of nucleic acid segments of the present invention may be performed using methods known to those of skill in the art, and will likely comprise expression vectors and promotor sequences such as those provided by lpp, tac, trp, lac, lacUV5 or T7 promotors. Alternatively, the inventors contemplate that a native or genetically-modified dbp promoter will also be useful in the construction of recombinant vectors expressing dbpA and/or dbpB genes.

For the expression of DbpA, DbpB, and DbpA- or DbpB-derived epitopes, once a suitable clone or clones have been obtained, whether they be native sequences or genetically-modified, one may proceed to prepare an expression system for the recombinant preparation of one or more DBP or DBP-derived peptides. The engineering of DNA segment(s) for expression in a prokaryotic or eukaryotic system may be performed by techniques generally known to those of skill in recombinant expression. It is believed that virtually any expression system may be employed in the expression of one or more DBPs or DBP-derived epitopes.

Alternatively, it may be desirable in certain embodiments to express one or more DBPs or DBP-derived epitopes in eukaryotic expression systems. The DNA sequences encoding the desired DBP(s) or DBP-derived epitope(s) (either native or mutagenized) may be separately expressed in bacterial systems, with the encoded proteins being expressed as fusions with β-galactosidase, ubiquitin, *Schistosoma japonicum* glutathione S-transferase, *S. aureus* Protein A, maltose binding protein, and the like. It is believed that bacterial expression will ultimately have advantages over eukaryotic expression in terms of ease of use and quantity of materials obtained thereby.

It is proposed that transformation of host cells with DNA segments encoding such epitopes will provide a convenient means for obtaining one or more DBPs or DBP-derived peptides. Genomic sequences are suitable for eukaryotic expression, as the host cell will, of course, process the genomic transcripts to yield functional mRNA for translation into protein.

It is similarly believed that almost any eukaryotic expression system may be utilized for the expression of one or more DBPs and DBP-derived epitopes, e.g., baculovirus-based, glutamine synthase-based or dihydrofolate reductase-based systems may be employed. In preferred embodiments it is contemplated that plasmid vectors incorporating an origin of replication and an efficient eukaryotic promoter, as exemplified by the eukaryotic vectors of the pCMV series, such as pCMV5, will be of most use.

For expression in this manner, one would position the coding sequences adjacent to and under the control of the promoter. It is understood in the art that to bring a coding sequence under the control of such a promoter, one positions the 5' end of the transcription initiation site of the transcriptional reading frame of the protein between about 1 and about 50 nucleotides "downstream" of (i.e., 3' of) the chosen promoter.

Where eukaryotic expression is contemplated, one will also typically desire to incorporate into the transcriptional unit which includes nucleic acid sequences encoding one or more DBPs or DBP-derived peptides, an appropriate polyadenylation site (e.g., 5'-AATAAA-3') if one was not contained within the original cloned segment. Typically, the poly-A addition site is placed about 30 to 2000 nucleotides "downstream" of the termination site of the protein at a position prior to transcription termination.

It is contemplated that virtually any of the commonly employed host cells can be used in connection with the expression of one or more DBPs and DBP-derived epitopes in accordance herewith. Examples include cell lines typically employed for eukaryotic expression such as 239, AtT-20, HepG2, VERO, HeLa, CHO, WI 38, BHK, COS-7, RIN and MDCK cell lines.

It is further contemplated that a DbpA, DbpB, or epitopic peptides derived from one or more native or recombinant DBPs may be "overexpressed", i.e., expressed in increased levels relative to its natural expression in human cells, or even relative to the expression of other proteins in a recombinant host cell containing a DBP-encoding DNA segment. Such overexpression may be assessed by a variety of methods, including radiolabeling and/or protein purification. However, simple and direct methods are preferred, for example, those involving SDS/PAGE and protein staining or Western blotting, followed by quantitative analyses, such as densitometric scanning of the resultant gel or blot. A specific increase in the level of the recombinant protein or peptide in comparison to the level in natural DBP-producing cells is indicative of overexpression, as is a relative abundance of the specific protein in relation to the other proteins produced by the host cell and, e.g., visible on a gel.

As used herein, the term "engineered" or "recombinant" cell is intended to refer to a cell into which a recombinant gene, such as a gene encoding a DBP has been introduced. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a single structural gene, an entire genomic clone comprising a structural gene and flanking DNA, or an operon or other functional nucleic acid segment which may also include genes positioned either upstream and/or downstream of the promotor, regulatory elements, or structural gene itself, or even genes not naturally associated with the particular structural gene of interest.

Where the introduction of a recombinant version of one or more of the foregoing genes is required, it will be important to introduce the gene such that it is under the control of a promoter that effectively directs the expression of the gene in the cell type chosen for engineering. In general, one will desire to employ a promoter that allows constitutive (constant) expression of the gene of interest. Commonly used constitutive eukaryotic promoters include viral promoters such as the cytomegalovirus (CMV) promoter, the Rous sarcoma long-terminal repeat (LTR) sequence, or the SV40 early gene promoter. The use of these constitutive promoters will ensure a high, constant level of expression of the introduced genes. The inventors have noticed that the level of expression from the introduced genes of interest can vary in different clones, or genes isolated from different strains or bacteria. Thus, the level of expression of a particular recombinant gene can be chosen by evaluating different clones derived from each transfection experiment; once that line is chosen, the constitutive promoter ensures that the desired level of expression is permanently maintained. It may also be possible to use promoters that are specific for cell type used for engineering, such as the insulin promoter in insulinoma cell lines, or the prolactin or growth hormone promoters in anterior pituitary cell lines.

2.3 Methods for Diagnosing Lyme Disease Using dbpA and dbpB Gene Compositions

Methods for diagnosing Lyme disease, and the detection of *B. burgdorferi* in clinical samples using nucleic acid compositions are also provided by the invention. The nucleic acid sequences encoding one or more DBPs, and in particular DbpA or DbpB are useful as diagnostic probes to detect the presence of *B. burgdorferi*, and related borrelias including *B. afzelii, B. andersonii, B. japonica*, and *B. garinii* in a test sample, using conventional techniques. In one such method of diagnosing Borrelia infection, dbpA and/or dbpB nucleic acid segments may be used in Southern hybridization analyses or Northern hybridization analyses to detect the presence of a dbpA- or dbpB-encoding nucleic acid segment within a clinical sample from a patient suspected of having such an infection. In a preferred embodiment, nucleic acid sequences as disclosed in any of SEQ ID NO:7, SEQ ID NO:10, SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63 or SEQ ID NO:65 are preferable as probes for such hybridization analyses.

2.4 Methods for Generating an Immune Response

A further aspect of the invention is the preparation of immunological compositions, and in particular anti-DbpA and anti-DbpB antibodies for diagnostic and therapeutic methods relating to the detection and treatment of infections caused by *B. burgdorferi* and related borrelias including *B. afzelii*, *B. andersonii*, *B. garinii*, and *B. japonica*.

Owing to a lack of significant amino acid identity between the DbpA and DbpB proteins of the invention, the inventors contemplate an important aspect of the invention is the identification of DbpA amino acid sequences which do cross-react with antibodies specific for DbpB, and the identification of DbpB amino acid sequences which do not cross-react with antibodies specific for DbpA. Methods are provided for identifying such proteins based on immunological methods such as ELISA, Western blots, and the like. In a preferred embodiment, the invention discloses a DbpB amino acid composition which does not cross-react with DbpA antibody compositions, and a DbpA amino acid composition which does not cross-react with DbpB antibody compositions.

Also disclosed in a method of generating an immune response in an animal. The method generally involves administering to an animal a pharmaceutical composition comprising an immunologically effective amount of a peptide composition disclosed herein. Preferred peptide compositions include the DbpA peptides disclosed in SEQ ID NO:8, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, and SEQ ID NO:52; as well as the DbpB peptides disclosed in SEQ ID NO:54, SEQ ID NO:56, SEQ ID NO:58, SEQ ID NO:60, SEQ ID NO:62, SEQ ID NO:64, and SEQ ID NO:66.

The invention also encompasses DBP and DBP-derived peptide antigen compositions together with pharmaceutically-acceptable excipients, carriers, diluents, adjuvants, and other components, such as additional peptides, antigens, or outer membrane preparations, as may be employed in the formulation of particular vaccines.

The nucleic acid sequences of the present invention encode DBP and are useful to generate pure recombinant DBP for administration to a host. Such administration is useful to prevent adherence of Borrelia spp., and in particular, *B. burgdorferi*, *B. afzelii*, *B. andersonii*, *B. garinii*, and *B. japonica*, to the host's tissues or as a vaccine to induce therapeutic antibodies.

It is shown herein that antisera raised against and reactive with one or more DBPs is inhibitory to in vitro and in vivo growth of various Borrelia strains. Thus, it is contemplated that administration of antibodies reactive with one or more DBPs to at-risk subjects will be effective for prophylaxis of, and in the case of infected subjects for therapy of, Lyme disease.

Antibodies may be of several types including those raised in heterologous donor animals or human volunteers immunized with DBPs, monoclonal antibodies (mAbs) resulting from hybridomas derived from fusions of B cells from DBP-immunized animals or humans with compatible myeloma cell lines, so-called "humanized" mAbs resulting from expression of gene fusions of combinatorial determining regions of mAb-encoding genes from heterologous species with genes encoding human antibodies, or DBP-reactive antibody-containing fractions of plasma from human donors residing in Lyme disease-endemic areas. It is contemplated that any of the techniques described above might be used for the vaccination of subjects for the purpose of antibody production. Optimal dosing of such antibodies is highly dependent upon the pharmacokinetics of the specific antibody population in the particular species to be treated, but it is anticipated that it will be necessary to maintain in these subjects a serum concentration of DBP-reactive antibodies that is at least twice that required for inhibition of in vitro growth of endemic borrelia strains. It is contemplated that the duration of dosing maintaining anti-DbpA and or anti-DbpB levels at these inhibitory antibody concentrations would be for at least four to eight weeks following presumptive exposure to a Borrelia, and in particular, *B. burgdorferi*, or throughout the duration of symptoms of Lyme disease and for at least four to eight weeks after cessation of these symptoms.

Using the peptide antigens described herein, the present invention also provides methods of generating an immune response, which methods generally comprise administering to an animal, a pharmaceutically-acceptable composition comprising an immunologically effective amount of one or more DBP peptide compositions. Preferred animals include mammals, and particularly humans. Other preferred animals include murines, bovines, equines, porcines, canines, and felines. The composition may include partially or significantly purified DBP epitopes, obtained from natural or recombinant sources, which proteins or peptides may be obtainable naturally or either chemically synthesized, or alternatively produced in vitro from recombinant host cells expressing DNA segments encoding such epitopes. Smaller peptides that include reactive epitopes, such as those between about 10 and about 50, or even between about 50 and about 100 amino acids in length will often be preferred. The antigenic proteins or peptides may also be combined with other agents, such as other borrelial peptide or nucleic acid compositions, if desired.

By "immunologically effective amount" is meant an amount of a peptide composition that is capable of generating an immune response in the recipient animal. This includes both the generation of an antibody response (B cell response), and/or the stimulation of a cytotoxic immune response (T cell response). The generation of such an immune response will have utility in both the production of useful bioreagents, e.g., CTLs and, more particularly, reactive antibodies, for use in diagnostic embodiments, and will also have utility in various prophylactic or therapeutic embodiments. Therefore, although these methods for the stimulation of an immune response include vaccination regimens designed to prevent or lessen significant infections caused by borrelias or other bacteria expressing a DBP, and treatment regimens that may lessen the severity or duration of any infection, it will be understood that achieving either of these end results is not necessary for practicing these aspects of the invention. Such treatment methods may be used particularly for the treatment of infections caused by pathogens such as *B. burgdorferi, B. afzelii, B. andersonii, B. garinii, B. japonica*, related borrelial species, and other bacteria which express one or more DBPs and in particular DbpA and/or DbpB and adhere to Dcn.

Further means contemplated by the inventors for generating an immune response in an animal includes administering to the animal, or human subject, a pharmaceutically-acceptable composition comprising an immunologically effective amount of a nucleic acid composition encoding a DBP epitope, or an immunologically effective amount of an attenuated live organism that includes and expresses such a nucleic acid composition. The "immunologically effective amounts" are those amounts capable of stimulating a B-cell and/or T-cell response.

Immunoformulations of this invention, whether intended for vaccination, treatment, or for the generation of antibodies useful in the detection of borrelias and in particular *B. burgdorferi*, the prevention of bacterial adhesion, or in the case of bacterial colonization, promotion of bacterial adhesion to ECM components such as Dcn, may comprise native, or synthetically-derived antigenic peptide fragments from these proteins. As such, antigenic functional equivalents of the proteins and peptides described herein also fall within the scope of the present invention. An "antigenically functional equivalent" protein or peptide is one that incorporates an epitope that is immunologically cross-reactive with one or more epitopes derived from any of the particular MSCRAMM proteins disclosed (e.g., DBPs), and particularly the DBP of *B. burgdorferi*. Antigenically functional equivalents, or epitopic sequences, may be first designed or predicted and then tested, or may simply be directly tested for cross-reactivity.

The identification or design of suitable DBP epitopes, and/or their functional equivalents, suitable for use in immunoformulations, vaccines, or simply as antigens (e.g., for use in detection protocols), is a relatively straightforward matter. For example, one may employ the methods of Hopp, as enabled in U.S. Pat. No. 4,554,101, incorporated herein by reference, that teaches the identification and preparation of epitopes from amino acid sequences on the basis of hydrophilicity. The methods described in several other papers, and software programs based thereon, can also be used to identify epitopic core sequences. For example, Chou and Fasman (1974a,b; 1978a,b; 1979); Jameson and Wolf (1988); Wolf et al. (1988); and Kyte and Doolittle (1982) all address this subject. The amino acid sequence of these "epitopic core sequences" may then be readily incorporated into peptides, either through the application of peptide synthesis or recombinant technology.

It is proposed that the use of shorter antigenic peptides, e.g., about 25 to about 50, or even about 15 to 25 amino acids in length, that incorporate epitopes of one or more DBPs will provide advantages in certain circumstances, for example, in the preparation of vaccines or in immunologic detection assays. Exemplary advantages include the ease of preparation and purification, the relatively low cost and improved reproducibility of production, and advantageous biodistribution.

In still further embodiments, the present invention concerns immunodetection methods and associated kits. It is contemplated that the proteins or peptides of the invention may be employed to detect antibodies having reactivity therewith, or, alternatively, antibodies prepared in accordance with the present invention, may be employed to detect DBPs or DBP-derived peptides. Either type of kit may be used in the immunodetection of compounds, present within clinical samples, that are indicative of Lyme disease or related infections caused by borrelias, and in particular *B. burgdorferi*. The kits may also be used in antigen or antibody purification, as appropriate.

In general, the preferred immunodetection methods will include first obtaining a sample suspected of containing a DBP-reactive antibody, such as a biological sample from a patient, and contacting the sample with a first DBP or peptide under conditions effective to allow the formation of an immunocomplex (primary immune complex). One then detects the presence of any primary immunocomplexes that are formed.

Contacting the chosen sample with the DBP or peptide under conditions effective to allow the formation of (primary) immune complexes is generally a matter of simply adding the protein or peptide composition to the sample. One then incubates the mixture for a period of time sufficient to allow the added antigens to form immune complexes with, i.e., to bind to, any antibodies present within the sample. After this time, the sample composition, such as a tissue section, ELISA plate, dot blot or western blot, will generally be washed to remove any non-specifically bound antigen species, allowing only those specifically bound species within the immune complexes to be detected.

The detection of immunocomplex formation is well known in the art and may be achieved through the application of numerous approaches known to the skilled artisan and described in various publications, such as, e.g., Nakamura et al. (1987), incorporated herein by reference. Detection of primary immune complexes is generally based upon the detection of a label or marker, such as a radioactive, fluorescent, biological or enzymatic label, with enzyme tags such as alkaline phosphatase, urease, horseradish peroxidase and glucose oxidase being suitable. The particular antigen employed may itself be linked to a detectable label, wherein one would then simply detect this label, thereby allowing the amount of bound antigen present in the composition to be determined.

Alternatively, the primary immune complexes may be detected by means of a second binding ligand that is linked to a detectable label and that has binding affinity for the first protein or peptide. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labelled secondary antibodies and the remaining bound label is then detected.

For diagnostic purposes, it is proposed that virtually any sample suspected of containing the antibodies of interest may be employed. Exemplary samples include clinical samples obtained from a patient such as blood or serum samples, cerebrospinal, synovial, or bronchoalveolar fluid, ear swabs, sputum samples, middle ear fluid or even perhaps urine samples may be employed. This allows for the diagnosis of Lyme disease and related infections caused by borrelias, and in particular, *B. burgdorferi*. Furthermore, it is contemplated that such embodiments may have application to non-clinical samples, such as in the titering of antibody samples, in the selection of hybridomas, and the like. Alternatively, the clinical samples may be from veterinary sources and may include such domestic animals as cattle, sheep, and goats. Samples from feline, canine, and equine sources may also be used in accordance with the methods described herein.

In related embodiments, the present invention contemplates the preparation of kits that may be employed to detect the presence of DBP-specific antibodies in a sample. Generally speaking, kits in accordance with the present invention will include a suitable protein or peptide together with an immunodetection reagent, and a means for containing the protein or peptide and reagent.

The immunodetection reagent will typically comprise a label associated with a DBP or peptide, or associated with a secondary binding ligand. Exemplary ligands might include a secondary antibody directed against the first DBP or peptide or antibody, or a biotin or avidin (or streptavidin) ligand having an associated label. Detectable labels linked to antibodies that have binding affinity for a human antibody are also contemplated, e.g., for protocols where the first reagent is a DBP peptide that is used to bind to a reactive antibody from a human sample. Of course, as noted above, a number of exemplary labels are known in the art and all such labels may be employed in connection with the present invention. The kits may contain antigen or antibody-label conjugates either in fully conjugated form, in the form of intermediates, or as separate moieties to be conjugated by the user of the kit.

The container means will generally include at least one vial, test tube, flask, bottle, syringe or other container means, into which the antigen may be placed, and preferably suitably allocated. Where a second binding ligand is provided, the kit will also generally contain a second vial or other container into which this ligand or antibody may be placed. The kits of the present invention will also typically include a means for containing the vials in close confinement for commercial sale, such as, e.g., injection or blow-molded plastic containers into which the desired vials are retained.

2.5 Methods for Inhibiting Bacterial Adhesion to Dcn

In addition, the DBP is useful as an agent to block *B. burgdorferi* adherence to Dcn, and proteoglycans which are structurally similar to Dcn such as Lmn, Fmn, Epn, and Bgn. In a preferred embodiment of the invention, a therapeutically effective dose of one or more DBPs, and in particular one or more DbpA or DbpB proteins, is administered to a subject to prevent or block adhesion of *B. burgdorferi* to the host's tissues by conventional methods. The composition is preferably systemically administered, but may be applied topically, e.g., to a localized lesion. The term "therapeutically effective dose" means that amount of a DBP composition which is sufficient to lessen or prevent adherence of *B. burgdorferi* to a subject or to neutralize the known deleterious effects of *B. burgdorferi* infection and may be determined by known clinical methods. Absent adhesion of the bacteria to the tissues, the disease-inducing effects of the microorganism are halted, thus the compositions of the present invention is useful as a therapeutic agent to prevent adhesion of *B. burgdorferi* and thereby lessen or prevent disease induced by this microorganism.

2.6 Probes and Primers for dbpA and dbpB Gene Segments

In addition to their use in directing the expression of Dbp and DbpB, the nucleic acid sequences disclosed herein also have a variety of other uses. For example, they also have utility as probes or primers in nucleic acid hybridization embodiments. As such, it is contemplated that nucleic acid segments that comprise a sequence region that consists of at least a 14 nucleotide long contiguous sequence that has the same sequence as, or is complementary to, a 14 nucleotide long contiguous sequence of SEQ ID NO:7, SEQ ID NO:10, SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63 or SEQ ID NO:65 will find particular utility. Longer contiguous identical or complementary sequences, e.g., those of about 20, 30, 40, 50, 100, 200, 500, 1000 (including all intermediate lengths) and even up to full length sequences will also be of use in certain embodiments.

The ability of such nucleic acid probes to specifically hybridize to DBP-encoding sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having sequence regions consisting of contiguous nucleotide stretches of 10–14, 15–20, 30, 50, or even of 100–200 nucleotides or so, identical or complementary to SEQ ID NO:7, SEQ ID NO:10, SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63 or SEQ ID NO:65, are particularly contemplated as hybridization probes for use in, e.g., Southern and Northern blotting. This would allow a DbpA or DbpB structural or regulatory gene to be analyzed, both in diverse cell types and also in various bacterial cells. The total size of fragment, as well as the size of the complementary stretch(es), will ultimately depend on the intended use or application of the particular nucleic acid segment. Smaller fragments will generally find use in hybridization embodiments, wherein the length of the contiguous complementary region may be varied, such as between about 14 and about 100 nucleotides, but larger contiguous complementarity stretches may be used, according to the length complementary sequences one wishes to detect.

The use of a hybridization probe of about 14–25 nucleotides in length allows the formation of a duplex molecule that is both stable and selective. Molecules having contiguous complementary sequences over stretches greater than 14 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 25 contiguous nucleotides, or even longer where desired.

Hybridization probes may be selected from any portion of any of the sequences disclosed herein. All that is required is to review the sequence set forth in SEQ ID NO:7, SEQ ID NO:10, SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63 or SEQ ID NO:65, or to any continuous portion of the sequence, from about 14–25 nucleotides in length up to and including the full length sequence, that one wishes to utilize as a probe or primer. The choice of probe and primer sequences may be governed by various factors, such as, by way of example only, one may wish to employ primers from towards the termini of the total sequence.

The process of selecting and preparing a nucleic acid segment that includes a contiguous sequence from within SEQ ID NO:7, SEQ ID NO:10, SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63 or SEQ ID NO:65, may alternatively be described as preparing a nucleic acid fragment. Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. No. 4,683,202 (incorporated herein by reference), by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of the entire dbp gene or gene fragments. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by about 0.02 M to about 0.15 M NaCl at temperatures of 50° C. to 70° C. Such selective conditions tolerate little, if any, mismatch between the probe and the template or target strand, and would be particularly suitable for isolating DBP genes.

Of course, for some applications, for example, where one desires to prepare mutants employing a mutant primer strand hybridized to an underlying template or where one seeks to isolate one or more DBP-encoding sequences, and in particular DbpA or DbpB sequences, from related species, functional equivalents, or the like, less stringent hybridization conditions will typically be needed in order to allow formation of the heteroduplex. In these circumstances, one may desire to employ conditions such as about 0.15 M to about 0.9 M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, calorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantitated, by means of the label.

2.7 Anti-DbpA and Anti-DbpB Antibody Compositions

In a preferred embodiment, administration of a therapeutically effective dose of DbpA and/or DbpB to a subject induces in the subject antibodies which bind and neutralize a Borrelia bacterium (and particularly B. burgdorferi, B. garinii, B. afzelii, B. andersonii, B. japonica and related Borrelia spp.), present in the subject, thereby preventing the deleterious effects of this microorganism. Alternatively, anti-Borrelial antibodies, and in particular, anti-B. burgdorferi, B. garinii, B. afzelii, B. andersonii, B. japonica and related Borrelia spp. antibodies generated in a first host animal provide antibodies which can be administered to a second subject for passive immunization or treatment against B. burgdorferi, B. garinii, B. afzelii, B. andersonii, or B. japonica infection. Such anti-Borrelia antibodies are also useful as a diagnostic screen for the presence of Borrelias, and in particular B. burgdorferi, B. garinii, B. afzelii, B. andersonii, B. japonica or related Borrelia spp. in a test sample, using conventional immunoassay techniques.

In the present invention, novel nucleic acid sequences (SEQ ID NO:7, SEQ ID NO:10, SEQ ID NO:11, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63 or SEQ ID NO:65) encode novel DBPs of B. burgdorferi, B. afzelii, and B. garinii. Strain variants are prepared and screened by amplification of nucleic acid sequences of other strains of B. burgdorferi or similar Lyme-disease inducing bacteria using oligonucleotide probes derived from the 2.5 kb insert of B. burgdorferi strain 297 (SEQ ID NO:7) and preferably from the approximate 0.6 kb open reading frame. Clones obtained from the amplification procedures are then used as hybridization probes to isolate the full length nucleic acid encoding strain variants. Alternatively, DNA libraries for each strain are constructed and screened for clones expressing a DBP, e.g., by their affinity for Dcn.

In certain aspects, the present invention concerns novel antibody compositions which inhibit Dcn binding to bacteria. In particular, antibodies to native and synthetically-modified epitopes from DBPs have been developed which inhibit Dcn binding to DBPs both in vitro and in vivo. In particular, proteins, peptides and peptide epitopes have been produced to provide vaccine compositions useful in the prevention of Lyme disease and antibody compositions useful in the prevention of Dcn binding to Borrelias.

In other embodiments, the present invention encompasses antibody compositions which enhance Dcn binding to bacterial cells. These aspects provide methods and compositions for producing bacterial colonization of an animal host with attenuated, or avirulent Borrelias expressing cell surface DBP epitopes.

In one aspect, the invention discloses an antibody that interacts with a DBP domain of a bacteria dbp gene product, and particularly, a DBP domain of a *B. burgdorferi dbp* gene product. Such antibody may be monoclonal, or preferably polyclonal. In another aspect, the invention discloses an antibody which inhibits bacterial adhesion, and the binding of the gene product to Dcn.

Also disclosed is a method for detecting a bacterium expressing a DBP in a sample. The method generally involves obtaining a sample suspected of containing a bacterium expressing such a protein, then contacting the sample with an antibody composition disclosed herein, and detecting the formation of immune complexes. In preferred embodiments, the bacterium is a borrelia, and most preferably, a *B. burgdorferi, B. afzelii, B. andersonii*, or *B. garinii* strain.

2.8 Immunodetection Kits and Methods

Another aspect of the invention are immunodetection kits containing antibodies of the present invention and suitable immunodetection reagents such as a detectable label linked to a protein, peptide or the antibody itself. Alternatively, the detectable label may be linked to a second antibody which binds to an antibody of the invention.

Related embodiments include diagnostic and therapeutic kits which include pharmaceutically-acceptable formulations of either the antibodies or peptide antigens disclosed herein. Such kits are useful in the detection of borrelias in clinical samples, and also useful for inhibiting or promoting the binding of borrelias to the ECM component, Dcn. In preferred embodiments, the bacteria detected using such kits include borrelias, and in particular, *B. burgdorferi, B. afzelii, B. andersonii, B. garinii, B. japonica*, and related species.

2.9 Methods for Inhibiting Bacterial Colonization

Other aspects of the invention include methods of inhibiting bacterial colonization, and particularly colonization by borrelias, in an animal by administering to the animal an antibody of the present invention which prevents or significantly reduces the binding of Dcn to the DBP expressed by the bacteria. Administration of the antibody composition may be prophylactically prior to and/or following diagnosis of Lyme disease or other multisystemic disorders caused by Borrelioses which may involve the skin, joints, heart, and central nervous system. The administration may also be made in passive immunization protocols designed to prevent and/or ameliorate systemic infections by susceptible pathogens, and in particular, to ameliorate the effects of infections by pathogenic *B. burgdorferi*.

2.10 Nucleic Acid Segments and Vectors

The present invention includes proteins expressed from genes encoding a DBP such as that protein expressed from the DNA insert of recombinant clone BG26:pB/2.5(5). Also included are strain variants of the gene derived from *B. burgdorferi* strain 297 present in the recombinant clone BG26:pB/2.5(5) which also encode proteins capable of binding Dcn, which may hybridize to DNA derived from BG26:pB/2.5(5) under conditions of moderate or high stringency, or which may serve as templates for gene amplification by PCR™ using oligonucleotide primers derived from BG26:pB/2.5(5). It is understood that these variants may include genes containing codons not identical in nucleotide sequence to those of the dbp gene of strain 297, but encoding the same, or functionally equivalent amino acid, as is anticipated by those practiced in the art who understand the degeneracy of the genetic code. These variants may also include those genes similar to the dbp gene from strain 297, but having codons specifying relatively few amino acids that are different from those of the protein(s) encoded by BG26:pB/2.5(5), or having somewhat fewer or greater numbers of these codons. Accordingly such sequences include those that have between about 60% and about 80%; or more preferably, between about 81% and about 90%; or even more preferably, between about 91% and about 99%; of amino acids that are identical or functionally equivalent to those of protein(s) encoded by BG26:pB/2.5(5).

It is also understood that amino acid sequences and nucleic acid sequences may include additional residues, such as additional N- or C-terminal amino acids, or 5' or 3' nucleic acid sequences, and yet still be as set forth herein, so long as the sequence meets the criteria set forth above including the expression of a DBP protein. These additional sequences may, for example, include various transcriptional promoters, enhancers, or terminators, various secretion-directing leader peptides, various amino acid sequences directing posttranslational modifications, amino acids or peptides which may facilitate isolation and purification of DBP(s), and the like. Naturally, alterations and additions to these sequences will be made given consideration of the cell type, organism, or animal that will be chosen for expression of DBP(s).

2.11 Vaccine Formulation and Compositions

It is expected that to achieve an "immunologically effective formulation" it may be desirable to administer DBPs to the human or animal subject in a pharmaceutically acceptable composition comprising an immunologically effective amount of DBPs mixed with other excipients, carriers, or diluents which may improve or otherwise alter stimulation of B cell and/or T cell responses, or immunologically inert salts, organic acids and bases, carbohydrates, and the like, which promote stability of such mixtures. Immunostimulatory excipients, often referred to as adjuvants, may include salts of aluminum (often referred to as Alums), simple or complex fatty acids and sterol compounds, physiologically acceptable oils, polymeric carbohydrates, chemically or genetically modified protein toxins, and various particulate or emulsified combinations thereof. DBPs or peptides within these mixtures, or each variant if more than one are present, would be expected to comprise about 0.0001 to 1.0 milligrams, or more preferably about 0.001 to 0.1 milligrams, or even more preferably less than 0.1 milligrams per dose.

It is also contemplated that attenuated organisms may be engineered to express recombinant DBP gene products and themselves be delivery vehicles for the invention. Particularly preferred are attenuated bacterial species such as Mycobacterium, and in particular *M. bovis, M. smegmatis*, or BCG. Alternatively, pox-, polio-, adeno-, or other viruses, and bacteria such as Salmonella, Shigella, Listeria, Streptococcus species may also be used in conjunction with the methods and compositions disclosed herein.

The naked DNA technology, often referred to as genetic immunization, has been shown to be suitable for protection against infectious organisms. Such DNA segments could be used in a variety of forms including naked DNA and plasmid DNA, and may administered to the subject in a variety of ways including parenteral, mucosal, and so-called microprojectile-based "gene-gun" inoculations. The use of dbp nucleic acid compositions of the present invention in such immunization techniques is thus proposed to be useful as a vaccination strategy against Lyme disease.

It is recognized by those skilled in the art that an optimal dosing schedule of a vaccination regimen may include as many as five to six, but preferably three to five, or even more preferably one to three administrations of the immunizing entity given at intervals of as few as two to four weeks, to as long as five to ten years, or occasionally at even longer intervals.

2.12 Compositions Comprising Transformed Host Cells and Recombinant Vectors

Particular aspects of the invention concern the use of plasmid vectors for the cloning and expression of recombinant peptides, and particular peptide epitopes comprising either native, or site-specifically mutated DBP epitopes. The generation of recombinant vectors, transformation of host cells, and expression of recombinant proteins is well-known to those of skill in the art. Prokaryotic hosts are preferred for expression of the peptide compositions of the present invention. An example of a preferred prokaryotic host is *E. coli*, and in particular, *E. coli* strains ATCC69791, BL21(DE3), JM101, XL1-Blue™, RR1, LE392, B, $\chi^{1776}$ (ATCC No. 31537), and W3110 (F$^-$, $\lambda^-$, prototrophic, ATCC273325). Alternatively, other Enterobacteriaceae species such as *Salmonella typhimurium* and *Serratia marcescens*, or even other Gram-negative hosts including various Pseudomonas species may be used in the recombinant expression of the genetic constructs disclosed herein. Borrelias themselves may be used to express these constructs, and in particular, *B. burgdorferi, B. afzelii, B. andersonii, B. japonica* and *B. garinii*.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* may be typically transformed using vectors such as pBR322, or any of its derivatives (Bolivar et al., 1977). pBR322 contains genes for ampicillin and tetracycline resistance and thus provides easy means for identifying transformed cells. pBR322, its derivatives, or other microbial plasmids or bacteriophage may also contain, or be modified to contain, promoters which can be used by the microbial organism for expression of endogenous proteins. A preferred vector for cloning the dbp constructs is pBlueScript™, and in particular the construct BG26:pB/2.5(5), or alternatively, vectors based on the pET vector series (Novagen, Inc., Madison, Wis.).

In addition, phage vectors containing replicon and control sequences that are compatible with the host microorganism can be used as transforming vectors in connection with these hosts. For example, bacteriophage such as λGEM™-11 may be utilized in making a recombinant vector which can be used to transform susceptible host cells such as *E. coli* LE392.

Those promoters most commonly used in recombinant DNA construction include the β-lactamase (penicillinase) and lactose promoter systems (Chang et al., 1978; Itakura et al., 1977; Goeddel et al., 1979) or the tryptophan (trp) promoter system (Goeddel et al., 1980). The use of recombinant and native microbial promoters is well-known to those of skill in the art, and details concerning their nucleotide sequences and specific methodologies are in the public domain, enabling a skilled worker to construct particular recombinant vectors and expression systems for the purpose of producing compositions of the present invention.

In addition to the preferred embodiment expression in prokaryotes, eukaryotic microbes, such as yeast cultures may also be used in conjunction with the methods disclosed herein. *Saccharomyces cerevisiae*, or common bakers' yeast is the most commonly used among eukaryotic microorganisms, although a number of other species may also be employed for such eukaryotic expression systems. For expression in Saccharomyces, the plasmid YRp7, for example, is commonly used (Stinchcomb et al., 1979; Kingsman et al., 1979; Tschemper et al., 1980). This plasmid already contains the trpL gene which provides a selection marker for a mutant strain of yeast lacking the ability to grow in tryptophan, for example ATCC No. 44076 or PEP4-1 (Jones, 1977). The presence of the trpL lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, an origin of replication, and termination sequences is suitable.

In addition to microorganisms, cultures of cells derived from multicellular organisms may also be used as hosts in the routine practice of the disclosed methods. In principle, any such cell culture is workable, whether from vertebrate or invertebrate culture. However, interest has been greatest in vertebrate cells, and propagation of vertebrate cells in culture (tissue culture) has become a routine procedure in recent years. Examples of such useful host cell lines are VERO and HeLa cells, Chinese hamster ovary (CHO) cell lines, and W138, BHK, COS-7, 293 and MDCK cell lines.

Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication (Fiers et al., 1978). Smaller or larger SV40 fragments may also be used, provided there is included the approximately 250 bp sequence extending from the HindIII site toward the BglI site located in the viral origin of replication. Further, it is also possible, and often desirable, to utilize promoter or control sequences normally associated with the desired gene sequence, provided such control sequences are compatible with the host cell systems.

The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

It will be further understood that certain of the polypeptides may be present in quantities below the detection limits of the Coomassie brilliant blue staining procedure usually employed in the analysis of SDS/PAGE gels, or that their presence may be masked by an inactive polypeptide of similar $M_r$. Although not necessary to the routine practice of the present invention, it is contemplated that other detection techniques may be employed advantageously in the visualization of particular polypeptides of interest. Immunologically-based techniques such as Western blotting using enzymatically-, radiolabel-, or fluorescently-tagged antibodies described herein are considered to be of particular use in this regard. Alternatively, the peptides of the present invention may be detected by using antibodies of the present invention in combination with secondary antibodies having affinity for such primary antibodies. This secondary antibody may be enzymatically- or radiolabeled, or alternatively, fluorescently-, or colloidal gold-tagged. Means for the labeling and detection of such two-step secondary antibody techniques are well-known to those of skill in the art.

3. BRIEF DESCRIPTION OF THE DRAWINGS

The drawings form part of the present specification and are included to further demonstrate certain aspects of the present invention. The invention may be better understood by reference to one or more of these drawings in combination with the detailed description of specific embodiments presented herein.

FIG. 1A. Identification of DBPs of *B. burgdorferi* N40. *B. burgdorferi* whole-cell lysate was subjected to SDS-PAGE (5 to 15%) under reducing conditions and stained with Coomassie brilliant blue. The same gel was transferred to a nitrocellulose membrane (FIG. 1B).

Figure 1B:
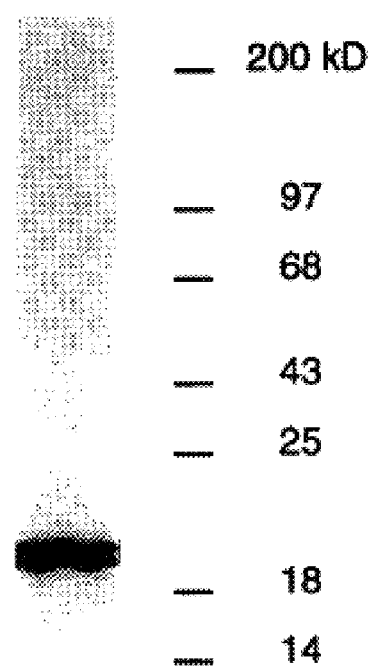

FIG. 1B. Identification of DBPs of *B. burgdorferi* N40. *B. burgdorferi* whole-cell lysate was subjected to SDS-PAGE (5 to 15%) under reducing conditions (FIG. 1A), then transferred to a nitrocellulose membrane. After blocking additional protein-binding sites, proteins on the membrane were probed with biotin-labeled Dcn and visualized by chemiluminescence. The migration of standard proteins with known molecular masses (in kDa) is shown on the left and right.

FIG. 2A. DNA sequence of a 2.5 kb insert of *B. burgdorferi* strain 297 DNA contained in the plasmid BG26:pB/2.5(5), which comprises a nucleic acid sequence which encodes DbpA and DbpB. The deduced amino acid sequences of DbpA and DbpB are shown in FIG. 3. Depicted in FIG. 2A are nucleotides 1–1400 (SEQ ID NO:10). The DNA sequence from position 1401 to 2653 (SEQ ID NO:11) is continued in FIG. 2B.

FIG. 2B. Continuation of the DNA sequence of a 2.5 kb insert of *B. burgdorferi* strain 297 DNA contained in the plasmid BG26:pB/2.5(5), which comprises a nucleic acid sequence which encodes DbpA and DbpB. Depicted in FIG. 2B are nucleotides 1401 to 2653 (SEQ ID NO:11). Nucleotides 1–1400 are shown in FIG. 2A.

FIG. 3. Nucleotide sequence of the dbpB gene from *B. burgdorferi* strains 297, SH2 and LP4 (SEQ ID NO:59), and amino acid sequence of the 187 amino-acid DbpB protein from *B. burgdorferi* strains 297, SH2 and LP4 (SEQ ID NO:60).

FIG. 4. Nucleotide sequence of the dbpA gene from *B. burgdorferi* strains 297 and LP7 (SEQ ID NO:29), and amino acid sequence of the 187 amino-acid DbpA from *B. burgdorferi* strains 297 and LP7 (SEQ ID NO:30).

FIG. 5. Nucleotide sequence of *B. burgdorferi* strains B31, BR4, and 3028 DNA encoding DbpA (SEQ ID NO:39). The translated amino acid sequence of the identical DbpAs from strains B31, BR4, and 3028 is given in SEQ ID NO:40.

FIG. 6. Nucleotide sequence of *B. burgdorferi* dbpB gene from strains HB19, G3940, LP5, ZS7, NCH01, FRED, and *B. garinii* dbpB gene from strain 20047. The sequence is identical for all seven strains (SEQ ID NO:63). The translated amino acid sequence of *B. burgdorferi* DbpB protein from strains HB19, G3940, LP5, ZS7, NCH01, FRED, and *B. garinii* DbpB protein from strain 20047 i also identical for all seven strains (SEQ ID NO:64).

FIG. 7. Nucleotide sequence of *B. burgdorferi* dbpB gene from strains N40, LP7, and *B. afzelii* strain PKo. The sequence is identical for all three strains (SEQ ID NO:61). The amino acid sequence of *B. burgdorferi* DbpB protein from strains N40, LP7, and *B. andersonii* strain PKo is also identical for all three strains (SEQ ID NO:62).

FIG. 8. Partial dbpB gene sequence from *B. garinii* strain IP90 (SEQ ID NO:65) and corresponding amino acid sequence of DbpB protein (SEQ ID NO:66).

FIG. 9. dbpB gene sequence from *B. burgdorferi* strain JD1 (SEQ ID NO:57) and corresponding amino acid sequence of DbpB protein (SEQ ID NO:58).

FIG. 10. dbpB gene sequence from *B. burgdorferi* strain IPS (SEQ ID NO:55) and corresponding amino acid sequence of DbpB protein (SEQ ID NO:56).

FIG. 11. dbpB gene sequence from *B. burgdorferi* strain CA287 (SEQ ID NO:53) and corresponding amino acid sequence of DbpB protein (SEQ ID NO:54).

FIG. 12. Nucleotide and deduced amino acid sequence of *B. garinii* strain IP90 dbpA gene (SEQ ID NO:51). The translated amino acid sequence of DbpA is given in SEQ ID NO:52.

FIG. 13. Nucleotide and deduced amino acid sequence of *B. afzelii* strain B023 dbpA gene (SEQ ID NO:49). The translated amino acid sequence of DbpA is given in SEQ ID NO:50.

FIG. 14. Nucleotide and deduced amino acid sequence of *B. afzelii* strain PGau dbpA gene (SEQ ID NO:47). The translated amino acid sequence of DbpA is given in SEQ ID NO:48.

FIG. 15. Nucleotide and deduced amino acid sequence of *B. burgdorferi* strain ZS7 dbpA gene (SEQ ID NO:45). The translated amino acid sequence of DbpA is given in SEQ ID NO:46.

FIG. 16. Nucleotide and deduced amino acid sequence of *B. burgdorferi* strain LP4 dbpA gene (SEQ ID NO:43). The translated amino acid sequence of DbpA is given in SEQ ID NO:44.

FIG. 17. Nucleotide and deduced amino acid sequence of *B. burgdorferi* strain G3940 dbpA gene (SEQ ID NO:41). The translated amino acid sequence of DbpA is given in SEQ ID NO:42.

FIG. 18. Nucleotide and deduced amino acid sequence of *B. burgdorferi* strain HB19 dbpA gene (SEQ ID NO:37). The translated amino acid sequence of DbpA is given in SEQ ID NO:38.

FIG. 19. Nucleotide and deduced amino acid sequence of *B. burgdorferi* strain JD1 dbpA gene (SEQ ID NO:35). The translated amino acid sequence of DbpA is given in SEQ ID NO:36.

FIG. 20. Nucleotide and deduced amino acid sequence of *B. burgdorferi* strain N40 dbpA gene (SEQ ID NO:33). The translated amino acid sequence of DbpA is given in SEQ ID NO:34.

FIG. 21. Nucleotide and deduced amino acid sequence of *B. burgdorferi* strain SH2 dbpA gene (SEQ ID NO:31). The translated amino acid sequence of DbpA is given in SEQ ID NO:32.

FIG. 22. Comparison of amino acid sequence identities for the DbpAs from related borrelias. The predicted DbpA amino acid sequences disclosed herein were compared in a pairwise fashion as to % identity using the BestFit algorithm of the University of Wisconsin Genetics Computer Group DNA analysis software package. Default parameters for gap weight and gap length weight were used.

Figure 23A:
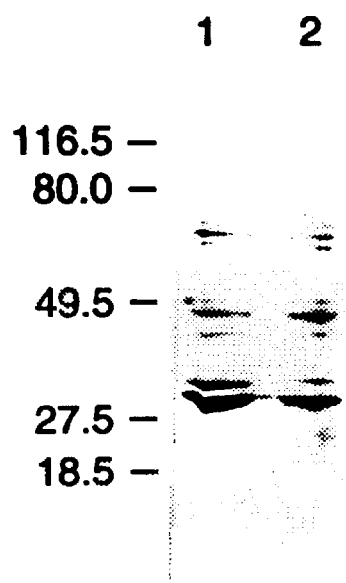

FIG. 23A. *B. burgdorferi* DBP expression, *B. burgdorferi* strain 297 (lane 1) and HP B31 (lane 2) whole-cell lysates were subjected to SDS-PAGE (5–15% gradient) under reducing conditions and stained with Coomassie.

Figure 23B:
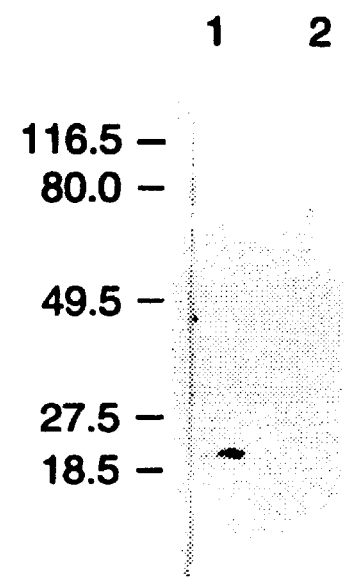

FIG. 23B. Gel from FIG. 23A transferred to a nitrocellulose membrane (B). After blocking additional protein-binding sites, proteins on the membrane were probed with digoxigenin-labeled Dcn and visualized by alkaline phosphatase reactivity. The migration of standard proteins with known molecular masses (in kilodaltons) are shown on the left and right.

Figure 23C:
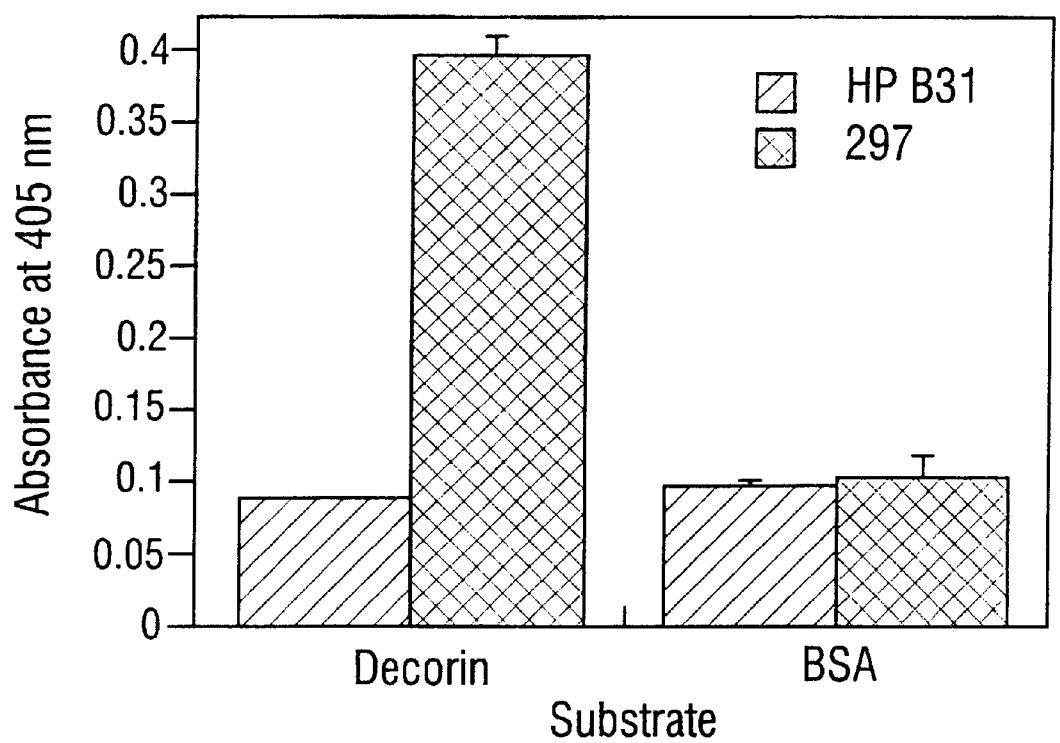

FIG. 23C. Attachment of *B. burgdorferi* to Dcn substrata. Dcn-coated microtiter wells were incubated with *B. burgdorferi* 297 or HP B3 1. Attachment to the substrate was quantitated by an ELISA.

Figure 24:
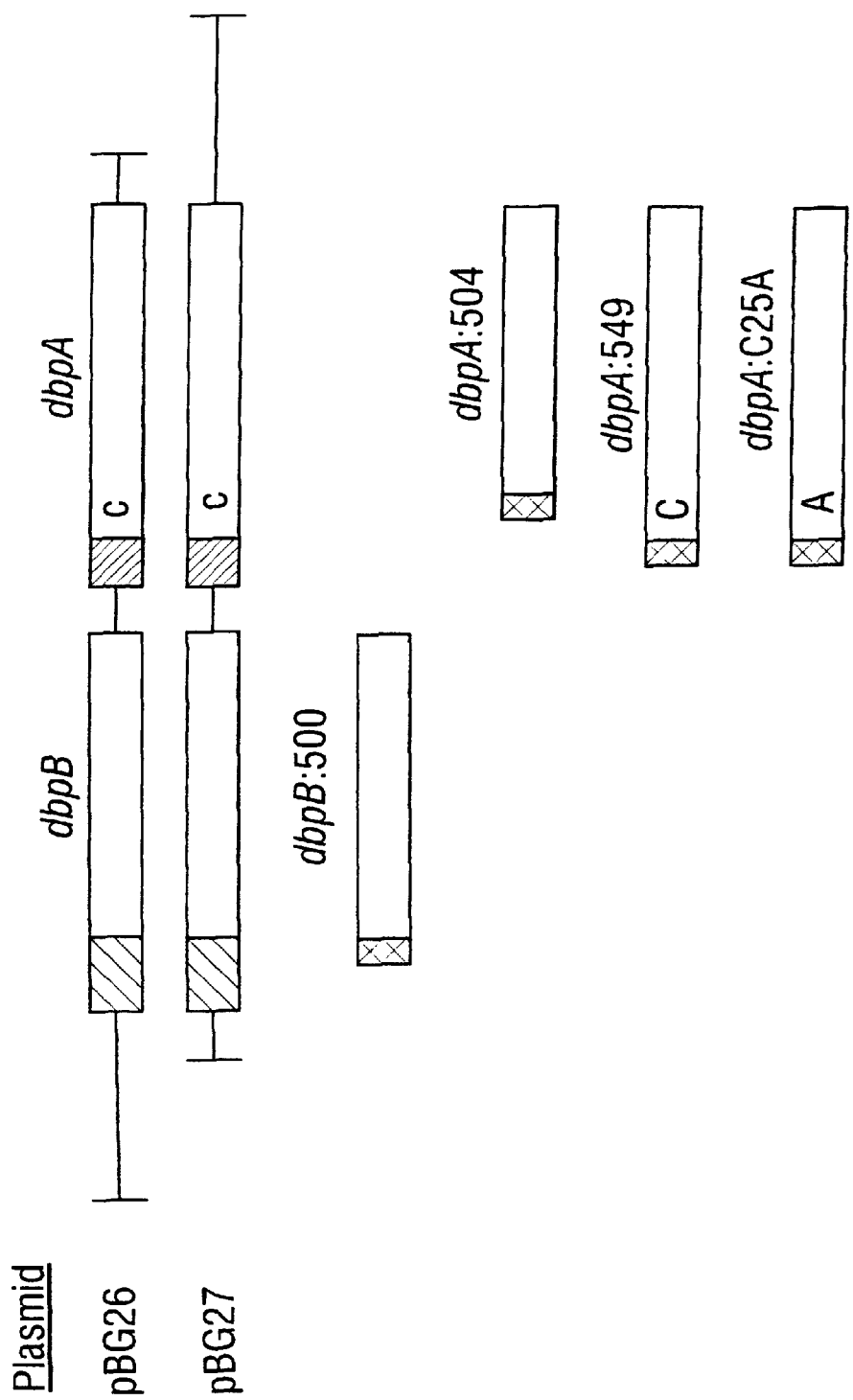

FIG. 24. Diagram of the dbpA and dbpB clones isolated from a λZAPII expression library and construction of recombinant polyhistidine fusion subclones (DbpB:500, DbpA:549, DbpA:504) and site-directed mutant (DbpA:C25A). The polyhistidine fusion (black), leader peptides (dotted, striped) and cysteine to alanine mutation are indicated.

Figure 25:
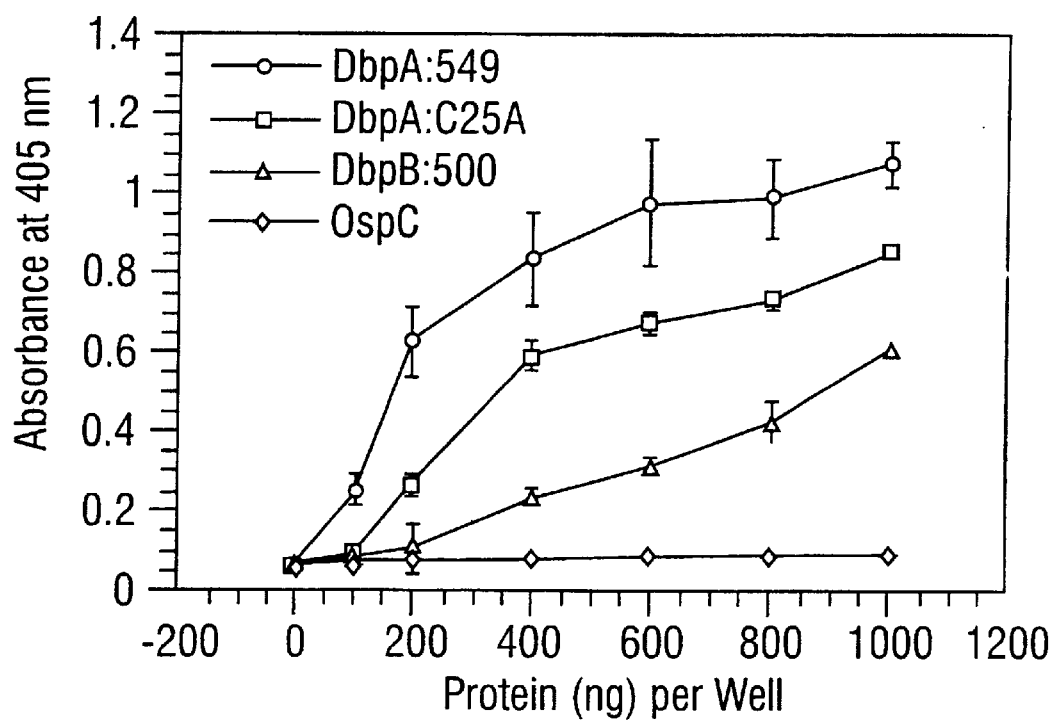

FIG. 25. Activity of recombinant Dcn-binding proteins. Microtiter wells were coated with DbpA:549, DbpB:500, DbpA:C25A, or OspC. Biotin-labeled Dcn was allowed to bind, followed by alkaline phosphatase conjugated streptavidin. Dcn binding was quantitated by measuring absorbance at 405 nm in the presence of phosphatase substrate.

Figure 26A:
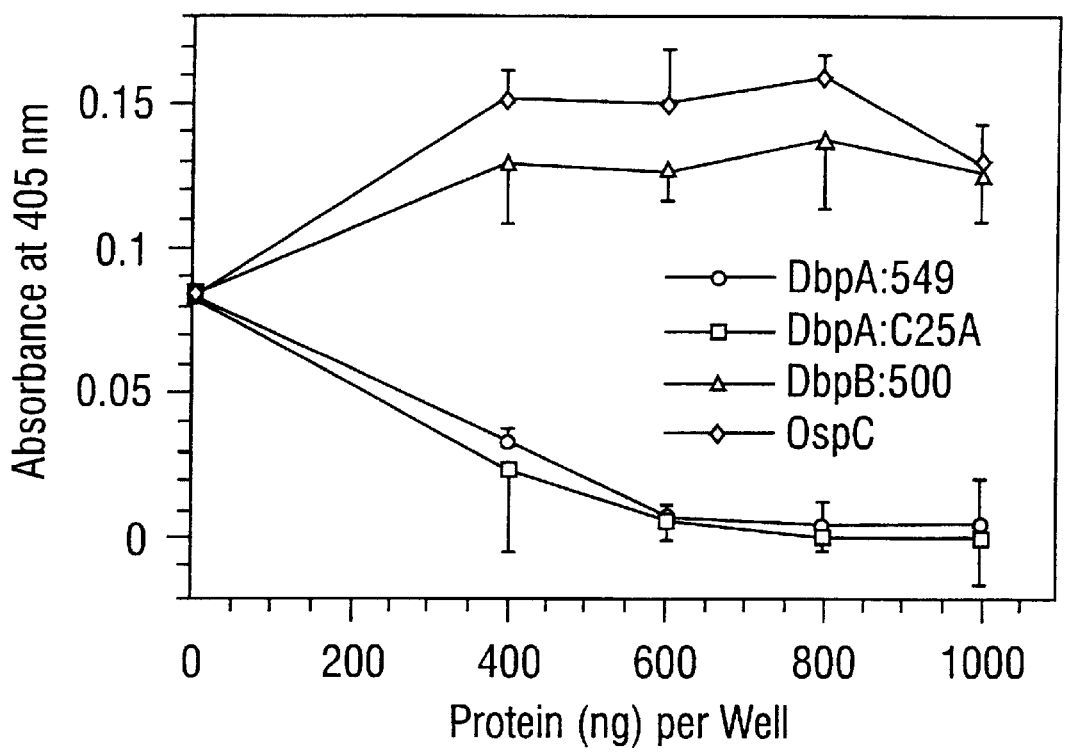

FIG. 26A. Inhibition of the attachment of *B. burgdorferi* 297 to Dcn substrata. Dcn-coated microtiter wells were preincubated with DbpA:549, DbpB:500, or DbpA:C25A before *B. burgdorferi* were allowed to attach. Attachment to the substrate was quantitated by an ELISA.

Figure 26B:
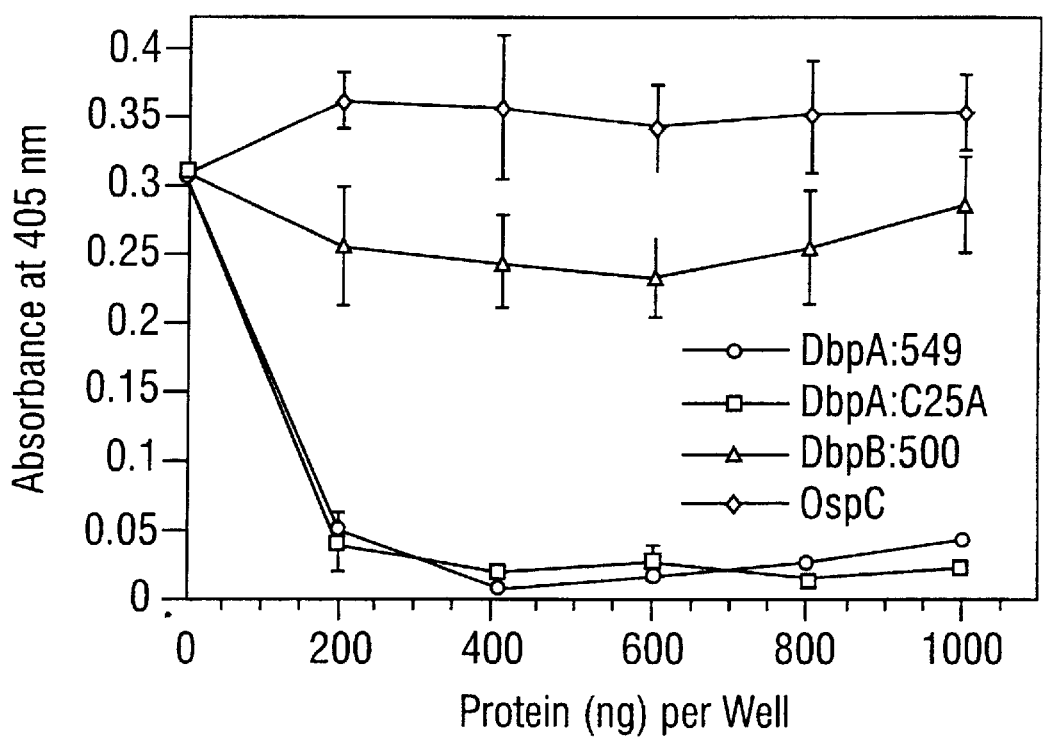

FIG. 26B. Inhibition of the attachment of *B. burgdorferi* N40 to Dcn substrata. Dcn-coated microtiter wells were preincubated with DbpA:549, DbpB:500, or DbpA:C25A before *B. burgdorferi* were allowed to attach. Attachment to the substrate was quantitated by an ELISA.

Figure 27:
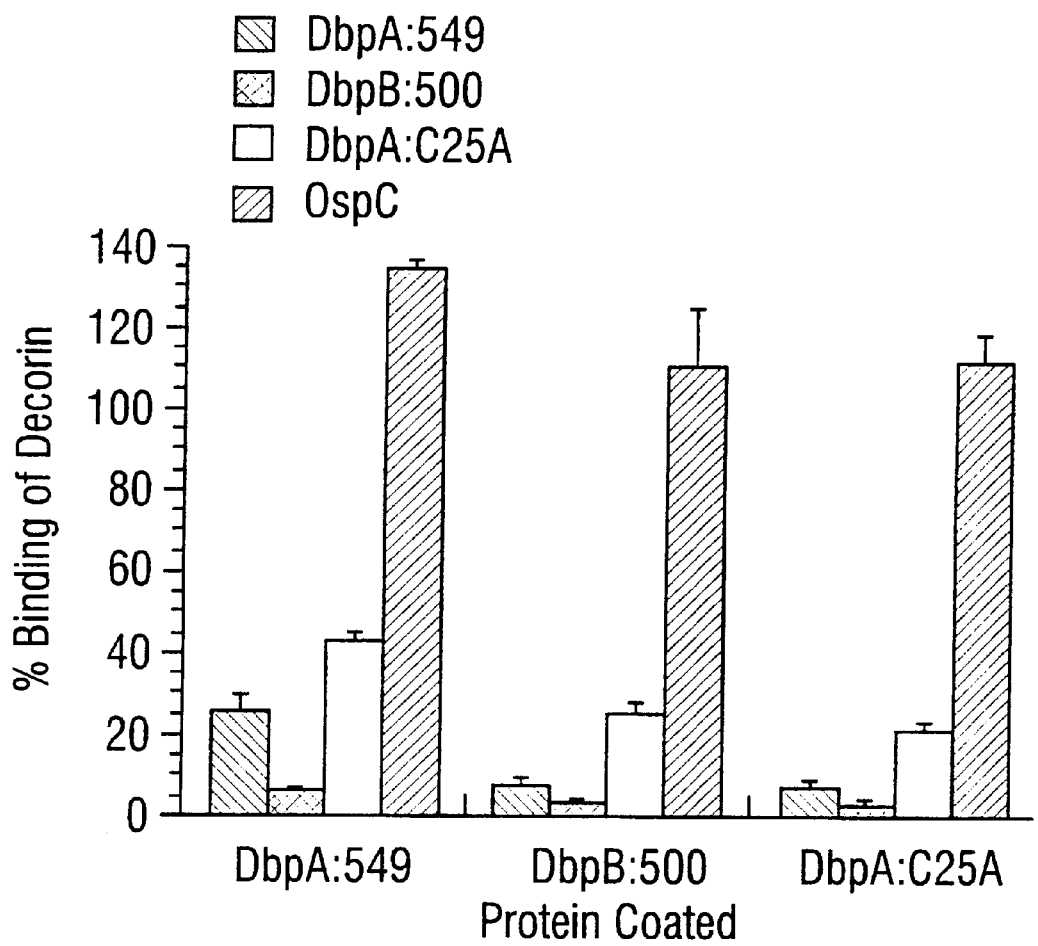

FIG. 27. Competition of DBPs for Dcn binding. Microtiter wells were coated with DbpA:549, DbpB:500, or DbpA:C25A. Biotin-labeled Dcn was preincubated with Dbps before being allowed to bind to Dbp coated wells. After incubating with alkaline phosphatase conjugated streptavidin, Dcn binding was quantitated by measuring absorbance at 405 nm in the presence of phosphatase substrate. Readings from BSA coated wells were subtracted background.

Figures 28A, 28B:
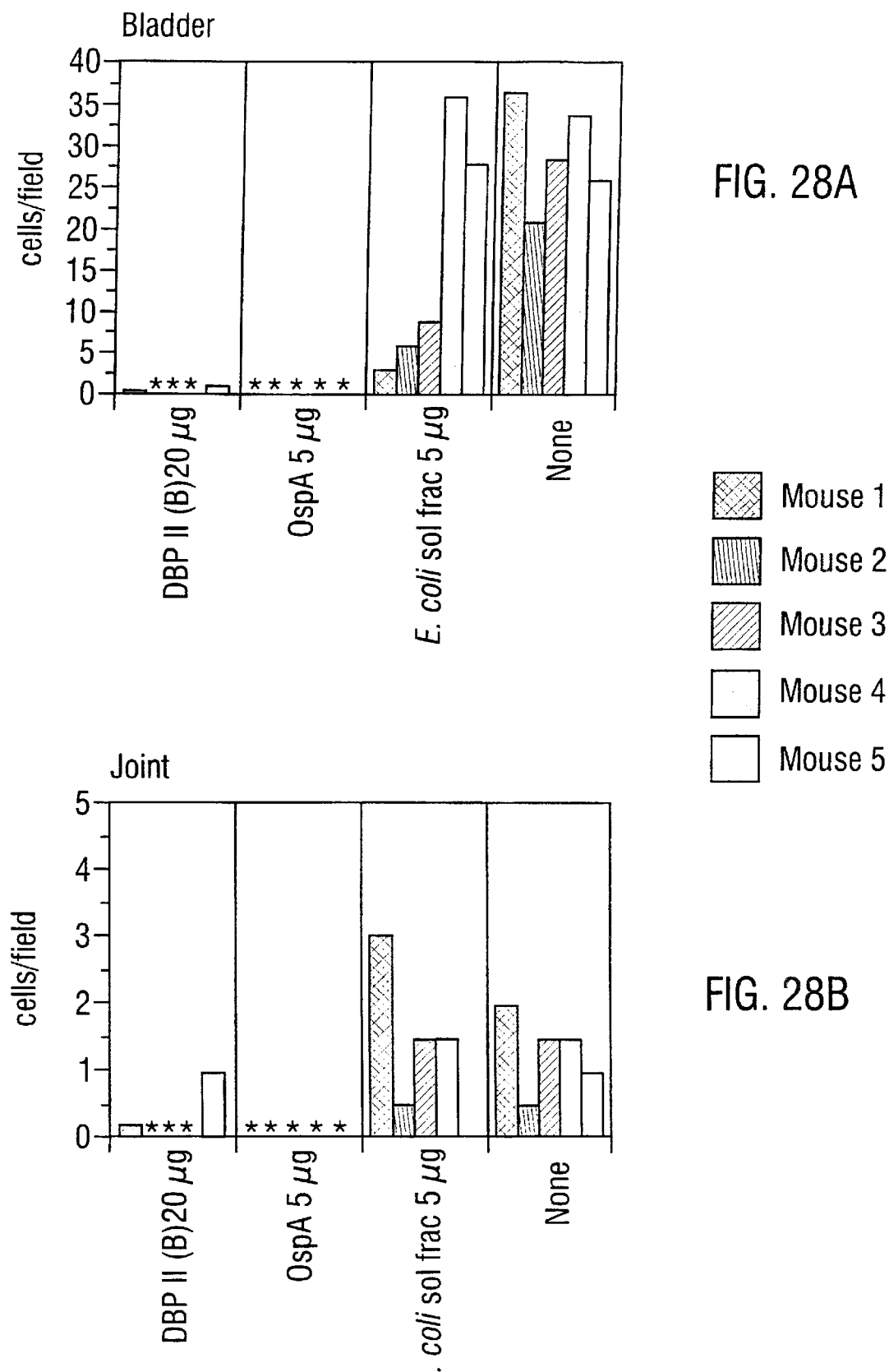

FIG. 28A. DbpB Active protection study in BALB/c mice.

FIG. 28B. DbpB Active protection study in BALB/c mice.

4. DESCRIPTION OF ILLUSTRATIVE EMBODIMENTS

The technology described herein is used to develop methods and compositions that specifically interfere with bacterial adhesion and the subsequent colonization host tissues, thus resulting in the prevention of infection. The technology is broadly applicable, has the potential to increase the effectiveness of antibiotic therapy in many situations, and replace antibiotic therapy in a number of other applications. The technology is anticipated to be especially effective in treatment regimens for Lyme disease, and as a cost-effective prophylaxis for prevention of borrelial infections.

4.1 Some Advantages of the Invention

Those of ordinary skill having the benefit of this disclosure will appreciate that the invention provides a number of advantages, including the following: Specifically the invention discloses:

(1) Serological variation of DbpA is less than that of OspA as antibodies reactive with DbpA-derived from *B. burgdorferi* sensu stricto are also growth-inhibitory to many strains of *B. garinii* and *B. afzelii*;

(2) Immunization of mice with either full-length DbpA or a recombinant truncated chimeric DBP protects against challenge with a heterologous *B. burgdorferi* strain;

(3) Antiserum against DbpA$_{297}$ provides either complete or partial protection against several additional heterologous *B. burgdorferi*, *B. afzelii*, and *B. garinii* strains;

(4) Antibodies (FAb fragments) against DBPs block the binding of recombinant DBPs to Dcn; and (5) The dbpA gene from *B. burgdorferi* 297 has been used to identify and isolate molecular clones of alleles of this gene present in different phylogenetic groups of Lyme disease spirochetes including *B. garinii*, *B. japonica*, *B. afzelii*, *B. andersonii*, and related Borrelia spp. by utilization of PCR™ techniques. These new dbp alleles have been shown to have a high level of sequence identity to the dbpA gene from strain 297. Indication was seen of important serologic differences among the various DBPs suggesting that it may be necessary to formulate a multiple-DBP antigen cocktail to achieve complete vaccine coverage of all clinically relevant *B. burgdorferi* strains.

4.1.1 DbpA and DbpB-Derived Antigens are Superior to OspA Antigens

The data from the biochemical and immunological characterization of the *B. burgdorferi* DbpA and DbpB herein show that Lyme disease vaccines derived from DbpA and/or DbpB do not suffer the limitations of the prior art, particularly with respect to OspA and other antigens previously investigated as antigens for development of borrelia vaccines. Indeed, vaccine compositions comprising one or more DBPs, and in particular, DbpA and/or DbpB, are likely to be superior to those previously available containing OspA alone.

4.2.2 Serological Variation of DbpA and DbpB

The serological variation of DbpA and DbpB appears to be less than that of OspA as antibodies reactive with DbpA and DbpB derived from *B. burgdorferi* sensu stricto are also growth-inhibitory to strains of *B. garinii* and *B. afzelii.*

4.2.3 rDbpA or rDbpB Immunization Protects Against Heterologous Strains

The data of the present invention demonstrate that immunization of mice with recombinant DbpA or DbpB protects against challenge from heterologous strains of *B. burgdorferi.*

4.2.4 DBP Vaccines Provide Superior Efficacy

Unlike OspA, DbpA and DbpB remain a target for immune intervention for several days after initiation of infection, and is the only antigen shown to date to possess this desirable property with respect to potential vaccine efficacy.

4.2.5 Anti-DbpA or Anti-DbpB Antibodies Eliminate Borrelias From Infected Animals DBP-targeted antibodies administered several days after initiation of infection can eliminate viable spirochetes from infected mice, suggesting that this antigen is also a potential target for immunotherapy of Lyme disease as well as for immunoprophylaxis. Biochemical data is provided showing that DbpA and DbpB are lipoproteins, and are exposed at the surface of the spirochetal outer membrane.

4.2.6 dbp Nucleic Acid Segments Are Useful in Identifying Borrelial Isolates

The novel dbpA and dbpB genes disclosed herein may be used to identify and isolate molecular clones of alleles of this gene present in different phylogenetic groups of Lyme disease spirochetes including *B. burgdorferi, B. garinii, B. afzelii, B. andersonii*, and *B. japonica* by utilization of such techniques as PCR™.

4.3 MSCRAMMs

Bacterial adherence to host tissue involves specific microbial surface adhesins of which a subfamily termed MSCRAMMs (microbial surface components recognizing adhesive matrix molecules, Patti et al., 1994; Patti and Hook, 1994) specifically recognize extracellular matrix components. Many pathogenic bacteria have been shown to specifically recognize and bind to various components of the extracellular matrix in an interaction which appears to represent a host tissue colonization mechanism.

MSCRAMMs (on the bacterial cell surface) and ligands (within the host tissue) are the molecules that interact in a lock and key fashion resulting in the adherence of bacteria to the host. Complete blockage of microbial adhesion is not required to prevent infection. It is only necessary to keep the bacterial inoculum below a critical mass. Several strategies have been developed which are particularly useful in combatting bacterial infections, such as infection by *B. burgdorferi*, by preventing bacterial adhesion to Dcn substrata including the extracellular matrix (ECM) of susceptible host cells. Such strategies are contemplated to be useful in the diagnosis, treatment, and prophylaxis of Lyme disease.

4.4 Extracellular Matrix

The ECM contains numerous glycoproteins and proteoglycans which, through inter- and intramolecular interactions, form insoluble matrices. The ECM has a structural function in the tissues but also affects the cellular physiology of the organism. Perhaps the best characterized biological functions of the ECM are related to its ability to serve as a substrata for the adhesion of host tissue cells. This process involves the integrins, a family of heterodimeric ($\alpha/\beta$) cell surface receptors which recognize specific structures in many of the ECM proteins. It is clear that many bacteria also have taken advantage of the ECM as a substrate for adhesion. Like most eukaryotic tissue cells, many bacteria have developed several parallel adhesion mechanisms and this apparent redundancy may reflect the importance of host tissue adherence for the prosperity of the bacteria.

The adherence of microbes to various cell-surface and extracellular matrix components has been widely reported (Abraham et al., 1983; Coburn et al., 1993; Fröman et al., 1984; Isaacs, 1994; Maxe et al., 1986; Van Nhieu and Isber, 1993). The present invention has identified a new class of bacterial MSCRAMMs which promotes bacterial adhesion to Dcn and other proteoglycans which are structurally similar to Dcn, which are found in conjunction with ECM components such as collagen. The identification and characterization of DbpA and DbpB and the genes which encode them represents the first known bacterial proteins with affinity for Dcn.

4.5 Collagen

Collagenous proteins are the major constituents of the ECM (Bornstein and Sage, 1980). Most collagens are synthesized intracellularly as precursor molecules and undergo extensive posttranslational processing prior to secretion and incorporation into the ECM or other collagen-rich tissues such as cartilage (Ramachandran and Reddi, 1976). To date over 18 different type of collagens have been defined, and they are loosely categorized into five groups (Vanderrest and Garrone, 1991). These groups are:

1) collagen types I, II, III, V, and XI which participate in quarter-staggered fibrils;
2) collagen types XII, XIV, and IX which are fibril-associated with interrupted triple helices;
3) collagen types IV, VIII, and X which form sheets;
4) collagen type VI which forms beaded filaments; and
5) collagen type VII, which forms anchoring fibrils.

The collagen network in skin is composed predominantly of collagens type I and type III. Dcn can inhibit transforming growth factor beta activity (TGFβ) (Yamaguchi et al., 1990) and inactivate the complement component Clq (Krumdieck et al., 1992) and has been proposed to act as an anti-inflammatory agent through these interactions.

4.6 Proteoglycans 4.6.1 Decorin

Dcn, also known as PG-40, PG-II, PG-S2 and CSIDS-PGII, is a small proteoglycan with a single chondroitin or dermatan sulfate chain attached to the fourth amino acid of the secreted 36–38 kDa protein (Chopra et al., 1985). Dcn has been found associated with collagen fibrils in virtually all connective tissues (Bianco et al., 1990), perhaps near the d and e bands in the D period (Pringle and Dodd, 1990). In vitro studies have shown that Dcn can change the kinetics of collagen fibril formation (Vogel et al., 1984, affect the morphology of forming collagen fibrils (Vogel and Trotter, 1987) and bind to TGF-β (Yamaguchi et al., 1990).

Dcn, so named because it "decorates" collagen fibers in the intracellular matrix, has been shown to bind different collagen types and is believed to act as a regulator of collagen fiber formation. The proteoglycan can be isolated from many different tissues, including skin, cartilage, and tendon.

Dcn consists of a 36 kDa core protein, a single, serine-linked glycosaminoglycan (GAG) chain of the chondroitin/dermatan sulfate type, and up to three N-linked oligosaccharide. The GAGs are unbranched polysaccharides consisting of repeating disaccharide units, highly sulfated and therefore highly negatively charged. Dcn containing a chondroitin-4-sulfate chain is isolated from developing bone (Fisher et al., 1987) while Dcn containing a dermatan sulfate chain is generally isolated from articular cartilage (Choi et al., 1989) or tendon (Vogel and Heinegård, 1985). The Dcn is heterogenous with respect to glycosaminoglycan chain size and the average size of the chains differ with tissue and developmental age, however, the Alcian blue or StainsAll band generally are centered from 100 to 250 kDa. While Dcn size may differ in different tissues, it is almost always smaller than the biglycan (Bgn) proteoglycan in the same tissue. Both the human (Krusius and Ruoslahti, 1986) and bovine (Day et al., 1987) cDNA have been published and show a ~36–38 kDa core protein. Dcn changes the kinetics of the generation of collagen fibrils in vitro (Vogel et al., 1984) and affects the final morphology of the resulting fibrils (Vogel and Trotter, 1987). While these results suggest that Dcn may play an important role in collagen fibril formation, it is still unknown why the small proteoglycan is maintained on the fibrils throughout life, well after the fibrils are crosslinked and stabilized. When the expression of high levels of Dcn is induced in Chinese hamster ovary (CHO) cells, their morphology and growth properties are dramatically changed (Yamaguchi and Ruoslahti, 1988).

The gene encoding Dcn has been localized to human chromosome 12 (McBride et al., 1990), and Dcn itself shows obvious homology to other small proteoglycans, including Bgn (Fisher et al., 1989), and Fmn (Oldberg et al., 1989), Epn, and Lmn. These proteoglycans are predominantly composed of 10–12 tandem repeats with each nominal 24 amino acid repeat having a pattern of hydrophobic amino acids (Fisher et al., 1989; Oldberg et al., 1989). These repeat sequences have been used many times in evolution when protein-protein, protein-cell or cell-cell interactions are required. While Dcn, like Fmn, is found associated with collagen fibrils (Oldberg et al., 1989), Bgn appears to be associated on or very near cell surfaces and not collagen bundles (Bianco et al., 1990).

4.6.2 Biglycan (Bgn)

Bgn (Fisher et al., 1989) is a small proteoglycan whose primary gene product is found associated with the cell surface or pericellular matrix of a variety of cells including specific subsets of developing mesenchymal (skeletal muscle, bone and cartilage), endothelial (blood vessels), and epithelial (keratinocytes cells) (Bianco et al., 1990). Other names for this proteoglycan includes; PG-1, PG-I, DS-PGI, PG-S1 and DS-I. Bgn is composed of two chondroitin (CS) or dermatan sulfate (DS) chains on a 38 kDa core protein that is predominantly made of 12 tandem 24 amino acid repeat structures, each characterized by ordered hydrophobic residues. Similar tandem repeat structures have been used throughout evolution when a protein is destined to bind another protein or perhaps a cell surface (Fisher et al., 1989; Patthy, 1987). The function of Bgn is unknown, but, like the homologous proteoglycan, Dcn, it may also bind to TGF-β.

The chondroitin sulfate containing Bgn is most commonly isolated from fetal or young bone (Fisher et al., 1987; 1983), while the dermatan sulfate containing form is isolated from articular cartilage (Choi et al., 1989). The Bgn is heterogeneous with respect to the size of the glycosaminoglycan chains which results in a broad band on SDS-PAGE centered anywhere from 200–350 kDa. Although Bgn may differ in size between tissues and developmental stage, it is almost always larger than the other small proteoglycan, Dcn, when Dcn is also present. Bgn may occasionally be present with a single CS/DS chain, thus making it the same size as Dcn. Removal of the glycosaminoglycan chains with the enzyme chondroitin ABC-lyase results in a 45 kDa band. The gene for Bgn is on the human X chromosome (Xq27ter) (Fisher et al., 1989) and its mRNA encodes a 42.5 kDa preproprotein. The human (cDNA) (Fisher et al., 1989), bovine protein (Neame et al., 1989) and rat (Dreher et al., 1990) sequences have been reported. Bgn probably contains three disulfide bonds. Unlike its close relatives, Dcn and Fmn, purified Bgn does not bind to collagen fibrils in vitro, nor is it found associated with classic collagen bundles in tissues. Bgn (both protein and mRNA) is expressed in a range of specialized cell types in developing human tissues including bone, cartilage, blood vessel endothelial cells, skeletal myofibrils, renal tubular epithelia, and differentiating keratinocytes (Bianco et al., 1990). Generally, the Bgn is immunolocalized to the cell surface or pericellular matrices, but in a tissue such as bone, the protein is detected in the matrix proper. This localization in the extracellular matrix may be due to the adsorption of the Bgn to hydroxylapatite crystals after having been shed from the osteoblasts. Localization of Bgn by immunoelectron microscopy has not yet been performed. The human Bgn gene has been cloned and partially sequenced.

4.6.3 Fibromodulin (Fmn)

Fmn (or 59-kDa cartilage protein) is a keratan/sulfate proteoglycan present in many types of connective tissues, e.g. cartilage, tendon and skin. Fmn is structurally related to the dermatan sulfate/chondroitin sulfate proteoglycans Dcn and Bgn. Fmn binds to collagen and affects the collagen fibrillogenesis in vitro (Heinegård and Oldberg, 1989).

The Fmn protein backbone consists of 357 amino acid residues (42 kDa) which can be divided into three structural domains (Oldberg et al., 1989). The N-terminal domain has four cysteine residues of which two are involved in an intrachain disulfide bond. This region of the protein also contains five to seven closely spaced tyrosine sulfate residues. The central domain, which constitutes 60% of the protein, consists of ten repeats of 25 amino acid residues. This central repeat domain, with preferentially leucine residues in conserved positions, is homologous to similar repeats in a number of proteins including the interstitial proteoglycans Dcn and Bgn (Oldberg et al., 1989). The C-terminal domain contains two cysteine residues which form an intrachain disulfide bond.

Fmn from cartilage, tendon and sclera contains asparagine-linked keratan sulfate chains (Oldberg et al., 1989; Plaas et al., 1990). Four of the five potential N-glycosylation sites in Fmn from bovine articular cartilage is substituted with keratan sulfate chains (Plaas et al., 1990). Fmn binds to type I and II collagen with a $K_d$ of 35 nM. The protein also delays the collagen fibrillation in vitro and causes the formation of thinner fibrils. This collagen binding property is shared by Dcn but not by the structurally related Bgn (Hedbom and Heinegård, 1989; Brown and Vogel, 1989).

4.6.4 Epiphycan (Epn)

A small dermatan sulfate proteoglycan containing leucine-rich repeats has been isolated from fetal bovine epiphyseal cartilage. This proteoglycan is referred to as Epn based on its preparation from that tissue. This proteoglycan which seems to have restricted expression is closely similar to other leucine-rich repeat containing proteoglycans, Dcn and Bgn (Krusius and Ruoslahti, 1986; Day et al. 1987; Fisher et al., 1989; Neame et al, 1989), as well as to osteoglycin (formerly osteoinductive factor) (Bentz et al., 1990), and is the mammalian equivalent to chick proteoglycan PG-Lβ (Shinomura and Kimata, 1992). Determination of the molecular weight of the intact proteoglycan, the core protein, as well as the glycosaminoglycan (GAG) chains was determined by radiolabeling by either iodination of the protein or tritiation of the GAG chain and subsequent analysis over FPLC chromatography and SDS-PAGE. The molecular weight of the intact proteoglycan was approximately 133 kDa while the core protein was ~46 kDa and the GAG chains were ~23–34 kDa. This analysis was determined in comparison with the fetal bovine epiphyseal Dcn and Bgn produced during the same preparation of Epn. Iodinated proteoglycan was analyzed for its ability to interact with collagens. Furthermore, tryptic peptides from this preparation of Epn were used to determine residues that have undergone posttranslational modification.

4.6.5 Lumican (Lmn)

A recent publication has identified a 1.9-kb cDNA clone encoding the chick Lmn (corneal keratan sulfate proteoglycan) (Blochberger et al., 1992). The cDNA clone contained an open reading frame coding for a 343-amino acid protein, $M_r$=38,640. The deduced sequence shows five potential N-linked glycosylation sites, four of which are in the leucine-rich region. These sites are also potential keratan sulfate attachment sites. The cDNA clone to Lmn hybridized to a 2.0-kb mRNA found in tissues other than cornea, predominantly muscle and intestine. The primary structure of lumican is similar to Fmn, Dcn, and Bgn.

4.7 DbpA and DbpB Binding To Dcn Requires Intact Proteoglycan

*B. burgdorferi* has now been found to adhere to Dcn, but does not directly adhere to collagen types I or III. High-affinity binding of *B. burgdorferi* to Dcn is specific and appears to require the intact proteoglycan, rather than the isolated core protein or GAG chain. Partial purification of the membrane constituents of *B. burgdorferi* and affinity chromatography using Dcn bound to a solid support has permitted visualization of at least two DBPs, designated DbpA and DbpB, having apparent molecular weights of about 18–20 kDa.

4.8 dbpA-and dbpB-Encoding Nucleic Acid Segments

As used herein, the term "dbp gene" is used to refer to a gene or DNA coding region that encodes a protein, polypeptide or peptide that is capable of binding Dcn, Fmn, Bgn, Epn, or Lmn. Exemplary and preferred dbp genes include the dbpA and dbpB genes isolated from Borrelia, and in particular, from *B. burgdorferi, B. afzelii, B. andersonii, B. garinii*, or *B. japonica*.

The definition of a "dbp gene", as used herein, is a gene that hybridizes, under relatively stringent hybridization conditions (see, e.g., Maniatis et al., 1982), to DNA sequences presently known to include a dbp gene sequence. The definition of a "dbpA gene", as used herein, is a gene that hybridizes, under relatively stringent hybridization conditions (see, e.g., Maniatis et al., 1982), to DNA sequences presently known to include a dbpA gene sequence. The definition of a "dbpB gene", as used herein, is a gene that hybridizes, under relatively stringent hybridization conditions (see, e.g., Maniatis et al., 1982), to DNA sequences presently known to include a dbpB gene sequence.

It will, of course, be understood that one or more than one genes encoding DBPs or peptides may be used in the methods and compositions of the invention. The nucleic acid compositions and methods disclosed herein may entail the administration of one, two, three, or more, genes or gene segments. The maximum number of genes that may be used is limited only by practical considerations, such as the effort involved in simultaneously preparing a large number of gene constructs or even the possibility of eliciting a significant adverse cytotoxic effect.

In using multiple dbp genes, they may be combined on a single genetic construct under control of one or more promoters, or they may be prepared as separate constructs of the same or different types. Thus, an almost endless combination of different dbp genes and genetic constructs may be employed. The inventors contemplate that under certain conditions, it may be desirable to express one or more dbpA genes in combination with one or more dbpB genes either on the same, or different DNA segments in order to produce the polypeptides of the invention. Such genes may either be on a single plasmid or vector, or, alternatively, present on more than one separate plasmids or vectors. Likewise, the genes may also be present as genomic or extragenomic sequences under the control or a single promoter or multiple independent promoters. Certain gene combinations may be designed to, or their use may otherwise result in, achieving synergistic effects on formation of an immune response, or the development of antibodies to the dbpA and/or dbpB gene products encoded by such nucleic acid segments, or in the production of diagnostic and treatment protocols for borrelia infection, and in particular, infection with *B. burgdorferi, B. afzelii, B. andersonii, B. japonica,* or *B. garinii*, and those infections leading to Lyme disease. Any and all such combinations are intended to fall within the scope of the present invention. Indeed, many synergistic effects have been described in the scientific literature, so that one of ordinary skill in the art would readily be able to identify likely synergistic gene combinations, or even gene-protein combinations.

It will also be understood that, if desired, the nucleic segment or gene could be administered in combination with further agents, such as, e.g., proteins or polypeptides or various pharmaceutically active agents. So long as genetic material forms part of the composition, there is virtually no limit to other components which may also be included, given that the additional agents do not cause a significant adverse effect upon contact with the target cells or tissues.

4.9 Therapeutic and Diagnostic Kits Comprising DBP Compositions

A therapeutic kit comprising, in suitable container means, one or more DBP composition(s) of the present invention in a pharmaceutically acceptable formulation represent another aspect of the invention. The DBP composition(s) may comprise:

1) one or more DBP proteins or peptides, and in particular DbpA and/or DbpB proteins or peptides;
2) one or more truncated DBP proteins or peptides, and in particular truncated DbpA and/or truncated DbpB proteins or peptides;
3) one or more site-specifically or randomly mutated DBP proteins or peptides, and in particular site-specifically or randomly mutated DbpA and/or DbpB proteins or peptides;
4) one or more DBP-encoded peptide epitopes, domains or motifs, and in particular DbpA- and/or DbpB-derived epitopes, domains or motifs;

5) one or more antibodies which bind to native, truncated, site-specifically or randomly mutated DBPs, or DBP-encoded peptide epitopes, domains or motifs, and in particular anti-DbpA and/or anti-DbpB;

6) one or more nucleic acid segments encoding all or a portion of one or more dbp genes, and in particular one or more dbpA and/or dbpB genes. These nucleic acid segments may encode native DBPs, truncated DBPs, site-specifically or randomly mutated DBPs, or DBP-derived peptide epitopes, domains or motifs, and may be either native, recombinant, or mutagenized DNA or RNA segments; or, alternatively, 7) a combination of one or more of the compositions 1) through 6).

The kit may comprise a single container means that contains the DBP composition(s). The container means may, if desired, contain a pharmaceutically acceptable sterile excipient, having associated with it, the DBP composition(s) and, optionally, a detectable label or imaging agent. The formulation may be in the form of a gelatinous composition (e.g., a collagenous composition), a powder, solution, matrix, lyophilized reagent, or any other such suitable means. In certain cases, the container means may itself be a syringe, pipette, or other such like apparatus, from which the DBP composition(s) may be applied to a tissue site, skin lesion, wound area, or other site of borrelial infection. However, the single container means may contain a dry, or lyophilized, mixture of one or more DBP composition(s), which may or may not require pre-wetting before use.

Alternatively, the kits of the invention may comprise distinct container means for each component. In such cases, one or more containers would contain each of the DBP composition(s), either as sterile solutions, powders, lyophilized forms, etc., and the other container(s) would include a matrix, solution, or other suitable delivery device for applying the DBP composition to the body, bloodstream, or to a tissue site, skin lesion, wound area, or other site of borrelial infection. Such delivery device may or may not itself contain a sterile solution, diluent, gelatinous matrix, carrier or other pharmaceutically-acceptable components.

The kits may also comprise a second or third container means for containing a sterile, pharmaceutically acceptable buffer, diluent or solvent. Such a solution may be required to formulate the DBP component into a more suitable form for application to the body, e.g., as a topical preparation, or alternatively, in oral, parenteral, or intravenous forms. It should be noted, however, that all components of a kit could be supplied in a dry form (lyophilized), which would allow for "wetting" upon contact with body fluids. Thus, the presence of any type of pharmaceutically acceptable buffer or solvent is not a requirement for the kits of the invention. The kits may also comprise a second or third container means for containing a pharmaceutically acceptable detectable imaging agent or composition.

The container means will generally be a container such as a vial, test tube, flask, bottle, syringe or other container means, into which the components of the kit may placed. The matrix and gene components may also be aliquoted into smaller containers, should this be desired. The kits of the present invention may also include a means for containing the individual containers in close confinement for commercial sale, such as, e.g., injection or blow-molded plastic containers into which the desired vials or syringes are retained.

Irrespective of the number of containers, the kits of the invention may also comprise, or be packaged with, an instrument for assisting with the placement of the ultimate matrix-gene composition within the body of an animal. Such an instrument may be a syringe, pipette, forceps, or any such medically approved delivery vehicle.

4.10 Affinity Chromatography

Affinity chromatography is generally based on the recognition of a protein by a substance such as a ligand or an antibody. The column material may be synthesized by covalently coupling a binding molecule, such as an activated dye, for example to an insoluble matrix. The column material is then allowed to adsorb the desired substance from solution. Next, the conditions are changed to those under which binding does not occur and the substrate is eluted. The requirements for successful affinity chromatography are:

1) that the matrix must specifically-adsorb the molecules of interest;

2) that other contaminants remain unadsorbed;

3) that the ligand must be coupled without altering its binding activity;

4) that the ligand must bind sufficiently tight to the matrix; and 5) that it must be possible to elute the molecules of interest without destroying them.

A preferred embodiment of the present invention is an affinity chromatography method for purification of antibodies from solution wherein the matrix contains DBPs or peptide epitopes derived from DBPs such as those derived from the DBP of *B. burgdorferi*, covalently-coupled to a Sepharose CL6B or CL4B. This matrix binds the antibodies of the present invention directly and allows their separation by elution with an appropriate gradient such as salt, GuHCl, pH, or urea. Another preferred embodiment of the present invention is an affinity chromatography method for the purification of DBPs and peptide epitopes from solution. The matrix binds the amino acid compositions of the present invention directly, and allows their separation by elution with a suitable buffer as described above.

4.11 Methods of Nucleic Acid Delivery and DNA Transfection

In certain embodiments, it is contemplated that the nucleic acid segments disclosed herein will be used to transfect appropriate host cells. Technology for introduction of DNA into cells is well-known to those of skill in the art. Four general methods for delivering a nucleic segment into cells have been described:

(1) chemical methods (Graham and Van der Eb, 1973);

(2) physical methods such as microinjection (Capecchi, 1980), electroporation (Wong and Neumann, 1982; Fromm et al., 1985) and the gene gun (Yang et al., 1990);

(3) viral vectors (Clapp, 1993; Eglitis and Anderson, 1988); and (4) receptor-mediated mechanisms (Curiel et al., 1991; Wagner et al., 1992).

4.12 Liposomes and Nanocapsules

In certain embodiments, the inventors contemplate the use of liposomes and/or nanocapsules for the introduction of particular peptides or nucleic acid segments into host cells. Such formulations may be preferred for the introduction of pharmaceutically-acceptable formulations of the nucleic acids, peptides, and/or antibodies disclosed herein. The formation and use of liposomes is generally known to those of skill in the art (see for example, Couvreur et al., 1977 which describes the use of liposomes and nanocapsules in the targeted antibiotic therapy of intracellular bacterial infections and diseases). Recently, liposomes were developed with improved serum stability and circulation half-times (Gabizon and Papahadjopoulos, 1988; Allen and Choun, 1987).

Nanocapsules can generally entrap compounds in a stable and reproducible way (Henry-Michelland et al., 1987). To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use in the present invention, and such particles may be are easily made, as described (Couvreur et al., 1977; 1988).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 Å, containing an aqueous solution in the core.

In addition to the teachings of Couvreur et al. (1988), the following information may be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. It often is difficult to determine which mechanism is operative and more than one may operate at the same time.

4.13 Methods for Preparing DBP and DBP-Derived Antibodies

In another aspect, the present invention contemplates an antibody that is immunoreactive with a polypeptide of the invention. As stated above, one of the uses for DBPs and DBP-derived epitopic peptides according to the present invention is to generate antibodies. Reference to antibodies throughout the specification includes whole polyclonal and monoclonal antibodies (mAbs), and parts thereof, either alone or conjugated with other moieties. Antibody parts include Fab and F(ab)$_2$ fragments and single chain antibodies. The antibodies may be made in vivo in suitable laboratory animals or in vitro using recombinant DNA techniques. In a preferred embodiment, an antibody is a polyclonal antibody.

Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of anti-antisera is a rabbit, a mouse, a rat, a hamster or a guinea pig. Because of the relatively large blood volume of rabbits, a rabbit is a preferred choice for production of polyclonal antibodies.

Antibodies, both polyclonal and monoclonal, specific for DBP and DBP-derived epitopes may be prepared using conventional immunization techniques, as will be generally known to those of skill in the art. A composition containing antigenic epitopes of particular DBPs can be used to immunize one or more experimental animals, such as a rabbit or mouse, which will then proceed to produce specific antibodies against DBP peptide. Polyclonal antisera may be obtained, after allowing time for antibody generation, simply by bleeding the animal and preparing serum samples from the whole blood.

The amount of immunogen composition used in the production of polyclonal antibodies varies upon the nature of the immunogen, as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate mAbs (below).

One of the important features provided by the present invention is a polyclonal sera that is relatively homogenous with respect to the specificity of the antibodies therein. Typically, polyclonal antisera is derived from a variety of different "clones," i.e., B-cells of different lineage. mAbs, by contrast, are defined as coming from antibody-producing cells with a common B-cell ancestor, hence their "mono" clonality.

When peptides are used as antigens to raise polyclonal sera, one would expect considerably less variation in the clonal nature of the sera than if a whole antigen were employed. Unfortunately, if incomplete fragments of an epitope are presented, the peptide may very well assume multiple (and probably non-native) conformations. As a result, even short peptides can produce polyclonal antisera with relatively plural specificities and, unfortunately, an antisera that does not react or reacts poorly with the native molecule.

Polyclonal antisera according to present invention is produced against peptides that are predicted to comprise whole, intact epitopes. It is believed that these epitopes are, therefore, more stable in an immunologic sense and thus express a more consistent immunologic target for the immune system. Under this model, the number of potential B-cell clones that will respond to this peptide is considerably smaller and, hence, the homogeneity of the resulting sera will be higher. In various embodiments, the present invention provides for polyclonal antisera where the clonality, i.e., the percentage of clone reacting with the same molecular determinant, is at least 80%. Even higher clonality—90%, 95% or greater—is contemplated.

To obtain mAbs, one would also initially immunize an experimental animal, often preferably a mouse, with a DBP-containing composition. One would then, after a period of time sufficient to allow antibody generation, obtain a population of spleen or lymph cells from the animal. The spleen or lymph cells can then be fused with cell lines, such as human or mouse myeloma strains, to produce antibody-secreting hybridomas. These hybridomas may be isolated to obtain individual clones which can then be screened for production of antibody to the desired peptide.

Following immunization, spleen cells are removed and fused, using a standard fusion protocol with plasmacytoma cells to produce hybridomas secreting mAbs against DBP. Hybridomas which produce mAbs to the selected antigens are identified using standard techniques, such as ELISA and Western blot methods. Hybridoma clones can then be cultured in liquid media and the culture supernatants purified to provide the DBP-specific mAbs.

It is proposed that the mAbs of the present invention will also find useful application in immunochemical procedures, such as ELISA and Western blot methods, as well as other procedures such as immunoprecipitation, immunocytological methods, etc. which may utilize antibodies specific to DBPs. In particular, DBP antibodies may be used in immunoabsorbent protocols to purify native or recombinant DBPs or DBP-derived peptide species or synthetic or natural variants thereof.

The antibodies disclosed herein may be employed in antibody cloning protocols to obtain cDNAs or genes encoding DBPs from other species or organisms, or to identify proteins having significant homology to DBP. They may also be used in inhibition studies to analyze the effects of DBP in cells, tissues, or whole animals. Anti-DBP antibodies will also be useful in immunolocalization studies to analyze the distribution of bacteria expressing DBPs during cellular infection, for example, to determine the cellular or tissue-specific distribution of borrelias under different physiological conditions. A particularly useful application of such antibodies is in purifying native or recombinant DBPs, for example, using an antibody affinity column. The operation of all such immunological techniques will be known to those of skill in the art in light of the present disclosure.

4.14 DBP Compositions for Treating Borrelia Infections

DBP-specific antibody compositions are used to bind to the bacteria and prevent adhesion to host tissues. Moreover, antibody coated bacteria are more easily recognized by the immune system resulting in more efficient killing of the bacteria. Dcn, Lmn, Epn, Fmn, Bgn, etc., or other molecules mimicking specific structure(s) within host tissues that pathogenic bacteria attach, may be used to saturate the DBPs on the surface of the bacteria, thereby preventing adhesion. Alternatively, DBP derivatives, or other molecules mimicking DBP may be used to saturate the binding site within host tissues, resulting in the inhibition of bacterial adhesion. A third alternative provided by the invention is anti-DBP antibody compositions which bind to DBP both in vitro and in vivo. Such antibodies make the DBPs unavailable for attachment to Dcn, and therefore, the bacteria expressing cell surface DBPs are unable to adhere to host tissues via Dcn binding.

4.15 Recombinant Expression of DBP

Recombinant clones expressing the dbp nucleic acid segments may be used to prepare purified recombinant DBP (rDBP), purified rDBP-derived peptide antigens as well as mutant or variant recombinant protein species in significant quantities. The selected antigens, and variants thereof, are proposed to have significant utility in diagnosing and treating infections cause by borrelias and in particular, *B. burgdorferi, B. garinii, B. andersonii, B. japonica* and *B. afzelii*. For example, it is proposed that rDBPs, peptide variants thereof, and/or antibodies against such rDBPs may also be used in immunoassays to detect borrelias or as vaccines or immunotherapeutics to treat borrelia infections, and to prevent bacterial adhesion to ECM components such as Dcn in the same manner as native DBP compositions. Additionally, by application of techniques such as DNA mutagenesis, the present invention allows the ready preparation of so-called "second generation" molecules having modified or simplified protein structures. Second generation proteins will typically share one or more properties in common with the full-length antigen, such as a particular antigenic/immunogenic epitopic core sequence. Epitopic sequences can be provided on relatively short molecules prepared from knowledge of the peptide, or encoding DNA sequence information. Such variant molecules may not only be derived from selected immunogenic/antigenic regions of the protein structure, but may additionally, or alternatively, include one or more functionally equivalent amino acids selected on the basis of similarities or even differences with respect to the natural sequence. This is particularly desirable in the preparation of blocking antibodies which prevent bacterial adhesion to Dcn, as outlined herein.

4.16 Antibody Compositions and Formulations Thereof

Means for preparing and characterizing antibodies are well known in the art (See, e.g., Harlow and Lane (1988); incorporated herein by reference). The methods for generating mAbs generally begin along the same lines as those for preparing polyclonal antibodies. Briefly, a polyclonal antibody is prepared by immunizing an animal with an immunogenic composition in accordance with the present invention and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobenzoyl-N-hydroxysuccinimide ester, carbodiimide and bis-biazotized benzidine.

mAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified protein, polypeptide or peptide. The immunizing composition is administered in a manner effective to stimulate antibody producing cells. Rodents such as mice and rats are preferred animals, however, the use of rabbit, sheep or frog cells is also possible. The use of rats may provide certain advantages (Goding, 1986), but mice are preferred, with the BALB/c mouse being most preferred as this is most routinely used and generally gives a higher percentage of stable fusions.

Following immunization, somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately about $5 \times 10^7$ to about $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render them incapable of growing in certain selective media which support the growth of only the desired fused cells (hybridomas).

Any one of a number of myeloma cells may be used, as are known to those of skill in the art (Goding, 1986; Campbell, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (v/v) PEG, by Gefter et al. (1977). The use of electrically induced fusion methods is also appropriate (Goding, 1986).

Fusion procedures usually produce viable hybrids at low frequencies, about $1 \times 10^{-6}$ to about $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific mAb produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

4.17 Immunoassays

As noted, it is proposed that native and synthetically-derived peptides and peptide epitopes of the invention will find utility as immunogens, e.g., in connection with vaccine development, or as antigens in immunoassays for the detection of reactive antibodies. Turning first to immunoassays, in their most simple and direct sense, preferred immunoassays of the invention include the various types of enzyme linked immunosorbent assays (ELISAs), as are known to those of skill in the art. However, it will be readily appreciated that the utility of DBP-derived proteins and peptides is not limited to such assays, and that other useful embodiments include RIAs and other non-enzyme linked antibody binding assays and procedures.

In preferred ELISA assays, proteins or peptides incorporating DBP, rDBP, or DBP-derived protein antigen sequences are immobilized onto a selected surface, preferably a surface exhibiting a protein affinity, such as the wells of a polystyrene microtiter plate. After washing to remove incompletely adsorbed material, one would then generally desire to bind or coat a nonspecific protein that is known to be antigenically neutral with regard to the test antisera, such as bovine serum albumin (BSA) or casein, onto the well. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological extract to be tested in a manner conducive to immune complex (antigen/antibody) formation. Such conditions preferably include diluting the antisera with diluents such as BSA, bovine gamma globulin (BGG) and phosphate buffered saline (PBS)/Tween®. These added agents also tend to assist in the reduction of nonspecific background. The layered antisera is then allowed to incubate for, e.g., from 2 to 4 hours, at temperatures preferably on the order of about 25° to about 27° C. Following incubation, the antisera-contacted surface is washed so as to remove nonimmunocomplexed material. A preferred washing procedure includes washing with a solution such as PBS/Tween®, or borate buffer.

Following formation of specific immunocomplexes between the test sample and the bound antigen, and subsequent washing, the occurrence and the amount of immunocomplex formation may be determined by subjecting the complex to a second antibody having specificity for the first. Of course, in that the test sample will typically be of human origin, the second antibody will preferably be an antibody having specificity for human antibodies. To provide a detecting means, the second antibody will preferably have an associated detectable label, such as an enzyme label, that will generate a signal, such as color development upon incubating with an appropriate chromogenic substrate. Thus, for example, one will desire to contact and incubate the antisera-bound surface with a urease or peroxidase-conjugated anti-human IgG for a period of time and under conditions that favor the development of immunocomplex formation (e.g., incubation for 2 hours at room temperature in a PBS-containing solution such as PBS-Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectrum spectrophotometer.

ELISAs may be used in conjunction with the invention. In one such ELISA assay, proteins or peptides incorporating antigenic sequences of the present invention are immobilized onto a selected surface, preferably a surface exhibiting a protein affinity such as the wells of a polystyrene microtiter plate. After washing to remove incompletely adsorbed material, it is desirable to bind or coat the assay plate wells with a nonspecific protein that is known to be antigenically neutral with regard to the test antisera such as bovine serum albumin (BSA), casein or solutions of powdered milk. This allows for blocking of nonspecific adsorption sites on the immobilizing surface and thus reduces the background caused by nonspecific binding of antisera onto the surface.

4.18 Immunoprecipitation

The anti-DBP antibodies of the present invention are particularly useful for the isolation of DBP antigens by immunoprecipitation. Immunoprecipitation involves the separation of the target antigen component from a complex mixture, and is used to discriminate or isolate minute amounts of protein. For the isolation of cell-surface localized proteins such as DBP, peptides must be solubilized from the bacterial cell wall by treatment with enzymes such as lysozyme, lysostaphin or mutanolysin, or alternatively, into detergent micelles. Nonionic salts are preferred, since other agents such as bile salts, precipitate at acid pH or in the presence of bivalent cations.

In an alternative embodiment the antibodies of the present invention are useful for the close juxtaposition of two antigens. This is particularly useful for increasing the localized concentration of antigens, e.g., enzyme-substrate pairs.

In a related embodiment, antibodies of the present invention are useful for promoting the binding of Dcn to dbp gene products. Such binding is readily measured by monitoring ligand binding using well-known procedures. Detection of the binding may be accomplished by using radioactively labeled antibodies or alternatively, radioactively-labeled Dcn. Alternatively, assays employing biotin-labeled antibodies are also well-known in the art as described (Bayer and Wilchek, 1980).

4.19 Western Blots

The compositions of the present invention will find great use in immunoblot or western blot analysis. The anti-DBP antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. This is especially useful when the antigens studied are immunoglobulins (precluding the use of immunoglobulins binding bacterial cell wall components), the antigens studied cross-react with the detecting agent, or they migrate at the same relative molecular weight as a cross-reacting signal. Immunologically-based detection methods in conjunction with Western blotting (including enzymatically-, radiolabel-, or fluorescently-tagged secondary antibodies against the toxin moiety) are considered to be of particular use in this regard.

4.20 Vaccines

The present invention contemplates vaccines for use in both active and passive immunization embodiments. Immunogenic compositions proposed to be suitable for use as a vaccine may be prepared most readily directly from the novel immunogenic proteins and/or peptide epitopes described herein. Preferably the antigenic material is extensively dialyzed to remove undesired small molecular weight molecules and/or lyophilized for more ready formulation into a desired vehicle.

The preparation of vaccines that contain peptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables, either as liquid solutions or suspensions, solid forms suitable for solution in, or suspension in, liquid prior to injection may also be prepared. The preparation may also be emulsified. The active immunogenic ingredient is often mixed with excipients that are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants that enhance the effectiveness of the vaccines.

A composition comprising DBP or DBP-derived proteins and/or native or modified epitopic peptides therefrom could also be the basis for human vaccines. The preparation of such compositions that are essentially free from endotoxin can be achieved by following the published methodology, for example, U.S. Pat. No. 4,271,147 (incorporated herein by reference) discloses methods for the preparation of *Neisseria meningitidis* membrane proteins for use in vaccines.

DBP and DBP-derived epitope-based vaccines may be conventionally administered parenterally, by injection, for example, either subcutaneously or intramuscularly. Additional formulations that are suitable for other modes of administration include suppositories and, in some cases, oral formulations. For suppositories, traditional binders and carriers may include, for example, polyalkalene glycols or triglycerides: such suppositories may be formed from mixtures containing the active ingredient in the range of 0.5% to 10%, preferably 1–2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain 10–95% of active ingredient, preferably 25–70%.

The proteins may be formulated into the vaccine as neutral or salt forms. Pharmaceutically acceptable salts, include the acid addition salts (formed with the free amino groups of the peptide) and those that are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines may be administered in a manner compatible with the dosage formulation, and in such amount as will be therapeutically effective and immunogenic. The quantity to be administered depends on the subject to be treated, including, e.g., the capacity of the individual's immune system to synthesize antibodies, and the degree of protection desired. Precise amounts of active ingredient required to be administered will be readily determinable by the skilled practitioner. However, suitable dosage ranges are of the order of several hundred micrograms active ingredient per vaccination. Suitable regimes for initial administration and booster shots are also variable, but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the size of the host.

Various methods of achieving adjuvant effect for the vaccine includes use of agents such as aluminum hydroxide or phosphate (alum), commonly used as 0.05 to 0.1 percent solution in phosphate buffered saline, admixture with synthetic polymers of sugars (Carbopol®) used as 0.25% solution, aggregation of the protein in the vaccine by heat treatment with temperatures ranging between about 70° and about 101° C. for 30 second to 2 minute periods respectively. Aggregation by reactivating with pepsin treated F(ab) antibodies to albumin, mixture with bacterial cells such as *C. parvum* or endotoxins or lipopolysaccharide components of gram-negative bacteria, emulsion in physiologically acceptable oil vehicles such as mannide monooleate (Aracel-A™) or emulsion with 20 percent solution of a perfluorocarbon (Fluosol-DA™) used as a block substitute may also be employed.

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1–5 years, usually three years, will be desirable to maintain protective levels of the antibodies. The course of the immunization may be followed by assays for antibodies for the supernatant antigens. The assays may be performed by labeling with conventional labels, such as radionuclides, enzymes, fluorescers, and the like. These techniques are well known and may be found in a wide variety of patents, such as U.S. Pat. Nos. 3,791,932; 4,174,384 and 3,949,064, as illustrative of these types of assays.

Of course, in light of the new technology on DNA vaccination, it will be understood that virtually all such vaccination regimens will be appropriate for use with DNA vectors and constructs, as described by Ulmer et al. (1993), Tang et al. (1992), Cox et al. (1993), Fynan et al. (1993), Wang et al. (1993) and Whitton et al. (1993), each incorporated herein by reference. In addition to parenteral routes of DNA inoculation, including intramuscular and intravenous injections, mucosal vaccination is also contemplated, as may be achieved by administering drops of DNA compositions to the nares or trachea. It is particularly contemplated that a gene-gun could be used to deliver an effectively immunizing amount of DNA to the epidermis (Fynan et al., 1993).

The present invention contemplates vaccines for use in both active and passive immunization embodiments. Immunogenic compositions, proposed to be suitable for use as a vaccine, may be prepared most readily directly from immunogenic peptides prepared in a manner disclosed herein. Preferably the antigenic material is extensively dialyzed to remove undesired small molecular weight molecules and/or lyophilized for more ready formulation into a desired vehicle. The preparation of vaccines which contain peptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables. Either as liquid solutions or suspensions: solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants which enhance the effectiveness of the vaccines.

4.21 Pharmaceutical Compositions

The pharmaceutical compositions disclosed herein may be orally administered, for example, with an inert diluent or with an assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral prophylaxis the polypeptide may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

The composition can be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

4.22 Screening Assays

Host cells that have been transformed could be used in the screening of natural and artificially derived compounds or mixtures to select those that are capable of complexing with the DBP and DBP-derived proteins of the present invention. This could be useful in the search for compounds that inhibit or otherwise disrupt, or even enhance the ability of the microorganism to bind Dcn. It is contemplated that effective pharmaceutical agents could be developed by identifying compounds that complex with the particular DBP epitopes, including, for example, compounds isolated from natural sources, such as plant, animal and marine sources, and various synthetic compounds. Natural or man-made compounds that may be tested in this manner could also include various minerals and proteins, peptides or antibodies.

4.23. Epitopic Core Sequences

The present invention is also directed to protein or peptide compositions, free from total cells and other peptides, which comprise a purified protein or peptide which incorporates an epitope that is immunologically cross-reactive with one or more of the antibodies of the present invention.

As used herein, the term "incorporating an epitope(s) that is immunologically cross-reactive with one or more anti-DBP antibodies" is intended to refer to a peptide or protein antigen which includes a primary, secondary or tertiary structure similar to an epitope located within a DBP polypeptide. The level of similarity will generally be to such a degree that monoclonal or polyclonal antibodies directed against the DBP polypeptide will also bind to, react with, or otherwise recognize, the cross-reactive peptide or protein antigen. Various immunoassay methods may be employed in conjunction with such antibodies, such as, for example, Western blotting, ELISA, RIA, and the like, all of which are known to those of skill in the art.

The identification of DBP epitopes such as those derived from dbp or dbp-like gene products and/or their functional equivalents, suitable for use in vaccines is a relatively straightforward matter. For example, one may employ the methods of Hopp, as taught in U.S. Pat. No. 4,554,101, incorporated herein by reference, which teaches the identification and preparation of epitopes from amino acid sequences on the basis of hydrophilicity. The methods described in several other papers, and software programs based thereon, can also be used to identify epitopic core sequences (see, for example, Jameson and Wolf, 1988; Wolf et al., 1988; U.S. Pat. No. 4,554,101). The amino acid sequence of these "epitopic core sequences" may then be readily incorporated into peptides, either through the application of peptide synthesis or recombinant technology.

Preferred peptides for use in accordance with the present invention will generally be on the order of about 5 to about 25 amino acids in length, and more preferably about 8 to about 20 amino acids in length. It is proposed that shorter antigenic peptide sequences will provide advantages in certain circumstances, for example, in the preparation of vaccines or in immunologic detection assays. Exemplary advantages include the ease of preparation and purification, the relatively low cost and improved reproducibility of production, and advantageous biodistribution.

It is proposed that particular advantages of the present invention may be realized through the preparation of synthetic peptides which include modified and/or extended epitopic/immunogenic core sequences which result in a "universal" epitopic peptide directed to DBP and DBP-related sequences, or other domains which bind Dcn or related proteoglycans. It is proposed that these regions represent those which are most likely to promote T-cell or B-cell stimulation in an animal, and, hence, elicit specific antibody production in such an animal.

An epitopic core sequence, as used herein, is a relatively short stretch of amino acids that is "complementary" to, and therefore will bind, antigen binding sites on DBP epitope-specific antibodies. Additionally or alternatively, an epitopic core sequence is one that will elicit antibodies that are cross-reactive with antibodies directed against the peptide compositions of the present invention. It will be understood that in the context of the present disclosure, the term "complementary" refers to amino acids or peptides that exhibit an attractive force towards each other. Thus, certain epitope core sequences of the present invention may be operationally defined in terms of their ability to compete with or perhaps displace the binding of the desired protein antigen with the corresponding protein-directed antisera.

In general, the size of the polypeptide antigen is not believed to be particularly crucial, so long as it is at least large enough to carry the identified core sequence or sequences. The smallest useful core sequence expected by the present disclosure would generally be on the order of about 5 amino acids in length, with sequences on the order of 8 or 25 being more preferred. Thus, this size will generally correspond to the smallest peptide antigens prepared in accordance with the invention. However, the size of the antigen may be larger where desired, so long as it contains a basic epitopic core sequence.

The identification of epitopic core sequences is known to those of skill in the art, for example, as described in U.S. Pat. No. 4,554,101, incorporated herein by reference, which teaches the identification and preparation of epitopes from amino acid sequences on the basis of hydrophilicity. Moreover, numerous computer programs are available for use in predicting antigenic portions of proteins (see e.g., Jameson and Wolf, 1988; Wolf et al., 1988). Computerized peptide sequence analysis programs (e.g., DNAStar® software, DNAStar, Inc., Madison, Wis.) may also be useful in designing synthetic DBP peptides and peptide analogs in accordance with the present disclosure. The peptides provided by this invention are ideal targets for use as vaccines or immunoreagents for the treatment of various borrelia-related diseases, and in particular, those caused by species which contain DBP and DBP-encoding genes, and hence those which express either dbp or dbp-like gene product(s) on the cell surface and in turn interact with ECM components such as Dcn to promote bacterial adhesion to host cells. In this regard, particular advantages may be realized through the preparation of synthetic peptides that include epitopic/immunogenic core sequences. These epitopic core sequences may be identified as hydrophilic and/or mobile regions of the polypeptides or those that include a T cell motif. It is known in the art that such regions represent those that are most likely to promote B cell or T cell stimulation, and, hence, elicit specific antibody production.

In the case of preventing bacterial adhesion, the preparation of epitopes which produce antibodies which inhibit the interaction of a Dcn-specific gene product and Dcn or proteoglycans which are structurally similar to Dcn such as Lmn, Bgn, Epn, or Fmn is particularly desirable.

To confirm that a protein or peptide is immunologically cross-reactive with, or a biological functional equivalent of, one or more epitopes of the disclosed peptides is also a straightforward matter. This can be readily determined using specific assays, e.g., of a single proposed epitopic sequence, or using more general screens, e.g., of a pool of randomly generated synthetic peptides or protein fragments. The screening assays may be employed to identify either equivalent antigens or cross-reactive antibodies. In any event, the principle is the same, i.e., based upon competition for binding sites between antibodies and antigens.

Suitable competition assays that may be employed include protocols based upon immunohistochemical assays, ELISAs, RIAs, Western or dot blotting and the like. In any of the competitive assays, one of the binding components, generally the known element, such as the DBP-derived peptide, or a known antibody, will be labeled with a detectable label and the test components, that generally remain unlabeled, will be tested for their ability to reduce the amount of label that is bound to the corresponding reactive antibody or antigen.

As an exemplary embodiment, to conduct a competition study between a DBP and any test antigen, one would first label DBP with a detectable label, such as, e.g., biotin or an enzymatic, radioactive or fluorogenic label, to enable subsequent identification. One would then incubate the labeled antigen with the other, test, antigen to be examined at various ratios (e.g., 1:1, 1:10 and 1:100) and, after mixing, one would then add the mixture to an antibody of the present invention. Preferably, the known antibody would be immobilized, e.g., by attaching to an ELISA plate. The ability of the mixture to bind to the antibody would be determined by detecting the presence of the specifically bound label. This value would then be compared to a control value in which no potentially competing (test) antigen was included in the incubation.

The assay may be any one of a range of immunological assays based upon hybridization, and the reactive antigens would be detected by means of detecting their label, e.g., using streptavidin in the case of biotinylated antigens or by using a chromogenic substrate in connection with an enzymatic label or by simply detecting a radioactive or fluorescent label. An antigen that binds to the same antibody as DBP, for example, will be able to effectively compete for binding to and thus will significantly reduce DBP binding, as evidenced by a reduction in the amount of label detected.

The reactivity of the labeled antigen, e.g., a DBP composition, in the absence of any test antigen would be the control high value. The control low value would be obtained by incubating the labeled antigen with an excess of unlabeled DBP antigen, when competition would occur and reduce binding. A significant reduction in labeled antigen reactivity in the presence of a test antigen is indicative of a test antigen that is "cross-reactive", i.e., that has binding affinity for the same antibody. "A significant reduction", in terms of the present application, may be defined as a reproducible (i.e., consistently observed) reduction in binding.

In addition to the peptidyl compounds described herein, the inventors also contemplate that other sterically similar compounds may be formulated to mimic the key portions of the peptide structure. Such compounds, which may be termed peptidomimetics, may be used in the same manner as the peptides of the invention and hence are also functional equivalents. The generation of a structural functional equivalent may be achieved by the techniques of modelling and chemical design known to those of skill in the art. It will be understood that all such sterically similar constructs fall within the scope of the present invention.

Syntheses of epitopic sequences, or peptides which include an antigenic epitope within their sequence, are readily achieved using conventional synthetic techniques such as the solid phase method (e.g., through the use of a commercially-available peptide synthesizer such as an Applied Biosystems Model 430A Peptide Synthesizer). Peptide antigens synthesized in this manner may then be aliquoted in predetermined amounts and stored in conventional manners, such as in aqueous solutions or, even more preferably, in a powder or lyophilized state pending use.

In general, due to the relative stability of peptides, they may be readily stored in aqueous solutions for fairly long periods of time if desired, e.g., up to six months or more, in virtually any aqueous solution without appreciable degradation or loss of antigenic activity. However, where extended aqueous storage is contemplated it will generally be desirable to include agents including buffers such as Tris or phosphate buffers to maintain a pH of about 7.0 to about 7.5. Moreover, it may be desirable to include agents which will inhibit microbial growth, such as sodium azide or Merthiolate. For extended storage in an aqueous state it will be desirable to store the solutions at 4° C., or more preferably, frozen. Of course, where the peptides are stored in a lyophilized or powdered state, they may be stored virtually indefinitely, e.g., in metered aliquots that may be rehydrated with a predetermined amount of water (preferably distilled) or buffer prior to use.

4.24 Site-Specific Mutagenesis

Site-specific mutagenesis is a technique useful in the preparation of individual peptides, or biologically functional equivalent proteins or peptides, through specific mutagenesis of the underlying DNA. The technique, well-known to those of skill in the art, further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 14 to about 25 nucleotides in length is preferred, with about 5 to about 10 residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially-available and their use is generally well-known to those skilled in the art. Double-stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double-stranded vector which includes within its sequence a DNA sequence which encodes the desired peptide. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected peptide-encoding DNA segments using site-directed mutagenesis is provided as a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al., 1994; Segal, 1976; Prokop and Bajpai, 1991; Kuby, 1994; and Maniatis et al., 1982, each incorporated herein by reference, for that purpose.

The PCR™-based strand overlap extension (SOE) (Ho et al., 1989) for site-directed mutagenesis is particularly preferred for site-directed mutagenesis of the nucleic acid compositions of the present invention. The techniques of PCR™ are well-known to those of skill in the art, as described hereinabove. The SOE procedure involves a two-step PCR™ protocol, in which a complementary pair of internal primers (B and C) are used to introduce the appropriate nucleotide changes into the wild-type sequence. In two separate reactions, flanking PCR™ primer A (restriction site incorporated into the oligo) and primer D (restriction site incorporated into the oligo) are used in conjunction with primers B and C, respectively to generate PCR™ products AB and CD. The PCR™ products are purified by agarose gel electrophoresis and the two overlapping PCR™ fragments AB and CD are combined with flanking primers A and D and used in a second PCR™ reaction. The amplified PCR™ product is agarose gel purified, digested with the appropriate enzymes, ligated into an expression vector, and transformed into *E. coli* JM101, XL1-Blue™ (Stratagene, LaJolla, Calif.), JM105, or TG1 (Carter et al., 1985) cells. Clones are isolated and the mutations are confirmed by sequencing of the isolated plasmids. Beginning with the native dbp gene sequence, suitable clones and subclones may be made in BG26:pB/2.5(5), from which site-specific mutagenesis may be performed. Alternatively, the use of pET vectors (Novagen, Inc., Madison, Wis.; U.S. Pat. No. 4,952,496, disclosed herein by reference) is contemplated in the recombinant production of DBP and DBP-derived polypeptides.

4.25 Biological Functional Equivalents

Modification and changes may be made in the structure of the peptides of the present invention and DNA segments which encode them and still obtain a functional molecule that encodes a protein or peptide with desirable characteristics. The following is a discussion based upon changing the amino acids of a protein to create an equivalent, or even an improved, second-generation molecule. The amino acid changes may be achieved by changing the codons of the DNA sequence, according to Table 1.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

TABLE 1

| Amino Acids | | Codons | | | | |
|---|---|---|---|---|---|---|
| Alanine | Ala A | GCA | GCC | GCG | GCU | |
| Cysteine | Cys C | UGC | UGU | | | |

TABLE 1-continued

| | | | | | | |
|---|---|---|---|---|---|---|
| Aspartic acid | Asp D | GAC | GAU | | | |
| Glutamic acid | Glu E | GAA | GAG | | | |
| Phenylalanine | Phe F | UUC | UUU | | | |
| Glycine | Gly G | GGA | GGC | GGG | GGU | |
| Histidine | His H | CAC | CAU | | | |
| Isoleucine | Ile I | AUA | AUC | AUU | | |
| Lysine | Lys K | AAA | AAG | | | |
| Leucine | Leu L | UUA | UUG | CUA | CUC | CUG CUU |
| Methionine | Met M | AUG | | | | |
| Asparagine | Asn N | AAC | AAU | | | |
| Proline | Pro P | CCA | CCC | CCG | CCU | |
| Glutamine | Gln Q | CAA | CAG | | | |
| Arginine | Arg R | AGA | AGG | CGA | CGC | CGG CGU |
| Serine | Ser S | AGC | AGU | UCA | UCC | UCG UCU |
| Threonine | Thr T | ACA | ACC | ACG | ACU | |
| Valine | Val V | GUA | GUC | GUG | GUU | |
| Tryptophan | Trp W | UGG | | | | |
| Tyrosine | Tyr Y | UAC | UAU | | | |

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred. It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

5. EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

5.1 EXAMPLE 1

Adherence of B. burgdorferi To Dcn

5.1.1 Materials and Methods

5.1.1.1 Bacterial Strains and Culture

Low-passage (fewer than 10 in vitro passages) *B. burgdorferi* N40 was used for all studies unless specified otherwise. High-passage *B. burgdorferi* B31 (ATCC 35210) has undergone numerous in vitro passages. *B. burgdorferi* was cultured in BSKII medium at 34° C. (Barbour, 1984). Cultures were incubated in a GasPak chamber (BBL, Baltimore, Md.) with 3 to 6% $O_2$ until the cells reached the mid-to late-log phase. Cells were harvested by centrifugation at 14,500×g for 30 min and gently washed in sterile, filtered phosphate-buffered saline (PBS; pH 7.4; 0.137 M NaCl, 3 mM KCl, 4 mM $Na_2HPO_4$, 1 mM $KH_2PO_4$) three times. The spirochetes were resuspended in PBS, and the cell density was adjusted to $10^9$ organisms per ml by use of a reference standard curve relating the $A_{600}$ to the organism number as determined by dark-field microscopy. The spirochetes were stored at 4° C. and retained Dcn-binding activity for up to 1 month.

*Staphylococcus aureus* Phillips (clinical osteomyelitis isolate) and PH100 (collagen adhesion-negative isogenic mutant of strain Phillips) were grown in brain heart fusion broth (Difco Laboratories, Detroit, Mich.) overnight at 37° C. without antibiotics (Patti et al., 1994). The cells were washed and resuspended in PBS.

5.1.1.2 Labeling of Dcn

Bovine Dcn from fetal skin was purified as described previously (Choi et al., 1989). Dcn was labeled with NHS-LC-Biotin (Pierce, Rockford, Ill.) as described in the manufacturer's directions and stored at −20° C.

Dcn was iodinated by the chloramine T method as described by Hunter (1978). Five microliters (0.5 mCi) of $Na^{125}I$ [Amersham Life Science, Arlington Heights, Ill.) was used to label 100 μg of Dcn in 1 ml of PBS. The specific activity of the radiolabeled proteoglycan was estimated to be approximately $2 \times 10^6$ cpm/μg.

5.1.1.3 Attachment Assay

Immulon-1® microtiter plate wells (Dynatech Labs, Chantilly, Va.) were coated with Dcn, collagen type I from rat tail (Collaborative Biomedical Products, Bedford, Mass.), or collagen type III from calf skin (Sigma Chemical Co., St. Louis, Mo.). Dcn was dissolved in PBS, and collagens type I and III were dissolved in 20 mM acetic acid and adjusted to a concentration of 1 mg/ml. Two micrograms of each protein in a total volume of 50 μl was incubated in the microtiter plate wells at 4° C. overnight. The wells were decanted and washed with 200 μl of PBS containing 0.1% bovine serum albumin (BSA) three times for 5 min each. Additional protein-binding sites were blocked by incubating the microtiter wells with 100 μl of a 1-mg/ml concentration of BSA in PBS for 2 h. The wells were washed and incubated for 1 h with 25 μl of a suspension containing $10^9$ organisms per ml of PBS-0.1% bovine serum albumin (BSA) three times for 5 min each. Additional protein-binding sites were blocked by incubating the microtiter wells with 100 μl of a 1 mg/ml concentration of BSA in PBS for 2 h. The wells were washed and incubated for 1 h with 25 μl of a suspension containing $10^9$ organisms per ml of PBS-0.1% BSA. After washing the wells to remove unattached bacteria, the wells were incubated for 1 h with 100 μl of a 1:1,000 dilution of anti-*B. burgdorferi* rabbit serum (rabbits were inoculated with $10^8$ organisms of washed *B. burgdorferi* B31 per ml, and serum was collected 3 weeks postinoculation) in PBS-0.1% BSA. This step was omitted when assaying *S. aureus* attachment because protein A on the surface of *S. aureus* binds the secondary antibody directly. The wells were washed and subsequently incubated with 100 μl of a 1:1,000 dilution of goat anti-rabbit alkaline phosphatase conjugate (Bio-Rad, Hercules, Calif.) in PBS-0.1% BSA for 1 h and then washed and subsequently incubated with 100 μl of a 1-mg/ml concentration of Sigma 104 phosphatase substrate dissolved in 1 M diethanolamine-0.5 mM $MgCl_2$ (pH 9.8) at 37° C. for 30 to 45 min. The $A_{405}$ was determined in a microplate reader (Molecular Devices, Menlo Park, Calif.).

To assay inhibition of attachment, 100-μl suspensions containing $10^9$ organisms of *B. burgdorferi* N40 per ml were preincubated with 2 μg of the potential competitor (or as otherwise stated) for 1 h at room temperature. The potential competitors included Dcn, BSA (The Binding Site, San Diego, Calif., or ICN, Costa Mesa, Calif.), fetuin type IV (Sigma), thyroglobulin type II (Sigma), fibrinogen (KabiVitrium, Stockholm, Sweden), aggrecan (Isolated from bovine cartilage), heparin (Sigma), and chondroitin sulfate type A (from whale and shark cartilage; Sigma). One microliter of 10% BSA was added to obtain a final concentration of 1% BSA. The suspensions were added to protein-coated microtiter wells, and the assay was continued as described above.

5.1.1.4 Binding Assay

*B. burgdorferi* N40 cells ($1.5 \times 10^8$) were incubated with approximately 50,000 cpm of $^{125}I$-labeled Dcn in a final volume of 0.5 ml of PBS containing 1% BSA for 1 h at room temperature. The reaction was stopped by the addition of 3 ml of PBS containing 1% BSA; centrifugation at 6,000×g for 30 min followed. Radiolabeled Dcn associated with the bacterial pellet was quantitated in a Cobra II Auto-Gamma Counter (Packard Instruments, Meriden, Conn.). Radioactivity recovered in tubes incubated as described above, but without bacteria, was regarded as background and subtracted from the values obtained with bacteria. Time dependence of binding was assayed by incubating *B. burgdorferi* with $^{125}I$-labeled Dcn as described above and stopping the reaction at the specified times.

Inhibition of binding was assayed by preincubating washed *B. burgdorferi* N40 ($10^8$ organisms per ml) with 5 μg of unlabeled competitor for 30 min. Radiolabeled Dcn (50,000 cpm) was added, and the incubation was continued for another 30 min. The reaction was stopped by the addition of 3 ml of PBS containing 1% BSA, and the assay was continued as described above.

5.1.1.5 SDS-PAGE and Western Blot-Type Assay

Proteins from *B. burgdorferi* whole-cell lysates were subjected to sodium dodecyl sulfate-polyacrylamide gel electrophoresis (SDS-PAGE) (Laemmli, 1970) and probed with a Western blot-type assay. For SDS-PAGE, $2 \times 10^7$ *B. burgdorferi* cells were lysed by boiling SDS under reducing conditions and subjected to electrophoresis through a 5 to 15% gradient acrylamide slab gel at 175 V for 30 min, or through a 12.5% acrylamide resolving gel at 200V for 35 min. For Western blot-type assays, the proteins were transferred from the polyacrylamide gel to a nitrocellulose membrane (Schleicher & Schuell, Inc., Keene, N.H.) by electroblot for 1.5 h at 4° C. Additional protein-binding sites on the membrane were blocked by incubating in 3% nonfat dry milk in TBST (0.15 M NaCl, 20 mM Tris-HCl, 0.05% Tween-20® [pH 7.4]) for 2 h at room temperature or overnight at 4° C. The membrane was incubated at room temperature with 0.1 $\mu$g of biotin-labeled Dcn per ml of TBST for 1 h, washed, and incubated with a 1:3,000 dilution of avidin D horseradish peroxidase conjugate (Vector Laboratories, Burlingame, Calif.) in TBST for 1 h. The membrane was washed and incubated in 1 ml of Enhanced Chemi-Luminescence detection reagents 1 and 2 (Amersham Life Science) for 1 min and exposed to X-ray film for 1 to 5 s.

5.1.2 Results 5.1.2.1 *B. burgdorferi* Adheres to Dcn

To determine whether any of the major macromolecular components of the dermal collagen fibers (i.e. collagens type I and III and Dcn) can support the adherence of *B. burgdorferi*, the inventors used an in vitro attachment assay. Microtiter wells were coated with Dcn or collagens, and a suspension of spirochetes was incubated for 1 h in the protein-coated wells. Adherent spirochetes were detected by an immunological method after nonadherent organisms were removed by washing. *B. burgdorferi* N40 adhered to wells coated with Dcn, whereas spirochete adherence to collagen-coated wells was only marginally greater than adherence to BSA-coated wells. Adherent spirochetes were detected by an immunological method after nonadherent organisms were removed by washing. *B. burgdorferi* N40 adhered to wells coated with Dcn, whereas spirochete adherence to collagen-coated wells was only marginally greater than adherence to BSA-coated controls wells. Furthermore, in this enzyme-linked immunosorbent assay (ELISA)-type test, the signals from the collagen-coated wells incubated with *B. burgdorferi* were comparable to those from protein-coated wells incubated in the absence of bacteria. As a control, the inventors demonstrated that the collagen-coated wells could support adherence of *S. aureus* Phillips, which expresses a collagen adhesin, but could not support adherence of strain PH100, a collagen adhesin-negative mutant. These data demonstrate that *B. burgdorferi* N40 adhered to Dcn but not to the other main components of dermal collagen fibers.

When the adherence of *B. burgdorferi* to Dcn-coated microtiter wells was assayed as a function of time, a time-dependent process in which maximal adherence was reached at ~1 h was observed. Continuing the incubation for another hour did not result in an increased number of adhering bacteria.

*B. burgdorferi* also appears to recognize soluble Dcn. Preincubation of the spirochetes with increasing concentrations of soluble Dcn resulted in a progressively reduced adherence to the Dcn substrate. A 50% reduction in attachment was observed when $2.5 \times 10^7$ spirochetes were preincubated with 0.1 $\mu$g of Dcn.

To determine the specificity of *B. burgdorferi* attachment to Dcn-coated wells, the inventors attempted to inhibit such attachment by preincubation of the spirochetes with various soluble extracellular components, such as fetuin, thyroglobulin, fibrinogen, aggrecan, and chondroitin sulfate chains. *B. burgdorferi* was preincubated with each component individually for 1 h, and the suspensions were transferred to microtiter wells whether the spirochetes were allowed to attach to Dcn-coated wells. Dcn inhibited attachment by 100%, whereas the other potential inhibitors only marginally affected attachment of the spirochetes, resulting in less than 20% inhibition. *B. burgdorferi* attachment to Dcn thus appears to be highly specific.

5.1.2.2 *B. burgdorferi* binds soluble $^{125}$I-labeled Dcn

A modified in vitro binding assay was used to determine whether *B. burgdorferi* binds to soluble $^{125}$I-labeled Dcn. Spirochetes were incubated in a suspension containing PBS, 1% BSA, and $^{125}$I-labeled Dcn. At the end of the incubation, the bacteria were collected by centrifugation and the amount of Dcn bound was assayed by measuring radioactivity in the pellet.

When binding was assayed as a function of time from 0 to 120 min, maximum binding was achieved in 15 min and remained constant for up to 2 h. Prolonged incubation for 3 to 4 h often resulted in a decrease of binding. A high-passage isolate of *B. burgdorferi* B31 showed no binding at any time points.

To correlate these results with the results of the attachment assay, inhibition of *B. burgdorferi* binding of $^{125}$I-labeled Dcn with different unlabeled components in suspension was attempted. The spirochetes were preincubated with the unlabeled potential competitor for 30 min in the absence of radiolabeled Dcn. After the addition of $^{125}$I-labeled Dcn, the incubation was continued for another 30 min. Dcn inhibited the binding of the radiolabeled ligand by 63%, whereas the other potential inhibitors tested (aggrecan, thyroglobulin, BSA, fetuin, chondroitin sulfate, fibrinogen, and heparin) were essentially without effect, all reducing binding by less than 10%. Thus, the effect of the unlabeled inhibitors on bacterial binding of soluble $^{125}$I-labeled Dcn is similar to that on the attachment of *B. burgdorferi* to Dcn substrates, indicating that the same bacterial molecule(s) is involved.

In attempts to determine which domain of Dcn is involved in binding to the spirochete, the inventors attempted to inhibit *B. burgdorferi* binding to intact $^{125}$I-labeled Dcn by use of isolated core protein, isolated GAG chain, or an equimolar mixture of both (Bidanset et al., 1992). Binding was inhibited by intact proteoglycan (containing the GAG chain covalently attached to the core protein) but was not inhibited by isolated core protein, isolated GAG chain, or a mixture of both.

When *B. burgdorferi* was incubated with increasing amounts of $^{125}$I-labeled Dcn, a concentration-dependent binding of the ligand was observed. Radioactivity recovered in tubes incubated in the absence of bacteria (nonspecific binding) also increased as the amount of labeled Dcn increased. Specific bacterial binding (total binding minus nonspecific binding) of $^{125}$I-labeled Dcn appeared to approach saturation. From these data, an approximate $K_d$ value was estimated for the interaction as well as the number (n) of Dcn-binding sites per bacteria. $[S]_{bound}/[S]_{free}$ was plotted versus $[S]_{bound}$, where the substrate, S, is Dcn. The $k_d$ was calculated at $3 \times 10^{-7}$ $M^{-1}$, indicating a moderate affinity, and n was calculated to be approximately $5 \times 10^4$ Dcn-binding sites per organism, indicating a small copy number. Although the standard deviation for Dcn bound is large, these values are semi-quantitative estimates of $K_d$ and n.

5.1.2.3 Identification of DBPs from *B. burgdorferi*

In an attempt to identify distinct DBPs expressed by *B. burgdorferi*, a Western lot-type assay with biotin-labeled Dcn was used as the probe. Proteins from whole-cell *B. burgdorferi* lysates were separated by SDS-PAGE under reducing conditions and transferred to a nitrocellulose membrane. After blocking additional protein-binding sites with a solution containing 3% nonfat dry milk, biotin-labeled Dcn was allowed to bind to proteins on the membrane, followed by binding of horseradish peroxidase-conjugated avidin to the biotin-labeled Dcn. DBPs were visualized by chemiluminescence. This assay revealed the presence of two DBPs with apparent molecular masses of 19 and 20 kDa in the mixture of proteins from *B. burgdorferi* N40. SDS-PAGE followed by staining with Coomassie brilliant blue indicated that these proteins constitute a small portion of the total proteins of *B. burgdorferi.* The two DBPs run directly beneath OspC (the prominent band at ~21 kDa) but are hardly visible, if at all, by Coomassie blue stain. When proteins from the high-passage, non-Dcn-binding B31 strain were analyzed in the same manner, no DBPs could be detected.

The inventors also attempted the inhibition of binding of biotin-labeled Dcn to *B. burgdorferi* proteins in the Western blot-type assay. The membrane was preincubated with the same unlabeled proteins as those used in attempts to block bacterial attachment to Dcn substrate or to inhibit the binding of $^{125}$I-labeled Dcn to intact spirochetes. The same type of specificity was observed in all three assays. Furthermore, the presence of isolated GAG chain or core protein did not interfere with binding of biotin-labeled Dcn to *B. burgdorferi* proteins. Taken together, these data suggest that the 19- and 20-kDa proteins identified as DBPs are responsible for binding of $^{125}$I-labeled Dcn to intact spirochetes and mediate adherence of bacteria to Dcn substrates.

Previous studies have revealed that *B. burgdorferi* is predominantly an extracellular pathogen and that the spirochetes are often found in intimate association with collagen fibers (Barthold et al., 1991; 1992; 1993; Duray, 1992). On the basis of this association, the inventors hypothesized that *B. burgdorferi* may express adhesins that specifically recognize a component of collagen fibers. In the skin, a tissue where *B. burgdorfei* is consistently found, the collagen network is composed mainly of collagen types I and III and the proteoglycan Dcn, which is associated with the collagen fibers.

*B. burgdorferi* adhered to substrata composed of Dcn but did not adhere to collagens type I or III. These data suggest that Dcn is a possible target for *B. burgdorferi* adherence in the skin. Previously, *B. burgdorferi* adherence to heparin Isaacs, 1994) and $\alpha_{IIb}\beta_3$ integrin (Coburn et al., 1993; 1994) has been reported. Furthermore, heparin inhibits the adherence of *B. burgdorferi* to cultured HeLa cells (Isaacs, 1994) but, as shown in this study, does not affect the binding of Dcn to the spirochete. *B. burgdorferi* most likely possesses several mechanisms of host tissue adherence; however, it is unlikely that any of the previously described adherence mechanisms are responsible for the observed colonization of collagen fibers in the dermis.

*B. burgdorferi* also binds to soluble Dcn in a process that exhibits saturation kinetics and occurs in a time- and concentration-dependent manner. Maximal binding was achieved more quickly when Dcn was in solution than when it was immobilized onto microtiter wells. The reason for this discrepancy is unknown. Both the binding of soluble $^{125}$I-labeled Dcn and the attachment of spirochetes to a Dcn substrate were effectively inhibited by Dcn. Other extracellular matrix proteins had only marginal effects, suggesting a high degree of specificity. Furthermore, neither isolated core protein nor GAG chain alone or in combination could inhibit binding.

The Borrelia binding site on the Dcn molecule has not been identified. Presumably, Dcn binds both collagen and borrelias at once, with the two interactions involving different sites on the proteoglycan. The requirement of intact Dcn adhesin on the spirochete may recognize a conformational motif that is destroyed upon separation of the core protein and the GAG chain.

The $K_d$ for the binding of *B. burgdorferi* to Dcn was estimated to be approximately $3\times10^{-7}$ $M^{-1}$, indicating moderate affinity. The number of binding sites, n, was calculated to be approximately $5\times10^4$ copies per organism, which is a low copy number. SDS-PAGE analysis also seems to indicate that the DBPs are not abundant *B. burgdorferi* proteins.

By Western blot-type assay, two putative Dcn adhesins with apparent molecular masses of 19 and 20 kDa were identified. The 19-kDa protein may be a truncated product derived from the same gene as the 20-kDa protein; alternatively, the two proteins may be genetically distinct. These data demonstrate that two proteins expressed by *B. burgdorferi* N40 may act as adhesins mediating attachment of spirochetes to dermal collagen via Dcn. Several other *B. burgdorferi* strains, including low-passage Sh-2.82 (*Ixodes dammini* tick isolate from Shelter Island, N.Y.), B31 (Barbour, 1984), and 297 (Isaacs, 1994), also bind $^{125}$I-labeled Dcn and express DBPs in the 20-kDa molecular mass range.

5.2 Example 2

Partial Purification of Native *B. burgdorferi* DbpA and DbpB

DBPs were partially purified by extracting membranes of *B. burgdorferi* strain N-40. To approximately $1\times10^9$ organisms/ml phosphate-buffered saline (PBS) was added N-octyl-glucopyranoside to a concentration of 1.5%. The mixture was incubated twenty min at room temperature, rotating end over end. The incubated mixture was spun down at 30,000 rpm for 5 min, and the supernatant containing the extracted membrane constituents was removed. The supernatant was dialyzed against PBS overnight at 4° C., changing the buffer once. The dialyzed membrane supernatant was then filtered thorough a 0.2 μm filter and poured through a Dcn affinity column.

The Dcn affinity column was prepared by first purifying Dcn from fetal bovine skin according to the method described by Choi. Purified Dcn was then covalently linked to CNBr-activated Sepharose® 4B (Pharmacia, Uppsala, SWEDEN), according to the manufacturer's instructions. The 2.0 ml Dcn column was equilibrated with PBS at room temperature, and the membrane preparation was poured through the column, followed by a 10 column volume wash with PBS. Protein bound to the Dcn column was eluted with 1 M NaCl, and eight 0.5 ml fractions were collected.

Twenty microliters of each collected fraction was electrophoresed in duplicate 5–15% gradient SDS polyacrylamide gels. One gel was stained with Coomassie Blue, and showed one major band at about 20 kDa. The second gel was transferred to nitrocellulose and probed with Dcn labeled with NHS-LC-Biotin (Pierce, Rockford, Ill.) according to the manufacturer's instructions. This biotinylated Western blot showed two Dcn-bound bands, one at about 18–19 kDa, and another at about 20 kDa.

A portion of the lower gel band, e.g., the 18–19 kDa band, was cut from the Coomassie Blue stained gel and transferred to a 5–20% gradient polyacrylamide gel together with endopeptidase. The separated proteins were transferred to PVDF (Immunoblon®, Pharmacia), stained with Coomassie Blue and destained in approximately 50% methanol/10% acetic acid. The resulting band at approximately 18 kDa was cut from the membrane and sent for commercial sequencing the Baylor College of Medicine Core Protein Facility (Houston, Tex.).

5.3 Example 3

Localization of DBPs to B. burgdorferi Membranes

The adhesive function of DBPs, and their role as targets for growth-inhibitory antibodies, imply that the DBPs are localized to the borrelia outer membrane. To provide additional biochemical support for this B. burgdorferi B3 total membranes were separated into inner and outer membranes (IM, OM) by a recently published isopycnic centrifugation technique (Bledsoe et al., 1994). By detergent phase portioning DbpA appears to be amphiphilic as are OspA and other borrelia membrane lipoproteins (Brandt et al., 1990). To confirm the presence of lipid on these proteins B. burgdorferi B31 was metabolically labeled with $^3$H-palmitate (Brandt et al., 1990), lysed, and used in an immunoprecipitation assay with rabbit anti-rDbpA and anti-rOspA. Both DbpA and OspA were found to incorporate $^3$H. Thus DbpA is a lipoprotein as predicted by its sequence and membrane fractionation properties.

5.4 Example 4

Nucleic Acid Sequences Encoding DbpA and DbpB

5.4.1 DNA Sequence of dbpA and dbpB

To isolate the dbpA and dbpB genes from B. burgdorferi strain N40 a λZAPU expression library was constructed from B. burgdorferi strain 297 genomic DNA. A Western blot-type assay was used to verify that strain 297 expresses DBPs. We demonstrated that despite their similar protein profiles by Coomassie Blue staining (FIG. 23A), B. burgdorferi strain 297 expresses Dbp(s) whereas strain HP B31 does not (FIG. 23B). We used an attachment assay to show that B. burgdorferi strain 297 can also attach to a Dcn substrate whereas strain HP B31 cannot (FIG. 23C).

Positive clones were sequenced, and an approximate 0.6 kb open reading frame identified. One clone, containing the 2.5 kb insert and the approximately 0.6 kb open reading frame was deposited with the American Type Culture Collection (ATCC) on Apr. 24, 1995, and has the accession number ATCC69791. A single major recombinant protein, DbpA, was expressed by this clone which was used to express DbpA, and the expressed protein was shown to bind Dcn by affinity chromatography and also by dot blot assay with a labeled Dcn probe. The expressed DbpA was also shown to prevent the adherence of B. burgdorferi to Dcn.

The λZAP™ expression library was obtained from Dr. Robin Isaacs of the V.A. Medical Center in Jackson, Miss. The library had been constructed using B. burgdorferi strain 297 DNA according to the manufacturer's instructions (Stratagene, La Jolla, Calif.). The library was created from DNA recovered from a B. burgdorferi 297 (p3) culture and included genomic and plasmid elements. The DNA was partially digested with Sau3A and partially end-filled to enable ligation into the vector digested with Xho1 and partially filled in. The initial library contained about $2.1 \times 10^5$ clones with greater than 95% recombinants. The average insert size was in the range of 2–4 kb.

The library was plated in six 90-mm plates and plaques were lifted onto HAFT nitrocellulose filters (Millipore, Bedford, Mass.) according to the protocol described by Sambrook et al., (1989). The filters were incubated in TBST (0.15 M NaCl, 0.02 M Tris HCl, 0.05% Tween-20®, pH 7.4) containing 3% (w/v) bovine serum albumin (BSA) for 2 hours at room temperature. The filters were washed with TBST three times for 5 min at room temperature. The washed filters were incubated with 1 µg of digoxigenin-labeled Dcn (prepared as described above) per ml of TBST for one h at room temperature, then washed as described above and incubated with 1:1000 anti-digoxigenin-POD Fab fragments in TBST for one h at room temperature. The antibody marker was developed by washing and incubating in chloronapthol solution (30 mg of 4-chloro-1-napthol [Bio-Rad, Hercules, Calif.] in 10 ml of methanol, chilled at −20° C. for ten min then 50 ml TBS [0.15 M NaCl, 0.02 M Tris HCl, pH 7.5] and 100 µl of 30% $H_2O_2$ was added) at room temperature for 5–20 min until color development was complete.

Positive plaques were pulled and stored in SM as described (Sambrook et al., 1989). The plaques were screened with digoxigenin-labeled Dcn as described above until a pure plaque was obtained (additional 2–4 rounds). DNA of the clones expressing DBPs was transferred to a pBlueScript® sequencing vector following the manufacturer's instructions enclosed with the λZAPII™ Vector. The DNA insert was sequenced using the dideoxy sequencing method.

Approximately 600,000 plaques from the library were screened with digoxigenin-labeled Dcn in search of functionally-active Dcn-binding proteins. Two clones, pBG26 and pBG27, were identified and sequenced. DNA sequencing revealed 1500 kb of overlapping sequence between the two clones. pBG26 contains an additional 500-bp of upstream sequence and pBG27 contains an additional 500-bp of downstream sequence (FIG. 24). Analysis of the DNA sequence revealed two ORFs each of exactly 561 bp, within the 1500-kb overlapping sequence. The ORFs are not arranged in an operon, but have separate promoters and are separated by a 177-bp DNA sequence. These ORFs were subsequently shown to be genes which encode for DBPs, therefore, they were designated dbpA and dbpB. Analysis of the deduced amino acid sequences revealed putative lipid attachment sites LISC (DbpA) and LVAC (DbpB). The nucleotide sequences for dbpA and dbpB were aligned using the MacVector program and were revealed to share 50% identity. The deduced amino acid sequences were aligned and shown to share only a 40% identity.

The sequence of the 2.5 kb (SEQ ID NO:7) insert is shown in FIG. 2A and FIG. 2B, with the approximate 0.6-kb open reading frame of dbpB beginning with the ATG sequence at nucleotide 791 and ending at nucleotide 1351; the approximate 0.6-kb open reading frame of dbpA begins with the ATG sequence at nucleotide 1471 and ends with the TCG at nucleotide 2031. The amino acid sequences of DbpA and DbpB are shown in SEQ ID NOs:8 and 28. The dbpB gene was not expressed at high levels by this clone, but its ORF was identical in length to dbpA. Surprisingly, the products of these two genes, however, share only about 40% amino acid sequence identity.

5.4.2 Expression and Purification of Recombinant DbpA and DbpB Proteins

The identification of putative lipid attachment sites within the deduced amino acid sequences of both genes suggested that they encode lipoproteins. Native DBPs are believed to be lipoproteins based on their partitioning into the Triton X-114 detergent phase as determined by Western blot analysis and incorporation of $^3$H palmitate (DbpA). Studies of other lipoproteins from *B. burgdorferi* have shown that signal peptidase II cleaves at the N-terminal side of cysteine after lipid attachment. To simulate the native proteins in their mature form, PCR was used to construct recombinant DBPs with the corresponding amino acid truncations; these constructs were designated DbpA:504 and DbpB:500 (FIG. 24). These proteins were expressed in *E. coli* M15 cells and polyhistidine (N-terminal) fusions.

The DBPs were purified by immobilized nickel chelating chromatography. When necessary, the proteins were also subsequently purified by cation exchange chromatography (Mono-S, Pharmacia, Uppsala, Sweden). DbpB:500 appeared as a single band at approximately 19 kDa by SDS-PAGE. DbpA:504 was highly insoluble so we created a construct lacking only nine amino terminal residues (designated DbpA:549, FIG. 23A and FIG. 23B). Purified DbpA:549 did appear to be soluble, however, when analyzed by SDS-PAGE, the protein exhibited two bands with apparent molecular masses of 20 and 40 kDa, indicating the formation of dimers. The 40 kDa protein was confirmed to be DbpA:549 by Western blot. Although the dimers could be detected even when SDS-PAGE was performed under reducing conditions. However, they were almost completely eliminated by adding excess (0.1M) β-mercaptoethanol to both the sample and running buffers, suggesting that the aggregation was due to intermolecular disulfide bonding. In an attempt to eliminate dimer formation, a site-directed mutant of DbpA:549 was created in which the sole cyestein at position 25 was mutated into an alanine residue (designated DbpA:C25A, FIG. 24). The resulting mutant did not appear to dimerize since it runs as a single band.

5.4.3 Recombinant DBPs Are Functionally Active

The activity of the recombinant Dbps was determined by Western blot-type assay and by a microtiter well binding assay. The Western blot-type assay is based on a traditional Western blot with the modification of using a labeled ligand, in this case digoxigenin-labeled Dcn, as the probe. Purified proteins were separated by SDS-PAGE under reducing conditions and transferred to a nitrocellulose membrane. After blocking additional protein-binding sites with a solution containing 5% nonfat dry milk, digoxigenin-labeled Dcn was allowed to bind to proteins on the membrane, followed by binding of alkaline phosphates-conjugated anti-digoxigenin $F_{ab}$ fragments to the digoxigenin-labeled Dcn. Dcn-binding proteins were visualized by phosphatase substrate reactivity. All three proteins, DbpA:549, DbpA:C25A and DbpB:500, showed roughly similar Dcn-binding activity as judged by relative band intensity.

To determine Dcn-binding activity by binding assay, separate microtiter wells were coated with increasing amounts of Dbps then biotin-labeled Dcn was allowed to bind for 1 hour. Using this assay, DbpA:549, DbpA:C25A, had at most approximately 80% activity compared with DbpA:549. It is possible that this discrepancy is due to differences in the proteins' affinity for the microtiter wells. It is significant to note that recombinant Osp used as a negative control (produced as a polyhistidine fusion protein from strain N40) did not exhibit any detectable Dcn-binding activity even at the highest concentration of 1000 ng per well.

5.4.4 Characterization of DBPs and Dcn Binding

Inhibition of attachment was assayed by coating microtiter wells with Dcn and preincubating the wells with increasing concentrations of DBPs for 1 hour before allowing a suspension of *B burgdorferi* to attach. Both DbpA:549 and DbpA:C25A can inhibit Borrelia attachment to Dcn-coated microtiter wells. Attachment of *B. burgdorferi* 297 is completely blocked when the wells are preincubated with 600 ng of either protein (FIG. 26A). Preincubation with either protein actually resulted in some enhancement of attachment for reasons that are unclear. Attachment of *B. burgdorferi* N40 is inhibited 93% when the wells were preincubated with 200 ng of either DbpA protein and completely blocked when preincubated with 400 ng (FIG. 26B). For N40, DbpB appeared to inhibit attachment weakly. This data suggested that different Borrelia strains may vary in their expression of DBPs. Alternatively, the two proteins could bind to different binding sites on Dcn.

A Western blot was used to address whether different Borrelia strains express different relative amounts of the two DBPs. Rabbit anti-sera were generated against DbpA:549 and DbpB:500. Surprisingly, these anti-sera showed minimal cross-reactivity as determined by ELISA. The few cross-reactive antibodies were adsorbed out using Dbps coupled to sepharose beads. The proteins in whole cell lysate of *B. burgdorferi* 297 and N40 were separated by SDS-PAGE under reducing conditions and transferred to a nitrocellulose membrane. The adsorbed anti-sera was used to probe for DbpA and DbpB in a Western blot. *B. burgdorferi* N40 appears to express more DbpB than DbpA whereas the reverse appears to be the case for *B. burgdorferi* 297.

A competitive binding assay was used to determine whether the DBPs bind to the same site on Dcn. DBPs were individually preincubated in approximately 1000 fold excess of biotin-labeled Dcn to saturate all of the binding sites on Dcn. The DBPs were coated onto microtiter wells before the Dcn-DBP mixture was allowed to bind. DbpA successfully competed the interaction between DbpB with Dcn and vice versa (FIG. 27). As expected, OspC did not inhibit binding of either DBP to Dcn and each DBP was able to inhibit Dcn binding with itself. Therefore, both proteins appear to bind to the same site on Dcn.

5.4.5 Discussion

Labeled Dcn was used as a probe to clone Dbp genes from a λZAPII genomic library constructed from *B. burgdorferi* 297 DNA. Two genes of exactly 561 bp were isolated. *E. coli* was able to recognize one or both of the DBP gene promoters since neither protein was being expressed as a fusion. The genes were localized by Southern hybridization to a 56-kb plasmid, the same plasmid on which the ospAB operon is located. The deduced amino acid sequences of DbpA and DbpB are 40% identical and their "normalized alignment score" was calculated to be 350, which indicates that the two proteins are evolutionarily related.

Both DBPs were produced in *E. coli* as polyhistidine fusions proteins lacking their leader peptides and purified by nickel chelating chromatography. The recombinant DBPs were active, but appeared to have different binding affinities for Dcn based on the microtiter well binding assay.

However, these discrepancies could be due to incomplete coating on the wells. No differences in binding as judged by band intensity were detectable by Western blot-type assay.

An attempt was made to inhibit the attachment of *B. burgdorferi* to Dcn-coated microtiter wells with the recombinant DBPs. DbpA:549 and DbpA:C25A were more efficient at inhibiting attachment compared with DbpB, but all three proteins inhibiting attachment to a significant degree. These results suggested that perhaps not all *B. burgdorferi* strains express both DbpA and DbpB. Only a single band could be detected by Western blot-type assay for *B. burgdorferi* 297, although two bands were readily apparent with strain N40. *B. burgdorferi* N40 and 297 whole cell lysates were probed in a Western blot with noncross-reactive polyclonal antisera recognizing DbpA and DbpB. There appeared to be more DbpB expressed by N40 and more DbpA expressed by 297. Therefore, DbpA is a more effective inhibitor of spirochete attachment to Dcn regardless of the relative expression of the DBPs.

To determine whether DbpA and DbpB bind to the same site on Dcn, a competitive binding assay was performed. It was shown that both DbpA and DbpB bind to the same site on Dcn. DbpA:C25A was a slightly less effective inhibitor compared to DbpA:549 and DbpB:500, which may be a result of the mutation. In this assay, DbpB is just as efficient as DbpA at competing for Dcn binding (FIG. 27), despite being unable to compete with intact spirochetes (FIG. 26A and FIG. 26B). This difference may be an artifact resulting from using purified proteins in an in vitro assay since the DBPs present in Borrelia membranes may not be fully accessible.

*B. burgdorferi* has two genes, designated dbpA and dbpB, encoding distinct Dcn-binding proteins, DbpA and DbpB, respectively. The proteins are similar in size, sequence and function, yet are expressed under the control of separate promoters and do not elicit cross-reactive antibodies.

5.5 Example 5

Identification of DBPs in Borrelial Isolates

One aspect of the present invention, is the identification of borrelias using the DBP compositions disclosed herein as diagnostic indicators of borrelial infection. As shown in Table 2, an assay of DBPs in borrelias using Western hybridization analyses, it was possible to identify the presence of DBPs in at least 13 strains of *B. burgdorferi*, 5 strains of *B. garinii*, and at least three strains of *B. afzelii*. These methods represent important diagnostic tools for the identification of bacteria in clinical isolates.

TABLE 2

Assay of DBPs in Borrelias By Western Blot

| Strain | Origin | DBP | Source |
|---|---|---|---|
| *B. burgdorferi* sensu stricto | | | |
| CA3 | tick | + | R. Lane |
| CA7 | tick | + | R. Lane |
| CA8 | tick | + | R Lane |
| CA20 | tick | + | J. Leong |
| B31 | *I. scapularis*, USA (NY) | +† | |
| 297 | CSF, USA (NY) | + | |
| Sh-2-82 | *I. scapularis*, USA (NY) | ++ | |
| N40 | *I. scapularis*, USA (NY) | +++† | |
| JD1 | *I. scapularis*, USA (MA) | ++† | |
| HB19 | Blood, USA | ± | |
| 3028 | (human plus), USA (TX) | +† | |
| G39/40 | *I. scapularis*, USA (CT) | ± | |
| LP4 | Skin (EM), USA (CT) | +† | |
| LP5 | Skin (EM), USA (CT) | +† | |
| LP7 | Skin (EM), USA (CT) | +† | |
| NCH-1 | Skin, USA | +† | |
| ZS7 | *I. ricinus*, Germany | ++ | |
| H11 | Blood, Italy | + | |
| CA-3-87 | *I. pacificus*, USA (CA) | ± | |
| FRED | (human), USA (MO) | − | |
| HBNC | Blood, USA (CA) | ± | |
| *B. garinii* | | | |
| PBr | CSF, Germany | ++ | |
| PBi | VSF, Germany | ++ | |
| Be 91 | Skin, Norway | ++ | |
| G2.22 | CSF, Germany | ++ | |
| Ip90 | *I. persulvatus*, Russia | + | |
| IP89 | *I. persulcatus*, Russia | ++ | |
| 2226 | *I. persulcatus*, China | + | |
| Fuji P1 | *I. persulcatus*, Japan | ++ | |
| 20047 | *I. ricinus*, France | ++ | |
| *B. afzelii* | | | |
| PKo | Skin (EM), Germany | ++† | |
| PGau | Skin (ACA), Germany | ++ | |
| ACA I | Skin (ACA), Sweden | + | |
| M7 | *I. persulcatus*, China | ± | |
| IPF | *I. persulcatus*, Japan | − | |
| BO23 | Skin, Germany | ++ | |
| ECM-1 | Skin (EM), Sweden | ++ | |
| PGau | skin | + | M. Hanson |
| *B. japonica* | | | |
| HO14 Group 25015 | *I. ovatus*, Japan | + | |
| 25015 | *I. scapularis*, USA | − | |
| "*B. andersonii* sp. nov." | | | |
| 21038 | *I. denatus*, USA | ++ | |

Strains were derived from Lyme patient material or Ixodes sp. ticks.
†two bands with activity at 18–20 kDa. CSF, cerebrospinal fluid, EM, reythema migrans; ACA, acrodermatitis chronicum atrophicans.

Example 6

Nucleic Acid Sequences Encoding Strain Variants of DbpA

Using the sequence of DbpA derived from *B. burgdorferi* strain 297, oligonucleotide amplification primers were constructed to amplify various regions of the gene. The primers used are summarized in Table 3.

The oligonucleotide primers were used in PCR™ to amplify portions of DbpA from the following strains of *B. burgdorferi*: N40, SH2, HB19, B31 (low passage); HPB31 (high passage), and 297. Amplification was carried out for 30 cycles of 94° C. for one min; 50° C. for 2 min; and 72° C. for three min using standard PCR™ conditions. (100 microliters total volume: 71.5 microliters water; 10 microliters 10X PCR™ buffer; 5 microliters of 5 mM MgCl$_2$; 2 microliters DNA; 2 μl each dNTP; 1.5 microliters of each primers; and 0.5 microliters of Taq polymerase (GIBCO). Each mixture was covered with 100 microliters of mineral oil and PCR™ cycles begun).

TABLE 3

Primers Used in DbpA Gene Amplification

| SEQ ID NO: | NAME | PRIMER SEQUENCE |
|---|---|---|
| 1 | BM-1-F | 5'-CGCGGATCCATGATTAAATGTAATAAT-3' |
| 2 | BN-10-F | 5'-CGCGGATCCACCAATCTTCTTAAACTA-3' |
| 3 | BG-26-F | 5'-CGCGGATCCGGACTAACAGGAGCAACA-3' |
| 4 | V-73 RP | 5'-GCGCTGCAGTTATACCCCACTACCCGT-3' |
| 5 | BA-145-F | 5'-CGCGGATCCCGACTTCTCTTAGGAGGT-3' |
| 6 | END-P | 5'-GCGCTGCAGTTACGATTTAGCAGTGCT-3' |

Five primer combinations were tested with each strain of bacteria as described in Table 4.

The amplification primers derived from the nucleotide sequence of dbpA of *B. burgdorferi* strain 297 produced products for each of the variant strains tested, although the ability of specific primers to amplify a product in each strain varied considerably. This implies variation between strains of the bacteria in the nucleic acid sequence encoding DbpA.

TABLE 4

PRIMER COMBINATIONS FOR dbpA AMPLIFICATIONS

| → | ↓ | PROD | N40 | SH2 | B31 | HB19 | HPB31 | 297 |
|---|---|---|---|---|---|---|---|---|
| BM-1F | END-P | 579 bp | − | + | − | − | + | + |
| BN10F | END-P | 549 bp | − | + | + | + | + | + |
| BG26F | V73RP | 159 bp | − | + | − | − | − | + |
| A145F | END-P | 147 bp | − | NA$^a$ | ND | ND | ND | − |
| BG26F | END-P | 504 bp | + | + | − | + | + | + |

$^a$ND = not determined.

Oligonucleotides derived from the DbpA DNA sequence of strain 297 were used as primers for PCR™ amplifications of dbp gene fragments from various borrelia strains. Using a western blot-like assay with tagged Dcn for assessment of Dcn binding activity, almost all strains were found to express a DBP in vitro of approximately the same size, 20 kDa±2 kDa. Thus these strains were predicted to contain alleles of the dbpA and dbpB genes of strain 297 as confirmed by PCR™.

These common sequences may be used to facilitate design of new primers to allow amplification of these strain variants. Alternately, these PCR™ products may be used to identify DNA fragments containing dbpA and dbpB strain variants by Southern hybridization, and ultimately derive molecular clones of these additional genes.

The sequence divergence of DbpA from some *B. afzelii* and *B. garinii* strains PGau with respect to the *B. burgdorferi* strains is consistent with the resistance of these strains to in vitro growth inhibition by anti-DbpA$_{297}$ serum. Availability of the dbpA sequences from *B. afzelii* and *B. garinii* provides a the basis for obtaining clones of additional *B. afzelii* and *B. garinii* dbpA gene sequences, elucidation of the common epitope motifs which may differ from *B. burgdorferi* and facilitate design of broad coverage multi-DbpA or multi DbpA/DbpB cocktail vaccines.

5.7 Example 7

DBP Compositions Block Adherence of Borrelias to Dcn

Microtiter test wells were coated with purified Dcn prepared as described for Example 1 and shaken at 4° C., covered, overnight. (One microgram of Dcn in 50 μl PBS, 50 μl/well.) Control wells were coated with 1% BSA in PBS. Dcn coated wells were also incubated with 1% BSA in PBS for 1 hr at room temperature to block uncovered sites.

Recombinant DBP was obtained by growing BG26:pB/2.5(5) in LB medium containing 100 μg/ml ampicillin overnight at 37° C. with shaking. 20 ml of the grown bacteria was placed in 1 l of LB medium containing 100 μg/ml ampicillin and shaken at 37° C. overnight till reaching an optical density of about 0.6–0.8 at $A_{600}$. IPTG was added to a concentration of 0.2 mM, and the mixture was shaken at 37° C. for about 2–3 hr. The cells were broken in a French press and the debris was pelleted at 40,000 rpm for about 15 min.

The supernatant was filtered through a 0.45 μm filter and 5 μl of the filtered supernatant was added to a 2-ml Dcn affinity column previously equilibrated in PBS. The column was washed with 10 volumes of PBS and the bound protein was eluted with 1 M NaCl. A 5–15% acrylamide gradient gel was prepared, and 20 μl of each fraction was added and the gel run to determine those fractions having the DBP. Those fractions containing the protein were pooled, and the pool dialyzed against PBS overnight at 4° C., changing the buffer at least once. The protein concentration of the dialyzed sample was determined by Lowry assay.

The coated microtiter plate was washed 3 times with 200 μl PBS containing 0.1% BSA, incubating about five min at room temperature on a shaker. DBP was diluted in PBS containing 0.1% BSA. 50 μl of the appropriate dilution was added to the well, and the plate was incubated for about 45 min at room temperature and on a shaker. The liquid was decanted and drained.

*B. burgdorferi* strain N40 was then added to the wells. Twenty five (25) microliters of bacteria ($1\times10^9$ organisms/ml) in PBS containing 0.1% BSA was added to each well and incubated 45 min at room temperature. The solution was decanted and drained, and the wells washed three times with PBS containing 0.1% BSA to remove unattached bacteria.

Anti-*B. burgdorferi* rabbit serum (1:1000, 100 μl/well) was added and incubated for 1 hr. (Rabbits were inoculated with $1\times10^8$ organisms per ml of washed *B. burgdorferi* strain B31, and serum was collected 3 weeks post-infection). After washing 3 times in PBS containing 0.1% BSA, the second antibody, 100 μl of 1:1000 goat anti-rabbit alkaline phosphatase conjugate (BioRad, Hercules, Calif.) diluted in PBS containing 0.1% BSA was added and incubated for 1 hr at room temperature. Sigma-104 phosphatase substrate (Sigma), 100 microliters of a 1 mg/ml stock dissolved in 1 M diethanolamine, 0.5 mM $MgCl_2$, pH 9.8, was added and incubated at 37° C. for 30 min. $A_{405}$ was calculated as a measure of binding to Dcn.

The results of the study are shown in Table 5, where the reported $A_{405}$ is the mean of three replicates. DBP was successful in blocking adherence of *B. burgdorferi* microorganisms to Dcn in a dose-dependant manner.

TABLE 5

**DbpA BLOCKS *B. burgdorferi* ADHESION**

| DbpA (μg) | +Den (A405) | +BSA (A405) |
|---|---|---|
| 0.0 | 0.380 | 0.098 |
| 0.5 | 0.208 | 0.127 |
| 2.5 | 0.119 | 0.165 |
| 5.0 | 0.141 | 0.131 |

5.8 Example 8

Inhibitory Activity of anti-rDbpA Serum Towards Borrelial Growth

Two other borrelial proteins, OspA and OspB, believed to be surface-exposed have been shown to be targets for bacterial killing by specific antibodies in the absence of complement (Sadziene et al., 1993). This prompted the inventors to examine antiserum against DbpA for a similar activity. Accessibility to bacteriostatic or bactericidal antibodies is one measure of a protein's exposure at the surface of a cell.

Table 6 shows the growth inhibitory activity of anti-rDbpA serum for diverse borrelia strains. The sensitivity of *B. burgdorferi* to growth in the presence of various antibodies in the absence of complement was assessed using a titration assay performed in microtiter plates. Rabbit antisera were serially diluted in 96-well plates in 0.1 ml BSKII medium, $10^5$ borrelia in the mid-log phase of growth in 0.1 ml BSKII medium were added per well, the mixture was incubated for three days and cell viability (motility) was assessed by microscopy. The results shown in Table 6 were those using rabbit serum raised against rDbpA derived from *B. burgdorferi* sensu stricto strain 297. This serum was strongly inhibitory to growth of twelve of seventeen *B. burgdorferi* sensu stricto strains tested expressing DbpA (HB-19, CA-3-87, and FRED express little or no DbpA in vitro), as well as several of the *B. garinii* and *B. afzelii* strains. Three *B. afzelii* strains and one *B. garinii* strain were slightly inhibited at a 1:50 serum dilution. Strain 25015 was also inhibited by 1:10 anti-DBP serum. *B. andersonii* strain 21038 was strongly sensitive. The strains inhibited by anti-DBP serum fall into at least four OspA serogroups, and have diverse geographic origins. Serum against an irrelevant antigen, OspA, was not inhibitory. The 36 *B. burgdorferi* sensu lato strains were also tested for their sensitivy to growth inhibition by rabbit serum against rOspA from strain B31. Of the 36 strains, 17 were sensitive to anti-OspA serum, and all but three of these were *B. burgdorferi* sensu stricto isolates. Thus, antibodies against DbpA from strain 297 inhibit the growth of more strains than anti-OspA serum, anti-DbpA antibodies inhibit more *B. afzelii* and *B. garinii* strains than OspA. As some strains failed to express DbpA in vitro (as judged by Den- and immuno-blotting, the determination that 20 of 36 strains are sensitive to inhibition by anti-DbpA may be an underestimate. Borrelia strains were obtained from Drs. Steve Norris, John Leong, Alan Barbour, Robert Lane, Robin Isaacs, David Dorward, and Steve Barthold.

TABLE 6

Comparison of Activities of Anti-DbpA and Anti-OspA Antibodies

| | | Anti-DbpA$_{297}$ | | Anti-IspA$_{B31}$ | |
|---|---|---|---|---|---|
| Strain | Origin | Inhibition Endpt. | Western | Inhibition Endpt. | Western |
| *B. burgdorferi* sensu stricto | | | | | |
| CA3 | tick | | | | |
| CA7 | tick | | | | |
| CA8 | tick | | | | |
| CA20 | tick | | | | |
| B31 | *I. scapularis*, USA (NY) | 5,120 | ++ | 51,200 | ++ |
| 297 | CSF, USA (NY) | 5,120 | ++ | 51,200 | ++ |
| Sh-2-82 | *I. scapularis*, USA (NY) | 5,120 | ++ | 51,200 | ++ |
| N40 | *I. scapularis*, USA (NY) | 12,800 | ++ | 51,200 | ++ |
| JD1 | *I. scapularis*, USA (MA) | 800 | ++ | 1,600 | ++ |
| HB19 | Blood, USA | <50 | ± | 100 | ++ |
| 3028 | (human plus), USA (TX) | <50* | ++ | 1,600 | ++ |
| G39/40 | *I. scapularis*, USA (CT) | 100 | ± | 3,200 | ++ |
| LP4 | Skin (EM), USA (CT) | 800 | ++ | <50 | ++ |
| LP5 | Skin (EM), USA (CT) | 800 | ++ | <50 | ++ |
| LP7 | Skin (EM), USA (CT) | 400 | ++ | <50 | ++ |
| NCH-1 | Skin, USA | <50* | ++ | 100 | ++ |
| ZS7 | *I. ricinus*, Germany | <50 | + | 400 | ++ |
| H11 | Blood, Italy | 200 | ++ | 400 | ++ |
| CA-3-87 | *I. pacificus*, USA (CA) | <50 | – | 1,600 | ++ |
| FRED | (human), USA (MO) | 1,600 | + | 3,200 | ++ |
| HBNC | Blood, USA (CA) | 3,200 | ± | 3,200 | ++ |
| | | 3 pos./7 | | 2 pos./17 | |
| *B. garinii* | | | | | |
| PBr | CSF, Germany | 12,800 | + | <50 | ++ |
| PBi | CSF, Germany | 800 | – | <50 | ++ |
| B4 91 | Skin, Norway | <100 | – | <50 | ++ |
| G2.22 | CSF, Germany | <50 | — | <50 | ++ |
| Ip90 | *I. persulcatus*, Russia | <50 | ± | <50 | ++ |

TABLE 6-continued

Comparison of Activities of Anti-DbpA and Anti-OspA Antibodies

|  |  | Anti-DbpA$_{297}$ | | Anti-IspA$_{B31}$ | |
| --- | --- | --- | --- | --- | --- |
| Strain | Origin | Inhibition Endpt. | Western | Inhibition Endpt. | Western |
| IP89 | *I. persulcatus*, Russia | <50 | − | <50 | + |
| 2226 | *I. persulcatus*, China | 200 | ± | <50 | ++ |
| Fuji P1 | *I. persulcatus*, Japan | 100 | ++ | <50 | ++ |
| 20047 | *I. ricinus*, France | <50* | ± | <100* | ++ |
|  |  | 12 pos./17 | 14 pos./17 |  |  |
| *B. afzelii* |  |  |  |  |  |
| PKo | Skin (EM), Germany | 12,800 | + | <50 | ++ |
| PGau | Skin (ACA), Germany | 50* | ++ | 50 | ++ |
| ACA I | Skin (ACA), Sweden | <50 | ± | <50 | ++ |
| M7 | *I. persulcatus*, China | 1,600 | + | <50 | ++ |
| IPF | *I. persulcatus*, Japan | 1,600 | ± | 200 | ++ |
| BO23 | Skin, Germany | <50* | ++ | <50 | + |
| ECM-1 | Skin (EM), Sweden | <50 | ++ | 100 | + |
| PGau | skin |  |  |  |  |
|  |  | 4 pos./9 |  | 0 pos./9 |  |
| *B. japonica* |  |  |  |  |  |
| HO14 | *I. ovatus*, Japan | <50 | ± | 50 | + |
|  |  | 0 pos./1 |  | 0 pos./1 |  |
| Group 25015 |  |  |  |  |  |
| 25015 | *I. scapularis*, USA | 10 | ± | 6,400 | ++ |
|  |  | 0 pos./1 |  | 1 pos./1 |  |
| "*B. andersonii* sp. nov." |  |  |  |  |  |
| 21038 | *I dentatus*, USA | 1,600 | + | <50 | ++ |
|  |  | 1 pos./1 |  | 0 pos./1 |  |
| TOTAL |  | 20 pos./36 |  | 17 pos./36 |  |

Strains were derived from Lyme patient material of Ixodes sp. ticks. Endpoint titer for GI was for >90% reduction in cell number and motility; titer ≦ 100 defined as positive inhibition.
*; partial reduction in cell number at lowest dilution tested.
CSF, cerebrospinal fluid;
EM erythema migrans;
ACA, acrodermatitis chronicum atrophicans.

Example 9

Recombinant Expression of DBPs Using dbp Constructs

To over-express the dbp-derived peptides of the present invention, DNA fragments encoding either one or more native or genetically-modified dbp genes of *B. burgdorferi* or dbp-derived nucleic acid segments encoding either DBP epitopes, truncated DBPs or nucleic acid segments encoding mutated DBPs or DBP-derived epitopes are cloned into appropriate expression vectors. Such vectors may contain a multiple restriction enzyme cloning site that situates the nucleic acid segment of interest such that its expression is controlled from an inducible promoter. Methods for determining orientation of the inserted segment, induction of the promotor, growth conditions, and restriction enzyme analysis, and recovery of the produced protein are well-known to those of skill in the art. Expression and quantitation of the peptides are determinable via standard methods such as SDS-PAGE, Western blot analysis, and protein determination assays.

A particular aspect of the present invention is the production of recombinant proteins in large quantity. Such methods are well-known to those of skill in the art, and have been described in detail hereinabove. In an overall and general sense, the production of a large number of recombinant proteins may be produced in either prokaryotic or eukaryotic cells using various expression systems depending upon the particular construct, and the particular advantages of the various expression systems available for such protein production. Particular aspects of the present invention include the use of the following expression systems:

Recombinant proteins so prepared find utility in the present invention in a variety of embodiments, including compositions for immunoassay reagents, antigen preparation for generation of immune responses in susceptible animals, vaccine formulations, and substrates for antibody production for use in passive and active immunization methods.

An example of a general procedure useful in the large-scale preparation of recombinant DBPs from a prokaryotic source, the following methods may be employed: Saturated overnight cultures of *E. coli* JM101 supE, endA, sbcB15, hsd R4, rpsL, thi Δ(lac-proAB) (F'traD36 $proAB^+$ $lacI^q$ ZΔM15), *E. coli* JM105 supE thi Δ(lac-proAB) (F'traD36 $proAB^+$ $lacI^q$ ZΔM15), TG1 (supE hsdΔ5 thi $\Delta(lac\text{-}proAB)^+$ ($F^+$traD36proAB $lacI^q$ lacZΔM15) (Carter et al., 1985), or XL1-Blue cells (Stratagene, La Jolla, Calif.) harboring expression plasmids are diluted 1:50 in Luria Broth (Gibco BRL, Grand Island, N.Y.) supplemented with ampicillin and allowed to grow until the culture reached an $OD_{600}$ of 0.6–0.7. Isopropyl-1-thio-β-D-galactopyranoside (IPTG; Gibco BRL, Grand Island, N.Y.) (final concentration 0.2 mM) is added to the cells and growth continued for another 2.5–5 hr at 37° C. The bacteria are collected by centrifugation and the bacterial pellets are resuspended in phosphate buffered saline (PBS; 10 mM phosphate, 0.14 M NaCl, pH 7.4). The cells are lysed by passage through a French press (SLM Instrument Inc., Urbana, Ill.) twice at 20,000 lb./in$^2$. The bacterial lysate is centrifuged at 102,000×g for 10 minutes to remove bacterial debris. The supernatant containing the soluble proteins is filtered through a 0.45 μM membrane (Nalgene, Rochester, N.Y.) and retained for further purification.

The present invention also concerns preparation of truncated DBPs expressed in recombinant systems. One such example is the construction of truncated DBPs which still retain the ability to bind Dcn. In a preferred embodiment, a vector was constructed to express proteins as fusions to the leader peptide and posttranslational modification sequence of the major *E. coli* lipoprotein, Lpp. Using the T7 promoter expression vector pET-30b (Novagen, Inc., Madison, Wis.) the NdeI-EcoRI restriction fragment containing the beginning of the translational region expressed from the T7 promoter was replaced with a synthetic sequence expressing the leader peptide of the Lpp protein and a peptide specifying lipoprotein posttranslational modifications generating the new vector pT7Lpp1. A fragment of the dbpA gene spanning amino acids Gly26 through Ser187 was amplified by PCR® with primer-added BamHI and HindIII sites. This fragment encoding a truncated DbpA protein was cloned into pT7Lpp1 to generate pMSH24. This plasmid was shown to express truncated DbpA as a chimeric lipoprotein when transformed into the *E. coli* host strain BL21(DE3) pLysS. Furthermore, this truncated DbpA retained the ability to bind Dcn in the tagged-Dcn blotting assay.

5.10 Example 10

Passive Immunization Using DbpA and DbpB Antibodies

The antibody compositions disclosed herein find particular utility in the passive immunization of animals to prevent bacterial adhesion to the ECM component Dcn, and related proteoglycans. Native DBPs, truncated DBPs, and site-specifically mutagenized DBPs, in particular, DbpA and DbpB, are contemplated to be particularly useful as antigens to immunize animal donors, and particularly mammalian donors such as humans. The immunoglobulin fraction (Ig) from the blood plasma of the donors can be purified and systemically administered to a target population. Those individuals at high risk for developing borrelia infections include, but are limited to, patients in intensive care units, immunocompromised patients, surgery patients, children, and persons in areas having high incidence of ixodid tick infestations such as the northeastern, midwestern, and western pacific United States. Two particular references which describe those at risk from borrelioses include Steere, 1994 and a report by the Centers for Disease Control, 1994.

The anti-DbpA and anti-DbpB Ig produced by immunization with peptides of the present invention find particular utility in several areas:

1) blocking the adhesion of bacteria to Dcn-coated substrata;

2) assisting the immune system in clearance by opsonization; and 3) lysing of bacteria by activation of the classical complement pathway.

5.10.1 Materials and Methods

Low-passage *B. burgdorferi* B31, which is infectious for mice, was used to demonstrate passive immunization using antibody compositions disclosed herein. This strain reacts with anti-rDbpA$_{297}$ and is killed by these antibodies in vitro. C3H/H3J mice, a widely used strain (Barthold et al., 1993) susceptible to both infection and disease were challenged with an intradermal inoculum of 10$^4$ spirochetes (100 LD$_{50}$) and passively immunized just before challenge with rabbit sera against rDbpA, rOspA, or rPspA.

5.10.2 Results

One means of demonstrating that accessibility of DbpA to antibodies is not an artifact of in vitro manipulation is to demonstrate passive protection from borrelia challenge with these antibodies. Even though common strains of inbred mice (such as C3H/HeJ, C3H/HeN, and Balb/cByJ) may differ in the severity of disease elicited by borrelia, their sensitivities to infectious borrelia strains is more uniform. Additionally mouse-virulent strains Sh.2.82, N40, and *B. afzelii* PKo were also evaluated for their in vivo sensitivity to anti-rDbpA$_{297}$ serum. C3H/HeJ mice, a widely-used strain susceptible to both infection and disease were challenged with an intradermal inoculum of 10$^4$ spirochetes and passively immunized just before challenge with rabbit sera against rDbpA, rOspA, or no serum. At two weeks post-challenge tissue samples (bladder, heart, synovial fluid) were placed in BSKII medium and evidence of borrelial outgrowth from these tissues were assessed microscopically after 2 and 3 weeks of in vitro culture. Protection was judged to be complete when no spirochetes are seen upon examination of 10–20 high power fields of samples from all three cultures. That bactericidal antibodies reactive with other antigens (OspA, OspB) also elicited passive protection against challenge with homologous or closely related strains, suggested that anti-rDbpA would also confer protection. Anti-DbpA serum confers protection against all *B. burgdorferi* strains evaluated even though these are heterologous from the source of antigen, *B. burgdorferi* strain 297. These results also confirm that DbpA remains a target for growth inhibition in vivo, at least for the duration the rabbit antibodies remained in circulation in the test mice.

5.11 Example 11

Active Immunization Using DbpA and DbpB Compositions

5.11.1 Materials and Methods

Groups of five mice (BALB/c and C3H/HeJ) were immunized with 20 μg rDbpA or soluble protein extract of *E. coli* JM101/pBSII, or 5 μg rOspA lipoprotein in complete Freund's adjuvant (CFA), and boosted with protein in incomplete Freund's adjuvant (IFA) at 4 wk. Groups of five BALB/c mice were also immunized with 20 μg rDbpB, or 5 μg rOspA or *E. coli* extract in CFA and boosted with protein in IFA at 3 weeks. At two week intervals sera were collected and analyzed for reactivity with the immunizing antigen by ELISA. At the time of challenge these serum ELISA titers were in excess of 1:100,000 indicating all antigen preparations were highly immunogenic by this immunization regimen.

5.11.2 Results

The rDbpA antigen preparation was able to confer complete protection for all BALB/c mice. Protection was also seen with rOspA, but not with the irrelevant *E. coli* antigen extract. Interestingly, spirochetes were absent from skin and joint tissue of rDbpA-immunized C3H (H-2$^k$ haplotype) and BALB/c (H-2$^d$ haplotype) mice.

The rDbpB antigen preparation was able to confer complete protection for three of five BALB/c mice, while the two infected mice had reduced levels of spirochetes in their tissues (FIG. 28A and FIG. 28B).

5.12 Example 12

Active Immunization Using Chimeric Lipoprotein-DbpA Truncate Compositions

Groups of five mice (C3H/HeJ) were immunized. At two week intervals sera were collected and analyzed for reactivity with the immunizing antigen by ELISA. At the time of challenge these serum ELISA titers were in excess of 1:100,000 indicating all antigen preparations were highly immunogenic by this immunization regimen. The rDbpA antigen preparation was similar to the chimeric lipoprotein DbpA truncate in its ability to confer protection for C3H/HeJ mice. Protection was also seen with rOspA, but not with the irrelevant E. coli antigen extracts. Serum against rDbpA raised in rabbits completely protected C3H mice. Again, protection against the heterologous B31 strain was seen using rDbpA and Lpp:DbpA derived from strain 297.

5.13 Example 13

Post-Infection Administration of Anti-rDbpA Serum Aborts Infection

A major concern for OspA-based vaccines, the leading candidate antigen for a Lyme disease vaccine, is that antibodies against this protein are effective only if present at high levels prior to infection. This suggests that an infection-induced memory response to OspA will be of little or no benefit. However, other borrelia surface proteins required for growth and persistence in vivo may not suffer this limitation as vaccine immunogens. Many bacterial pathogens including borrelias initiate infection following adhesion to specific macromolecules of the host target tissue. These adhesins are exposed at the bacterial surface. Adhesins are effective vaccines against human and animal diseases, as demonstrated in several animal models. Several of the recently developed acellular pertussis vaccines include the B. pertussis adhesins pertactin, FHA, and fimbriae (Cherry, 1992). The following example illustrates the effectiveness of DbpA in passive immunization studies.

C3H/HeJ mice (three per group) were challenged with an intradermal inoculum of $10^4$ spirochetes (100 $ID_{50}$) and passively immunized with one administration just before challenge with 0.1 ml rabbit sera against rDbpA, rOspA, or rPspA (day 0), or at days 2, 4, 7, or 10 post-challenge. Mice were sacrificed at day 17 and infection was assessed by culture of skin, bladder, and joint tissues as before.

As shown in Table 7 anti-DbpA serum was effective until day four, while anti-OspA serum was ineffective after day 0. This shows that DbpA, even after a period of four days to grow and adapt to in vivo conditions present in the host remains a target for antibody-mediated elimination. This was not the case for OspA. It is possible this post-infection therapeutic effects can be extended to later in the infection process if multiple doses of antibody, or antibody from the homologous species, are administered to gain more favorable pharmacokinetics. The studies measured only infection rather than disease, however, antibody levels which are not sufficient to eliminate all borrelia may in fact be sufficient to prevent disease pathologies.

Significantly, these results indicate that an infection-induced memory immune response to a priming vaccination with DbpA may be effective at eliminating infection or disease. This may also be possible based on the results obtained for DbpB.

5.14 Example 14

Isolation of Nucleic Acid Sequences Encoding DBPs from *B. burgdorferi, B. afzelii,* and *B. garinii*

Oligonucleotides were used as primers for PCR™ amplifications of dbpA gene fragments from borrelia strains representing the three major phylogenetic groups of Lyme disease spirochetes. Primers derived from the dbpA gene of strain 297 are able to function in the PCR™ to amplify candidate dbpA alleles of the expected size from seven of eight strains tested under a limited set of different amplification conditions. Strains having variant dbpA alleles not yet amplified by the conditions described, such as PBi, may yield detectable PCR™ products under less stringent annealing conditions, or with other combinations of these primers, or both. Determining the nucleotide sequences of these alleles will allow elucidation of the most highly conserved regions which presumably would be common among all genes expressing DbpA. These common sequences would then be used to facilitate design of new primers to allow amplification of these strain variants. Alternately, these PCR™ products could be used to identify DNA fragments containing dbpA strain variants by Southern hybridization, and ultimately derive molecular clones of these genes.

Identification of candidate dbpA alleles from *B. burgdorferi, B. afzelii,* and *B. garinii* was accomplished using oligonucleotides as primers for PCR™ amplifications of dbpA gene fragments from borrelia strains representing the three major phylogenetic groups of Lyme disease spirochetes. Portions of the PCR™ amplification reactions were electrophoresed on 1% agarose gels and the approximate sizes of the DNA products were estimated relative to size standards. Where a given primer pair yielded an amplification product of the size expected from the strain 297 sequence this is indicated with a check mark. In some cases additional amplification products were also obtained. All amplifications were initiated with a 15 sec denaturation at 96° C., followed by annealing, then by a 30 sec extension period at 72° C. "Full-length" and "truncated" products of the dbpA gene with primers within the DbpA coding sequence were obtained using a 15 sec annealing period at 42° C. Longer amplification products with primer pairs 1, 2, and 3 outside of the DbpA coding sequence were obtained with a 15 sec annealing period at either 45° C. or 49° C. The indicated products were detected after 30 cycles of amplification in the presence of Taq polymerase (Perkin Elmer-Cetus).

Table 9 shows a summary of the heterologous borrelia strain passive protection results discussed in Example 5.10. Data were compiled in tabular form and expressed as % of mice protected by anti-$DBP_{297}$ serum and anti-$OspA_{B31}$ serum. Under these challenge conditions, broader protection was achieved with anti-DBP serum.

TABLE 7

Effect of Post-Challenge Passive Administration of Antisera on Borrelia Enfection in C3H/HeJ Mice

| | Number of Mice Infected at Each Day of Serum Administration | | | | |
|---|---|---|---|---|---|
| Antiserum | 0 | 2 | 4 | 7 | 10 |
| DbpA | 0/3 | 0/3 | 0/3 | 3/3 | 3/3 |
| OspA | 0/3 | 3/3 | 3/3 | — | |
| PspA | 3/3 | — | — | — | |
| None | 3/3 | — | — | — | |

Identification of candidate dbpB alleles from *B. burgdorferi, B. atzelii* and *B. garinii* was accomplished using oligonucleotides derived from the strain 297 dbpB gene sequence as PCR™ primers in a manner similar to the strategy for dbpA. In addition to *B. burgdorferi* strain 297, 15 dbpB genes were amplified and sequenced from a variety of *B. burgdorferi* (2P4, Sh2, FRED, G39/40, WB19, LP5, NCH-1, Zs7, LP7, N40, CA-2-87, JD1, IPS, *B. afzelii* (Pko), and *B. garinii* (20047) strains. At the amino acid level the DbpB proteins expressed by these 16 dbpB genes share >98% amino acid sequence identity. Only four amino acid substitutions were observed among these alleles; thse are listed in Table 10.

TABLE 8

Amplification of a DBP Allele from Various Borrelia spp.

| Species | Strain | Expected | DBP Full Length 564 bp | DBP Truncate 448 bp | DBP Pair 1 852 bp | DBP Pair 2 700 bp | DBP Pair 3 954 bp |
|---|---|---|---|---|---|---|---|
| *B. burgdorferi* | B31 | | − | + | − | + | − |
| | 297 | | + | + | + | + | + |
| | Sh.2.82 | | + | + | + | + | + |
| *B. afzelii* | ACA-1 | | + | − | − | + | − |
| | PGau | | + | + | − | − | − |
| *B. garinii* | IP90 | | + | + | − | − | '1 |
| | B491 | | + | − | − | − | − |
| | pBi | | − | − | − | − | − |

TABLE 9

| | Anti-DBP Serum Culture Positive Tissues | | | Anti-OspA Serum Culture Positive Tissues | | |
|---|---|---|---|---|---|---|
| Challenge Borrelia Strain | Bladder | Ear | % of Mice Protected | Bladder | Ear | % of Mice Protected |
| *B. burgdorferi* sensu stricto | | | | | | |
| B31 | 0/5 | 0/5 | 100% | 0/5 | 0/5 | 100% |
| Sh.2.82 | 0/5 | 0/5 | 100% | 1/5 | 1/5 | 80% |
| N40 | 0/5 | 0/5 | 100% | 5/5 | 3/5 | 0% |
| *B. afzelii* | | | | | | |
| Pko | 2/5 | 0/5 | 60% | 5/5 | 4/5 | 0% |

TABLE 10

Amino Acid Sequence Identities of Strain Variants of DbpB

| Strain | Identity as Compared To Styrain 297 |
|---|---|
| 297 | Identical |
| LP4 | Identical |
| SH2 | Identical |
| 20047 | Identical, except 1 amino acid difference: D50E (Asp → Glu at A.A. 50) |
| FRED | Identical, except 1 amino acid difference: D50E (Asp → Glu at A. A. 50) |
| G3940 | Identical, except 1 amino acid difference: D50E (Asp → Glu at A.A. 50) |
| HB19 | Identical, except 1 amino acid difference: D50E (Asp → Glu at A. A. 50) |
| LP5 | Identical, except 1 amino acid difference: D50E (Asp → Glu at A.A. 50) |
| NCH-1 | Identical, except 1 amino acid difference: D50E (Asp → Glu at A. A. 50) |
| ZS7 | Identical, except 1 amino acid difference: D50E (Asp → Glu at A.A. 50) |
| IP5 | Identical, except 2 amino acid differencs: K16D, D50E (Lys → Asp at A.A. 16; Asp → Glu at A.A. 50) |
| LP7 | Identical with 2 amino acid differences: K16D, D50E (Lys → Asp at A.A. 16; Asp → Glu at A.A. 50) |
| N40 | Identical with 2 amino acid differences: K16D, D50E (Lys → Asp at A.A. 16; Asp → Glu at A.A. 50) |
| pKo | Identical with 2 amino acid differences: K16D, D50E (Lys → Asp at A.A. 16; Asp → Hlu at A.A. 50) |
| JD1 | Identical with 2 amino acid differences: D50E, G53E (Asp → Glu at A.A. 50; Gly → Gly at A.A. 53) |
| CA287 | Identical with 3 amino acid differences: K16D, A31T, D50E (Lys → Asp at A.A. 16; Ala → Thr at A.A. 31; Asp → Glu at A.A. 50) |

5.14 Example 14

Preparation of DBP-Specific Proteoglycan Derivatives

Another aspect of the invention is the preparation of novel compositions comprising proteoglycans and/or their derivatives which recognize the native DBPs and synthetically-modified DBP-derived epitopes disclosed herein. Such compositions are useful in the preparation of therapeutic formulations for preventing bacterial adhesion in an animal, and particularly, in humans. Novel ligands mimicking native Dcn present in the ECM serve as chemopreventatives in bacterial infection by effectively saturating the MSCRAMM components present on the bacterial cell surface.

6. BRIEF DESCRIPTION OF THE SEQUENCE IDENTIFIERS

SEQ ID NO:1–SEQ ID NO:6, Primers listed in Table 3.

SEQ ID NO:7, DNA sequence of 2.5-kb dbpA/dbpB from *B. burgdorferi* 297.

SEQ ID NO:8, DbpA sequence of 0.6-kb ORF from *B. burgdorferi* 297.

SEQ ID NO:9, DbpA sequence of 0.6-kb ORF from *B. burgdorferi* 297.

SEQ ID NO:10, Nucleotides 1–1400 of 2.5-kb insert DNA of BG26:pB/2.5(5).

SEQ ID NO:11, Nucleotides 1401–2653 of 2.5-kb insert DNA of BG26:pB/2.5(5). BG26:pB/2.5(5).

SEQ ID NO:12, dbpA gene of *B. burgdorferi* strain B31.

SEQ ID NO:13, DbpA protein of *B. burgdorferi* strain B31.

SEQ ID NO:14, dbpA gene from *B. burgdorferi* strain Sb.2.82.

SEQ ID NO:15, DbpA protein from *B. burgdorferi* strain Sb.2.82.

SEQ ID NO:16,dbpA gene from *B. burgdorferi* strain HB-19.

SEQ ID NO:17, DbpA protein from *B. burgdorferi* strain HB-19.

SEQ ID NO:18, dbpA gene from *B. afzelii* strain PGau.

SEQ ID NO:19, DbpA protein from *B. afzelii* strain PGau.

SEQ ID NO:20, dbpA gene from *B. garinii* stain P90.

SEQ ID NO:21, DbpA protein from *B. garinii* strain IP90.

SEQ ID NO:22, dbpa gene from *B. burgdorferi* stain LP4.

SEQ ID NO:23, DbpA protein from *B. burgdorferi* strain LP4.

SEQ ID NO:24, dbpA gene from *B. burgdorferi* strain LP7.

SEQ ID NO:25, DbpA protein from *B. burgdorferi* strain LP7.

SEQ ID NO:26, dbpA gene from *B. burgdorferi* strain JD1.

SEQ ID NO:27, DbpA protein from *B. burgdorferi* strain JD1.

SEQ ID NO:28, DbpB protein from *B. burgdorferi* 297.

SEQ ID NO:29, dbpA gene from *B. burgdorferi* 297, LP4.

SEQ ID NO:30, DbpA protein from *B. burgdorferi* 297, LP4.

SEQ ID NO:31, dbpA gene from *B. burgdorferi* SH2.

SEQ ID NO:32, DbpA protein from *B. burgdorferi* SH2.

SEQ ID NO:33, dbpA gene from *B. burgdorferi* N40.

SEQ ID NO:34, DbpA protein from *B. burgdorferi* N40.

SEQ ID NO:35, dbpA gene from *B. burgdorferi* JD1.

SEQ ID NO:36, DbpA protein from *B. burgdorferi* JD1.

SEQ ID NO:37, dbpA gene from *B. burgdorferi* HB19.

SEQ ID NO:38, DbpA protein from *B. burgdorferi* HB19.

SEQ ID NO:39, dbpA gene from *B. burgdorferi* B31, BR4, 3028.

SEQ ID NO:40, DbpA protein from *B. burgdorferi* B31, BR4, 3028.

SEQ ID NO:41, dbpA gene from *B. burgdorferi* G3940.

SEQ ID NO:42, DbpA protein from *B. burgdorferi* G3940.

SEQ ID NO:43, dbpA gene from *B. burgdorferi* IP90.

SEQ ID NO:44, DbpA protein from *B. burgdorferi* LP4.

SEQ ID NO:45, dbpA gene from *B. burgdorferi* ZS7.

SEQ ID NO:46, DbpA protein from *B. burgdorferi* ZS7.

SEQ ID NO:47, dbpA gene from *B. afzelii* PGau.

SEQ ID NO:48, DbpA protein from *B. afzelii* PGau.

SEQ ID NO:49, dbpA gene from *B. afzelii* B023.

SEQ ID NO:50, DbpA protein from *B. afzelii* B023.

SEQ ID NO:51, dbpA gene from *B. garinii* IP90.

SEQ ID NO:52, DbpA protein from *B. garinii* IP90.

SEQ ID NO:53, dbpB gene from *B. burgdorferi* CA287.

SEQ ID NO:54, DbpB protein from *B. burgdorferi* CA287.

SEQ ID NO:55, dbpB gene from *B. burgdorferi* IPS.

SEQ ID NO:56, DbpB protein from *B. burgdorferi* IPS.

SEQ ID NO:57, dbpB gene from *B. burgdorferi* JD1.

SEQ ID NO:58, DbpB protein from *B. burgdorferi* JD1.

SEQ ID NO:59, dbpB gene from *B. burgdorferi* 297, SH2 and LP4.

SEQ ID NO:60, DbpB protein from *B. burgdorferi* 297, SH2 and LP4.

SEQ ID NO:61, dbpB gene from *B. burgdorferi* N40, LP7, and *B. afzelii* PKo.

SEQ ID NO:62, DbpB from *B. burgdorferi* N40, LP7, and *B. afzelii* PKo.

SEQ ID NO:63, dbpB gene from *B. burgdorferi* HB19, G3940, LP5, ZS7, NCH-1, FRED, and *B. garinii* 20047.

SEQ ID NO:64, DbpB protein from *B. burgdorferi* HB29, G3940, LPS, ZS7, NCH-1, FRED, and *B. garinii* 20047.

SEQ ID NO:65, Partial dbpB gene from *B. garinii* IP90.

SEQ ID NO:66, Partial DbpB protein from *B. garinii* IP90.

7. REFERENCES

The following literature citations as well as those cited above are incorporated in pertinent part by reference herein for the reasons cited in the above text:

U.S. Pat. No. 3,791,932.
U.S. Pat. No. 3,949,064.
U.S. Pat. No. 4,174,384.
U.S. Pat. No. 4,196,265.
U.S. Pat. No. 4,271,147.
U.S. Pat. No. 4,554,101.
U.S. Pat. No. 4,578,770.
U.S. Pat. No. 4,596,792.
U.S. Pat. No. 4,599,230.
U.S. Pat. No. 4,599,231.
U.S. Pat. No. 4,601,903.
U.S. Pat. No. 4,608,251.
U.S. Pat. No. 4,683,195.
U.S. Pat. No. 4,683,202.
U.S. Pat. No. 4,952,496.
U.S. Pat. No. 5,168,050.

Abraham et al., "Adherence of *Streptococcus pyogenes, Escherichia coli,* and *Pseudomonas aeruginosa* to Fibronectin-Coated and Uncoated Epithelial Cells," *Infect. Immun.,* 41:1261–1268, 1983.

Allen and Choun, "Large Unilamellar Liposomes with Low Uptake into the Reticuloendothelial System," *FEBS Lett.,* 223:42–46, 1987.

Barbour, "Isolation and Cultivation of Lyme Disease Spirochetes," *Yale J. Biol Med.,* 47:521–525, 1984.

Barthold and Bockenstedt, *Infect. Immun.,* 61:4696–4702, 1993.

Barthold et al., "Animal Model: Chronic Lyme borreliosis in the Laboratory Mouse," *Am. J. Pathol.,* 143:959–971, 1993.

Barthold et al., "Kinetics of *Borrelia burgdorferi* Dissemination and Evolution of Disease After Intradermal Inoculation of Mice," *Am. J. Pathol.,* 139:263–273, 1991.

Barthold et al., "Lyme borreliosis in the Laboratory Mouse," *In: Lyme Disease: Molecular and Immunology Approaches,* S. E. Schutzer (ed.), Cold Spring Harbor Press, Plainview, N.Y., p. 223–242, 1992.

Barthold et al., *Infect. Immun.,* 63:2255–2261, 1995.

Bayer and Wilchek, "The use of the avidin-biotin complex as a tool for molecular biology" In Glick, D., "Methods of Biochemical Analysis," John Wiley and Sons, New York, 1980.

Bianco et al., *J. Histochem. Cytochem.,* 38:1549–1563, 1990.

Bidanset et al., "Binding of the Proteoglycan Decorin to Collagen Type VI," *J. Biol. Chem.,* 267:5250–5256, 1992.

Bledsoe et al., *J. Bacteriol.,* 176:7447–7455, 1994.

Blockgerger et al., *J. Biol. Chem.,* 267:347–352, 1992.

Bolivar et al., *Gene,* 2:95, 1977.

Bornstein and Sage, *Ann. Rev. Biochem.,* 49:957–1003, 1980.

Brandt et al., *Infect. Immun.,* 58:983–991, 1990.

Brown and Vogel, *Matrix,* 9:468–478, 1989.

Campbell, "Monoclonal Antibody Technology, Laboratory Techniques in Biochemistry and Molecular Biology," Vol. 13, Burden and Von Knippenberg, Eds. pp. 75–83, Elsevier, Amsterdam, 1984.

Capecchi, "High efficiency transformation by direct microinjection of DNA into cultured mammalian cells," Cell, 22(2):479–488, 1980.

Carter et al, Nucl. Acids Res., 12:4431–4443, 1985.

Casjens et al., J. Bacteriol, 177:2769, 1995.

Centers for Disease Control, "Lyme Disease, United States, 1994," Morbid. Mortal. W. Rep., 44(24):459–463, 1994.

Chang et al., Nature, 375:615, 1978.

Cherry, Vaccine, 10:1033–1038, 1992.

Choi et al., J. Biol. Chem., 264:2876–2884, 1989.

Choi et al., "Characterization of the Dermatan Sulfate Proteoglycans, DS-PGI and DS-PGII, From Bovine Articular Cartilage and Skin Isolated by Octyl-Sepharose Chromatography," J. Biol. Chem., 264:2876–2884, 1989.

Chopra et al., Biochem. J., 232:277–279, 1985.

Chou and Fasman, "Conformational Parameters for Amino Acids in Helical, β-Sheet, and Random Coil Regions Calculated from Proteins," Biochemistry, 13(2):211–222, 1974b.

Chou and Fasman, "Empirical Predictions of Protein Conformation," Ann. Rev. Biochem., 47:251–276, 1978b.

Chou and Fasman, "Prediction of β-Turns," Biophys. J., 26:367–384, 1979.

Chou and Fasman, "Prediction of Protein Conformation," Biochemistry, 13(2):222–245, 1974a.

Clapp, "Somatic gene therapy into hematopoietic cells. Current status and future implications," Clin. Perinatol., 20(1):155–168, 1993.

Coburn et al., "Diverse Lyme Disease Spirochetes Bind Integrin $\alpha_{IIb}\beta_3$ on Human Platelets," Infect. Immun., 62:5559–5567, 1994.

Coburn et al., "Integrin $\alpha_{IIb}\beta_3$ Mediates Binding of the Lyme Disease Agent Borrelia burgdorferi to Human Platelets," Proc. Natl. Acad. Sci. USA, 90:7059–7063, 1993.

Couvreur, "Polyalkyleyanoacrylates as Colloidal Drug Carriers," Crit. Rev. Ther. Drug Carrier Syst., 5:1–20, 1988.

Couvreur et al., "Nanocapsules, a New Lysosomotropic Carrier," FEBS Lett., 84:323–326, 1977.

Cox et al., J. Virol., 67(9):5664–5667, 1993.

Curiel et al., "Adenovirus enhancement of transferrin-polylysine-mediated gene delivery," Proc. Natl. Acad. Sci. USA, 88(19):8850–8854, 1991.

Day et al, Biochem. J, 248:801–805, 1987.

de Silva et al, J. Exp. Med. 183:271–275, 1996.

Dreher et al., Eur. J. Cell Biol., 53:296–304, 1990.

Duray, "Target Organs of Borrelia burgdorferi Infections: Functional Responses and Histology," In: Lyme Disease: Molecular and Immunologic Approaches, S. E. Schutzer (ed.), Cold Spring Harbor Press, Plainview, N.Y., p. 11–30, 1992.

Eglitis and Anderson, "Retroviral vectors for introduction of genes into mammalian cells," Biotechniques, 6(7):608–614, 1988.

Fiers et al., Nature, 273:113, 1978.

Fikrig et al., J. Exp. Med., 181:215–221, 1995.

Fikrig et al., Science, 250:553–556, 1990.

Fisher et al., Connect. Tissue Res., 21:43–50, 1989.

Fisher et al., J. Biol. Chem., 258:6588–6594, 1983.

Fisher et al., J. Biol. Chem., 262:9702–9708, 1987.

Fisher et al., J. Biol. Chem., 264:4571–4576, 1989.

Fröman et al., "Binding of Escherichia coli to Fibronectin: A Mechanism of Tissue Adherence," J. Biol. Chem., 259:14899–14905, 1984.

Fromm et al., "Expression of genes transferred into monocot and dicot plant cells by electroporation," Proc. Natl. Acad. Sci. USA, 82(17):5824–5828, 1985.

Funderburgh et al., Dev. Biol., 116:267–277, 1986.

Fynan et al., "DNA vaccines: protective immunizations by parenteral, mucosal, and gene gun inoculations," Proc. Natl. Acad. Sci. USA, 90(24):11478–11482, 1993.

Gabizon and Papahadjopoulos, "Liposomes formulations with prolonged circulation time in blood and enhanced uptake by tumors," Proc. Natl. Acad. Sci. USA, 85:6949–6953, 1988.

Goding, "Monoclonal Antibodies: Principles and Practice," pp. 60–74. 2nd Edition, Academic Press, Orlando, Fla., 1986.

Goeddel et al., Nature, 281:544, 1979.

Goeddel et al., Nucl. Acids Res., 8:4057, 1980.

Graham and van der Eb, "Transformation of rat cells by DNA of human adenovirus 5," Virology, 54(2):536–539, 1973.

Harlow and Lane, "Antibodies: a Laboratory Manual," Cold Spring Harbor Laboratory, Cold Spring Harbor, N.Y. 1988.

Häupl et al., "Persistence of Borrelia burgdorferi in Ligamentous Tissue From a Patient With Chronic Lyme borreliosis," Arthritis Rheum., 36:1621–1626, 1993.

Hedborn and Heinegard, J. Biol. Chem., 264:6898–6905, 1989.

Henry-Michelland et al., "Attachment of Antibiotics to Nanoparticles; Preparation, Drug-Release and Antimicrobial Activity in vitro," Int. J. Pharm., 35:121–127, 1987.

Hess et al., J. Adv. Enzyme Reg., 7:149, 1968.

Hitzeman et al., J. Biol. Chem., 255:2073, 1980.

Ho et al., "Site-Directed Mutagenesis by Overlap Extension Using the Polymerase Chain Reaction," Gene, 77:51–59, 1989.

Holland et al., Biochemistry, 17:4900, 1978.

Hunter, "Radioimmunoassay," In: Handbook of Experimental Immunology, D. M. Weir (ed.), Blackwell Scientific Publications, Ltd., Oxford, U.K., p. 14.1–14.40, 1978.

Isaacs, "Borrelia burgdorferi Bind to Epithelial Cell Proteoglycans," J. Clin. Invest., 93:809–819, 1994.

Itakura et al., Science, 198:1056, 1977.

Jameson and Wolf, Compu. Appl. Biosci., 4(1):181–6, 1988.

Jones, Genetics, 85:12 1977.

Keller et al., J. Am. Med. Assoc., 271:1764–1768, 1994.

Kingsman et al., Gene, 7:141, 1979.

Kohler and Milstein, Eur. J. Immunol., 6:511–519, 1976.

Kohler and Milstein, Nature, 256:495–497, 1975.

Kolbert et al., *Res. Microbiol.*, 146:5, 1995.

Kreis and Vale (eds.), *Guidebook to the Extracellular Matrix and Adhesion Proteins*, A Sambrook and Tooze Publication at Oxford University Press, p. 48–56. 1993.

Krumdieck et al., "The Proteoglycan Decorin Binds C1q and Inhibits the Activity of the C1 Complex," *J. Immunol.*, 149:3695–3701, 1992.

Krusius and Ruoslahti, *Proc. Natl. Acad Sci. USA*, 83:7683–7687, 1986.

Kuby, "Immunology" 2nd Edition. W. H. Freeman & Company, New York, 1994.

Kyte and Doolittle, *J. Mol. Biol.*, 157(1):105–132, 1982.

Laemmli, "Cleavage of Structural Proteins During the Assembly of the Head of Bacteriophage T4," *Nature (London)*, 227:680–685, 1970.

Lovrich et al., *Infect. Immun.*, 63:2113–2119, 1995.

Maloy, et al., "Microbial Genetics" 2nd Edition. Jones and Bartlett Publishers, Boston, Mass., 1994.

Maniatis et al., "Molecular Cloning: a Laboratory Manual," Cold Spring Harbor Laboratory, Cold Spring Harbor, N.Y., 1982.

Maxe et al., "Specific Attachment of *Staphylococcus aureus* to Immobilized Fibronectin," *Infect. Immun.*, 54:695–704, 1986.

McBride et al., *Genomics*, 6:219–225, 1990.

Nakamura et al., "Enzyme Immunoassays: Heterogenous and Homogenous Systems," Chapter 27., 1987.

Neame et al., *J. Biol. Chem.*, 264:8653–8661, 1989.

Oldberg et al., *EMBO J.*, 8:2601–2606, 1989.

Patthy, *J. Mol. Biol.*, 198:567–577, 1987.

Patti et al., "The *Staphylococcus aureus* Collagen Adhesin is a Virulence Determinant in Experimental Septic Arthritis," *Infect. Immun.* 62:152–161, 1994.

Plaas et al., *J. Biol. Chem.*, 265:20634–20640, 1990.

Pringle and Dodd, *J. Histochem. Cytochem.*, 38:1405–1411, 1990.

Probert and LeFebvre, Abst. Annu. Meet. Am. Soc. Microbiol., #E-56, 1995.

Prokop and Bajpai, "Recombinant DNA Technology I" *Ann. N.Y. Acad Sci.*, Vol. 646, 1991.

Ramachandran and Reddi, "Biochemistry of Collagen," Plenum Press, New York, 1976.

Sadziene et al., *J. Infect. Dis.*, 167:165–172, 1993.

Sambrook et al., "Molecular Cloning: A Laboratory Manual," 2nd Edition, Chapter 12.6, Cold Spring Harbor Laboratory, Cold Spring Harbor, N.Y., 1989.

Schaible et al., *Proc. Natl. Acad. Sci. USA*, 87:3768–3772, 1990.

Schaible et al., *Vaccine*, 11:1049–1054, 1993.

Schwan et al., *Proc. Natl. Acad Sci. USA*, 92:2909–2913, 1995.

Segal, "Biochemical Calculations" 2nd Edition. John Wiley and Sons, New York, 1976.

Steere, *New Engl. J. Med.*, 321:586–596, 1989.

Steere, *Proc. Nat. Acad. Sci. USA.*, 91:2378–2383, 1994.

Stinchcomb et al., *Nature*, 282:39, 1979.

Studier et al., "Use of T7 RNA Polymerase to Direct Expression of Cloned Genes" *Methods Enzymol.* 185, 1990.

Tang et al, *Nature*, 356:152–154, 1992.

Tschemper et al., *Gene*, 10:157, 1980.

Ulmer et al., "Heterologous Protection Against Influenza by Injection of DNA Encoding a Viral Protein," *Science*, 259:1745–1749, 1993.

Urioste et al., *J. Exp. Med*, 180:1077–1085, 1994.

Van Nhieu et al., "Bacterial Internalization Medicated by $\beta_1$ Chain Integrins is Determined by Ligand Affinity and Receptor Density," *EMBO J.*, 12:1887–1895, 1993.

Vanderrest and Garrone, *FASEB. J.*, 5:2814–2823, 1991.

Vogel and Heinegard, *J. Biol. Chem.*, 260:9298–9306, 1985.

Vogel and Trotter, *Collagen Rel. Res.*, 7:105–114, 1987.

Vogel et al., *Biochem. J.*, 223:587–597, 1984.

Wagner et al, "Coupling of adenovirus to transferrin-polylysine/DNA complexes greatly enhances receptor-mediated gene delivery and expression of transfected genes," *Proc. Natl. Acad. Sci. USA*, 89(13):6099–6103, 1992.

Wang et al., *J. Exp. Med.*, 177:699, 1993.

Wang et al., *J. Immunol.*, 150:3022, 1993.

Whitton et al., *J. Virol.*, 67:(1)348–352, 1993.

Wilske et al., *Infect. Immun.*, 61:2182–2191, 1993.

Wilske et al., *J. Clin. Microbiol.*, 31:340, 1993.

Wilske et al., *Scand. J. Infect. Dis. Suppl.*, 77:108–129, 1991.

Wolf et al., *Compu. Appl. Biosci.*, 4(1):187–91, 1988.

Wong and Neumann, "Electric field mediated gene transfer," *Biochim. Biophys. Res. Commun.* 107(2):584–587, 1982.

Yamaguchi et al., "Negative Regulation of Transforming Growth Factor-$\beta$ by the Proteoglycan Decorin," *Nature (London)*, 346:281–284, 1990.

Yang and Russel, *Proc. Natl. Acad. Sci. USA*, 87:4144–4148, 1990.

Zimmer et al, "Lyme Carditis in Immunodeficient Mice During Experimental Infection of *Borrelia burgdorferi*," *Virchows Arch. A Pathol. Anat.*, 417:129–135, 1990.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. Accordingly, the exclusive rights sought to be patented are as described in the claims below.

What is claimed is:

1. A composition comprising:
   (a) an isolated decorin binding protein comprising the contiguous amino acid sequence of SEQ ID NO:34;
   (b) an isolated decorin binding protein comprising an amino acid sequence of at least about 100 contiguous amino acids from SEQ ID NO:42;
   (c) an isolated decorin binding protein comprising an amino acid sequence of at least about 100 contiguous amino acids from SEQ ID NO:46; or
   (d) an isolated decorin binding protein or decorin binding peptide comprising an amino acid sequence of at least about 25 contiguous amino acids from SEQ ID NO:50.

2. The composition of claim 1, comprising an isolated decorin binding protein comprising the contiguous amino acid sequence of SEQ ID NO:34.

3. The composition of claim 1, comprising an isolated decorin binding protein comprising an amino acid sequence of at least about 100 contiguous amino acids from SEQ ID NO:42.

4. The composition of claim 3, comprising an isolated decorin binding protein comprising the contiguous amino acid sequence of SEQ ID NO:42.

5. The composition of claim 1, comprising an isolated decorin binding protein comprising an amino acid sequence of at least about 100 continuous amino acids from SEQ ID NO:46.

6. The composition of claim 5, comprising an isolated decorin binding protein comprising the contiguous amino acid sequence of SEQ ID NO: 46.

7. The composition of claim 1, comprising an isolated decorin binding protein or decorin binding peptide comprising an amino acid sequence of at least about 25 contiguous amino acids from SEQ ID NO:50.

8. The composition of claim 7, comprising an isolated decorin binding protein or decorin binding peptide comprising an amino acid sequence of at least about 50 contiguous amino acids from SEQ ID NO:50.

9. The composition of claim 8, comprising an isolated decorin binding protein comprising an amino acid sequence of at least about 100 contiguous amino acids from SEQ ID NO:50.

10. The composition of claim 9, comprising an isolated decorin binding protein comprising the contiguous amino acid sequence of SEQ ID NO:50.

11. The composition of claim 1, dispersed in a pharmaceutically acceptable carrier.

12. The composition of claim 1, comprising an isolated decorin binding protein comprising the contiguous amino acid sequence of SEQ ID NO:34 and an isolated decorin binding protein comprising an amino acid sequence of at least about 100 contiguous amino acids from SEQ ID NO:42.

13. The composition of claim 1, comprising an isolated decorin binding protein comprising the contiguous amino acid sequence of SEQ ID NO:34 and an isolated decorin binding protein comprising an amino acid sequence of at least about 100 contiguous amino acids from SEQ ID NO:46.

14. The composition of claim 1, comprising an isolated decorin binding protein comprising the contiguous amino acid sequence of SEQ ID NO:34 and an isolated decorin binding protein or decorin binding peptide comprising an amino acid sequence of at least about 25 contiguous amino acids from SEQ ID NO:50.

15. The composition of claim 14, comprising an isolated decorin binding protein comprising the contiguous amino acid sequence of SEQ ID NO:34 and an isolated decorin binding protein or decorin binding peptide comprising an amino acid sequence of at least about 50 contiguous amino acids from SEQ ID NO:50.

16. The composition of claim 15, comprising an isolated decorin binding protein comprising the contiguous amino acid sequence of SEQ ID NO:34 and an isolated decorin binding protein comprising an amino acid sequence of at least about 100 contiguous amino acids from SEQ ID NO:50.

17. The composition of claim 1, comprising an isolated decorin binding protein comprising an amino acid sequence of at least about 100 contiguous amino acids from SEQ ID NO:42 and an isolated decorin binding protein comprising the contiguous amino acid sequence of SEQ ID NO:46.

18. The composition of claim 1, comprising an isolated decorin binding protein comprising the contiguous amino acid sequence of SEQ ID NO:42 and an isolated decorin binding protein comprising an amino acid sequence of at least about 100 contiguous amino acids from SEQ ID NO:46.

19. The composition of claim 1, comprising an isolated decorin binding protein comprising an amino acid sequence of at least about 100 contiguous amino acids from SEQ ID NO:42 and an isolated decorin binding protein or decorin binding peptide comprising an amino acid sequence of at least about 25 contiguous amino acids from SEQ ID NO:50.

20. The composition of claim 19, comprising an isolated decorin binding protein comprising the contiguous amino acid sequence of SEQ ID NO:42 and an isolated decorin binding protein comprising an amino acid sequence of at least about 100 contiguous amino acids from SEQ ID NO:50.

21. The composition of claim 1, comprising an isolated decorin binding protein comprising an amino acid sequence of at least about 100 contiguous amino acids from SEQ ID NO:46 and an isolated decorin binding protein or decorin binding peptide comprising an amino acid sequence of at least about 25 contiguous amino acids from SEQ ID NO:50.

22. The composition of claim 21, comprising an isolated decorin binding protein comprising the contiguous amino acid sequence of SEQ ID NO:46 and an isolated decorin binding protein comprising an amino acid sequence of at least about 100 contiguous amino acids from SEQ ID NO:50.

23. The composition of claim 1, comprising an isolated decorin binding protein comprising the contiguous amino acid sequence of SEQ ID NO:34, an isolated decorin binding protein comprising an amino acid sequence of at least about 100 contiguous amino acids from SEQ ID NO:42 and an isolated decorin binding protein comprising an amino acid sequence of at least about 100 contiguous amino acids from SEQ ID NO:46.

24. The composition of claim 1, comprising an isolated decorin binding protein comprising the contiguous amino acid sequence of SEQ ID NO:34, an isolated decorin binding protein comprising an amino acid sequence of at least about 100 contiguous amino acids from SEQ ID NO:42 and an isolated decorin binding protein or decorin binding peptide comprising an amino acid sequence of at least about 25 contiguous amino acids from SEQ ID NO:50.

25. The composition of claim 24, comprising an isolated decorin binding protein comprising the contiguous amino acid sequence of SEQ ID NO:34, an isolated decorin binding protein comprising an amino acid sequence of at least about 100 contiguous amino acids from SEQ ID NO:42 and an isolated decorin binding protein comprising an amino acid sequence of at least about 100 contiguous amino acids from SEQ ID NO:50.

26. The composition of claim 1, comprising an isolated decorin binding protein comprising an amino acid sequence of at least about 100 contiguous amino acids from SEQ ID NO:42, an isolated decorin binding protein comprising an amino acid sequence of at least about 100 contiguous amino acids from SEQ ID NO:46 and an isolated decorin binding protein or decorin binding peptide comprising an amino acid sequence of at least about 25 contiguous amino acids from SEQ ID NO:50.

27. The composition of claim 26, comprising an isolated decorin binding protein comprising an amino acid sequence of at least about 100 contiguous amino acids from SEQ ID NO:42, an isolated decorin binding protein comprising an amino acid sequence of at least about 100 contiguous amino acids from SEQ ID NO:46 and an isolated decorin binding protein comprising an amino acid sequence of at least about 100 contiguous amino acids from SEQ ID NO:50.

28. The composition of claim 1, comprising an isolated decorin binding protein comprising the contiguous amino acid sequence of SEQ ID NO:34, an isolated decorin binding protein comprising an amino acid sequence of at least about 100 contiguous amino acids from SEQ ID NO:42, an isolated decorin binding protein comprising an amino acid sequence of at least about 100 contiguous amino acids from SEQ ID NO:46 and an isolated decorin binding protein or decorin binding peptide comprising an amino acid sequence of at least about 25 contiguous amino acids from SEQ ID NO:50.

29. The composition of claim 28, comprising an isolated decorin binding protein comprising the contiguous amino acid sequence of SEQ ID NO:34, an isolated decorin binding protein comprising an amino acid sequence of at least about 100 contiguous amino acids from SEQ ID NO:42, an isolated decorin binding protein comprising an amino acid sequence of at least about 100 contiguous amino acids from SEQ ID NO:46 and an isolated decorin binding protein comprising an amino acid sequence of at least about 100 contiguous amino acids from SEQ ID NO:50.

30. The composition of claim 12, comprising an isolated decorin binding protein comprising the contiguous amino acid sequence of SEQ ID NO:34 and an isolated decorin binding protein comprising the contiguous amino acid sequence of SEQ ID NO:42.

31. The composition of claim 13, comprising an isolated decorin binding protein comprising the contiguous amino acid sequence of SEQ ID NO:34 and an isolated decorin binding protein comprising the contiguous amino acid sequence of SEQ ID NO:46.

32. The composition of claim 16, comprising an isolated decorin binding protein comprising the contiguous amino acid sequence of SEQ ID NO:34 and an isolated decorin binding protein comprising the contiguous amino acid sequence of SEQ ID NO:50.

33. The composition of claim 18, comprising an isolated decorin binding protein comprising the contiguous amino acid sequence of SEQ ID NO:42 and an isolated decorin binding protein comprising the contiguous amino acid sequence of SEQ ID NO:46.

34. The composition of claim 20, comprising an isolated decorin binding protein comprising the contiguous amino acid sequence of SEQ ID NO:42 and an isolated decorin binding protein comprising the contiguous amino acid sequence of SEQ ID NO:50.

35. The composition of claim 22, comprising an isolated decorin binding protein comprising the contiguous amino acid sequence of SEQ ID NO:46 and an isolated decorin binding protein comprising the contiguous amino acid sequence of SEQ ID NO:50.

36. The composition of claim 23, comprising an isolated decorin binding protein comprising the contiguous amino acid sequence of SEQ ID NO:34, an isolated decorin binding protein comprising the contiguous amino acid sequence of SEQ ID NO:42 and an isolated decorin binding protein comprising the contiguous amino acid sequence of SEQ ID NO:46.

37. The composition of claim 25, comprising an isolated decorin binding protein comprising the contiguous amino acid sequence of SEQ ID NO:34, an isolated decorin binding protein comprising the contiguous amino acid sequence of SEQ ID NO:42 and an isolated decorin binding protein comprising the contiguous amino acid sequence of SEQ ID NO:50.

38. The composition of claim 27, comprising an isolated decorin binding protein comprising the contiguous amino acid sequence of SEQ ID NO:42, an isolated decorin binding protein comprising the contiguous amino acid sequence of SEQ ID NO:46 and an isolated decorin binding protein comprising the contiguous amino acid sequence of SEQ ID NO:50.

39. The composition of claim 29, comprising an isolated decorin binding protein comprising the contiguous amino acid sequence of SEQ ID NO:34, an isolated decorin binding protein comprising the contiguous amino acid sequence of SEQ ID NO:42, an isolated decorin binding protein comprising the contiguous amino acid sequence of SEQ ID NO:46 and an isolated decorin binding protein comprising the contiguous amino acid sequence of SEQ ID NO:50.

* * * * *

SEQUENCE LISTING

<160> NUMBER OF SEQ ID NOS: 66

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 1
cgcggatcca tgattaaatg taataat                                              27

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 2
cgcggatcca ccaatcttct taaacta                                              27

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 3
cgcggatccg gactaacagg agcaaca                                              27

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 4
gcgctgcagt tataccccac tacccgt                                              27

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 5
cgcggatccc gacttctctt aggaggt                                              27

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

```
<400> SEQUENCE: 6
gcgctgcagt tacgatttag cagtgct                                          27

<210> SEQ ID NO 7
<211> LENGTH: 2656
<212> TYPE: DNA
<213> ORGANISM: Borrelia burgdorferi
<220> FEATURE:
<221> NAME/KEY: CDS
<222> LOCATION: (1474)..(2034)

<400> SEQUENCE: 7
ctcgatctat tttttaaata taataaaatt aataaaaata agtggtaaaa ggagaaaaga      60
atatttaaaa caaatatat tctgttgcca gtaataacat tattgtgtaa tatgtatagt     120
gaggtattta ctcaaagagc aagaaacaaa atcaaaaaa atcgttgtta acgaacaaaa     180
tgaaagatta aaacgcttaa taaagcttta tggaaaata catctagtaa aagtttaaaa     240
gacatgacaa ttaaagtaaa aaacaaaata gcctcaggag caagcaaaaa aggatacttc    300
tttaaaggcc taagggtat ttttatgcct tttaagcctg ccaatcctta tactcctaat    360
taaaaaaaat aaagcaatat caaaatagtc aaaatactca aagagaagc caataaattg    420 cgggagatgg cttctctttt attttttaaga cctaattatt ttagactttg attcaatttg    480
caaaataacc aatttgaaat attttggcaa actggaaaca agtcttaaat tacaagccag    540
attgatagaa acttgtaatt ccaaacaatg ttactgctat atttgcataa aacaaattca    600
cactaacaat aaaaataata aaataaaact taaactgata cgcttttaaa ataaaagttt    660
taaactttag tacaaatcta gacattatat taacttttta catcaacata ctaactaatt    720
tattttattt tattttttcat aaagtgggct aaaatttaaa tttaactaaa tttaatagaa    780
ggaggaaaaa atgaaaattg gaaagctaaa ttcaatagtt atagccttgt tttttaaact    840
attggtcgca tgtagtattg gattagtaga aagaacaaat gcagctcttg aatcgtcctc    900
taaggattta aaaacaaaa ttttaaaaat aaaaaaagat gccacgggaa aagtgtgtact    960 ttttgaagct tttacaggtc ttaaaaccgg ttccaaggta acaagtggtg gactagcctt   1020
aagagaagca aaagtacaag ccattgttga acaggaaag ttccttaaga taatagaaga   1080
agaagcttta aagcttaaag aaactggaaa cagtggtcaa ttcttggcta tgtttgactt   1140
aatgcttgag gttgtagaat cgctagaaga cgttggaata ataggcttaa aagcccgtgt   1200
tttagaggaa tctaaaaata atcctataaa cacagctgaa agattgcttg cggctaaagc   1260
tcaaatagaa aatcaactta aagtggttaa ggaaaaacaa atattgaaa atggtggaga   1320 gaaaaaaaat aacaaaagca aaaaaagaa ataaatatta aaaatattgt cattagaatg   1380
gactaaaagt aaaattttta gctcgtccta atatttacaa tttaataata ttggtttatt   1440
gcttttacta aaatacaaaa aaaggataat gtt atg att aaa tgt aat aat aaa    1494
                                   Met Ile Lys Cys Asn Asn Lys
                                    1               5 act ttt aac aat tta ctt aaa cta act ata ctt gtt aac cta ctt ata     1542
Thr Phe Asn Asn Leu Leu Lys Leu Thr Ile Leu Val Asn Leu Leu Ile
        10                  15                  20 tca tgt gga cta aca gga gca aca aaa atc aaa tta gaa tca tca gct     1590
Ser Cys Gly Leu Thr Gly Ala Thr Lys Ile Lys Leu Glu Ser Ser Ala
    25                  30                  35 aaa gcc att gta gat gaa ata gat gca att aaa aaa aag gct gct tct     1638
Lys Ala Ile Val Asp Glu Ile Asp Ala Ile Lys Lys Lys Ala Ala Ser
40                  45                  50                  55
```

```
atg ggt gta aat ttt gat gcc ttt aaa gat aaa aaa acg ggt agt ggg     1686
Met Gly Val Asn Phe Asp Ala Phe Lys Asp Lys Lys Thr Gly Ser Gly
            60                  65                  70 gta tca gaa aat cca ttc ata ctt gaa gca aaa gtg cga gct act aca     1734
Val Ser Glu Asn Pro Phe Ile Leu Glu Ala Lys Val Arg Ala Thr Thr
        75                  80                  85 gta gcg gaa aaa ttc gta ata gca ata gaa gag gaa gct act aaa ctt     1782
Val Ala Glu Lys Phe Val Ile Ala Ile Glu Glu Glu Ala Thr Lys Leu
    90                  95                  100 aaa gaa act gga agt agt ggt gaa ttc tca gca atg tat gat tta atg     1830
Lys Glu Thr Gly Ser Ser Gly Glu Phe Ser Ala Met Tyr Asp Leu Met
105                 110                 115 ttt gaa gtc tca aaa cca tta caa gaa ttg gga ata caa gag atg aca     1878
Phe Glu Val Ser Lys Pro Leu Gln Glu Leu Gly Ile Gln Glu Met Thr
120                 125                 130                 135 aaa aca gtc tca atg gca gct gaa gag aat cct cca act aca gct caa     1926
Lys Thr Val Ser Met Ala Ala Glu Glu Asn Pro Pro Thr Thr Ala Gln
            140                 145                 150 gga gtg ctt gaa att gca aaa aaa atg aga gaa aaa tta caa agg gtt     1974
Gly Val Leu Glu Ile Ala Lys Lys Met Arg Glu Lys Leu Gln Arg Val
        155                 160                 165 cac aag aaa aac caa gac acc tta aag aaa aaa aat acc gaa gac agc     2022
His Lys Lys Asn Gln Asp Thr Leu Lys Lys Lys Asn Thr Glu Asp Ser
    170                 175                 180 act gct aaa tcg taataaacac cattttata tgcaactcaa aataatagac          2074
Thr Ala Lys Ser
    185 caaacaacca cctgtgttgg gctgtttggt cttacaattt aaatgttaat tctgcaatgc   2134 aaaaaacaaa tattaagctc ttcaaccagc attcaaaagc taaattaag gttaaagcaa    2194 ttaacccaaa ggatttaaaa tttaaaaaat actgtaataa acattaaaag ttataaaatg   2254 taattattat tttcaaacaa aataattaaa tatcctttt gatgttattt ggaatttctt    2314 tcctttagac tttaaatcaa gactgtcgta aagcaccta ttattatcca ttacaagaaa    2374 atgcacaaaa acccgacttt accttaactc tgttatttca aactctcagc cagctttagg   2434 caaataaagt ggactctctg atctaacctt ggaaatatt ttataacaac taagaatttt    2494 acatggattt aaaatataac aatcctttct aatgtagcct aattccaaaa accgctgata   2554 atttaaatta acgtcttttg ctgtaaaatc aaaccccttt aaaacaaata tcaatagtgc   2614 aaagacaaaa aataacatcg gactttttgaa tgtctttaaa ca                    2656

<210> SEQ ID NO 8
<211> LENGTH: 187
<212> TYPE: PRT
<213> ORGANISM: Borrelia burgdorferi

<400> SEQUENCE: 8

Met Ile Lys Cys Asn Asn Lys Thr Phe Asn Asn Leu Leu Lys Leu Thr
1               5                   10                  15

Ile Leu Val Asn Leu Leu Ile Ser Cys Gly Leu Thr Gly Ala Thr Lys
            20                  25                  30

Ile Lys Leu Glu Ser Ser Ala Lys Ala Ile Val Asp Glu Ile Asp Ala
        35                  40                  45

Ile Lys Lys Lys Ala Ala Ser Met Gly Val Asn Phe Asp Ala Phe Lys
    50                  55                  60

Asp Lys Lys Thr Gly Ser Gly Val Ser Glu Asn Pro Phe Ile Leu Glu
65                  70                  75                  80
```

```
Ala Lys Val Arg Ala Thr Thr Val Ala Glu Lys Phe Val Ile Ala Ile
                85                  90                  95

Glu Glu Glu Ala Thr Lys Leu Lys Glu Thr Gly Ser Ser Gly Glu Phe
            100                 105                 110

Ser Ala Met Tyr Asp Leu Met Phe Glu Val Ser Lys Pro Leu Gln Glu
        115                 120                 125

Leu Gly Ile Gln Glu Met Thr Lys Thr Val Ser Met Ala Ala Glu Glu
    130                 135                 140

Asn Pro Pro Thr Thr Ala Gln Gly Val Leu Glu Ile Ala Lys Lys Met
145                 150                 155                 160

Arg Glu Lys Leu Gln Arg Val His Lys Lys Asn Gln Asp Thr Leu Lys
                165                 170                 175

Lys Lys Asn Thr Glu Asp Ser Thr Ala Lys Ser
            180                 185
```

<210> SEQ ID NO 9
<211> LENGTH: 187
<212> TYPE: PRT
<213> ORGANISM: Borrelia burgdorferi

<400> SEQUENCE: 9

```
Met Ile Lys Cys Asn Asn Lys Thr Phe Asn Asn Leu Leu Lys Leu Thr
 1               5                  10                  15

Ile Leu Val Asn Leu Leu Ile Ser Cys Gly Leu Thr Gly Ala Thr Lys
                20                  25                  30

Ile Lys Leu Glu Ser Ser Ala Lys Ala Ile Val Asp Glu Ile Asp Ala
            35                  40                  45

Ile Lys Lys Lys Ala Ala Ser Met Gly Val Asn Phe Asp Ala Phe Lys
        50                  55                  60

Asp Lys Lys Thr Gly Ser Gly Val Ser Glu Asn Pro Phe Ile Leu Glu
 65                 70                  75                  80

Ala Lys Val Arg Ala Thr Thr Val Ala Glu Lys Phe Val Ile Ala Ile
                85                  90                  95

Glu Glu Glu Ala Thr Lys Leu Lys Glu Thr Gly Ser Ser Gly Glu Phe
            100                 105                 110

Ser Ala Met Tyr Asp Leu Met Phe Glu Val Ser Lys Pro Leu Gln Glu
        115                 120                 125

Leu Gly Ile Gln Glu Met Thr Lys Thr Val Ser Met Ala Ala Glu Glu
    130                 135                 140

Asn Pro Pro Thr Thr Ala Gln Gly Val Leu Glu Ile Ala Lys Lys Met
145                 150                 155                 160

Arg Glu Lys Leu Gln Arg Val His Lys Lys Asn Gln Asp Thr Leu Lys
                165                 170                 175

Lys Lys Asn Thr Glu Asp Ser Thr Ala Lys Ser
            180                 185
```

<210> SEQ ID NO 10
<211> LENGTH: 1400
<212> TYPE: DNA
<213> ORGANISM: Artificial Sequence
<220> FEATURE:
<223> OTHER INFORMATION: Description of Artificial Sequence: SYNTHETIC OLIGONUCLEOTIDE

<400> SEQUENCE: 10

```
ctcgatctat ttttaaata taataaaatt aataaaaata agtggtaaaa ggagaaaaga     60
atatttaaaa caaatatat tctgttgcca gtaataacat tattgtgtaa tatgtatagt    120
```

-continued

```
gaggtatttta ctcaaagagc aagaaacaaa aatcaaaaaa atcgttgtta acgaacaaaa      180
tgaaagatta aaacgcttaa taaaagctta tggaaaaata catctagtaa aagtttaaaa      240
gacatgacaa ttaaagtaaa aaacaaaata gcctcaggag caagcaaaaa aggatacttc      300
tttaaaggcc taaagggtat ttttatgcct tttaagcctg ccaatcctta tactcctaat      360
taaaaaaaat aaagcaatat caaatagtc aaaatactca aaagagaagc caataaattg       420
cgggagatgg cttctctttt attttaaga cctaattatt ttagactttg attcaatttg        480
caaaataacc aatttgaaat attttggcaa actggaaaca agtcttaaaa tacaagccag      540
attgatagaa acttgtaatt ccaaacaatg ttactgctat atttgcataa aacaaattca      600
cactaacaat aaaaataata aataaaact taaactgata cgcttttaaa ataaaagttt        660
taaactttag tacaaatcta gacattatat taacttttta catcaacata ctaactaatt      720
tattttattt tatttttcat aaagtgggct aaaatttaaa tttaactaaa tttaatagaa      780
ggaggaaaaa atgaaaattg gaaagctaaa ttcaatagtt atagccttgt tttttaaact      840
attggtcgca tgtagtattg gattagtaga aagaacaaat gcagctcttg aatcgctcta      900
aggatttaaa aacaaaattt taaaaataaa aaaagatgcc acgggaaaag gtgtacttt       960 tgaagctttt acaggtctta aaaccggttc caagtaaca agtggtggac tagccttaag       1020
agaagcaaaa gtacaagcca ttgttgaaac aggaaagttc cttaagataa tagaagaaga    1080
agctttaaag cttaaagaaa ctggaaacag tggtcaattc ttggctatgt ttgacttaat      1140
gcttgaggtt gtagaatcgc tagaagacgt tggaataata ggcttaaaag cccgtgtttt      1200
agaggaatct aaaaataatc tataaacaca gctgaaagat tgcttgcggc taaagctcaa     1260
atagaaaatc aacttaaagt ggttaaggaa aaacaaaata ttgaaaatgg tggagagaaa     1320
aaaaataaca aaagcaaaaa aagaaataa atattaaaaa tattgtcatt agaatggact      1380
aaaagtaaaa ttttttggctc                                                1400
```

<210> SEQ ID NO 11
<211> LENGTH: 1253
<212> TYPE: DNA
<213> ORGANISM: Artificial Sequence
<220> FEATURE:
<223> OTHER INFORMATION: Description of Artificial Sequence: SYNTHETIC OLIGONUCLEOTIDE

<400> SEQUENCE: 11

```
gtcctaatat ttacaattta ataatattgg tttattgctt ttatctaaaa tacaaaaaaa       60
ggataatgtt atgattaaat gtaataataa aacttttaac aatttactta aactaactat       120
acttgttaac ctacttatat catgtggact aacaggagca acaaaaatca aattagaatc      180
atcagctaaa gccattgtag atgaaataga tgcaattaaa aaaaggctg cttctatggg      240 tgtaaatttt gatgcctta aagataaaaa aacgggtagt ggggtatcag aaaatccatt       300
catacttgaa gcaaaagtgc gagctactac agtagcggaa aaattcgtaa tagcaataga     360
agaggaagct actaaactta agaaactgg aagtagtggt gaattctcag caatgtatga     420
tttaatgttt gaagtctcaa aaccattaca agaattggga atacaagaga tgacaaaaac    480
agtctcaatg gcagctgaag agaatcctcc aactacagct caaggagtgc ttgaaattgc     540
aaaaaaaatg agagaaaaat tacaaagggt tcacaagaaa aaccaagaca ccttaaagaa     600
aaaaaatacc gaagacagca ctgctaaatc gtaataaaca ccattttat atgcaactca     660 aaataatagg ccaaacaacc acctgtgttg ggctgtttgg tcttacaatt taaatgttaa     720
```

```
ttctgcaatg caaaaaacaa atattaagct cttcaaccag cattcaaaag ctaaaattaa    780
ggttaaagca attaacccaa aggatttaaa atttaaaaaa tactgtaata aacattaaaa    840
gttataaaat gtaattatta ttttcaaaca aaataattaa atatccttttt tgatgttatt    900
```
<br>
```
gttataaaat gtaattatta ttttcaaaca aaataattaa atatccttttt tgatgttatt    900 tggaatttct ttcctttaga ctttaaatca agactgtcgt aaagcacctt attattatcc    960
attacaagaa aatgcacaaa aacccgactt taccttaact ctgttatttc aaactctcag   1020
ccagctttag gcaaataaag tggactctcg tatctaacct tggaaaatat tttataacaa   1080
ctaagaattt tacatggatt taaaatataa caatcctttc taatgtagcc taattccaaa   1140
aaccgctgat aatttaaatt aacgtctttt gctgtaaaat caaacccctt taaaacaaat   1200
atcaatagtg caaagacaaa aaataacatc ggactttga atgtctttaa aca          1253
```

<210> SEQ ID NO 12
<211> LENGTH: 573
<212> TYPE: DNA
<213> ORGANISM: Borrelia burgdorferi
<220> FEATURE:
<221> NAME/KEY: CDS
<222> LOCATION: (1)..(573)

<400> SEQUENCE: 12

```
atg att aaa tgt aat aat aaa act ttt aac aat tta ctt aaa cta act     48
Met Ile Lys Cys Asn Asn Lys Thr Phe Asn Asn Leu Leu Lys Leu Thr
 1               5                  10                  15 ata ctt gtt aac cta ctt ata tca tgt gga cta aca gga gca aca aaa     96
Ile Leu Val Asn Leu Leu Ile Ser Cys Gly Leu Thr Gly Ala Thr Lys
             20                  25                  30 att aga tta gaa cga agc gct aaa gac att aca gat gaa ata gat gca    144
Ile Arg Leu Glu Arg Ser Ala Lys Asp Ile Thr Asp Glu Ile Asp Ala
         35                  40                  45 att aaa aaa gac gct gct ctt aag ggc gta aat ttt gat gcc ttt aaa    192
Ile Lys Lys Asp Ala Ala Leu Lys Gly Val Asn Phe Asp Ala Phe Lys
     50                  55                  60 gat aaa aaa acg ggt agt ggg gta tca gaa aat cca ttc ata ctt gaa    240
Asp Lys Lys Thr Gly Ser Gly Val Ser Glu Asn Pro Phe Ile Leu Glu
 65                  70                  75                  80 gca aaa gtg cga gct act aca gta gcg gaa aaa ttc gta ata gca ata    288
Ala Lys Val Arg Ala Thr Thr Val Ala Glu Lys Phe Val Ile Ala Ile
                 85                  90                  95 gaa gag gaa gct act aaa ctc aaa gaa act gga agt agt ggt gaa ttt    336
Glu Glu Glu Ala Thr Lys Leu Lys Glu Thr Gly Ser Ser Gly Glu Phe
            100                 105                 110 tca gca atg tat gat tta atg ttt gaa gtc tca aaa cca tta caa aaa    384
Ser Ala Met Tyr Asp Leu Met Phe Glu Val Ser Lys Pro Leu Gln Lys
        115                 120                 125 ttg gga ata caa gag atg aca aaa aca gtc tca gat gca gct gaa gag    432
Leu Gly Ile Gln Glu Met Thr Lys Thr Val Ser Asp Ala Ala Glu Glu
    130                 135                 140 aat cct cca act aca gct caa gga gtg ctt gaa att gca aaa aaa atg    480
Asn Pro Pro Thr Thr Ala Gln Gly Val Leu Glu Ile Ala Lys Lys Met
145                 150                 155                 160 aga gaa aaa tta caa agg gtt cat aca aaa aac tac tgc acc ctt aaa    528
Arg Glu Lys Leu Gln Arg Val His Thr Lys Asn Tyr Cys Thr Leu Lys
                165                 170                 175 aag aag gaa aat tct act ttt act gat gaa aaa tgc aaa aat aac        573
Lys Lys Glu Asn Ser Thr Phe Thr Asp Glu Lys Cys Lys Asn Asn
            180                 185                 190
```

```
<210> SEQ ID NO 13
<211> LENGTH: 191
<212> TYPE: PRT
<213> ORGANISM: Borrelia burgdorferi

<400> SEQUENCE: 13

Met Ile Lys Cys Asn Asn Lys Thr Phe Asn Asn Leu Leu Lys Leu Thr
 1               5                  10                  15

Ile Leu Val Asn Leu Leu Ile Ser Cys Gly Leu Thr Gly Ala Thr Lys
             20                  25                  30

Ile Arg Leu Glu Arg Ser Ala Lys Asp Ile Thr Asp Glu Ile Asp Ala
         35                  40                  45

Ile Lys Lys Asp Ala Ala Leu Lys Gly Val Asn Phe Asp Ala Phe Lys
     50                  55                  60

Asp Lys Lys Thr Gly Ser Gly Val Ser Glu Asn Pro Phe Ile Leu Glu
 65                  70                  75                  80

Ala Lys Val Arg Ala Thr Thr Val Ala Glu Lys Phe Val Ile Ala Ile
                 85                  90                  95

Glu Glu Glu Ala Thr Lys Leu Lys Glu Thr Gly Ser Ser Gly Glu Phe
            100                 105                 110

Ser Ala Met Tyr Asp Leu Met Phe Glu Val Ser Lys Pro Leu Gln Lys
        115                 120                 125

Leu Gly Ile Gln Glu Met Thr Lys Thr Val Ser Asp Ala Ala Glu Glu
    130                 135                 140

Asn Pro Pro Thr Thr Ala Gln Gly Val Leu Glu Ile Ala Lys Lys Met
145                 150                 155                 160

Arg Glu Lys Leu Gln Arg Val His Thr Lys Asn Tyr Cys Thr Leu Lys
                165                 170                 175

Lys Lys Glu Asn Ser Thr Phe Thr Asp Glu Lys Cys Lys Asn Asn
            180                 185                 190

<210> SEQ ID NO 14
<211> LENGTH: 561
<212> TYPE: DNA
<213> ORGANISM: Borrelia burgdorferi
<220> FEATURE:
<221> NAME/KEY: CDS
<222> LOCATION: (1)..(561)

<400> SEQUENCE: 14 atg att aaa tgt aat aat aaa act ttt aac aat tta ctt aaa cta act      48
Met Ile Lys Cys Asn Asn Lys Thr Phe Asn Asn Leu Leu Lys Leu Thr
 1               5                  10                  15 ata ctt gtt aac cta ctt ata tca tgt gga cta aca gga gca aca aaa      96
Ile Leu Val Asn Leu Leu Ile Ser Cys Gly Leu Thr Gly Ala Thr Lys
             20                  25                  30 atc aaa tta gaa tca tca gct aaa gcc att gta gat gaa ata gat gca     144
Ile Lys Leu Glu Ser Ser Ala Lys Ala Ile Val Asp Glu Ile Asp Ala
         35                  40                  45 att aaa aaa aag gct gct tct atg ggt gta aat ttt gat gcc tct aaa     192
Ile Lys Lys Lys Ala Ala Ser Met Gly Val Asn Phe Asp Ala Ser Lys
     50                  55                  60 gat aaa aaa acg ggt agt ggg gta tca gaa aat cca ttc ata ctt gaa     240
Asp Lys Lys Thr Gly Ser Gly Val Ser Glu Asn Pro Phe Ile Leu Glu
 65                  70                  75                  80 gca aaa gtg cga gct act aca gta gcg gaa aaa ttc gta ata gca ata     288
Ala Lys Val Arg Ala Thr Thr Val Ala Glu Lys Phe Val Ile Ala Ile
                 85                  90                  95 gaa gag gaa gct act aaa ctt aaa gaa act gga agt agt ggt gaa ttc     336
```

```
Glu Glu Glu Ala Thr Lys Leu Lys Glu Thr Gly Ser Ser Gly Glu Phe
            100                 105                 110 tca gca atg tat gat tta atg ttt gaa gtc tca aaa cca tta caa gaa          384
Ser Ala Met Tyr Asp Leu Met Phe Glu Val Ser Lys Pro Leu Gln Glu
        115                 120                 125 ttg gga ata caa gag atg aca aaa aca gtc tca atg gca gct gaa gag          432
Leu Gly Ile Gln Glu Met Thr Lys Thr Val Ser Met Ala Ala Glu Glu
    130                 135                 140 aat cct cca act aca gct caa gga gtg ctt gaa att gca aaa aaa atg          480
Asn Pro Pro Thr Thr Ala Gln Gly Val Leu Glu Ile Ala Lys Lys Met
145                 150                 155                 160 aga gaa aaa tta caa agg gtt cac aag aaa aac caa gac acc tta aag          528
Arg Glu Lys Leu Gln Arg Val His Lys Lys Asn Gln Asp Thr Leu Lys
                165                 170                 175 aaa aaa aat acc gaa gac agc act gct aaa tcg                              561
Lys Lys Asn Thr Glu Asp Ser Thr Ala Lys Ser
            180                 185
```

<210> SEQ ID NO 15
<211> LENGTH: 187
<212> TYPE: PRT
<213> ORGANISM: Borrelia burgdorferi

<400> SEQUENCE: 15

```
Met Ile Lys Cys Asn Asn Lys Thr Phe Asn Asn Leu Leu Lys Leu Thr
 1               5                  10                  15

Ile Leu Val Asn Leu Leu Ile Ser Cys Gly Leu Thr Gly Ala Thr Lys
                20                  25                  30

Ile Lys Leu Glu Ser Ser Ala Lys Ala Ile Val Asp Glu Ile Asp Ala
            35                  40                  45

Ile Lys Lys Lys Ala Ala Ser Met Gly Val Asn Phe Asp Ala Ser Lys
        50                  55                  60

Asp Lys Lys Thr Gly Ser Gly Val Ser Glu Asn Pro Phe Ile Leu Glu
65                  70                  75                  80

Ala Lys Val Arg Ala Thr Thr Val Ala Glu Lys Phe Val Ile Ala Ile
                85                  90                  95

Glu Glu Glu Ala Thr Lys Leu Lys Glu Thr Gly Ser Ser Gly Glu Phe
            100                 105                 110

Ser Ala Met Tyr Asp Leu Met Phe Glu Val Ser Lys Pro Leu Gln Glu
        115                 120                 125

Leu Gly Ile Gln Glu Met Thr Lys Thr Val Ser Met Ala Ala Glu Glu
    130                 135                 140

Asn Pro Pro Thr Thr Ala Gln Gly Val Leu Glu Ile Ala Lys Lys Met
145                 150                 155                 160

Arg Glu Lys Leu Gln Arg Val His Lys Lys Asn Gln Asp Thr Leu Lys
                165                 170                 175

Lys Lys Asn Thr Glu Asp Ser Thr Ala Lys Ser
            180                 185
```

<210> SEQ ID NO 16
<211> LENGTH: 582
<212> TYPE: DNA
<213> ORGANISM: Borrelia burgdorferi
<220> FEATURE:
<221> NAME/KEY: CDS
<222> LOCATION: (1)..(582)

<400> SEQUENCE: 16

```
atg aat aaa tat caa aaa att ttc aaa atc ttt aat ttt aaa aat tta          48
```

```
Met Asn Lys Tyr Gln Lys Ile Phe Lys Ile Phe Asn Phe Lys Asn Leu
 1               5                  10                  15 ctt aaa cta agt tta ctt gtt gcc ctc ata tca tgc gga tta aaa gga        96
Leu Lys Leu Ser Leu Leu Val Ala Leu Ile Ser Cys Gly Leu Lys Gly
                 20                  25                  30 gaa aca aaa atc ata tta gaa cga agt gct aaa gac att aca gat gaa       144
Glu Thr Lys Ile Ile Leu Glu Arg Ser Ala Lys Asp Ile Thr Asp Glu
             35                  40                  45 ata aat aaa att aaa aaa gac gct gct gat aac aat gta aat ttt gct       192
Ile Asn Lys Ile Lys Lys Asp Ala Ala Asp Asn Asn Val Asn Phe Ala
 50                  55                  60 gcc ttt aca gat agt gaa aca ggt agc aag gta tca gaa aat tca ttc       240
Ala Phe Thr Asp Ser Glu Thr Gly Ser Lys Val Ser Glu Asn Ser Phe
 65                  70                  75                  80 ata ctt gaa gca aaa gtg cga gct act aca gta gca gaa aaa ttt gta       288
Ile Leu Glu Ala Lys Val Arg Ala Thr Thr Val Ala Glu Lys Phe Val
                 85                  90                  95 aca gcg atc gaa ggg gaa gct aca aaa ctt aaa aag act gga agt agt       336
Thr Ala Ile Glu Gly Glu Ala Thr Lys Leu Lys Lys Thr Gly Ser Ser
            100                 105                 110 ggt gaa ttc tca gca atg tac aac atg atg ctt gag gtc tca ggc cca       384
Gly Glu Phe Ser Ala Met Tyr Asn Met Met Leu Glu Val Ser Gly Pro
            115                 120                 125 tta gaa gaa tta gga gta cta aga atg aca aag aca gtt aca gat gcg       432
Leu Glu Glu Leu Gly Val Leu Arg Met Thr Lys Thr Val Thr Asp Ala
130                 135                 140 gct gaa caa cac cct aca act aca gct gaa gga ata ctt gaa att gca       480
Ala Glu Gln His Pro Thr Thr Thr Ala Glu Gly Ile Leu Glu Ile Ala
145                 150                 155                 160 aaa aaa atg aga gaa aaa tta caa agg gtt cat aca aaa aac tac tgc       528
Lys Lys Met Arg Glu Lys Leu Gln Arg Val His Thr Lys Asn Tyr Cys
                165                 170                 175 gcc ctt aaa aag aag gaa aat tct act ttt act gat gaa aaa tgc aaa       576
Ala Leu Lys Lys Lys Glu Asn Ser Thr Phe Thr Asp Glu Lys Cys Lys
                180                 185                 190 aat aac                                                                582
Asn Asn <210> SEQ ID NO 17
<211> LENGTH: 194
<212> TYPE: PRT
<213> ORGANISM: Borrelia burgdorferi

<400> SEQUENCE: 17

Met Asn Lys Tyr Gln Lys Ile Phe Lys Ile Phe Asn Phe Lys Asn Leu
 1               5                  10                  15

Leu Lys Leu Ser Leu Leu Val Ala Leu Ile Ser Cys Gly Leu Lys Gly
                 20                  25                  30

Glu Thr Lys Ile Ile Leu Glu Arg Ser Ala Lys Asp Ile Thr Asp Glu
             35                  40                  45

Ile Asn Lys Ile Lys Lys Asp Ala Ala Asp Asn Asn Val Asn Phe Ala
 50                  55                  60

Ala Phe Thr Asp Ser Glu Thr Gly Ser Lys Val Ser Glu Asn Ser Phe
 65                  70                  75                  80

Ile Leu Glu Ala Lys Val Arg Ala Thr Thr Val Ala Glu Lys Phe Val
                 85                  90                  95

Thr Ala Ile Glu Gly Glu Ala Thr Lys Leu Lys Lys Thr Gly Ser Ser
            100                 105                 110
```

```
Gly Glu Phe Ser Ala Met Tyr Asn Met Met Leu Glu Val Ser Gly Pro
            115                 120                 125

Leu Glu Glu Leu Gly Val Leu Arg Met Thr Lys Thr Val Thr Asp Ala
            130                 135                 140

Ala Glu Gln His Pro Thr Thr Thr Ala Glu Gly Ile Leu Glu Ile Ala
145                 150                 155                 160

Lys Lys Met Arg Glu Lys Leu Gln Arg Val His Thr Lys Asn Tyr Cys
                165                 170                 175

Ala Leu Lys Lys Lys Glu Asn Ser Thr Phe Thr Asp Glu Lys Cys Lys
            180                 185                 190

Asn Asn
```

```
<210> SEQ ID NO 18
<211> LENGTH: 543
<212> TYPE: DNA
<213> ORGANISM: Borrelia afzelii
<220> FEATURE:
<221> NAME/KEY: CDS
<222> LOCATION: (1)

```
<212> TYPE: PRT
<213> ORGANISM: Borrelia afzelii

<400> SEQUENCE: 19

Met Ile Lys Tyr Asn Lys Ile Ile Leu Thr Leu Thr Leu Leu Ala Ser
 1               5                  10                  15

Leu Leu Ala Ala Cys Gly Leu Thr Gly Glu Thr Lys Leu Arg Leu Glu
            20                  25                  30

Ser Ser Ala Gln Glu Ile Lys Asp Glu Val Asp Lys Ile Arg Ala Glu
        35                  40                  45

Ala Val Thr Glu Gly Val Asn Phe Asp Ala Phe Thr Asp Thr Gln Thr
    50                  55                  60

Gly Ser Lys Val Ala Glu Asn Pro Phe Ile Ile Lys Ala Lys Ile Arg
 65                 70                  75                  80

Thr Thr Ser Val Ala Leu Lys Phe Ile Gln Ala Ile Lys Glu Glu Ala
                85                  90                  95

Glu Lys Leu Lys Glu Ser Gly Ser Ser Ser Gln Phe Ser Ala Leu Tyr
            100                 105                 110

Asp Ile Met Leu Asp Ile Ala Ala Pro Ile Gln Lys Ile Gly Ile Lys
        115                 120                 125

Asp Met Ile Lys Thr Val Thr Gln Glu Ala Glu Lys Thr Pro Thr Thr
    130                 135                 140

Thr Ala Glu Gly Ile Ile Thr Ile Ala Lys Ala Met Glu Val Lys Leu
145                 150                 155                 160

Asn Arg Val Lys Asn Lys Asn Glu Glu Ala Leu Lys Lys Lys Ser Glu
                165                 170                 175

Asn Ala Thr Thr Thr
            180

<210> SEQ ID NO 20
<211> LENGTH: 552
<212> TYPE: DNA
<213> ORGANISM: Borrelia garinii
<220> FEATURE:
<221> NAME/KEY: CDS
<222> LOCATION: (1)..(552)

<400> SEQUENCE: 20 atg act aaa cac acc aaa aat tta ctt aaa cta agt tta att gtt agc      48
Met Thr Lys His Thr Lys Asn Leu Leu Lys Leu Ser Leu Ile Val Ser
 1               5                  10                  15 ctg tta gta gca tgt ggc tta aca gga gaa act aaa atc aaa tta gaa      96
Leu Leu Val Ala Cys Gly Leu Thr Gly Glu Thr Lys Ile Lys Leu Glu
            20                  25                  30 tca tca gct caa gaa att aaa gat gaa ata aat aaa att aaa gct aat     144
Ser Ser Ala Gln Glu Ile Lys Asp Glu Ile Asn Lys Ile Lys Ala Asn
        35                  40                  45 gct aaa aaa gaa ggc gta aat ttc gag gct ttc aca gat aaa caa aca     192
Ala Lys Lys Glu Gly Val Asn Phe Glu Ala Phe Thr Asp Lys Gln Thr
    50                  55                  60 ggc agt aag gta tca aaa aag cct gaa ttc ata ctt aaa gca aaa ata     240
Gly Ser Lys Val Ser Lys Lys Pro Glu Phe Ile Leu Lys Ala Lys Ile
 65                 70                  75                  80 caa gct att caa gtg gca gga aaa ttt gta aaa gca ata aaa gag gaa     288
Gln Ala Ile Gln Val Ala Gly Lys Phe Val Lys Ala Ile Lys Glu Glu
                85                  90                  95 gca gaa aaa ctt aaa aag agt gga agt agc ggt gca ttc tcg gca atg     336
Ala Glu Lys Leu Lys Lys Ser Gly Ser Ser Gly Ala Phe Ser Ala Met
            100                 105                 110
```

```
tat gat tta atg ctt gat gta tca aaa cca cta gaa gag att gga ata      384
Tyr Asp Leu Met Leu Asp Val Ser Lys Pro Leu Glu Glu Ile Gly Ile
            115                 120                 125 caa aaa atg aca gga aca gtt aca cag gca gct gaa aaa acc cct cca      432
Gln Lys Met Thr Gly Thr Val Thr Gln Ala Ala Glu Lys Thr Pro Pro
        130                 135                 140 act aca gct gag ggg ata ctt gct att gca aaa gca atg gaa gat aaa      480
Thr Thr Ala Glu Gly Ile Leu Ala Ile Ala Lys Ala Met Glu Asp Lys
145                 150                 155                 160 tta aac aat gtt aat aca aaa caa cac gag gct ctc aaa aac ctc gag      528
Leu Asn Asn Val Asn Thr Lys Gln His Glu Ala Leu Lys Asn Leu Glu
                165                 170                 175 gga aaa gaa gcc aaa act cct aaa                                      552
Gly Lys Glu Ala Lys Thr Pro Lys
            180
```

<210> SEQ ID NO 21
<211> LENGTH: 184
<212> TYPE: PRT
<213> ORGANISM: Borrelia garinii

<400> SEQUENCE: 21

```
Met Thr Lys His Thr Lys Asn Leu Leu Lys Leu Ser Leu Ile Val Ser
  1               5                  10                  15

-continued

```
ata ctt gtt aac cta ctt ata tca tgt gga cta aca gga gca aca aaa    96
Ile Leu Val Asn Leu Leu Ile Ser Cys Gly Leu Thr Gly Ala Thr Lys
             20                  25                  30 atc aaa tta gaa tca tca gct aaa gcc att gta gat gaa ata gat gca   144
Ile Lys Leu Glu Ser Ser Ala Lys Ala Ile Val Asp Glu Ile Asp Ala
         35                  40                  45 att aaa aaa aag gct gct tct atg ggt gta aat ttt gat gcc ttt aaa   192
Ile Lys Lys Lys Ala Ala Ser Met Gly Val Asn Phe Asp Ala Phe Lys
     50                  55                  60 gat aaa aaa acg ggt ggt ggg gta tca aaa aat cca ttc ata ctt gaa   240
Asp Lys Lys Thr Gly Gly Gly Val Ser Lys Asn Pro Phe Ile Leu Glu
 65                  70                  75                  80 gca aaa gtg cga gct act aca gta gcg gaa aaa ttc gta ata gca ata   288
Ala Lys Val Arg Ala Thr Thr Val Ala Glu Lys Phe Val Ile Ala Ile
                 85                  90                  95 gaa gag gaa gct act aaa ctt aaa gaa act gga agt agt ggt gaa ttc   336
Glu Glu Glu Ala Thr Lys Leu Lys Glu Thr Gly Ser Ser Gly Glu Phe
            100                 105                 110 tca gca atg tat gat tta atg ttt gaa gtc tca aaa cca tta caa gaa   384
Ser Ala Met Tyr Asp Leu Met Phe Glu Val Ser Lys Pro Leu Gln Glu
        115                 120                 125 ttg gga ata caa gag atg aca aaa aca gtc tca atg gca gct gaa gag   432
Leu Gly Ile Gln Glu Met Thr Lys Thr Val Ser Met Ala Ala Glu Glu
    130                 135                 140 aat cct cca act aca gct caa gga gtg ctt gaa att gca aaa aaa atg   480
Asn Pro Pro Thr Thr Ala Gln Gly Val Leu Glu Ile Ala Lys Lys Met
145                 150                 155                 160 aga gaa aaa tta caa agg gtt cac aag aaa aac caa gac acc tta aag   528
Arg Glu Lys Leu Gln Arg Val His Lys Lys Asn Gln Asp Thr Leu Lys
                165                 170                 175 aaa aaa aat acc gaa gac agc act gct aaa tcg                       561
Lys Lys Asn Thr Glu Asp Ser Thr Ala Lys Ser
            180                 185
```

<210> SEQ ID NO 23
<211> LENGTH: 187
<212> TYPE: PRT
<213> ORGANISM: Borrelia burgdorferi

<400> SEQUENCE: 23

```
Met Ile Lys Cys Asn Asn Lys Thr Phe Asn Asn Leu Leu Lys Leu Thr
 1               5                  10                  15

Ile Leu Val Asn Leu Leu Ile Ser Cys Gly Leu Thr Gly Ala Thr Lys
             20                  25                  30

Ile Lys Leu Glu Ser Ser Ala Lys Ala Ile Val Asp Glu Ile Asp Ala
         35                  40                  45

Ile Lys Lys Lys Ala Ala Ser Met Gly Val Asn Phe Asp Ala Phe Lys
     50                  55                  60

Asp Lys Lys Thr Gly Gly Gly Val Ser Lys Asn Pro Phe Ile Leu Glu
 65                  70                  75                  80

Ala Lys Val Arg Ala Thr Thr Val Ala Glu Lys Phe Val Ile Ala Ile
                 85                  90                  95

Glu Glu Glu Ala Thr Lys Leu Lys Glu Thr Gly Ser Ser Gly Glu Phe
            100                 105                 110

Ser Ala Met Tyr Asp Leu Met Phe Glu Val Ser Lys Pro Leu Gln Glu
        115                 120                 125

Leu Gly Ile Gln Glu Met Thr Lys Thr Val Ser Met Ala Ala Glu Glu
```

```
                130              135              140
Asn Pro Pro Thr Thr Ala Gln Gly Val Leu Glu Ile Ala Lys Lys Met
145             150                  155                  160

Arg Glu Lys Leu Gln Arg Val His Lys Lys Asn Gln Asp Thr Leu Lys
                165                  170                  175

Lys Lys Asn Thr Glu Asp Ser Thr Ala Lys Ser
            180                  185
```

<210> SEQ ID NO 24
<211> LENGTH: 561
<212> TYPE: DNA
<213> ORGANISM: Borrelia burgdorferi
<220> FEATURE:
<221> NAME/KEY: CDS
<222> LOCATION: (1)..(561)

<400> SEQUENCE: 24

```
atg att aaa tgt aat aat aaa act ttt aac aat tta ctt aaa cta act       48
Met Ile Lys Cys Asn Asn Lys Thr Phe Asn Asn Leu Leu Lys Leu Thr
  1               5                  10                  15 ata ctt gtt aac cta ctt ata tca tgt gga cta aca gga gca aca aaa       96
Ile Leu Val Asn Leu Leu Ile Ser Cys Gly Leu Thr Gly Ala Thr Lys
             20                  25                  30 atc aaa tta gaa tca tca gct aaa gcc att gta gat gaa ata gat gca      144
Ile Lys Leu Glu Ser Ser Ala Lys Ala Ile Val Asp Glu Ile Asp Ala
         35                  40                  45 att aaa aaa aag gct gct tct atg ggt gta aat ttt gat gcc ttt aaa      192
Ile Lys Lys Lys Ala Ala Ser Met Gly Val Asn Phe Asp Ala Phe Lys
     50                  55                  60 gat aaa aaa acg ggt agt ggg gta tca gaa aat cca ttc ata ctt gaa      240
Asp Lys Lys Thr Gly Ser Gly Val Ser Glu Asn Pro Phe Ile Leu Glu
 65                  70                  75                  80 gca aaa gtg cga gct act aca gta gcg gaa aaa ttc gta ata gca ata      288
Ala Lys Val Arg Ala Thr Thr Val Ala Glu Lys Phe Val Ile Ala Ile
                 85                  90                  95 gaa gag gaa gct act aaa ctt aaa gaa act gga agt agt ggt gaa ttc      336
Glu Glu Glu Ala Thr Lys Leu Lys Glu Thr Gly Ser Ser Gly Glu Phe
            100                 105                 110 tca gca atg tat gat tta atg ttt gaa gtc tca aaa cca tta caa gaa      384
Ser Ala Met Tyr Asp Leu Met Phe Glu Val Ser Lys Pro Leu Gln Glu
        115                 120                 125 ttg gga ata caa gag atg aca aaa aca gtc tca atg gca gct gaa gag      432
Leu Gly Ile Gln Glu Met Thr Lys Thr Val Ser Met Ala Ala Glu Glu
    130                 135                 140 aat cct cca act aca gct caa gga gtg ctt gaa att gca aaa aaa atg      480
Asn Pro Pro Thr Thr Ala Gln Gly Val Leu Glu Ile Ala Lys Lys Met
145                 150                 155                 160 aga gaa aaa tta caa agg gtt cac aag aaa aac caa gac acc tta aag      528
Arg Glu Lys Leu Gln Arg Val His Lys Lys Asn Gln Asp Thr Leu Lys
                165                 170                 175 aaa aaa aat acc gaa gac agc act gct aaa tcg                          561
Lys Lys Asn Thr Glu Asp Ser Thr Ala Lys Ser
            180                 185
```

<210> SEQ ID NO 25
<211> LENGTH: 187
<212> TYPE: PRT
<213> ORGANISM: Borrelia burgdorferi

<400> SEQUENCE: 25

Met Ile Lys Cys Asn Asn Lys Thr Phe Asn Asn Leu Leu Lys Leu Thr

```
  1               5                  10                 15
Ile Leu Val Asn Leu Leu Ile Ser Cys Gly Leu Thr Gly Ala Thr Lys
                 20                 25                 30

Ile Lys Leu Glu Ser Ser Ala Lys Ala Ile Val Asp Glu Ile Asp Ala
             35                 40                 45

Ile Lys Lys Lys Ala Ala Ser Met Gly Val Asn Phe Asp Ala Phe Lys
         50                 55                 60

Asp Lys Lys Thr Gly Ser Gly Val Ser Glu Asn Pro Phe Ile Leu Glu
 65                 70                 75                 80

Ala Lys Val Arg Ala Thr Thr Val Ala Glu Lys Phe Val Ile Ala Ile
                 85                 90                 95

Glu Glu Glu Ala Thr Lys Leu Lys Glu Thr Gly Ser Ser Gly Glu Phe
            100                 105                110

Ser Ala Met Tyr Asp Leu Met Phe Glu Val Ser Lys Pro Leu Gln Glu
            115                 120                125

Leu Gly Ile Gln Glu Met Thr Lys Thr Val Ser Met Ala Ala Glu Glu
        130                 135                140

Asn Pro Pro Thr Thr Ala Gln Gly Val Leu Glu Ile Ala Lys Lys Met
145                 150                 155                160

Arg Glu Lys Leu Gln Arg Val His Lys Lys Asn Gln Asp Thr Leu Lys
                165                 170                175

Lys Lys Asn Thr Glu Asp Ser Thr Ala Lys Ser
            180                 185
```

<210> SEQ ID NO 26
<211> LENGTH: 564
<212> TYPE: DNA
<213> ORGANISM: Borrelia burgdorferi
<220> FEATURE:
<221> NAME/KEY: CDS
<222> LOCATION: (1)..(564)

<400> SEQUENCE: 26

```
atg att aaa tgt aat aat aaa act ttt aac aat tta ctt aaa cta act       48
Met Ile Lys Cys Asn Asn Lys Thr Phe Asn Asn Leu Leu Lys Leu Thr
 1               5                  10                 15 ata ctt gtt aac cta ctt ata tca tgt gga cta aca gga gca aca aaa       96
Ile Leu Val Asn Leu Leu Ile Ser Cys Gly Leu Thr Gly Ala Thr Lys
                 20                 25                 30 atc aaa tta gaa tca tca gct aaa gcc att gta gat gaa ata gat gca      144
Ile Lys Leu Glu Ser Ser Ala Lys Ala Ile Val Asp Glu Ile Asp Ala
             35                 40                 45 att aaa aaa gag gct gct ctt aag ggt gta aat ttt gat gcc ttt aaa      192
Ile Lys Lys Glu Ala Ala Leu Lys Gly Val Asn Phe Asp Ala Phe Lys
         50                 55                 60 gat aaa aaa acg ggt agt ggg gta tca aaa aat cca ttc ata ctt gaa      240
Asp Lys Lys Thr Gly Ser Gly Val Ser Lys Asn Pro Phe Ile Leu Glu
 65                 70                 75                 80 gca aaa gtg cga gct act aca gta gcg gaa aaa ttc gta ata gca ata      288
Ala Lys Val Arg Ala Thr Thr Val Ala Glu Lys Phe Val Ile Ala Ile
                 85                 90                 95 gaa gag gaa gct act aaa ctt aaa gaa act gga agt agt ggt gaa ttc      336
Glu Glu Glu Ala Thr Lys Leu Lys Glu Thr Gly Ser Ser Gly Glu Phe
            100                 105                110 tca gca atg tat gat tta atg ttt gaa gtc tca aaa cca tta caa gaa      384
Ser Ala Met Tyr Asp Leu Met Phe Glu Val Ser Lys Pro Leu Gln Glu
            115                 120                125 ttg gga ata caa gag atg aca aaa aca gtc tca atg gca gct gaa gag      432
```

```
Leu Gly Ile Gln Glu Met Thr Lys Thr Val Ser Met Ala Ala Glu Glu
        130                 135                 140 aat cct cca act aca gct caa gga gtg ctt gaa att gca aaa aaa atg      480
Asn Pro Pro Thr Thr Ala Gln Gly Val Leu Glu Ile Ala Lys Lys Met
145                 150                 155                 160 aga gaa aaa tta caa agg gtt cac aag aaa aac caa caa acc tta aag      528
Arg Glu Lys Leu Gln Arg Val His Lys Lys Asn Gln Gln Thr Leu Lys
                165                 170                 175 aaa aaa aat acc gaa gaa agc act gct aaa tcg aaa                      564
Lys Lys Asn Thr Glu Glu Ser Thr Ala Lys Ser Lys
                180                 185

<210> SEQ ID NO 27
<211> LENGTH: 188
<212> TYPE: PRT
<213> ORGANISM: Borrelia burgdorferi

<400> SEQUENCE: 27

Met Ile Lys Cys Asn Asn Lys Thr Phe Asn Asn Leu Leu Lys Leu Thr
  1               5                  10                  15

Ile Leu Val Asn Leu Leu Ile Ser Cys Gly Leu Thr Gly Ala Thr Lys
                 20                  25                  30

Ile Lys Leu Glu Ser Ser Ala Lys Ala Ile Val Asp Glu Ile Asp Ala
             35                  40                  45

Ile Lys Lys Glu Ala Ala Leu Lys Gly Val Asn Phe Asp Ala Phe Lys
         50                  55                  60

Asp Lys Lys Thr Gly Ser Gly Val Ser Lys Asn Pro Phe Ile Leu Glu
 65                  70                  75                  80

Ala Lys Val Arg Ala Thr Thr Val Ala Glu Lys Phe Val Ile Ala Ile
                 85                  90                  95

Glu Glu Glu Ala Thr Lys Leu Lys Glu Thr Gly Ser Ser Gly Glu Phe
            100                 105                 110

Ser Ala Met Tyr Asp Leu Met Phe Glu Val Ser Lys Pro Leu Gln Glu
        115                 120                 125

Leu Gly Ile Gln Glu Met Thr Lys Thr Val Ser Met Ala Ala Glu Glu
    130                 135                 140

Asn Pro Pro Thr Thr Ala Gln Gly Val Leu Glu Ile Ala Lys Lys Met
145                 150                 155                 160

Arg Glu Lys Leu Gln Arg Val His Lys Lys Asn Gln Gln Thr Leu Lys
                165                 170                 175

Lys Lys Asn Thr Glu Glu Ser Thr Ala Lys Ser Lys
                180                 185

<210> SEQ ID NO 28
<211> LENGTH: 187
<212> TYPE: PRT
<213> ORGANISM: Borrelia burgdorferi

<400> SEQUENCE: 28

Met Lys Ile Gly Lys Leu Asn Ser Ile Val Ile Ala Leu Phe Phe Lys
  1               5                  10                  15

Leu Leu Val Ala Cys Ser Ile Gly Leu Val Glu Arg Thr Asn Ala Ala
                 20                  25                  30

Leu Glu Ser Ser Ser Lys Asp Leu Lys Asn Lys Ile Leu Lys Ile Lys
             35                  40                  45

Lys Asp Ala Thr Gly Lys Gly Val Leu Phe Glu Ala Phe Thr Gly Leu
         50                  55                  60
```

```
Lys Thr Gly Ser Lys Val Thr Ser Gly Gly Leu Ala Leu Arg Glu Ala
 65                  70                  75                  80

Lys Val Gln Ala Ile Val Glu Thr Gly Lys Phe Leu Lys Ile Ile Glu
                 85                  90                  95

Glu Glu Ala Leu Lys Leu Lys Glu Thr Gly Asn Ser Gly Gln Phe Leu
                100                 105                 110

Ala Met Phe Asp Leu Met Leu Glu Val Val Ser Leu Glu Asp Val
            115                 120                 125

Gly Ile Ile Gly Leu Lys Ala Arg Val Leu Glu Ser Lys Asn Asn
130                 135                 140

Pro Ile Asn Thr Ala Glu Arg Leu Leu Ala Ala Lys Ala Gln Ile Glu
145                 150                 155                 160

Asn Gln Leu Lys Val Val Lys Glu Lys Gln Asn Ile Glu Asn Gly Gly
                165                 170                 175

Glu Lys Lys Asn Asn Lys Ser Lys Lys Lys
            180                 185
```

<210> SEQ ID NO 29
<211> LENGTH: 564
<212> TYPE: DNA
<213> ORGANISM: Borrelia burgdorferi

<400> SEQUENCE: 29

```
atgattaaat gtaataataa aacttttaac aatttactta aactaactat acttgttaac    60
ctacttatat catgtggact aacaggagca acaaaaatca aattagaatc atcagctaaa   120
gccattgtag atgaaataga tgcaattaaa aaaaaggctg cttctatggg tgtaaatttt   180
gatgccttta agataaaaa aacgggtagt ggggtatcag aaaatccatt catacttgaa   240
gcaaaagtgc gagctactac agtagcggaa aaattcgtaa tagcaataga gaggaagct    300
actaaactta agaaactgg aagtagtggt gaattctcag caatgtatga tttaatgttt   360
gaagtctcaa aaccattaca agaattggga atacaagaga tgacaaaaac agtctcaatg   420
gcagctgaag agaatcctcc aactacagct caaggagtgc ttgaaattgc aaaaaaaatg   480
agagaaaaat tacaaagggt tcacaagaaa aaccaagaca ccttaaagaa aaaaaatacc   540
gaagacagca ctgctaaatc gtaa                                          564
```

<210> SEQ ID NO 30
<211> LENGTH: 188
<212> TYPE: PRT
<213> ORGANISM: Borrelia burgdorferi

<400> SEQUENCE: 30

```
Met Ile Lys Cys Asn Asn Lys Thr Phe Asn Asn Leu Leu Lys Leu Thr
  1               5                  10                  15

Ile Leu Val Asn Leu Leu Ile Ser Cys Gly Leu Thr Gly Ala Thr Lys
                 20                  25                  30

Ile Lys Leu Glu Ser Ser Ala Lys Ala Ile Val Asp Glu Ile Asp Ala
             35                  40                  45

Ile Lys Lys Lys Ala Ala Ser Met Gly Val Asn Phe Asp Ala Phe Lys
 50                  55                  60

Asp Lys Lys Thr Gly Ser Gly Val Ser Glu Asn Pro Phe Ile Leu Glu
 65                  70                  75                  80

Ala Lys Val Arg Ala Thr Thr Val Ala Glu Lys Phe Val Ile Ala Ile
                 85                  90                  95

Glu Glu Glu Ala Thr Lys Leu Lys Glu Thr Gly Ser Ser Gly Glu Phe
```

-continued

```
                    100                 105                 110
Ser Ala Met Tyr Asp Leu Met Phe Glu Val Ser Lys Pro Leu Gln Glu
            115                 120                 125

Leu Gly Ile Gln Glu Met Thr Lys Thr Val Ser Met Ala Ala Glu Glu
        130                 135                 140

Asn Pro Pro Thr Thr Ala Gln Gly Val Leu Glu Ile Ala Lys Lys Met
145                 150                 155                 160

Arg Glu Lys Leu Gln Arg Val His Lys Lys Asn Gln Asp Thr Leu Lys
                165                 170                 175

Lys Lys Asn Thr Glu Asp Ser Thr Ala Lys Ser Glx
            180                 185
```

<210> SEQ ID NO 31
<211> LENGTH: 564
<212> TYPE: DNA
<213> ORGANISM: Borrelia burgdorferi

<400> SEQUENCE: 31

```
atgattaaat gtaataataa aacttttaac aatttactta aactaactat acttgttaac      60
ctacttatat catgtggact aacaggagca acaaaaatca aattagaatc atcagctaaa     120
gccattgtag atgaaataga tgcaattaaa aaaaaggctg cttctatggg tgtaaatttt     180
gatgcctcta agataaaaaa aacgggtagt ggggtatcag aaaatccatt catacttgaa     240
gcaaaagtgc gagctactac agtagcggaa aaattcgtaa tagcaataga agaggaagct     300
actaaactta agaaactgg aagtagtggt gaattctcag caatgtatga tttaatgttt     360
gaagtctcaa aaccattaca agaattggga atacaagaga tgacaaaaac agtctcaatg     420
gcagctgaag agaatcctcc aactacagct caaggagtgc ttgaaattgc aaaaaaaatg     480
agagaaaaat tacaaagggt tcacaagaaa aaccaagaca ccttaaagaa aaaaaatacc     540
gaagacagca ctgctaaatc gtaa                                             564
```

<210> SEQ ID NO 32
<211> LENGTH: 187
<212> TYPE: PRT
<213> ORGANISM: Borrelia burgdorferi

<400> SEQUENCE: 32

```
Met Ile Lys Cys Asn Asn Lys Thr Phe Asn Asn Leu Leu Lys Leu Thr
  1               5                  10                  15

Ile Leu Val Asn Leu Leu Ile Ser Cys Gly Leu Thr Gly Ala Thr Lys
             20                  25                  30

Ile Lys Leu Glu Ser Ser Ala Lys Ala Ile Val Asp Glu Ile Asp Ala
         35                  40                  45

Ile Lys Lys Lys Ala Ala Ser Met Gly Val Asn Phe Asp Ala Ser Lys
     50                  55                  60

Asp Lys Lys Thr Gly Ser Gly Val Ser Glu Asn Pro Phe Ile Leu Glu
 65                  70                  75                  80

Ala Lys Val Arg Ala Thr Thr Val Ala Glu Lys Phe Val Ile Ala Ile
                 85                  90                  95

Glu Glu Glu Ala Thr Lys Leu Lys Leu Thr Gly Ser Ser Gly Glu Phe
            100                 105                 110

Ser Ala Met Tyr Asp Leu Met Phe Glu Val Ser Lys Pro Leu Gln Glu
        115                 120                 125

Leu Gly Ile Gln Glu Met Thr Lys Thr Val Ser Met Ala Ala Glu Glu
    130                 135                 140
```

```
Asn Pro Pro Thr Thr Ala Gln Gly Val Leu Glu Ile Ala Lys Lys Met
145                 150                 155                 160

Arg Glu Lys Leu Gln Arg Val His Lys Lys Asn Gln Asp Thr Leu Lys
                165                 170                 175

Lys Lys Asn Thr Glu Asp Ser Thr Ala Lys Ser
            180                 185
```

<210> SEQ ID NO 33
<211> LENGTH: 585
<212> TYPE: DNA
<213> ORGANISM: Borrelia burgdorferi

<400> SEQUENCE: 33

```
atgaataaat atcaaaaaac tttcaaaatc tttaatttta aaaatttact taaactaagt    60
ttacttgttg ccctcatatc atgcggatta aaggagaaa caaaaatcat attagaacga   120
agcgctaaag acattacaga tgaaataaat aaaattaaaa aagacgctgc tgataacaat   180
gtaaattttg ctgcctttac agatagtgaa acagtagca aggtatcaga aaattcattc   240
atacttgaag caaaagtgcg agctactaca gtagcagaaa aatttgtaac agcgatcgaa   300
ggggaagcta caaaacttaa aaagactgga agtagtggtg aattctcagc aatgtacaac   360
atgatgcttg aggtctcagg cccattagaa gaattaggag tactaagaat gacaaagaca   420
gttacagatg cggctgaaca acaccctaca actacagctg aaggaatact tgaaattgct   480
aaaataatga aacaaaatt acaaagggtt catacaaaaa actactgcgc ccttgaaaag   540
aagaaaaatc ctaattttac tgatgaaaaa tgcaaaaata actaa                   585
```

<210> SEQ ID NO 34
<211> LENGTH: 195
<212> TYPE: PRT
<213> ORGANISM: Borrelia burgdorferi

<400> SEQUENCE: 34

```
Met Asn Lys Tyr Gln Lys Thr Phe Lys Ile Phe Asn Phe Lys Asn Leu
1               5                   10                  15

Leu Lys Leu Ser Leu Leu Val Ala Leu Ile Ser Cys Gly Leu Lys Gly
            20                  25                  30

Glu Thr Lys Ile Ile Leu Glu Arg Ser Ala Lys Asp Ile Thr Asp Glu
        35                  40                  45

Ile Asn Lys Ile Lys Lys Asp Ala Ala Asp Asn Val Asn Phe Ala
    50                  55                  60

Ala Phe Thr Asp Ser Glu Thr Gly Ser Lys Val Ser Glu Asn Ser Phe
65                  70                  75                  80

Ile Leu Glu Ala Lys Val Arg Ala Thr Thr Val Ala Glu Lys Phe Val
                85                  90                  95

Thr Ala Ile Glu Gly Glu Ala Thr Lys Leu Lys Lys Thr Gly Ser Ser
            100                 105                 110

Gly Glu Phe Ser Ala Met Tyr Asn Met Met Leu Glu Val Ser Gly Pro
        115                 120                 125

Leu Glu Glu Leu Gly Val Leu Arg Met Thr Lys Thr Val Thr Asp Ala
    130                 135                 140

Ala Glu Gln His Pro Thr Thr Thr Ala Glu Gly Ile Leu Glu Ile Ala
145                 150                 155                 160

Lys Ile Met Lys Thr Lys Leu Gln Arg Val His Thr Lys Asn Tyr Cys
                165                 170                 175
```

```
Ala Leu Glu Lys Lys Lys Asn Pro Asn Phe Thr Asp Glu Lys Cys Lys
            180                 185                 190

Asn Asn Glx
        195

<210> SEQ ID NO 35
<211> LENGTH: 567
<212> TYPE: DNA
<213> ORGANISM: Borrelia burgdorferi

<400> SEQUENCE: 35
atgattaaat gtaataataa aacttttaac aatttactta aactaactat acttgttaac      60
ctacttatat catgtggact aacaggagca acaaaaatca aattagaatc atcagctaaa     120
gccattgtag atgaaataga tgcaattaaa aaagaggctg ctcttaaggg tgtaaatttt     180 gatgcctta  aagataaaaa aacgggtagt ggggtatcaa aaaatccatt catacttgaa     240
gcaaaagtgc gagctactac agtagcggaa aaattcgtaa tagcaataga agaggaagct     300
actaaactta agaaactgg  aagtagtggt gaattctcag caatgtatga tttaatgttt     360
gaagtctcaa aaccattaca agaattggga atacaagaga tgacaaaaac agtctcaatg     420
gcagctgaag agaatcctcc aactacagct caaggagtgc ttgaaattgc aaaaaaaatg     480
agagaaaaat tacaaagggt tcacaagaaa aaccaacaaa ccttaaagaa aaaaaatacc     540
gaagaaagca ctgctaaatc gaaataa                                         567

<210> SEQ ID NO 36
<211> LENGTH: 191
<212> TYPE: PRT
<213> ORGANISM: Borrelia burgdorferi

<400> SEQUENCE: 36

Met Ile Lys Cys Asn Asn Lys Thr Phe Asn Asn Leu Leu Lys Leu Thr
 1               5                  10                  15

Ile Leu Val Asn Leu Leu Ile Ser Cys Gly Leu Thr Gly Ala Thr Lys
            20                  25                  30

Ile Lys Leu Glu Ser Ser Ala Lys Ala Ile Val Asp Glu Ile Asp Ala
        35                  40                  45

Ile Lys Lys Glu Ala Ala Leu Lys Gly Val Asn Phe Asp Ala Phe Lys
    50                  55                  60

Asp Lys Lys Thr Gly Ser Gly Val Ser Lys Asn Pro Phe Ile Leu Glu
65                  70                  75                  80

Ala Lys Val Arg Ala Thr Thr Val Ala Glu Lys Phe Val Ile Ala Ile
                85                  90                  95

Glu Glu Glu Ala Thr Lys Leu Lys Glu Thr Gly Ser Ser Gly Glu Phe
            100                 105                 110

Ser Ala Met Tyr Asp Leu Met Phe Glu Val Ser Lys Pro Leu Gln Glu
        115                 120                 125

Leu Gly Ile Gln Glu Met Thr Lys Thr Val Ser Met Ala Ala Glu Glu
    130                 135                 140

Asn Pro Pro Thr Thr Ala Gln Gly Val Leu Glu Ile Ala Lys Lys Met
145                 150                 155                 160

Arg Glu Lys Leu Gln Arg Val His Ile Ser Lys Asn Gln Gln Thr
                165                 170                 175

Leu Lys Lys Lys Asn Thr Glu Glu Ser Thr Ala Lys Ser Lys Glx
            180                 185                 190
```

<210> SEQ ID NO 37
<211> LENGTH: 585
<212> TYPE: DNA
<213> ORGANISM: Borrelia burgdorferi

<400> SEQUENCE: 37

| | | | | | |
|---|---|---|---|---|---|
| atgaataaat | atcaaaaaat | tttcaaaatc | tttaatttta | aaaatttact | taaactaagt | 60 |
| ttacttgttg | ccctcatatc | atgcggatta | aaggagaaa | caaaaatcat | attagaacga | 120 |
| agtgctaaag | acattacaga | tgaaataaat | aaaattaaaa | aagacgctgc | tgataacaat | 180 |
| gtaaattttg | ctgcctttac | agatagtgaa | acaggtagca | aggtatcaga | aaattcattc | 240 |
| atacttgaag | caaaagtgcg | agctactaca | gtagcagaaa | aatttgtaac | agcgatcgaa | 300 |
| ggggaagcta | caaaacttaa | aaagactgga | agtagtggtg | aattctcagc | aatgtacaac | 360 |
| atgatgcttg | aggtctcagg | cccattagaa | gaattaggag | tactaagaat | gacaaagaca | 420 |
| gttacagatg | cggctgaaca | acaccctaca | actcagctg | aaggaatact | tgaaattgca | 480 |
| aaaaaaatga | gagaaaaatt | acaaggggtt | catacaaaaa | actactgcgc | ccttaaaaag | 540 |
| aaggaaaatt | ctacttttac | tgatgaaaaa | tgcaaaaata | actaa | | 585 |

<210> SEQ ID NO 38
<211> LENGTH: 160
<212> TYPE: PRT
<213> ORGANISM: Borrelia burgdorferi

<400> SEQUENCE: 38

Met Asn Lys Tyr Gln Lys Ile Phe Lys Ile Phe Asn Phe Lys Asn Leu
1               5                   10                  15

Leu Lys Leu Ser Leu Leu Val Ala Leu Ile Ser Cys Gly Leu Lys Gly
            20                  25                  30

Glu Thr Lys Ile Ile Leu Glu Arg Ser Ala Lys Asp Ile Thr Asp Glu
        35                  40                  45

Ile Asn Lys Ile Lys Lys Asp Ala Ala Asp Asn Asn Val Asn Phe Ala
    50                  55                  60

Ala Phe Thr Asp Ser Glu Thr Gly Ser Lys Val Ser Glu Asn Ser Phe
65                  70                  75                  80

Ala Lys Val Arg Ala Thr Thr Val Ala Glu Lys Phe Val Thr Ala Ile Glu
                85                  90                  95

Lys Lys Lys Thr Gly Ser Ser Gly Ser Ala Met Tyr Asn Met Met Val
            100                 105                 110

Ser Gly Gly Val Arg Met Thr Lys Thr Val Thr Asp Ala Ala His Thr
        115                 120                 125

Thr Thr Ala Gly Ala Lys Lys Met Arg Lys Arg Val His Thr Lys Asn
    130                 135                 140

Tyr Cys Ala Lys Lys Asn Ser Thr Thr Asp Lys Cys Lys Asn Asn
145                 150                 155                 160

<210> SEQ ID NO 39
<211> LENGTH: 576
<212> TYPE: DNA
<213> ORGANISM: Borrelia burgdorferi

<400> SEQUENCE: 39

| | | | | | |
|---|---|---|---|---|---|
| atgattaaat | gtaataataa | aacttttaac | aatttactta | aactaactat | acttgttaac | 60 |
| ctacttatat | catgtggact | aacaggagca | acaaaaatta | gattagaacg | aagcgctaaa | 120 |
| gacattacag | atgaaataga | tgcaattaaa | aaagacgctg | ctcttaaggg | cgtaaatttt | 180 |

```
gatgccttta aagataaaaa aacgggtagt ggggtatcag aaaatccatt catacttgaa    240
gcaaaagtgc gagctactac agtagcggaa aaattcgtaa tagcaataga agaggaagct    300
actaaactca aagaaactgg aagtagtggt gaattttcag caatgtatga tttaatgttt    360
gaagtctcaa aaccattaca aaaattggga atacaagaga tgacaaaaac agtctcagat    420
gcagctgaag agaatcctcc aactacagct caaggagtgc ttgaaattgc aaaaaaaatg    480
agagaaaaat tacaaagggt tcatacaaaa aactactgca cccttaaaaa gaaggaaaat    540
tctactttta ctgatgaaaa atgcaaaaat aactaa                              576
```

<210> SEQ ID NO 40
<211> LENGTH: 192
<212> TYPE: PRT
<213> ORGANISM: Borrelia burgdorferi

<400> SEQUENCE: 40

```
Met Ile Lys Cys Asn Asn Lys Thr Phe Asn Asn Leu Leu Lys Leu Thr
  1               5                  10                  15

Ile Leu Val Asn Leu Leu Ile Ser Cys Gly Leu Thr Gly Ala Thr Lys
                 20                  25                  30

Ile Arg Leu Glu Arg Ser Ala Lys Asp Ile Thr Asp Glu Ile Asp Ala
             35                  40                  45

Ile Lys Lys Asp Ala Ala Leu Lys Gly Val Asn Phe Asp Ala Phe Lys
         50                  55                  60

Asp Lys Lys Thr Gly Ser Gly Val Ser Glu Asn Pro Phe Ile Leu Glu
 65                  70                  75                  80

Ala Lys Val Arg Ala Thr Thr Val Ala Glu Lys Phe Val Ile Ala Ile
                 85                  90                  95

Glu Glu Glu Ala Thr Lys Leu Lys Glu Thr Gly Ser Ser Gly Glu Phe
            100                 105                 110

Ser Ala Met Tyr Asp Leu Met Phe Glu Val Ser Lys Pro Leu Gln Lys
        115                 120                 125

Leu Gly Ile Gln Glu Met Thr Lys Thr Val Ser Asp Ala Ala Glu Glu
    130                 135                 140

Asn Pro Pro Thr Thr Ala Gln Gly Val Leu Glu Ile Ala Lys Lys Met
145                 150                 155                 160

Arg Glu Lys Leu Gln Arg Val His Thr Lys Asn Tyr Cys Thr Leu Lys
                165                 170                 175

Lys Lys Glu Asn Ser Thr Phe Asp Glu Lys Cys Lys Asn Asn Glx
            180                 185                 190
```

<210> SEQ ID NO 41
<211> LENGTH: 549
<212> TYPE: DNA
<213> ORGANISM: Borrelia burgdorferi

<400> SEQUENCE: 41

```
atgattaaat gtaataataa aactttttaac aatttactta aactaactat acttgttaac    60
ctacttatat catgtggact aacaggagca acaaaaatca aattagaatc atcagctaaa   120
gccattgtag atgaaataga tgcaattaaa aaagaggctg cttctatggg tgtaaatttt   180
gaagccttta cagatagtga aacaggtaga aaggcagcag gatcaggagg ggatttcata   240
aaacaagcaa agtacgagc tattaaagta gcagaaaact tcttaacagc aatagaagag   300
gaggctacta aacttaaaga aactggaagt agtggtgaat ttcagcaat gtatgattta   360 atgtttgaag tctcagaacc attagaaaga attggggtac aaaaaatgaa aaaaacagtc   420
```

```
tcaatggcag ctgaagagaa tcctccaact acagctcaag gagtgcttga aattgcaaaa      480
aaaatgagag aaaaattaat acaagttaaa ggaaaacaaa aattaaatcc agaaactact      540
acggaataa                                                              549
```

<210> SEQ ID NO 42
<211> LENGTH: 183
<212> TYPE: PRT
<213> ORGANISM: Borrelia burgdorferi

<400> SEQUENCE: 42

```
Met Ile Lys Cys Asn Asn Lys Thr Phe Asn Leu Leu Lys Leu Thr
 1               5                  10                  15

Ile Leu Val Asn Leu Leu Ile Ser Cys Gly Leu Thr Gly Ala Thr Lys
                20                  25                  30

Ile Lys Leu Glu Ser Ser Ala Lys Ala Ile Val Asp Glu Ile Asp Ala
            35                  40                  45

Ile Lys Lys Glu Ala Ala Ser Met Gly Val Asn Phe Glu Ala Phe Thr
    50                  55                  60

Asp Ser Glu Thr Gly Arg Lys Ala Ala Gly Ser Gly Gly Asp Phe Ile
65                  70                  75                  80

Lys Gln Ala Lys Val Arg Ala Ile Lys Val Ala Glu Asn Phe Leu Thr
                85                  90                  95

Ala Ile Glu Glu Glu Ala Thr Lys Leu Lys Glu Thr Gly Ser Ser Gly
            100                 105                 110

Glu Phe Ser Ala Met Tyr Asp Leu Met Phe Glu Val Ser Glu Pro Leu
        115                 120                 125

Glu Arg Ile Gly Val Gln Lys Met Lys Lys Thr Val Ser Met Ala Ala
    130                 135                 140

Glu Glu Asn Pro Pro Thr Thr Ala Gln Gly Val Leu Glu Ile Ala Lys
145                 150                 155                 160

Lys Met Arg Glu Lys Leu Ile Gln Val Lys Gly Lys Gln Lys Leu Asn
                165                 170                 175

Pro Glu Thr Thr Thr Glu Glx
            180
```

<210> SEQ ID NO 43
<211> LENGTH: 564
<212> TYPE: DNA
<213> ORGANISM: Borrelia burgdorferi

<400> SEQUENCE: 43

```
atgattaaat gtaataataa aacttttaac aatttactta aactaactat acttgttaac       60
ctacttatat catgtggact aacaggagca acaaaaatca aattagaatc atcagctaaa      120
gccattgtag atgaaataga tgcaattaaa aaaaggctg cttctatggg tgtaaatttt       180
gatgccttta agataaaaa aacgggtggt ggggtatcaa aaaatccatt catacttgaa       240
gcaaaagtgc gagctactac agtagcggaa aaattcgtaa tagcaataga agaggaagct      300
actaaactta agaaactgg aagtagtggt gaattctcag caatgtatga tttaatgttt       360
gaagtctcaa aaccattaca agaattggga atacaagaga tgacaaaaac agtctcaatg      420
gcagctgaag agaatcctcc aactacagct caaggagtgc ttgaaattgc aaaaaaaatg      480
agagaaaaat tacaaagggt tcacaagaaa aaccaagaca ccttaaagaa aaaaaatacc      540
gaagacagca ctgctaaatc gtaa                                             564
```

<210> SEQ ID NO 44
<211> LENGTH: 188
<212> TYPE: PRT
<213> ORGANISM: Borrelia burgdorferi

<400> SEQUENCE: 44

Met Ile Lys Cys Asn Asn Lys Thr Phe Asn Asn Leu Leu Lys Leu Thr
 1               5                  10                  15

Ile Leu Val Asn Leu Leu Ile Ser Cys Gly Leu Thr Gly Ala Thr Lys
                20                  25                  30

Ile Lys Leu Glu Ser Ser Ala Lys Ala Ile Val Asp Glu Ile Asp Ala
            35                  40                  45

Ile Lys Lys Lys Ala Ala Ser Met Gly Val Asn Phe Asp Ala Phe Lys
    50                  55                  60

Asp Lys Lys Thr Gly Gly Val Ser Lys Asn Pro Phe Ile Leu Glu
65                  70                  75                  80

Ala Lys Val Arg Ala Thr Thr Val Ala Glu Lys Phe Val Ile Ala Ile
                85                  90                  95

Glu Glu Glu Ala Thr Lys Leu Lys Glu Thr Gly Ser Ser Gly Glu Phe
            100                 105                 110

Ser Ala Met Tyr Asp Leu Met Phe Glu Val Ser Lys Pro Leu Gln Glu
        115                 120                 125

Leu Gly Ile Gln Glu Met Thr Lys Thr Val Ser Met Ala Ala Glu Glu
    130                 135                 140

Asn Pro Pro Thr Thr Ala Gln Gly Val Leu Glu Ile Ala Lys Lys Met
145                 150                 155                 160

Arg Glu Lys Leu Gln Arg Val His Lys Lys Asn Gln Asp Thr Leu Lys
                165                 170                 175

Lys Lys Asn Thr Glu Asp Ser Thr Ala Lys Ser Glx
            180                 185

<210> SEQ ID NO 45
<211> LENGTH: 585
<212> TYPE: DNA
<213> ORGANISM: Borrelia burgdorferi

<400> SEQUENCE: 45
atgaataaat atcaaaaaac tttcaaaatc tttaatttta aaaatttact taaactaagt      60
ttacttgttg ccctcatatc atgcggatta aaggagaaa caaaaatcat attagaacga     120
agcgccaaag acattataga tgaaataaat aaaattaaaa aagacgctgc tgataacaat     180
gtaaattttg ctgcctttaa agaagacaaa acaggcagca aggtatcaga aaattcattc     240
atacttgaag caaaaatgcg cggtactaca gtagcagaaa aatttgtaac agcgatcgaa     300
ggggaagcta caaacttaa aaagactgga agtagtggtg aattctcagc aatgtacaac     360
atgatgcttg aggtctcagg cccattagaa gaattaggag tactaagaat gacaaagaca     420
gttacagatg cggctgaaca cacccctaca actacagctg aaggaatact tgaaattgct     480
aaaataatga aacaaaatt acaaagggtt catacaaaaa actactgtgc ccttaaaaag     540
aaggaaaatc cttcttttac tggtgaaaaa tgcaaaaata actaa                    585

<210> SEQ ID NO 46
<211> LENGTH: 195
<212> TYPE: PRT
<213> ORGANISM: Borrelia burgdorferi

<400> SEQUENCE: 46

```
Met Asn Lys Tyr Gln Lys Thr Phe Lys Ile Phe Asn Phe Lys Asn Leu
 1               5                  10                  15

Leu Lys Leu Ser Leu Leu Val Ala Leu Ile Ser Cys Gly Leu Lys Gly
             20                  25                  30

Glu Thr Lys Ile Ile Leu Glu Arg Ser Ala Lys Asp Ile Ile Asp Glu
         35                  40                  45

Ile Asn Lys Ile Lys Lys Asp Ala Ala Asp Asn Asn Val Asn Phe Ala
     50                  55                  60

Ala Phe Lys Glu Asp Lys Thr Gly Ser Lys Val Ser Glu Asn Ser Phe
 65                  70                  75                  80

Ile Leu Glu Ala Lys Met Arg Gly Thr Thr Val Ala Glu Lys Phe Val
                 85                  90                  95

Thr Ala Ile Glu Gly Glu Ala Thr Lys Leu Lys Lys Thr Gly Ser Ser
            100                 105                 110

Gly Glu Phe Ser Ala Met Tyr Asn Met Met Leu Glu Val Ser Gly Pro
            115                 120                 125

Leu Glu Glu Leu Gly Val Leu Arg Met Thr Lys Thr Val Thr Asp Ala
        130                 135                 140

Ala Glu Gln His Pro Thr Thr Thr Ala Glu Gly Ile Leu Glu Ile Ala
145                 150                 155                 160

Lys Ile Met Lys Thr Lys Leu Gln Arg Val His Thr Lys Asn Tyr Cys
                165                 170                 175

Ala Leu Lys Lys Glu Asn Pro Ser Phe Thr Gly Glu Lys Cys Lys
            180                 185                 190

Asn Asn Glx
        195

<210> SEQ ID NO 47
<211> LENGTH: 546
<212> TYPE: DNA
<213> ORGANISM: Borrelia afzelii

<400> SEQUENCE: 47
atgattaaat ataataaaat tatacttaca ctaactttac ttgctagcct gttagcagca      60
tgtggcttaa caggagaaac taaacttaga ttagaatcat cagctcaaga aattaaagat     120
gaggtggata aaattagagc cgaagctgtt acagaaggcg taaatttcga tgctttcaca     180
gatacacaaa caggtagcaa ggtagcagaa aacccattca taattaaagc aaaaatacga     240
actactagtg tagcattaaa gttcatacaa gcaataaaag aggaagcaga aaaactcaaa     300
gaaagcggga gcagcagcca attctcagca ttgtatgata taatgcttga catcgcagcc     360
ccaatacaaa aaattggaat aaaagacatg ataaaaacgg ttacacagga agctgaaaaa     420
actcctacaa ctacagctga aggaataatt acgattgcaa aagcaatgga agttaaatta     480
aacagagtta aaaataaaaa tgaagaagcc ctcaaaaaaa agtcagaaaa cgctactact     540
acataa                                                               546

<210> SEQ ID NO 48
<211> LENGTH: 182
<212> TYPE: PRT
<213> ORGANISM: Borrelia afzelii

<400> SEQUENCE: 48

Met Ile Lys Tyr Asn Lys Ile Ile Leu Thr Leu Thr Leu Leu Ala Ser
 1               5                  10                  15
```

```
Leu Leu Ala Ala Cys Gly Leu Thr Gly Glu Thr Lys Leu Arg Leu Glu
             20                  25                  30

Ser Ser Ala Gln Glu Ile Lys Asp Glu Val Asp Lys Ile Arg Ala Glu
         35                  40                  45

Ala Val Thr Glu Gly Val Asn Phe Asp Ala Phe Thr Asp Thr Gln Thr
     50                  55                  60

Gly Ser Lys Val Ala Glu Asn Pro Phe Ile Ile Lys Ala Lys Ile Arg
 65                  70                  75                  80

Thr Thr Ser Val Ala Leu Lys Phe Ile Gln Ala Ile Lys Glu Ala
                 85                  90                  95

Glu Lys Leu Lys Glu Ser Gly Ser Ser Gln Phe Ser Ala Leu Tyr
            100                 105                 110

Asp Ile Met Leu Asp Ile Ala Ala Pro Ile Gln Lys Ile Gly Ile Lys
            115                 120                 125

Asp Met Ile Lys Thr Val Thr Gln Glu Ala Glu Lys Thr Pro Thr Thr
        130                 135                 140

Thr Ala Glu Gly Ile Ile Thr Ile Ala Lys Ala Met Glu Val Lys Leu
145                 150                 155                 160

Asn Arg Val Lys Asn Lys Asn Glu Gly Ala Leu Lys Lys Ser Glu
                165                 170                 175

Asn Ala Thr Thr Thr Glx
            180
```

```
<210> SEQ ID NO 49
<211> LENGTH: 510
<212> TYPE: DNA
<213> ORGANISM: Borrelia afzelii

<400> SEQUENCE: 49
atgattaaat ataataaaat tatacttaca ctaactttac ttgctagcct gttagcagca    60
tgtagtttaa caggaaaagc tagattggaa tcatcagtta agacattac aaatgaaata   120 gataaagcta taaagcagc taagacgct ggtgtaaata cagacgcgtt cacagaaaca    180
caaacaggtg gcaaggtggc gggctctcaa ataagagacg caaaaaagct cgtcgctgac   240
ttaacaatcg aatttctaaa agcaacagaa gaggaaacta ttacatttaa agaaaatgga   300
gcgggggaag atgaattctc aggaatatat gatttaatat acagaaccgc agaagcagta   360
gaaaaaattg ggatgaaagt gaaacaagcg gtcgaagcag ctgccaaaga aaatcctaaa   420
actacagcta atgggataat tgagattgta aagtaatga agcaaaagt ggaaaacatt    480 aaagaaaaac aaactaaaaa tcaaaaataa                                    510
```

```
<210> SEQ ID NO 50
<211> LENGTH: 170
<212> TYPE: PRT
<213> ORGANISM: Borrelia afzelii

<400> SEQUENCE: 50

Met Ile Lys Tyr Asn Lys Ile Ile Leu Thr Leu Thr Leu Leu Ala Ser
  1               5                  10                  15

Leu Leu Ala Ala Cys Ser Leu Thr Gly Lys Ala Arg Leu Glu Ser Ser
             20                  25                  30

Val Lys Asp Ile Thr Asn Glu Ile Asp Lys Ala Ile Lys Ala Ala Lys
         35                  40                  45

Asp Ala Gly Val Asn Thr Asp Ala Phe Thr Glu Thr Gln Thr Gly Gly
     50                  55                  60
```

```
Lys Val Ala Gly Ser Gln Ile Arg Asp Ala Lys Lys Leu Val Ala Asp
 65                  70                  75                  80

Leu Thr Ile Glu Phe Leu Lys Ala Thr Glu Glu Thr Ile Thr Phe
                 85                  90                  95

Lys Glu Asn Gly Ala Gly Glu Asp Glu Phe Ser Gly Ile Tyr Asp Leu
                100                 105                 110

Ile Tyr Arg Thr Ala Glu Ala Val Glu Lys Ile Gly Met Lys Val Lys
            115                 120                 125

Gln Ala Val Glu Ala Ala Ala Lys Glu Asn Pro Lys Thr Thr Ala Asn
        130                 135                 140

Gly Ile Ile Glu Ile Val Lys Val Met Lys Ala Lys Val Glu Asn Ile
145                 150                 155                 160

Lys Glu Lys Gln Thr Lys Asn Gln Lys Glx
                165                 170
```

<210> SEQ ID NO 51
<211> LENGTH: 555
<212> TYPE: DNA
<213> ORGANISM: Borrelia garinii

<400> SEQUENCE: 51

| | | | | | |
|---|---|---|---|---|---|
| atgactaaac | acaccaaaaa | tttacttaaa | ctaagtttaa | ttgttagcct | gttagtagca | 60 |
| tgtggcttaa | caggagaaac | taaaatcaaa | ttagaatcat | cagctcaaga | aattaaagat | 120 |
| gaaataaata | aaattaaagc | taatgctaaa | aagaaggcg | taaatttcga | ggctttcaca | 180 |
| gataaacaaa | caggcagtaa | ggtatcaaaa | aagcctgaat | tcatacttaa | agcaaaaata | 240 |
| caagctattc | aagtggcagg | aaaatttgta | aaagcaataa | aagaggaagc | agaaaaactt | 300 |
| aaaaagagtg | gaagtagcgg | tgcattctcg | gcaatgtatg | atttaatgct | tgatgtatca | 360 |
| aaaccactag | aagagattgg | aatacaaaaa | atgacaggaa | cagttacaca | ggcagctgaa | 420 |
| aaaccccctc | caactacagc | tgagggata | cttgctattg | caaaagcaat | ggaagataaa | 480 |
| ttaaacaatg | ttaatacaaa | acaacacgag | gctctcaaaa | acctcgaggg | aaaagaagcc | 540 |
| aaaactccta | aataa | | | | | 555 |

<210> SEQ ID NO 52
<211> LENGTH: 185
<212> TYPE: PRT
<213> ORGANISM: Borrelia garinii

<400> SEQUENCE: 52

```
Met Thr Lys His Thr Lys Asn Leu Leu Lys Leu Ser Leu Ile Val Ser
  1               5                  10                  15

Leu Leu Val Ala Cys Gly Leu Thr Gly Glu Thr Lys Ile Lys Leu Glu
                 20                  25                  30

Ser Ser Ala Gln Glu Ile Lys Asp Glu Ile Asn Lys Ile Lys Ala Asn
             35                  40                  45

Ala Lys Lys Glu Gly Val Asn Phe Glu Ala Phe Thr Asp Lys Gln Thr
         50                  55                  60

Gly Ser Lys Val Ser Lys Lys Pro Glu Phe Ile Leu Lys Ala Lys Ile
 65                  70                  75                  80

Gln Ala Ile Gln Val Ala Gly Lys Phe Val Lys Ala Ile Lys Glu Glu
                 85                  90                  95

Ala Glu Lys Leu Lys Lys Ser Gly Ser Ser Gly Ala Phe Ser Ala Met
                100                 105                 110

Tyr Asp Leu Met Leu Asp Val Ser Lys Pro Leu Glu Glu Ile Gly Ile
```

```
                    115                 120                 125
Gln Lys Met Thr Gly Thr Val Thr Gln Ala Ala Glu Lys Thr Pro Pro
        130                 135                 140

Thr Thr Ala Glu Gly Ile Leu Ala Ile Ala Lys Ala Met Glu Asp Lys
145                 150                 155                 160

Leu Asn Asn Val Asn Thr Lys Gln His Glu Ala Leu Lys Asn Leu Glu
                165                 170                 175

Gly Lys Glu Ala Lys Thr Pro Lys Glx
        180                 185
```

<210> SEQ ID NO 53
<211> LENGTH: 564
<212> TYPE: DNA
<213> ORGANISM: Borrelia burgdorferi

<400> SEQUENCE: 53

```
atgaaaattg gaaagctaaa ttcaatagtt atggtcttgt tttttgatct attggtcgca      60
tgtagtattg gattagtaga aagaacaaat acagctcttg aatcgtcctc taaggattta     120
aaaacaaaa ttttaaaaat aaaaaaagaa gccacgggaa aaggtgtact ttttgaagct     180
tttacaggtc ttaaaaccgg ttccaaggta acaagtggtg gactagcctt aagagaagca     240
aaagtacaag ccattgttga acaggaaag ttccttaaga taatagaaga agaagcttta      300
aagcttaaag aaactggaaa cagtggtcaa ttcttggcta tgtttgactt aatgcttgag     360
gttgtagaat cgctagaaga cgttggaata ataggcttaa aagcccgtgt tttagaggaa     420
tctaaaaata atcctataaa cacagctgaa agattgcttg cggctaaagc tcaaatagaa     480
aatcaactta aagtggttaa ggaaaaacaa aatattgaaa atggtggaga gaaaaaaaat     540
aacaaaagca aaaaaaataa ataa                                             564
```

<210> SEQ ID NO 54
<211> LENGTH: 187
<212> TYPE: PRT
<213> ORGANISM: Borrelia burgdorferi

<400> SEQUENCE: 54

```
Met Lys Ile Gly Lys Leu Asn Ser Ile Val Met Val Leu Phe Phe Asp
1               5                   10                  15

Leu Leu Val Ala Cys Ser Ile Gly Leu Val Glu Arg Thr Asn Thr Ala
                20                  25                  30

Leu Glu Ser Ser Ser Lys Asp Leu Lys Asn Lys Ile Leu Lys Ile Lys
            35                  40                  45

Lys Glu Ala Thr Gly Lys Gly Val Leu Phe Glu Ala Phe Thr Gly Leu
        50                  55                  60

Lys Thr Gly Ser Lys Val Thr Ser Gly Gly Leu Ala Leu Arg Glu Ala
65                  70                  75                  80

Lys Val Gln Ala Ile Val Glu Thr Gly Lys Phe Leu Lys Ile Glu
                85                  90                  95

Glu Glu Ala Leu Lys Leu Lys Glu Thr Gly Asn Ser Gly Gln Phe Leu
                100                 105                 110

Ala Met Phe Asp Leu Met Leu Glu Val Val Glu Ser Leu Glu Asp Val
            115                 120                 125

Gly Ile Ile Gly Leu Lys Ala Arg Val Leu Glu Glu Ser Lys Asn Asn
        130                 135                 140

Pro Ile Asn Thr Ala Glu Arg Leu Leu Ala Ala Lys Ala Gln Ile Glu
145                 150                 155                 160
```

```
Asn Gln Leu Lys Val Val Lys Glu Lys Gln Asn Ile Glu Asn Gly Gly
                165                 170                 175
Glu Lys Lys Asn Asn Lys Ser Lys Lys Asn Lys
            180                 185

<210> SEQ ID NO 55
<211> LENGTH: 564
<212> TYPE: DNA
<213> ORGANISM: Borrelia burgdorferi

<400> SEQUENCE: 55
atgaaaattg gaaagctaaa ttcaatagtt atggtcttgt tttttgatct attggtcgca      60
tgtagtattg gattagtaga aagaacaaat gcagctcttg aatcgtcctc taaggattta     120
aaaaacaaaa ttttaaaaat aaaaaaagaa gccacgggaa aaggtgtact ttttgaagct     180
tttacaggtc ttaaaaccgg ttccaaggta acaagtggtg gactagcctt aagagaagca     240
aaagtacaag ccattgttga acaggaaag ttccttaaga taatagaaga agaagcttta     300
aagcttaaag aaactggaaa cagtggtcaa ttcttggcta tgtttgactt aatgcttgag     360
gttgtagaat cgctagaaga cgttggaata ataggcttaa aagcccgtgt tttagaggaa     420
tctaaaaata tcctataaa cacagctgaa agattgcttg cggctaaagc tcaaatagaa     480
aatcaactta aagtggttaa ggaaaaacaa atattgaaa atggtggaga gaaaaaaat     540 aacaaaagca aaaaaataa ataa                                             564

<210> SEQ ID NO 56
<211> LENGTH: 187
<212> TYPE: PRT
<213> ORGANISM: Borrelia burgdorferi

<400> SEQUENCE: 56

Met Lys Ile Gly Lys Leu Asn Ser Ile Val Met Val Leu Phe Phe Asp
  1               5                  10                  15

Leu Leu Val Ala Cys Ser Ile Gly Leu Val Glu Arg Thr Asn Ala Ala
                 20                  25                  30

Leu Glu Ser Ser Lys Asp Leu Lys Asn Lys Ile Leu Lys Ile Lys
             35                  40                  45

Lys Glu Ala Thr Gly Lys Gly Val Leu Phe Glu Ala Phe Thr Gly Leu
 50                  55                  60

Lys Thr Gly Ser Lys Val Thr Ser Gly Gly Leu Ala Leu Arg Glu Ala
 65                  70                  75                  80

Lys Val Gln Ala Ile Val Glu Thr Gly Lys Phe Leu Lys Ile Ile Glu
                 85                  90                  95

Glu Glu Ala Leu Lys Leu Lys Glu Thr Gly Asn Ser Gly Gln Phe Leu
                100                 105                 110

Ala Met Phe Asp Leu Met Leu Glu Val Val Glu Ser Leu Glu Asp Val
            115                 120                 125

Gly Ile Ile Gly Leu Lys Ala Arg Val Leu Glu Ser Lys Asn Asn
            130                 135                 140

Pro Ile Asn Thr Ala Glu Arg Leu Leu Ala Ala Lys Ala Gln Ile Glu
145                 150                 155                 160

Asn Gln Leu Lys Val Val Lys Glu Lys Gln Asn Ile Glu Asn Gly Gly
                165                 170                 175

Glu Lys Lys Asn Asn Lys Ser Lys Lys Asn Lys
            180                 185
```

<210> SEQ ID NO 57
<211> LENGTH: 564
<212> TYPE: DNA
<213> ORGANISM: Borrelia burgdorferi

<400> SEQUENCE: 57

| | | | | | |
|---|---|---|---|---|---|
| atgaaaattg | gaaagctaaa | ttcaatagtt | atagccttgt | tttttaaact | attggtcgca | 60 |
| tgtagtattg | gattagtaga | agaacaaat | gcagctcttg | aatcgtcctc | taaggattta | 120 |
| aaaacaaaa | ttttaaaaat | aaaaaaagaa | gccacggaaa | aaggtgtact | ttttgaagct | 180 |
| tttacaggtc | ttaaaaccgg | ttccaaggta | acaagtggtg | gactagcctt | aagagaagca | 240 |
| aaagtacaag | ccattgttga | acaggaaag | ttccttaaga | taatagaaga | agaagcttta | 300 |
| aagcttaaag | aaactggaaa | cagtggtcaa | ttcttggcta | tgtttgactt | aatgcttgag | 360 |
| gttgtagaat | cgctagaaga | cgttggaata | ataggcttaa | aagcccgtgt | tttagaggaa | 420 |
| tctaaaaata | atcctataaa | cacagctgaa | agattgcttg | cggctaaagc | tcaaatagaa | 480 |
| aatcaactta | aagtggttaa | ggaaaaacaa | atattgaaa | atggtggaga | gaaaaaaat | 540 |
| aacaaaagca | aaaaaagaa | ataa | | | | 564 |

<210> SEQ ID NO 58
<211> LENGTH: 187
<212> TYPE: PRT
<213> ORGANISM: Borrelia burgdorferi

<400> SEQUENCE: 58

Met Lys Ile Gly Lys Leu Asn Ser Ile Val Ile Ala Leu Phe Phe Lys
1               5                   10                  15

Leu Leu Val Ala Cys Ser Ile Gly Leu Val Glu Arg Thr Asn Ala Ala
                20                  25                  30

Leu Glu Ser Ser Ser Lys Asp Leu Lys Asn Lys Ile Leu Lys Ile Lys
            35                  40                  45

Lys Glu Ala Thr Glu Lys Gly Val Leu Phe Glu Ala Phe Thr Gly Leu
    50                  55                  60

Lys Thr Gly Ser Lys Val Thr Ser Gly Gly Leu Ala Leu Arg Glu Ala
65                  70                  75                  80

Lys Val Gln Ala Ile Val Glu Thr Gly Lys Phe Leu Lys Ile Ile Glu
                85                  90                  95

Glu Glu Ala Leu Lys Leu Lys Glu Thr Gly Asn Ser Gly Gln Phe Leu
            100                 105                 110

Ala Met Phe Asp Leu Met Leu Glu Val Val Glu Ser Leu Glu Asp Val
        115                 120                 125

Gly Ile Ile Gly Leu Lys Ala Arg Val Leu Glu Ser Lys Asn Asn
    130                 135                 140

Pro Ile Asn Thr Ala Glu Arg Leu Leu Ala Ala Lys Ala Gln Ile Glu
145                 150                 155                 160

Asn Gln Leu Lys Val Val Lys Glu Lys Gln Asn Ile Glu Asn Gly Gly
                165                 170                 175

Glu Lys Lys Asn Asn Lys Ser Lys Lys Lys
            180                 185

<210> SEQ ID NO 59
<211> LENGTH: 564
<212> TYPE: DNA
<213> ORGANISM: Borrelia burgdorferi

<400> SEQUENCE: 59

```
atgaaaattg gaaagctaaa ttcaatagtt atagccttgt tttttaaact attggtcgca        60
tgtagtattg gattagtaga aagaacaaat gcagctcttg aatcgtcctc taaggattta       120
aaaaacaaaa ttttaaaaat aaaaaaagat gccacgggaa aaggtgtact ttttgaagct       180
tttacaggtc ttaaaaccgg ttccaaggta acaagtggtg gactagcctt aagagaagca       240
aaagtacaag ccattgttga aacaggaaag ttccttaaga taatagaaga agaagcttta       300
aagcttaaag aaactggaaa cagtggtcaa ttcttggcta tgtttgactt aatgcttgag       360
gttgtagaat cgctagaaga cgttggaata ataggcttaa aagcccgtgt tttagaggaa       420
tctaaaaata tcctataaa cacagctgaa agattgcttg cggctaaagc tcaaatagaa        480
aatcaactta aagtggttaa ggaaaaacaa aatattgaaa atggtggaga gaaaaaaaat       540
aacaaaagca aaaaaaagaa ataa                                              564
```

`<210>` SEQ ID NO 60
`<211>` LENGTH: 188
`<212>` TYPE: PRT
`<213>` ORGANISM: Borrelia burgdorferi

`<400>` SEQUENCE: 60

```
Met Lys Ile Gly Lys Leu Asn Ser Ile Val Ile Ala Leu Phe Phe Lys
 1               5                  10                  15

Leu Leu Val Ala Cys Ser Ile Gly Leu Val Glu Arg Thr Asn Ala Ala
                20                  25                  30

Leu Glu Ser Ser Ser Lys Asp Leu Lys Asn Lys Ile Leu Lys Ile Lys
            35                  40                  45

Lys Asp Ala Thr Gly Lys Gly Val Leu Phe Glu Ala Phe Thr Gly Leu
        50                  55                  60

Lys Thr Gly Ser Lys Val Thr Ser Gly Gly Leu Ala Leu Arg Glu Ala
 65                  70                  75                  80

Lys Val Gln Ala Ile Val Glu Thr Gly Lys Phe Leu Lys Ile Ile Glu
                85                  90                  95

Glu Glu Ala Leu Lys Leu Lys Glu Thr Gly Asn Ser Gly Gln Phe Leu
            100                 105                 110

Ala Met Phe Asp Leu Met Leu Glu Val Val Glu Ser Leu Glu Asp Val
        115                 120                 125

Gly Ile Ile Gly Leu Lys Ala Arg Val Leu Glu Glu Ser Lys Asn Asn
    130                 135                 140

Pro Ile Asn Thr Ala Glu Arg Leu Leu Ala Ala Lys Ala Gln Ile Glu
145                 150                 155                 160

Asn Gln Leu Lys Val Val Lys Glu Lys Gln Asn Ile Glu Asn Gly Gly
                165                 170                 175

Glu Lys Lys Asn Asn Lys Ser Lys Lys Lys Glx
            180                 185
```

`<210>` SEQ ID NO 61
`<211>` LENGTH: 564
`<212>` TYPE: DNA
`<213>` ORGANISM: Borrelia burgdorferi

`<400>` SEQUENCE: 61

```
atgaaaattg gaaagctaaa ttcaatagtt atggtcttgt tttttgatct attggtcgca        60
tgtagtattg gattagtaga aagaacaaat gcagctcttg aatcgtcctc taaggattta       120
aaaaacaaaa ttttaaaaat aaaaaaagaa gccacgggaa aaggtgtact ttttgaagct       180
```

```
tttacaggtc ttaaaaccgg ttccaaggta acaagtggtg gactagcctt aagagaagca        240
aaagtacaag ccattgttga acaggaaag ttccttaaga taatagaaga agaagcttta         300
aagcttaaag aaactggaaa cagtggtcaa ttcttggcta tgtttgactt aatgcttgag        360
gttgtagaat cgctagaaga cgttggaata ataggcttaa aagcccgtgt tttagaggaa        420
tctaaaaata atcctataaa cacagctgaa agattgcttg cggctaaagc tcaaatagaa        480
aatcaactta aagtggttaa ggaaaaacaa atattgaaa atggtggaga gaaaaaaaat        540
aataaaagca aaaaaaagaa ataa                                                564
```

<210> SEQ ID NO 62
<211> LENGTH: 187
<212> TYPE: PRT
<213> ORGANISM: Borrelia burgdorferi

<400> SEQUENCE: 62

```
Met Lys Ile Gly Lys Leu Asn Ser Ile Val Met Val Leu Phe Phe Asp
  1               5                  10                  15

Leu Leu Val Ala Cys Ser Ile Gly Leu Val Glu Arg Thr Asn Ala Ala
                 20                  25                  30

Leu Glu Ser Ser Ser Lys Asp Leu Lys Asn Lys Ile Leu Lys Ile Lys
             35                  40                  45

Lys Glu Ala Thr Gly Lys Gly Val Leu Phe Glu Ala Phe Thr Gly Leu
         50                  55                  60

Lys Thr Gly Ser Lys Val Thr Ser Gly Gly Leu Ala Leu Arg Glu Ala
 65                  70                  75                  80

Lys Val Gln Ala Ile Val Glu Thr Gly Lys Phe Leu Lys Ile Ile Glu
                 85                  90                  95

Glu Glu Ala Leu Lys Leu Lys Glu Thr Gly Asn Ser Gly Gln Phe Leu
            100                 105                 110

Ala Met Phe Asp Leu Met Leu Glu Val Val Glu Ser Leu Glu Asp Val
        115                 120                 125

Gly Ile Ile Gly Leu Lys Ala Arg Val Leu Glu Glu Ser Lys Asn Asn
    130                 135                 140

Pro Ile Asn Thr Ala Glu Arg Leu Leu Ala Ala Lys Ala Gln Ile Glu
145                 150                 155                 160

Asn Gln Leu Lys Val Val Lys Glu Lys Gln Asn Ile Glu Asn Gly Gly
                165                 170                 175

Glu Lys Lys Asn Asn Lys Ser Lys Lys Lys
            180                 185
```

<210> SEQ ID NO 63
<211> LENGTH: 564
<212> TYPE: DNA
<213> ORGANISM: Borrelia burgdorferi

<400> SEQUENCE: 63

```
atgaaaattg gaaagctaaa ttcaatagtt atagccttgt ttttaaact attggtcgca         60 tgtagtattg gattagtaga aagaacaaat gcagctcttg aatcgtcctc taaggattta        120
aaaaacaaaa ttttaaaaat aaaaaaagaa gccacgggaa aaggtgtact ttttgaagct        180
tttacaggtc ttaaaaccgg ttccaaggta acaagtggtg gactagcctt aagagaagca        240
aaagtacaag ccattgttga acaggaaag ttccttaaga taatagaaga agaagcttta         300
aagcttaaag aaactggaaa cagtggtcaa ttcttggcta tgtttgactt aatgcttgag        360
gttgtagaat cgctagaaga cgttggaata ataggcttaa aagcccgtgt tttagaggaa        420
```

```
tctaaaaata atcctataaa cacagctgaa agattgcttg cggctaaagc tcaaatagaa      480
aatcaactta aagtggttaa ggaaaaacaa atattgaaa atggtggaga gaaaaaaat        540 aacaaaagca aaaaaagaa ataa                                              564
```

<210> SEQ ID NO 64
<211> LENGTH: 187
<212> TYPE: PRT
<213> ORGANISM: Borrelia burgdorferi

<400> SEQUENCE: 64

```
Met Lys Ile Gly Lys Leu Asn Ser Ile Val Ile Ala Leu Phe Phe Lys
  1               5                  10                  15

Leu Leu Val Ala Cys Ser Ile Gly Leu Val Glu Arg Thr Asn Ala Ala
             20                  25                  30

Leu Glu Ser Ser Lys Asp Leu Lys Asn Lys Ile Leu Lys Ile Lys
         35                  40                  45

Lys Glu Ala Thr Gly Lys Gly Val Leu Phe Glu Ala Phe Thr Gly Leu
     50                  55                  60

Lys Thr Gly Ser Lys Val Thr Ser Gly Gly Leu Ala Leu Arg Glu Ala
 65                  70                  75                  80

Lys Val Gln Ala Ile Val Glu Thr Gly Lys Phe Leu Lys Ile Ile Glu
                 85                  90                  95

Glu Glu Ala Leu Lys Leu Lys Glu Thr Gly Asn Ser Gly Gln Phe Leu
            100                 105                 110

Ala Met Phe Asp Leu Met Leu Glu Val Val Glu Ser Leu Glu Asp Val
        115                 120                 125

Gly Ile Ile Gly Leu Lys Ala Arg Val Leu Glu Glu Ser Lys Asn Asn
    130                 135                 140

Pro Ile Asn Thr Ala Glu Arg Leu Leu Ala Ala Lys Ala Gln Ile Glu
145                 150                 155                 160

Asn Gln Leu Lys Val Val Lys Glu Lys Gln Asn Ile Glu Asn Gly Gly
                165                 170                 175

Glu Lys Lys Asn Asn Lys Ser Lys Lys Lys Lys
            180                 185
```

<210> SEQ ID NO 65
<211> LENGTH: 282
<212> TYPE: DNA
<213> ORGANISM: Borrelia garinii

<400> SEQUENCE: 65

```
gacggccagt gccaagcttt aatacttaaa aaaatggaa atagtagtca attcttggct        60
atgtttgatt tcatgcttga agttacagga tcattagatg agattggaat aaaaggaata      120
aaaagttcca tttcagagga agctaaatct aaccctgtaa acacagctga agattggtt       180 gaggttaagg ctaaaataga aataagcta gaaggtgtca agaaaagaca aaaacttgac      240
gatgaggaga aaaaatagg taaaagcaaa aaaaagcaat aa                         282
```

<210> SEQ ID NO 66
<211> LENGTH: 93
<212> TYPE: PRT
<213> ORGANISM: Borrelia garinii

<400> SEQUENCE: 66

```
Asp Gly Gln Cys Gln Ala Leu Ile Leu Lys Lys Asn Gly Asn Ser Ser
  1               5                  10                  15
```

-continued

```
Gln Phe Leu Ala Met Phe Asp Phe Met Leu Glu Val Thr Gly Ser Leu
             20              25                  30

Asp Glu Ile Gly Ile Lys Gly Ile Lys Ser Ser Ile Ser Glu Glu Ala
             35              40                  45

Lys Ser Asn Pro Val Asn Thr Ala Glu Arg Leu Val Glu Val Lys Ala
         50              55                  60

Lys Ile Glu Asn Lys Leu Glu Gly Val Lys Lys Arg Gln Lys Leu Asp
 65              70                  75                  80

Asp Glu Glu Lys Lys Ile Gly Lys Ser Lys Lys Lys Gln
             85              90
```